US010273505B2

(12) United States Patent
Garcez Lopes et al.

(10) Patent No.: US 10,273,505 B2
(45) Date of Patent: *Apr. 30, 2019

(54) MODIFIED MICROORGANISMS AND METHODS OF MAKING BUTADIENE USING SAME

(71) Applicant: Braskem S.A., Camacari—BA (BR)

(72) Inventors: Mateus Schreiner Garcez Lopes, Camacari (BR); Avram Michael Slovic, Camacari (BR); Iuri Estrada Gouvea, Camacari (BR); Johana Rincones Perez, Camacari (BR); Lucas Pedersen Parizzi, Camacari (BR)

(73) Assignee: BRASKEM S.A., Camacari (BR)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,594

(22) Filed: Jul. 23, 2018

(65) Prior Publication Data

US 2018/0346936 A1 Dec. 6, 2018

Related U.S. Application Data

(60) Division of application No. 14/885,311, filed on Oct. 16, 2015, now Pat. No. 10,059,963, which is a continuation of application No. 14/365,441, filed as application No. PCT/US2012/070161 on Dec. 17, 2012, now Pat. No. 9,518,273.

(60) Provisional application No. 61/606,035, filed on Mar. 2, 2012, provisional application No. 61/576,788, filed on Dec. 16, 2011.

(51) Int. Cl.

*C12P 5/02* (2006.01)
*C12N 15/52* (2006.01)
*C12N 9/88* (2006.01)

(52) U.S. Cl.

CPC ................ *C12P 5/026* (2013.01); *C12N 9/88* (2013.01); *C12N 15/52* (2013.01); *C12P 5/02* (2013.01); *C12Y 402/01127* (2013.01)

(58) Field of Classification Search

None
See application file for complete search history.

(56) References Cited

U.S. PATENT DOCUMENTS

| | | | |
|---|---|---|---|
| 2009/0155869 A1 | 6/2009 | Buelter et al. |
| 2011/0165644 A1 | 7/2011 | Marliere |
| 2011/0172476 A1 | 7/2011 | Dumesic et al. |
| 2011/0262975 A1 | 10/2011 | Berry et al. |
| 2011/0300597 A1 | 12/2011 | Burk et al. |
| 2012/0021478 A1 | 1/2012 | Osterhout et al. |
| 2013/0189753 A1 | 7/2013 | Pearlman et al. |

OTHER PUBLICATIONS

Slater et al., "Multiple beta-Ketothiolases Mediate Poly(beta-Hydroxyalkanoate) Copolymer Synthesis in Ralstonia eutropha," Journal of Bacteriology, American Society for Microbiology, US, vol. 180, No. 8, Apr. 1, 1998, pp. 1979-1987.
Tseng et al., "Controlled biosynthesis of odd-chain fuels and chemicals via engineered modular metabolic pathways," Proceedings of the National Academy of Sciences, vol. 109,No. 44, Oct. 30, 2012, pp. 17925-17930.
Office Action issued in corresponding Canadian Patent Application No. 2,859,556 dated Aug. 7, 2017.
Office Action issued in corresponding European Patent Application No. 12857162.7 dated Aug. 24, 2017.
Office Action issued in corresponding Chinese Patent Application No. 201280069265.6 dated Jul. 31, 2017 and English translation of same.

*Primary Examiner* — Suzanne M Noakes
*Assistant Examiner* — Jae W Lee
(74) *Attorney, Agent, or Firm* — K&L Gates LLP

(57) ABSTRACT

The present disclosure generally relates to methods of using microorganisms that comprise one or more polynucleotides coding for enzymes in one or more pathways that catalyze a conversion of a fermentable carbon source to butadiene and products and processes derived therefrom.

9 Claims, 3 Drawing Sheets

Specification includes a Sequence Listing.

MODIFIED MICROORGANISMS AND METHODS OF MAKING BUTADIENE USING SAME

CROSS-REFERENCE TO RELATED APPLICATIONS

This application is a divisional of U.S. application Ser. No. 14/885,311 which is a continuation of U.S. application Ser. No. 14/365,441, filed Jun. 13, 2014, now U.S. Pat. No. 9,518,273, issued on Dec. 13, 2016, which is a 371 National Stage Application of International Application No. PCT/US2012/70161, filed Dec. 17, 2012, which claims priority to and the benefit of U.S. Provisional Application No. 61/606,035, filed on Mar. 2, 2012, and U.S. Provisional Application No. 61/576,788, filed Dec. 16, 2011, the disclosures of each of which are incorporated by reference herein in their entirety.

BACKGROUND

Butadiene (1,3-butadiene, $CH_2$=CH—CH=$CH_2$, CAS 106-99-0) is a linear, conjugated 4-carbon hydrocarbon typically manufactured (along with other 4-carbon molecules) by steam cracking petroleum-based hydrocarbons. This process involves harsh conditions and high temperatures (at least about 850° C.). Other methods of butadiene production involve toxic and/or expensive catalysts, highly flammable and/or gaseous carbon sources, and high temperatures. Globally, several million tons of butadiene-containing polymers are produced annually. Butadiene can be polymerized to form polybutadiene, or reacted with hydrogen cyanide (prussic acid) in the presence of a nickel catalyst to form adiponitrile, a precursor to nylon. More commonly, however, butadiene is polymerized with other olefins to form copolymers such as acrylonitrile-butadiene-styrene (ABS), acrylonitrile-butadiene (ABR), or styrene-butadiene (SBR) copolymers.

SUMMARY

The present disclosure generally relates to microorganisms (e.g., non-naturally occurring microorganisms, also referred to herein as modified microorganisms) that comprise one or more polynucleotides coding for enzymes in one or more pathways that catalyze a conversion of a carbon source to butadiene and the uses of such microorganisms in industrial processes including, for use in the production of butadiene and products derived therefrom.

The present disclosure provides methods of producing butadiene from a fermentable carbon source, comprising: providing a fermentable carbon source; contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and expressing the one or more polynucleotides coding for the enzymes in the pathway that catalyzes a conversion of the fermentable carbon source to one or more intermediates in a pathway for the production of butadiene and the one or more polynucleotides coding for enzymes in a pathway that catalyze a conversion of the one or more intermediates to butadiene in the microorganism to produce butadiene.

In some embodiments which may be combined with any of the above or below mentioned embodiments, the enzymes that catalyze the conversion of the fermentable carbon source to one or more intermediates in the pathway for the production of butadiene are set forth in any one of Tables 1-3.

In some embodiments which may be combined with any of the above or below mentioned embodiments, the enzymes that catalyze the conversion of the one or more intermediates to butadiene are set forth in any one of Tables 1-3.

In some embodiments which may be combined with any of the above or below mentioned embodiments, butadiene is produced via an acetyl-CoA and propionyl-CoA intermediate; a crotonyl-CoA intermediate; and/or a formic acid intermediate.

In some embodiments which may be combined with any of the above or below mentioned embodiments, the one or more polynucleotides coding for enzymes in a pathway that catalyze a conversion of acetyl-CoA and propionyl-CoA to ketovaleryl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of ketovaleryl-CoA to (R) or (S) 3-hydroxyaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S) hydroxyaleryl-CoA to 2-pentenoyl-CoA code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of 2-pentenoyl-CoA to 2-pentenoic acid code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 2-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of 2-pentenoic acid to 4-pentenoic acid code for an isomerase including, for example, and isomerase encoded by a polynucleotide as set forth in any one of SEQ ID NOs: 99-102.

In some embodiments which may be combined with any of the above or below mentioned embodiments, the one or more polynucleotides coding for enzymes in a pathway that catalyze a conversion of 4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more more polynucleotides coding for enzymes in a pathway that catalyze a conversion of 2-pentenoyl-CoA to pent-2,4-dienoyl-CoA code for a dehydrogenase including, for example, a dehydrogenase encoded by a polynucleotide as set forth in any one of SEQ ID NOs: 124-139.

In some embodiments which may be combined with any of the above or below mentioned embodiments, the one or more polynucleotides coding for enzymes in a pathway that catalyze a conversion of pent-2,4-dienoyl-CoA to pent-2,4-dienoic code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 2,4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the one or more polynucleotides coding for enzymes in a pathway that catalyze a conversion of crotonyl-CoA to crotonyl alcohol code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of crotonyl-CoA to crotonaldehyde code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of crotonaldehyde to crotonyl alcohol code for an oxidoreductase or CoA synthetase including, for example, an oxidoreductase or synthetase encoded by a polynucleotide as set forth in any one of SEQ ID NOs: 103-123 or SEQ ID NOs: 34-36, respectively.

In some embodiments which may be combined with any of the above or below mentioned embodiments, the one or more polynucleotides coding for enzymes in a pathway that catalyze a conversion of crotonyl alcohol to butadiene code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of $CO_2$ to formic acid code for a dehydrogenase including, for example, a dehydrogenase encoded by a polynucleotide as set forth in any one of SEQ ID NOs: 124-139.

In some embodiments which may be combined with any of the above or below mentioned embodiments, the one or more polynucleotides coding for enzymes in a pathway that catalyze a conversion of pyruvate and CoA to acetyl-CoA and formic acid code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of formic acid to formyl-CoA code for a transferase or a CoA synthetase including, for example, a transferase or a CoA synthetase encoded by a polynucleotide as set forth in any one of SEQ ID NOs: 1-28 or 34-36, respectively.

In some embodiments which may be combined with any of the above or below mentioned embodiments, the one or more polynucleotides coding for enzymes in a pathway that catalyze a conversion of 2 acetyl-CoA to acetoacetyl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of acetoacetyl-CoA and formyl-CoA to 3,5-ketovaleryl-CoA code for a ketothiolase including, for example, a ketothiolase encoded by a polynucleotide as set forth in any one of SEQ ID NOs: 58-78.

In some embodiments which may be combined with any of the above or below mentioned embodiments, the one or more polynucleotides coding for enzymes in a pathway that catalyze a conversion of 3,5-ketovaleryl-CoA to (R) or (S)-5-hydroxy-3-ketovaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S)-5-hydroxy-3-ketovaleryl-CoA to (R) or (S)-3,5-dihydroxyaleryl-CoA code for an oxidoreductase including, for example, an oxidoreductase encoded by a polynucleotide as set forth in any one of SEQ ID NOs: 103-123.

In some embodiments which may be combined with any of the above or below mentioned embodiments, the one or more polynucleotides coding for enzymes in a pathway that catalyze a conversion of (R) or (S)-3,5-dihydroxyaleryl-CoA to (R) or (S) 3-hydroxy-4-pentenoyl-CoA code for a dehydratase including, for example, a dehydratase encoded by a polynucleotide as set forth in any one of SEQ ID NOs: 37-55.

In some embodiments which may be combined with any of the above or below mentioned embodiments, the one or more polynucleotides coding for enzymes in a pathway that catalyze a conversion of (R) or (S)-3-hydroxy-4-pentenoyl-CoA to 3-hydroxy-4-pentenoic acid code for a transferase or a hydrolase including, for example, a transferase or a hydrolase encoded by a polynucleotide as set forth in any one of SEQ ID NOs: 1-28 or 29-33, respectively.

In some embodiments which may be combined with any of the above or below mentioned embodiments, the one or more polynucleotides coding for enzymes in a pathway that catalyze a conversion of 3-hydroxy-4-pentenoic acid to butadiene code for a decarboxylase including, for example, a decarboxylase encoded by a polynucleotide as set forth in any one of SEQ ID NOs: 79-98.

In some embodiments which may be combined with any of the above or below mentioned embodiments, the microorganism is a bacterium is selected from the genera consisting of: *Burkholderia, Propionibacterium, Propionispira, Clostridium, Bacillus, Escherichia, Pelobacter*, or *Lactobacillus.*

In some embodiments which may be combined with any of the above or below mentioned embodiments, the microorganism is a eukaryote is a yeast, filamentous fungi, protozoa, or algae.

In some embodiments which may be combined with any of the above or below mentioned embodiments, the yeast is *Saccharomyces cerevisiae, Zymomonas mobilis*, or *Pichia pastoris*.

In some embodiments which may be combined with any of the above or below mentioned embodiments, the carbon source is sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof.

In some embodiments which may be combined with any of the above or below mentioned embodiments, the carbon source is a monosaccharide, oligosaccharide, or polysaccharide.

In some embodiments which may be combined with any of the above or below mentioned embodiments, the butadiene is secreted by the microorganism into the fermentation media.

In some embodiments which may be combined with any of the above or below mentioned embodiments, the methods may further comprise recovering the butadiene from the fermentation media.

In some embodiments which may be combined with any of the above or below mentioned embodiments, the microorganism has been genetically modified to express the one or more polynucleotides coding for enzymes in a pathway that catalyzes a conversion of the fermentable carbon source to one or more intermediates in the pathway for the production of butadiene and the one or more polynucleotides coding for enzymes in a pathway that catalyze a conversion of one or more intermediates to butadiene.

In some embodiments which may be combined with any of the above or below mentioned embodiments, the conversion of the fermentable carbon source to butadiene is ATP positive (e.g., generates a net of ATP per mol of butadiene produced) and may be additionally combined with a NADH consuming pathway to provide an anaerobic process for butadiene production.

The present disclosure also provides microorganisms comprising one or more polynucleotides coding for enzymes in a pathway that catalyzes a conversion of a fermentable carbon source to one or more intermediates in a pathway for the production of butadiene and one or more polynucleotides coding for enzymes in a pathway that catalyze a conversion of the one or more intermediates to butadiene.

In some embodiments which may be combined with any of the above or below mentioned embodiments, the enzymes that catalyze the conversion of the fermentable carbon source to one or more intermediates in the pathway for the production of butadiene are set forth in any one of Tables 1-3.

In some embodiments which may be combined with any of the above or below mentioned embodiments, the enzymes that catalyze the conversion of the one or more intermediates to butadiene are set forth in any one of Tables 1-3.

In some embodiments which may be combined with any of the above or below mentioned embodiments, butadiene is produced via an acetyl-CoA and propionyl-CoA intermediate; a crotonyl-CoA intermediate; and/or a formic acid intermediate.

In some embodiments which may be combined with any of the above or below mentioned embodiments, the microorganism is a bacterium is selected from the genera consisting of: *Burkholderia, Propionibacterium, Propionispira, Clostridium, Bacillus, Escherichia, Pelobacter*, or *Lactobacillus*.

In some embodiments which may be combined with any of the above or below mentioned embodiments, the microorganism is a eukaryote is a yeast, filamentous fungi, protozoa, or algae.

In some embodiments which may be combined with any of the above or below mentioned embodiments, the yeast is *Saccharomyces cerevisiae, Zymomonas mobilis*, or *Pichia pastoris*.

In some embodiments which may be combined with any of the above or below mentioned embodiments, the microorganism has been genetically modified to express the one or more polynucleotides coding for enzymes in a pathway that catalyzes a conversion of the fermentable carbon source to one or more intermediates in the pathway for the production of butadiene and the one or more polynucleotides coding for enzymes in a pathway that catalyze a conversion of one or more intermediates to butadiene.

The present disclosure also provides a method for producing butadiene, the method comprising: catalyzing a conversion of crotonyl alcohol to butadiene with an enzyme having an amino acid sequence at least 70% identical to linalool dehydratase (GI: 302064203).

In some embodiments, which may be combined with any of the above or below mentioned embodiments, the enzyme is at least 80% identical to linalool dehydratase (GI: 302064203).

In some embodiments, which may be combined with any of the above or below mentioned embodiments, the enzyme is at least 95% identical to linalool dehydratase (GI: 302064203).

In some embodiments, which may be combined with any of the above or below mentioned embodiments, the enzyme is linalool dehydratase (GI: 302064203).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity In some embodiments, which may be combined with any of the above or below mentioned embodiments, the enzyme has dehydratase and isomerase activity.

In some embodiments, which may be combined with any of the above or below mentioned embodiments, the method is performed in a microorganism.

The present disclosure also provides a method for producing butadiene, the method comprising: catalyzing a conversion of crotonyl alcohol to butadiene with an enzyme having an amino acid sequence at least 70% identical to a linalool dehydratase (EC 4.2.1.127).

In some embodiments, which may be combined with any of the above or below mentioned embodiments, the enzyme is at least 80% identical to a linalool dehydratase (EC 4.2.1.127).

In some embodiments, which may be combined with any of the above or below mentioned embodiments, the enzyme is at least 95% identical to a linalool dehydratase (EC 4.2.1.127).

In some embodiments, which may be combined with any of the above or below mentioned embodiments, the enzyme is a linalool dehydratase (EC 4.2.1.127).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity.

In some embodiments, which may be combined with any of the above or below mentioned embodiments, the enzyme has dehydratase and isomerase activity.

In some embodiments, which may be combined with any of the above or below mentioned embodiments, the method is performed in a microorganism.

The present disclosure also provides a modified microorganism comprising a polynucleotide coding for an enzyme that catalyzes a conversion of crotonyl alcohol to butadiene, wherein enzyme has an amino acid sequence at least 70% identical to linalool dehydratase (GI: 302064203).

In some embodiments, which may be combined with any of the above or below mentioned embodiments, the enzyme has an amino acid sequence at least 80% identical to linalool dehydratase (GI: 302064203).

In some embodiments, which may be combined with any of the above or below mentioned embodiments, the enzyme has an amino acid sequence at least 95% identical to linalool dehydratase (GI: 302064203).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity.

In some embodiments, which may be combined with any of the above or below mentioned embodiments, the enzyme has dehydratase and isomerase activity.

The present disclosure also provides a modified microorganism comprising a polynucleotide coding for an enzyme that catalyzes a conversion of crotonyl alcohol to butadiene, wherein the enzyme has an amino acid sequence at least 70% identical to a linalool dehydratase (EC 4.2.1.127).

In some embodiments, which may be combined with any of the above or below mentioned embodiments, the enzyme has an amino acid sequence at least 80% identical to linalool dehydratase (EC 4.2.1.127).

In some embodiments, which may be combined with any of the above or below mentioned embodiments, the enzyme has an amino acid sequence at least 95% identical to linalool dehydratase (EC 4.2.1.127).

In some embodiments, which may be combined with any of the above or below mentioned embodiments, the enzyme accepts crotonyl alcohol as a substrate.

In some embodiments, which may be combined with any of the above or below mentioned embodiments, the enzyme has dehydratase activity.

In some embodiments, which may be combined with any of the above or below mentioned embodiments, the enzyme has isomerase activity.

In some embodiments, which may be combined with any of the above or below mentioned embodiments, the enzyme has dehydratase and isomerase activity.

These and other embodiments of the present disclosure will be disclosed in further detail herein below.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
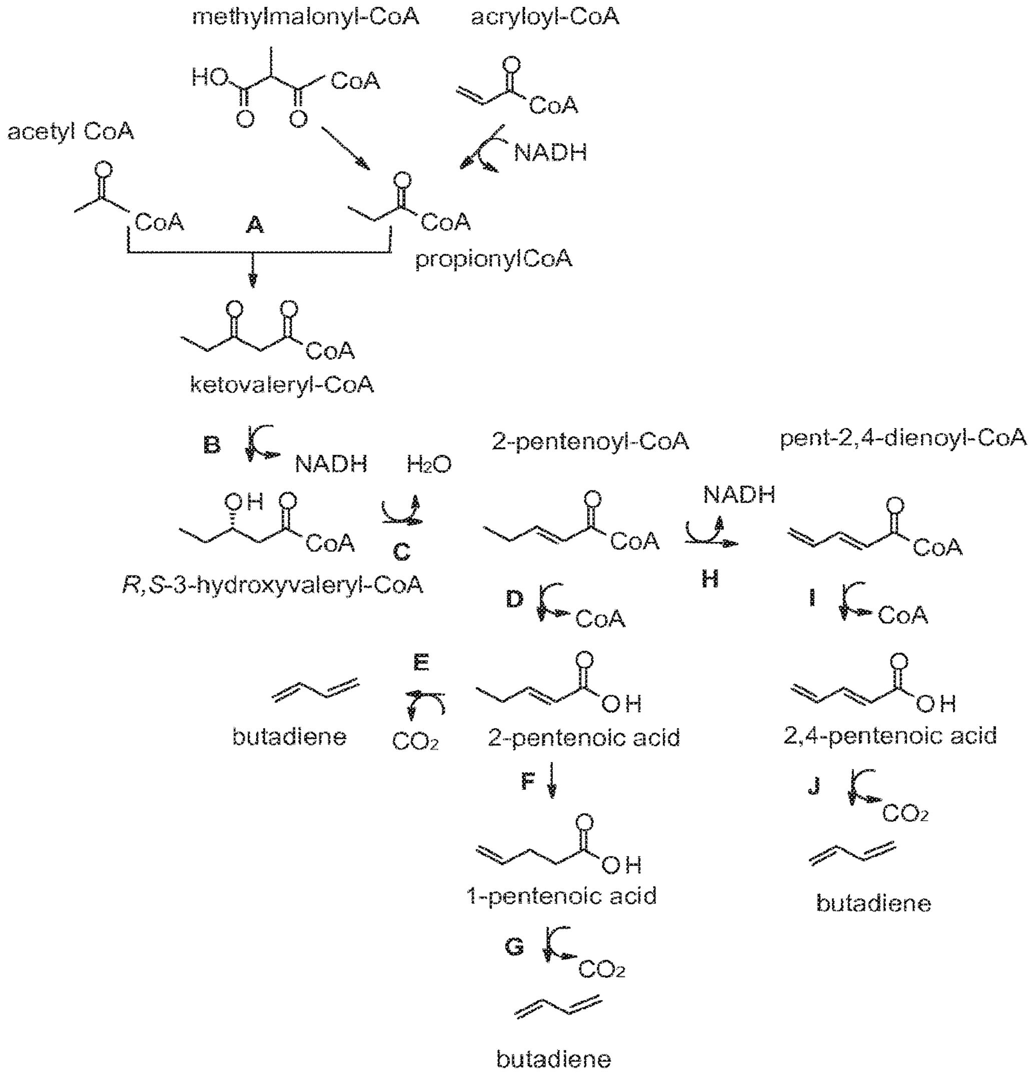
FIG. 1 depicts an exemplary pathway for the production of butadiene from a fermentable carbon source via an acetyl-CoA and propionyl-CoA intermediate.
Figure 2:
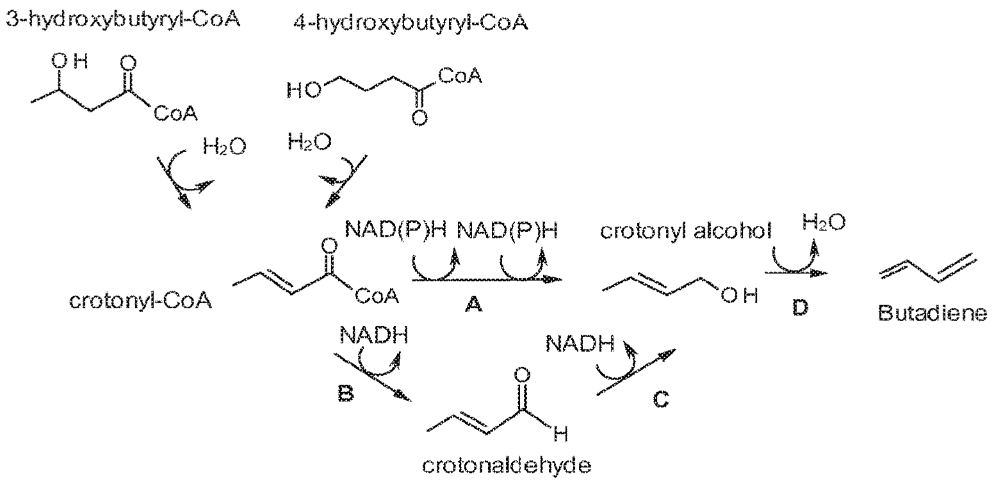
FIG. 2 depicts an exemplary pathway for the production of butadiene from a fermentable carbon source via a crotonyl-CoA intermediate.
Figure 3:
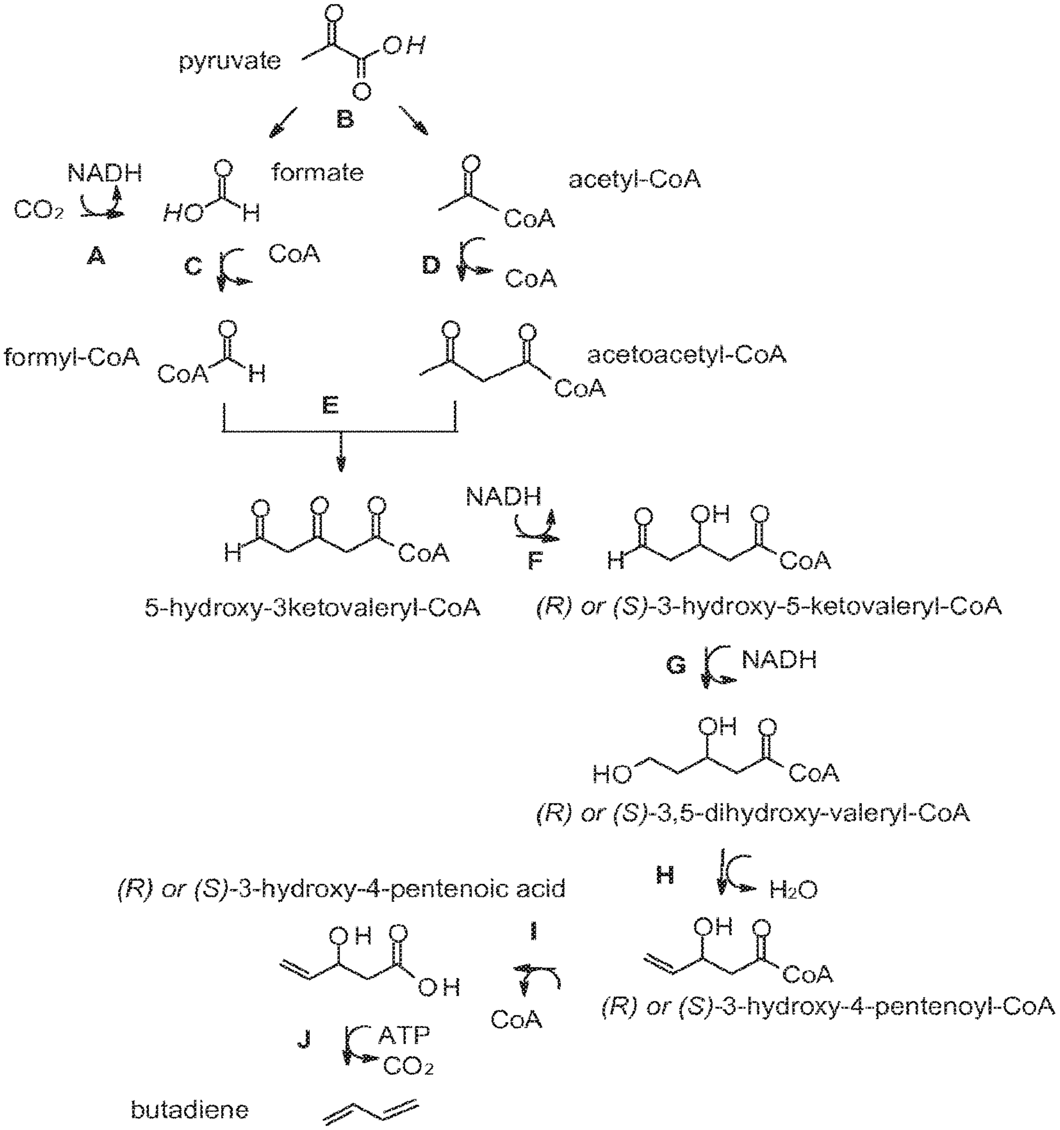
FIG. 3 depicts an exemplary pathway for the production of butadiene from a fermentable carbon source via a formic acid intermediate.

The present disclosure generally relates to microorganisms (e.g., non-naturally occurring microorganisms; modified microorganisms) that comprise a genetically modified pathway and uses of the microorganisms for the conversion of a fermentable carbon source to butadiene (see, FIGS. 1-3). Such microorganisms comprise one or more polynucleotides coding for enzymes that catalyze a conversion of a fermentable carbon source to butadiene via novel enzymatic pathways. Optionally, the produced butadiene may subsequently be converted to polybutadiene or any number of other butadiene-containing polymers.

This disclosure provides, in part, the discovery of novel enzymatic pathways including, for example, novel combinations of enzymatic pathways, for the production of butadiene from a carbon source (e.g., a fermentable carbon source). The enzymatic pathways disclosed herein permit the enzymatic production of butadiene via: an acetyl-CoA and propionyl-CoA intermediate; a crotonyl-CoA intermediate; and/or a formic acid intermediate.

The methods provided herein provide end-results similar to those of sterilization without the high capital expenditure and continuing higher management costs that are typically required to establish and maintain sterility throughout a production process. In this regard, most industrial-scale butadiene production processes are operated in the presence of measurable numbers of bacterial contaminants due to the aerobic nature of their processes. It is believed that bacterial contamination of a butadiene production processes causes a reduction in product yield and an inhibition of growth of the microorganism producing butadiene. Such drawbacks of prior methods are avoided by the presently disclosed methods as the toxic nature of the produced butadiene reduces contaminants in the production process.

The enzymatic pathways disclosed herein are advantageous over prior known enzymatic pathways for the production of butadiene in that the enzymatic pathways disclosed herein are ATP positive and when combined with a NADH consuming pathway it can provide an anaerobic pathway for butadiene. While it is possible to use aerobic processes to produce butadiene, anaerobic processes are preferred due to the risk incurred when olefins (which are by nature are explosive) are mixed with oxygen during the fermentation process, especially for butadiene fermentation. Moreover, the supplementation of oxygen and nitrogen in a fermenter requires an additional investment for air compressor, fermenters (bubble column or air-lift fermenter), temperature control and nitrogen. The presence of oxygen can also catalyze the polymerization of butadiene and can promote the growth of aerobic contaminants in the fermenter broth. Additionally, aerobic fermentation processes for the production of butadiene present several drawbacks at industrial scale (where it is technically challenging to maintain aseptic conditions) such as the fact that: (i) greater biomass is obtained reducing overall yields on carbon for the desired products; (ii) the presence and oxygen favors the growth of contaminants (Weusthuis et al., 2011, *Trends in Biotechnology,* 2011, Vol. 29, No. 4, 153-158) and (iii) the mixture of oxygen and gaseous compounds such as butadiene, poses serious risks of explosion, (iv) the oxygen can catalyze the unwanted reaction of polymerization of the olefin and, finally, (v) higher costs of fermentation and purification in aerobic conditions. Additionally, the butadiene produced by the processes disclosed herein is not diluted by $O_2$ and $N_2$ thus preventing both costly and time-consuming purification of the produced butadiene.

It will be understood that the steps involved in any and all of the methods described herein may be performed in any order and are not to be limited or restricted to the order in which they are particularly recited. For example, the present disclosure provides methods of producing butadiene from a fermentable carbon source, comprising: providing a fermentable carbon source; contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media; and expressing the one or more polynucleotides coding for the enzymes in the pathway that catalyzes a conversion of the fermentable carbon source to one or more intermediates in a pathway for the production of butadiene and one or more polynucleotides coding for enzymes in a pathway that catalyze a conversion of the one or more intermediates to butadiene in the microorganism to produce butadiene. As such, expression of the one or more polynucleotides coding for the enzymes in the pathway that catalyzes a conversion of the fermentable carbon source to one or more intermediates in a pathway for the production of butadiene and one or more polynucleotides coding for enzymes in a pathway that catalyze a conversion of the one or more intermediates to butadiene in the microorganism to produce butadiene may be performed prior to or after contacting the fermentable carbon source with a microorganism comprising one or more polynucleotides coding for enzymes in a pathway that catalyzes a conversion of the fermentable carbon source to one or more intermediates in a pathway for the production of butadiene, and one or more polynucleotides coding for enzymes in a pathway that catalyze a conversion of the one or more intermediates to butadiene in a fermentation media.

It will also be understood that the microorganisms disclosed herein may comprise the entire pathway disclosed in any of FIGS. 1-3 including, comprising all of the polynucleotides that code for enzymes that catalyze a conversion of a fermentable carbon source to butadiene. Alternatively, it will also be understood that the microorganisms disclosed herein may comprises one or more of the polynucleotides coding for enzymes that catalyze a conversion of a fermentable carbon source to butadiene in any of FIGS. 1-3 (e.g., a microorganism may comprise 2, 3, 4, 5, 6, 7, 8, 9, 10 or more polynucleotides that code for enzymes that catalyze a conversion of a fermentable carbon source to butadiene as disclosed in any of FIGS. 1-3.

In some embodiments, the ratio of grams of the produced butadiene to grams of the fermentable carbon source is 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or 1.00.

In some embodiments, a number of moles of carbon in the produced butadiene comprises 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of a number of moles of carbon in the fermentable carbon source.

As used herein, "butadiene" is intended to mean buta-1,3-diene or 1,3-butadiene (CAS 106-99-0), with a general formula $CH_2$=CH—CH=$CH_2$, and a molecular mass of 54.09 g/mol.

As used herein, the term "biological activity" or "functional activity," when referring to a protein, polypeptide or peptide, may mean that the protein, polypeptide or peptide exhibits a functionality or property that is useful as relating to some biological process, pathway or reaction. Biological or functional activity can refer to, for example, an ability to interact or associate with (e.g., bind to) another polypeptide or molecule, or it can refer to an ability to catalyze or regulate the interaction of other proteins or molecules (e.g., enzymatic reactions).

As used herein, the term "culturing" may refer to growing a population of cells, e.g., microbial cells, under suitable conditions for growth, in a liquid or on solid medium.

As used herein, the term "derived from" may encompass the terms originated from, obtained from, obtainable from, isolated from, and created from, and generally indicates that one specified material finds its origin in another specified material or has features that can be described with reference to the another specified material.

As used herein, the term "an expression vector" may refer to a DNA construct containing a polynucleotide or nucleic acid sequence encoding a polypeptide or protein, such as a DNA coding sequence (e.g., gene sequence) that is operably linked to one or more suitable control sequence(s) capable of affecting expression of the coding sequence in a host. Such control sequences include a promoter to affect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome (e.g., independent vector or plasmid), or may, in some instances, integrate into the genome itself (e.g., integrated vector). The plasmid is the most commonly used form of expression vector. However, the disclosure is intended to include such other forms of expression vectors that serve equivalent functions and which are, or become, known in the art.

As used herein, the term "expression" may refer to the process by which a polypeptide is produced based on a nucleic acid sequence encoding the polypeptides (e.g., a gene). The process includes both transcription and translation.

As used herein, the term "gene" may refer to a DNA segment that is involved in producing a polypeptide or protein (e.g., fusion protein) and includes regions preceding and following the coding regions as well as intervening sequences (introns) between individual coding segments (exons).

As used herein, the term "heterologous," with reference to a nucleic acid, polynucleotide, protein or peptide, may refer to a nucleic acid, polynucleotide, protein or peptide that does not naturally occur in a specified cell, e.g., a host cell. It is intended that the term encompass proteins that are encoded by naturally occurring genes, mutated genes, and/or synthetic genes. In contrast, the term homologous, with reference to a nucleic acid, polynucleotide, protein or peptide, refers to a nucleic acid, polynucleotide, protein or peptide that occurs naturally in the cell.

As used herein, the term a "host cell" may refer to a cell or cell line, including a cell such as a microorganism which a recombinant expression vector may be transfected for expression of a polypeptide or protein (e.g., fusion protein). Host cells include progeny of a single host cell, and the progeny may not necessarily be completely identical (in morphology or in total genomic DNA complement) to the original parent cell due to natural, accidental, or deliberate mutation. A host cell may include cells transfected or transformed in vivo with an expression vector.

As used herein, the term "introduced," in the context of inserting a nucleic acid sequence or a polynucleotide sequence into a cell, may include transfection, transformation, or transduction and refers to the incorporation of a nucleic acid sequence or polynucleotide sequence into a eukaryotic or prokaryotic cell wherein the nucleic acid sequence or polynucleotide sequence may be incorporated into the genome of the cell (e.g., chromosome, plasmid, plastid, or mitochondrial DNA), converted into an autonomous replicon, or transiently expressed.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Non-naturally occurring microbial organisms of the disclosure can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely. Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

As used herein, "butadiene" is intended to mean a conjugated linear diene with the molecular formula C4H6, a general formula of $CH_2{=}CH{-}CH{=}CH_2$ and a molecular mass of 54.09 g/mol. Butadiene is also known in the art as 1,3-butadiene, but-1,3-diene, biethylene, erythrene, divinyl, and vinylethylene.

As used herein, the term "operably linked" may refer to a juxtaposition or arrangement of specified elements that allows them to perform in concert to bring about an effect. For example, a promoter may be operably linked to a coding sequence if it controls the transcription of the coding sequence.

As used herein, the term "a promoter" may refer to a regulatory sequence that is involved in binding RNA polymerase to initiate transcription of a gene. A promoter may be an inducible promoter or a constitutive promoter. An inducible promoter is a promoter that is active under environmental or developmental regulatory conditions.

As used herein, the term "a polynucleotide" or "nucleic acid sequence" may refer to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Such polynucleotides or nucleic acid sequences may encode amino acids (e.g., polypeptides or proteins such as fusion proteins). Because the genetic code is degenerate, more than one codon may be used to encode a particular amino acid, and the present disclosure encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms polynucleotide, nucleic acid, and oligonucleotide are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S (thioate), P(S)S (dithioate), $(O)NR_2$ (amidate), P(O)R, P(O)OR', $COCH_2$ (formacetal), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term a "protein" or "polypeptide" may refer to a composition comprised of amino acids and recognized as a protein by those of skill in the art. The conventional one-letter or three-letter code for amino acid residues is used herein. The terms protein and polypeptide are used interchangeably herein to refer to polymers of amino acids of any length, including those comprising linked (e.g., fused) peptides/polypeptides (e.g., fusion proteins). The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, related proteins, polypeptides or peptides may encompass variant proteins, polypeptides or peptides. Variant proteins, polypeptides or peptides differ from a parent protein, polypeptide or peptide and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "recovered," "isolated," "purified," and "separated" may refer to a material (e.g., a protein, peptide, nucleic acid, polynucleotide or cell) that is removed from at least one component with which it is naturally associated. For example, these terms may refer to a material which is substantially or essentially free from components which normally accompany it as found in its native state, such as, for example, an intact biological system.

As used herein, the term "recombinant" may refer to nucleic acid sequences or polynucleotides, polypeptides or proteins, and cells based thereon, that have been manipulated by man such that they are not the same as nucleic acids, polypeptides, and cells as found in nature. Recombinant may also refer to genetic material (e.g., nucleic acid sequences or polynucleotides, the polypeptides or proteins they encode, and vectors and cells comprising such nucleic acid sequences or polynucleotides) that has been modified to alter its sequence or expression characteristics, such as by mutating the coding sequence to produce an altered polypeptide, fusing the coding sequence to that of another coding sequence or gene, placing a gene under the control of a different promoter, expressing a gene in a heterologous organism, expressing a gene at decreased or elevated levels, expressing a gene conditionally or constitutively in manners different from its natural expression profile, and the like.

As used herein, the term "selective marker" or "selectable marker" may refer to a gene capable of expression in a host cell that allows for ease of selection of those hosts containing an introduced nucleic acid sequence, polynucleotide or vector. Examples of selectable markers include but are not limited to antimicrobial substances (e.g., hygromycin, bleomycin, or chloramphenicol) and/or genes that confer a metabolic advantage, such as a nutritional advantage, on the host cell.

As used herein, the term "substantially similar" and "substantially identical" in the context of at least two nucleic acids, polynucleotides, proteins or polypeptides may mean that a nucleic acid, polynucleotide, protein or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) nucleic acid, polynucleotide, protein or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et aL (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "transfection" or "transformation" may refer to the insertion of an exogenous nucleic acid or polynucleotide into a host cell. The exogenous nucleic acid or polynucleotide may be maintained as a non-integrated vector, for example, a plasmid, or alternatively, may be integrated into the host cell genome. The term transfecting or transfection is intended to encompass all conventional techniques for introducing nucleic acid or polynucleotide into host cells. Examples of transfection techniques include, but are not limited to, calcium phosphate precipitation, DEAE-dextran-mediated transfection, lipofection, electroporation, and microinjection.

As used herein, the term "transformed," "stably transformed," and "transgenic" may refer to a cell that has a non-native (e.g., heterologous) nucleic acid sequence or polynucleotide sequence integrated into its genome or as an episomal plasmid that is maintained through multiple generations.

As used herein, the term "vector" may refer to a polynucleotide sequence designed to introduce nucleic acids into one or more cell types. Vectors include cloning vectors, expression vectors, shuttle vectors, plasmids, phage particles, single and double stranded cassettes and the like.

As used herein, the term "wild-type," "native," or "naturally-occurring" proteins may refer to those proteins found in nature. The terms wild-type sequence refers to an amino acid or nucleic acid sequence that is found in nature or naturally occurring. In some embodiments, a wild-type sequence is the starting point of a protein engineering project, for example, production of variant proteins.

Unless defined otherwise herein, all technical and scientific terms used herein have the same meaning as commonly understood by one of ordinary skill in the art to which this disclosure belongs. Singleton, et al., Dictionary of Microbiology and Molecular Biology, second ed., John Wiley and Sons, New York (1994), and Hale & Markham, The Harper Collins Dictionary of Biology, Harper Perennial, N.Y. (1991) provide one of skill with a general dictionary of many of the terms used in this disclosure. Further, it will be understood that any of the substrates disclosed in any of the pathways herein may alternatively include the anion or the cation of the substrate.

Numeric ranges provided herein are inclusive of the numbers defining the range.

Unless otherwise indicated, nucleic acids sequences are written left to right in 5' to 3' orientation; amino acid sequences are written left to right in amino to carboxyl orientation, respectively.

While the present disclosure is capable of being embodied in various forms, the description below of several embodiments is made with the understanding that the present disclosure is to be considered as an exemplification of the disclosure, and is not intended to limit the disclosure to the specific embodiments illustrated. Headings are provided for convenience only and are not to be construed to limit the disclosure in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

Modification of Microorganism

A microorganism may be modified (e.g., genetically engineered) by any method known in the art to comprise and/or express (e.g., including over express) one or more polynucleotides (e.g., heterologous polynucleotides and/or non-heterologous polynucleotides) coding for enzymes in one or more pathways that are capable of converting a fermentable carbon source to butadiene. The microorganism may naturally express all of the enzymes in one or more pathways needed to convert a fermentable carbon source to butadiene or may be modified to express including, for example, over express, one or more enzymes in the one or more pathways. In some embodiments, the microorganism may comprise fewer than all of the enzymes in such pathway and polynucleotides coding for the missing enzymes may be genetically introduced into the microorganism. For example, the modified microorganism may be modified to comprise one or more polynucleotides coding for enzymes that catalyze a conversion of a fermentable carbon source (e.g., glucose) to one or more intermediates (e.g., acetyl-CoA and propionyl-CoA; crotonyl-CoA; and/or formic acid) in a pathway for the production of butadiene. Additionally or alternatively, the modified microorganism may be modified to comprise one or more polynucleotides coding for enzymes that catalyze a conversion of the one or more intermediates (e.g., acetyl-CoA and propionyl-CoA; crotonyl-CoA; and/or formic acid) to butadiene. In some embodiments, a polynucleotide may code for an enzyme that catalyzes a conversion of one or more intermediates in a pathway for the production of butadiene. In some embodiments, polynucleotides may be modified (e.g., genetically engineered) to modulate (e.g., increase or decrease) the substrate specificity of the encode enzyme, or the polynucleotides may be modified to change the substrate specificity of the encoded enzyme (e.g., a polynucleotide that codes for an enzyme with specificity for a substrate may be modified such that the enzyme has specificity for another substrate). Preferred microorganisms may comprise polynucleotides coding for one or more of the enzymes as set forth in any one of Tables 1-3 and FIG. 1-3.

A microorganism may comprise one or more polynucleotides coding for enzymes in a pathway that catalyze a conversion of acetyl-CoA and propionyl-CoA to butadiene. In some embodiments, the one or more polynucleotides coding for enzymes in a pathway that catalyze a conversion of acetyl-CoA and propionyl-CoA to butadiene may include, but are not limited to:

one or more polynucleotides coding for enzymes in a pathway that catalyze a conversion of acetyl-CoA and propionyl-CoA to ketovaleryl-CoA (e.g., a thiolase);

one or more polynucleotides coding for enzymes in a pathway that catalyze a conversion of ketovaleryl-CoA to (R) or (S) 3-hydroxyaleryl-CoA (e.g., a hydroxyvaleryl-CoA dehydrogenase);

one or more polynucleotides coding for enzymes in a pathway that catalyze a conversion of (R) or (S) hydroxyaleryl-CoA to 2-pentenoyl-CoA (e.g., a hydroxyvaleryl-CoA dehydratase);

one or more polynucleotides coding for enzymes in a pathway that catalyze a conversion of 2-pentenoyl-CoA to 2-pentenoic acid (e.g., a pentenoyl-CoA hydrolase or transferase);

one or more polynucleotides coding for enzymes in a pathway that catalyze a conversion of 2-pentenoic acid to butadiene (e.g., a 2-pentenoic acid decarboxylase);

one or more polynucleotides coding for enzymes in a pathway that catalyze a conversion of 2-pentenoic acid to 4-pentenoic acid (e.g., a transposing C═C bonds isomerase);

one or more polynucleotides coding for enzymes in a pathway that catalyze a conversion of 4-pentenoic acid to butadiene (e.g., a 4-pentenoic acid decarboxylase);

one or more polynucleotides coding for enzymes in a pathway that catalyze a conversion of 2-pentenoyl-CoA to pent-2,4-dienoyl-CoA (e.g., a pentenoyl-CoA dehydrogenase);

one or more polynucleotides coding for enzymes in a pathway that catalyze a conversion of pent-2,4-dienoyl-CoA to pent-2,4-dienoic (e.g., a pent-2,4-dienoyl-CoA hydrolase, or transferase); and/or one or more polynucleotides coding for enzymes in a pathway that catalyze a conversion of 2,4-pentenoic acid to butadiene (e.g., a pent,2,4-dienoic acid decarboxylase).

In some embodiments, the microorganism further comprises one or more polynucleotides coding for enzymes in a pathway that catalyze a conversion of a fermentable carbon source (e.g., glucose) to methylmalonyl-CoA and/or acryloyl-CoA.

In some embodiments, a microorganism is provided that comprises one or more of the above polynucleotides including, all, of the polynucleotides above.

Exemplary enzymes which convert acetyl-CoA and propionyl-CoA to butadiene are presented in Table 1 below, as well as, the substrates that they act upon and product that they produce. The enzyme number represented in Table 1 correlates with the enzyme numbering used in FIG. 1 which schematically represents the enzymatic conversion of a fermentable carbon source to butadiene through an acetyl-CoA and propionyl-CoA intermediate.

TABLE 1

Production of butadiene via acetyl-CoA and propionyl-CoA intermediates.

| Enzyme No. | Enzyme Name | E.C. number | Mediated Conversion |
|---|---|---|---|
| A | thiolase | 2.3.1. | acetyl-CoA + propionyl-CoA → ketovaleryl-CoA |
| B | hydroxyvaleryl-CoA dehydrogenase | 1.1.1. 1.1.1. | ketovaleryl-CoA + NADH→ (R) or (S) 3-hydroxyaleryl-CoA |
| C | hydroxyvaleryl-CoA dehydratase | 4.2.1. | (R) or (S) hydroxyaleryl-CoA→ 2-pentenoyl-CoA |
| D | pentenoyl-CoA hydrolase or transferase | 3.1.2, 2.8.3 or 2.3.3 | 2-pentenoyl-CoA → 2-pentenoic acid |
| E | 2-pentenoic acid decarboxylase | 4.1.1. | 2-pentenoic acid → butadiene |
| F | transposing C=C bonds isomerase | 5.3.3 | 2-pentenoic acid → 4-pentenoic acid |
| G | 4-pentenoic acid decarboxylase | 4.1.1.33 | 4-pentenoic acid → butadiene |
| H | pentenoyl-CoA dehydrogenase | 1.3.1. | 2-pentenoyl-CoA → pent-2,4-dienoyl-CoA |
| I | pent-2,4-dienoyl-CoA hydrolase, or transferase | 3.1.2, 2.8.3 or 2.3.3 | pent-2,4-dienoyl-CoA → pent-2,4-dienoic |
| J | pent,2,4-dienoic acid decarboxylase | 4.1.1. | 2,4-pentenoic acid → butadiene |

A microorganism may comprise one or more polynucleotides coding for enzymes in a pathway that catalyze a conversion of crotonyl-CoA to butadiene. In some embodiments, the one or more polynucleotides coding for enzymes in a pathway that catalyze a conversion of crotonyl-CoA to butadiene may include, but are not limited to:

one or more polynucleotides coding for enzymes in a pathway that catalyze a conversion of crotonyl-CoA to crotonyl alcohol (e.g., a crotonyl-CoA reductase (bifunctional));

one or more polynucleotides coding for enzymes in a pathway that catalyze a conversion of crotonyl-CoA to crotonaldehyde (e.g., a crotonaldehyde dehydrogenase);

one or more polynucleotides coding for enzymes in a pathway that catalyze a conversion of crotonaldehyde to crotonyl alcohol (e.g., a crotonyl alcohol dehydrogenase); and/or one or more polynucleotides coding for enzymes in a pathway that catalyze a conversion of crotonyl alcohol to butadiene (e.g., a crotonyl alcohol dehydratase).

In some embodiments, a microorganism is provided that comprises one or more of the above polynucleotides including, all, of the polynucleotides above.

In preferred embodiments, the microorganism further comprises one or more polynucleotides coding for enzymes in a pathway that catalyze a conversion of a fermentable carbon source (e.g., glucose) to crotonyl-CoA.

In some embodiments, the microorganism may further comprise one or more polynucleotides coding for enzymes in a pathway that catalyze a conversion of a fermentable carbon source (e.g., glucose) to 3-hydroxybutyryl-CoA and/or 4-hydroxybutyryl-CoA. In such embodiments, the microorganism further comprises one or more polynucleotides coding for enzymes in a pathway that catalyze a conversion of 3-hydroxybutyryl-CoA to crotonyl-CoA and/or one or more polynucleotides coding for enzymes in a pathway that catalyze a conversion of 4-hydroxybutyryl-CoA to crotonyl-CoA.

Exemplary enzymes which convert crotonyl-CoA to butadiene are presented in Table 1 below, as well as, the substrates that they act upon and product that they produce. The enzyme number represented in Table 1 correlates with the enzyme numbering used in FIG. 1 which schematically represents the enzymatic conversion of a fermentable carbon source to butadiene through a crotonyl-CoA intermediate.

TABLE 2

Production of butadiene via a crotonyl-CoA intermediate.

| Enzyme No. | Enzyme Name | E.C. number | Mediated Conversion |
|---|---|---|---|
| A | crotonyl-CoA reductase (bifuncional) | 1.1.1 | crotonyl-CoA → crotonyl alcohol |
| B | crotonaldehyde dehydrogenase | 1.2.1 | crotonyl-CoA → crotonaldehyde |
| C | crotonyl alcohol dehydrogenase | 1.1.1 1.1.1.1 | crotonaldehyde → crotonyl alcohol |
| D | crotonyl alcohol dehydratase | 4.2.1 4.2.1.127 | crotonyl alcohol → butadiene |

A microorganism may comprise one or more polynucleotides coding for enzymes in a pathway that catalyze a conversion of formic acid to butadiene. In some embodiments, the one or more polynucleotides coding for enzymes in a pathway that catalyze a conversion of formic acid to butadiene may include, but are not limited to:

one or more polynucleotides coding for enzymes in a pathway that catalyze a conversion of $CO_2$ to formic acid (e.g., a formate dehydrogenase);

one or more polynucleotides coding for enzymes in a pathway that catalyze a conversion of pyruvate and CoA to acetyl-CoA and formic acid (e.g., an acetyl-CoA:formate C-acetyltransferase);

one or more polynucleotides coding for enzymes in a pathway that catalyze a conversion of formic acid to formyl-CoA (e.g., a formyl-CoA transferase or synthase);

one or more polynucleotides coding for enzymes in a pathway that catalyze a conversion of 2 acetyl-CoA to acetoacetyl-CoA (e.g., an acetoacetyl-CoA thiolase);

one or more polynucleotides coding for enzymes in a pathway that catalyze a conversion of acetoacetyl-CoA and formyl-CoA to 3,5-ketovaleryl-CoA (e.g., a 3,5-ketovaleryl-CoA thiolase);

one or more polynucleotides coding for enzymes in a pathway that catalyze a conversion of 3,5-ketovaleryl-CoA to (R) or (S)-5-hydroxy-3-ketovaleryl-CoA (e.g., a 3,5-ketovaleryl-CoA dehydrogenase);

one or more polynucleotides coding for enzymes in a pathway that catalyze a conversion of (R) or (S)-5-hydroxy-3-ketovaleryl-CoA to (R) or (S)-3,5-dihydroxyaleryl-CoA (e.g., a 5-hydroxy-3-ketovaleryl-CoA dehydrogenase);

one or more polynucleotides coding for enzymes in a pathway that catalyze a conversion of (R) or (S)-3,5-dihydroxyaleryl-CoA to (R) or (S) 3-hydroxy-4-pentenoyl-CoA (e.g., a 3,5-hydroxyvaleryl-CoA dehydratase);

one or more polynucleotides coding for enzymes in a pathway that catalyze a conversion of (R) or (S)-3-hydroxy-4-pentenoyl-CoA to 3-hydroxy-4-pentenoic acid (e.g., a 3-hydroxy-4-pentenoyl-CoA hydrolase, transferase or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase).

In some embodiments, the microorganism further comprises one or more polynucleotides coding for enzymes in a pathway that catalyze a conversion of a fermentable carbon source (e.g., glucose) to pyruvate.

In some embodiments, a microorganism is provided that comprises one or more of the above polynucleotides including, all, of the polynucleotides above.

Exemplary enzymes which convert formic acid to butadiene are presented in Table 3 below, as well as, the substrates that they act upon and product that they produce. The enzyme number represented in Table 3 correlates with the enzyme numbering used in FIG. 3 which schematically represents the enzymatic conversion of a fermentable carbon source to butadiene through a formic acid intermediate.

TABLE 3

Production of butadiene via a formic acid intermediate.

| Enzyme No. | Enzyme Name | E.C. number | Mediated Conversion |
|---|---|---|---|
| A | formate dehydrogenase | 1.2.1.2 | $CO_2$ → Formate |
| B | acetyl-CoA:formate C-acetyltransferase | 2.3.1.54 | pyruvate + CoA → acetyl-CoA + formic acid |
| C | formyl-CoA transferase or synthase | 2.8.3.16<br>6.2.1 | formic acid → formyl-CoA |
| D | acetoacetyl-CoA thiolase | 2.3.1.16 | 2 acetyl-CoA → acetoacetyl-CoA |
| E | 3,5-ketovaleryl-CoA thiolase | 2.3.1.<br>2.3.1.16 | acetoacetyl-CoA + formyl-CoA → 3,5-ketovaleryl-CoA |
| F | 3,5-ketovaleryl-CoA dehydrogenase | | 3,5-ketovaleryl-CoA → (R) or (S)-5-hydroxy-3-Ketovaleryl-CoA |
| G | 5-hydroxy-3-ketovaleryl-CoA dehydrogenase | 1.1.1.35<br>1.1.1.36 | (R) or (S)-5-hydroxy-3-ketovaleryl-CoA → (R) or (S)-3,5-dihydroxyaleryl-CoA |
| H | 3,5-hydroxyvaleryl-CoA dehydratase | 4.2.1.17<br>4.2.1.54 | (R) or (S)-3,5-dihydroxyaleryl-CoA→ (R) or (S) 3-hydroxy-4-pentenoyl-CoA |
| I | 3-hydroxy-4-pentenoyl-CoA hydrolase, transferase or synthase | 3.1.2,<br>2.8.3 or<br>2.3.3 | (R) or (S)-3-hydroxy-4-pentenoyl-CoA → 3-hydroxy-4-pentenoic acid |
| J | 3-hydroxy-4-pentenoic acid decarboxylase | 4.1.1.33 | 3-hydroxy-4-pentenoic acid → butadiene |

A microorganism is also provided that comprises one or more polynucleotides coding for enzymes in a pathway that catalyze a conversion of a fermentable carbon source to acetyl-CoA and propionyl-CoA and one or more polynucleotides coding for enzymes in a pathway that catalyze a conversion of acetyl-CoA and propionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to methylmalonyl-CoA; one or more polynucleotides coding for enzymes in a pathway that catalyze a conversion of methylmalonyl-CoA to propionyl-CoA; one or more polynucleotides coding for enzymes in a pathway that catalyze a conversion of pyruvate to acryloyl-CoA; one or more polynucleotides coding for enzymes in a pathway that catalyze a conversion of acryloyl-CoA to propionyl-CoA; one or more polynucleotides coding for enzymes in a pathway that catalyze a conversion of acetyl-CoA and propionyl-CoA to ketovaleryl-CoA (e.g., a thiolase); one or more polynucleotides coding for enzymes in a pathway that catalyze a conversion of ketovaleryl-CoA to (R) or (S) 3-hydroxyvaleryl-CoA (e.g., a hydroxyvaleryl-CoA dehydrogenase); one or more polynucleotides coding for enzymes in a pathway that catalyze a conversion of (R) or (S) 3-hydroxyvaleryl-CoA to 2-pentenoyl-CoA (e.g., a hydroxyvaleryl-CoA dehydratase); one or more polynucleotides coding for enzymes in a pathway that catalyze a conversion of 2-pentenoyl-CoA to 2-pentenoic acid (e.g., a pentenoyl-CoA hydrolase, a pentenoyl-CoA transferase or a pentenoyl-CoA synthase); one or more polynucleotides coding for enzymes in a pathway that catalyze a conversion of 2-pentenoic acid to 4-pentenoic acid (e.g., a transposing bonds C═C isomerase); and/or one or more polynucleotides coding for enzymes in a pathway that catalyze a conversion of 4-pentenoic acid to butadiene (e.g., a 4-pentenoic fatty acid decarboxylase or a 2-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to ethyl-malonyl-CoA and one or more polynucleotides coding for enzymes in a pathway that catalyze a conversion of ethyl-malonyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyzes a conversion of pyruvate to acetyl-CoA; one or more polynucleotides coding for enzymes in a pathway that catalyzes a conversion of acetyl-CoA to acetoacetyl-CoA (e.g., an acetoacetyl-CoA thiolase); one or more polynucleotides coding for enzymes in a pathway that catalyzes a conversion of acetoacetyl-CoA to 3-hydroxybutyryl-CoA (e.g., a 3-hydroxybutyryl-CoA dehydrogenase); one or more polynucleotides coding for enzymes in a pathway that catalyzes a conversion of 3-hydroxybutyryl-CoA to crotonyl-CoA (e.g., a crotonase); one or more polynucleotides coding for enzymes in a pathway that catalyzes a conversion of crotonyl-CoA to ethyl-malonyl-CoA (e.g., a crotonyl-CoA carboxylase/reductase); one or more polynucleotides coding for enzymes in a pathway that catalyzes a conversion of crotonyl-CoA to butyric acid (e.g., butyryl-CoA dehydrogenase); one or more polynucleotides coding for enzymes in a pathway that catalyzes a conversion of butyric acid to ethyl-malonyl-CoA (e.g., a butanoyl-CoA:carbon-dioxide ligase); one or more polynucleotides coding for enzymes in a pathway that catalyze a conversion of ethyl-malonyl-CoA to 2-(formol)butanoic acid (e.g., an ethyl-malonyl-CoA reductase (aldehyde forming)); one or more polynucleotides coding for enzymes in a pathway that catalyze a conversion of 2-(formol)butanoic acid to 2-(hydroxymethyl)butanoic acid (e.g., a 2-(formyl)butanoic acid reducatase (alcohol forming)); one or more polynucleotides coding for enzymes in a pathway that catalyze a conversion of ethyl malonyl-CoA to 2-(hydroxymethyl)butanoic acid (e.g., an ethyl-malonyl-CoA reductase (alcohol forming)); one or more polynucleotides coding for enzymes in a pathway that catalyze a conversion of 2-(hydroxymethyl)butanoic acid to 2-(phosphanyloxymethyl)butanoic acid (e.g., a 2-(hydroxymethyl)butanoic acid kinase); one or more polynucleotides coding for enzymes in a pathway that catalyze a conversion of 2-(phosphanyloxymethyl)butanoic acid to 2-(diphosphanyloxymethyl)butanoic acid (e.g., a 2-(phosphanyloxymethyl)butanoic acid kinase); one or more polynucleotides coding for enzymes in a pathway that catalyze a conversion of 2-(diphosphanyloxymethyl)butanoic acid to [(E)-but-2-enoxy]-phosphanyl-phosphane (e.g., 2-(diphosphanyloxymethyl)butanoic acid decarboxylase); and/or one or more polynucleotides coding for enzymes in a pathway that catalyze a conversion of [(E)-but-2-enoxy]-phosphanyl-phosphane to butadiene (e.g., butadiene synthetase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to 4-hydroxybutyryl-CoA and 3-hydroxybutyryl-CoA and one or more polynucleotides coding for enzymes in a pathway that catalyze a conversion of 4-hydroxybutyryl-CoA and 3-hydroxybutyryl-CoA to butadiene including, but not limited to: one or more polynucleotides coding for enzymes in a pathway that catalyze a conversion of a fermentable carbon source (e.g., glucose) to PEP; one or more polynucleotides coding for enzymes in a pathway that catalyze a conversion of PEP to oxaloacetate (e.g., a PEP carboxykinase or PEP carboxylase); one or more polynucleotides coding for enzymes in a pathway that catalyze a conversion of PEP to pyruvate; one or more polynucleotides coding for enzymes in a pathway that catalyze a conversion of pyruvate to acetyl-CoA (e.g., a pyruvate dehydrogenase or a pyruvate ferrodoxin oxirreductase) or oxaloacetate (e.g., a PEP carboxykinase or PEP carboxylase); one or more polynucleotides coding for enzymes in a pathway that catalyze a conversion of acetyl-CoA to acetoacetyl-CoA (e.g., an acetoacetyl-CoA thiolase); one or more polynucleotides coding for enzymes in a pathway that catalyze a conversion of acetoacetyl-CoA to 3-hydroxybutyryl-CoA (e.g., 3-hydroxybutyryl-CoA dehydrogenase); one or more polynucleotides coding for enzymes in a pathway that catalyze a conversion of oxaloacetate to malate (e.g., a malate dehydrogenase); one or more polynucleotides coding for enzymes in a pathway that catalyze a conversion of malate to fumarate (e.g., a fumarase); one or more polynucleotides coding for enzymes in a pathway that catalyze a conversion of fumarate to succinate (e.g., a fumarate reductase); one or more polynucleotides coding for enzymes in a pathway that catalyze a conversion of succinate to succinyl-CoA (e.g., a succinyl-CoA transferase or a succinyl-CoA synthase); one or more polynucleotides coding for enzymes in a pathway that catalyze a conversion of succinyl-CoA to succinyl semialdehyde (e.g., a succinyl-CoA reductase); one or more polynucleotides coding for enzymes in a pathway that catalyze a conversion of succinyl semialdehyde to 4-hydroxybutyrate (e.g., a 4-hydroxybutyrate dehydrogenase); one or more polynucleotides coding for enzymes in a pathway that catalyze a conversion of succinate to 4-hydroxybutyrate (e.g., a succinate reductase, phosphopantatheinylase or 4-hydroxybutyrate dehydrogenase); one or more polynucleotides coding for enzymes in a pathway that catalyze a conversion of 4-hydroxybutyrate to 4-hydroxybutyryl-CoA (e.g., a 4-hydroxybutyryl-CoA transferase or a 4-hydroxybutyryl-CoA synthase); one or more polynucleotides coding for enzymes in a pathway that catalyze a conversion of 4-hydroxybutyryl-CoA to crotonyl-CoA (e.g., a 4-hydroxybutyryl-CoA dehydratase); one or more polynucleotides coding for enzymes in a pathway that catalyze a conversion of 3-hydroxybutyryl-CoA to crotonyl-CoA (e.g., a crotonase); one or more polynucleotides coding for enzymes in a pathway that catalyze a conversion of crotonyl-CoA to crotonaldehyde (e.g., a crotonaldehyde dehydrogenase); one or more polynucleotides coding for enzymes in a pathway that catalyze a conversion of crotonaldehyde to crotonyl alcohol (e.g., an alcohol dehydrogenase); one or more polynucleotides coding for enzymes in a pathway that catalyze a conversion of crotonyl-CoA to crotonyl alcohol (e.g., a crotonyl-CoA reductase (bifunctional); and/or one or more polynucleotides coding for enzymes in a pathway that catalyze a conversion of crotonyl alcohol to butadiene (e.g., a crotonyl alcohol dehydratase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source to acryloyl-CoA and acetyl-CoA and one or more polynucleotides coding for enzymes in a pathway that catalyze a conversion of acryloyl-CoA and acetyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to lactate (e.g., a lactate dehydrogenase); one or more polynucleotides coding for enzymes in a pathway that catalyze a conversion of lactate to lactoyl-CoA (e.g., a lactoyl-CoA transferase or synthase); one or more polynucleotides coding for enzymes in a pathway that catalyze a conversion of lactoyl-CoA to acryloyl-CoA; one or more polynucleotides coding for enzymes in a pathway that catalyze a conversion of pyruvate to acetyl-CoA; one or more polynucleotides coding for enzymes in a pathway that catalyze a conversion of acryloyl-CoA and acetyl-CoA to 3-keto-4-pentenoyl-CoA (e.g., a thiolase); one or more polynucleotides coding for enzymes in a pathway that catalyze a conversion of 3-keto-4-pentenoyl-CoA to (R) or (S) 3-hydroxy-4-pentenoyl-CoA (e.g., a 3-keto-4-pentenoyl-CoA dehydrogenase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA transferase, a hydrolase, or a synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetyl-CoA and 3-hydroxypropionyl-CoA and one or more polynucleotides coding for enzymes in a pathway that catalyze a conversion of acetyl-CoA and 3-hydroxypropionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to lactate; one or more polynucleotides coding for enzymes in a pathway that catalyze a conversion of lactate to lactoyl-CoA (e.g., lactoyl-CoA transferase or synthase); one or more polynucleotides coding for enzymes in a pathway that catalyze a conversion of lactoyl-CoA to acryloyl-CoA (e.g., lactoyl-CoA dehydratase); one or more polynucleotides coding for enzymes in a pathway that catalyze a conversion of acryloyl-CoA to 3-hydroxypropionyl-CoA (e.g., acryloyl-CoA hydratase); one or more polynucleotides coding for enzymes in a pathway that catalyze a conversion of pyruvate to 3-hydroxypropionate; one or more polynucleotides coding for enzymes in a pathway that catalyze a conversion of 3-hydroxypropionate to 3-hydroxypropionyl-CoA; one or more polynucleotides coding for enzymes in a pathway that catalyze a conversion of acetyl-CoA and 3-hydroxypropionyl-CoA to 5-hydroxy-3-ketovaleryl-CoA (e.g., a thiolase); one or more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-ketovaleryl-CoA dehydrogenase); one or more polynucleotides coding for enzymes in a pathway that catalyze a conversion of (R) or (S) 3,5-dihydroxy-valeryl-CoA to (R) or (S) 3-hydroxy-4-pentenoyl-CoA (e.g., a 3,5-hydroxyvaleryl-CoA dehydratase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA hydrolase, transferase, or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetoacetyl-CoA and formyl-CoA and one or more polynucleotides coding for enzymes in a pathway that catalyze a conversion acetoacetyl-CoA and formyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to acetyl-CoA and formate (e.g., a pyruvate formate-lyase); one or more polynucleotides coding for enzymes in a pathway that catalyze a conversion of acetyl-CoA to acetoacetyl-CoA (e.g., thiolase); one or more polynucleotides coding for enzymes in a pathway that catalyze a conversion of $CO_2$ to formate (e.g., formate dehydrogenase); one or more polynucleotides coding for enzymes in a pathway that catalyze a conversion of formate to formyl-CoA (e.g., a formyl-CoA transferase, or formyl-CoA synthase); one or more polynucleotides coding for enzymes in a pathway that catalyze a conversion of formyl-CoA and acetoacetyl-CoA to 3,5-ketovaleryl-CoA (e.g., a thiolase); one or more polynucleotides coding for enzymes in a pathway that catalyze a conversion of 3,5-ketovaleryl-CoA to 5-hydroxy-3-ketovaleryl-CoA; one or more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-Ketovaleryl-CoA dehydrogenase); one or more polynucleotides coding for enzymes in a pathway that catalyze a conversion of (R) or (S) 3,5-dihydroxy-valeryl-CoA to (R) or (S) 3-hydroxy-4-pentenoyl-CoA (e.g., a 3,5-hydroxyvaleryl-CoA dehydratase); one or more polynucleotides coding for enzymes in a pathway that catalyze a conversion of (R) or (S) 3-hydroxy-4-pentenoyl-CoA to 3-hydroxy-4-pentenoic acid (e.g., a 3-hydroxy-4-pentenoyl-CoA hydrolase, transferase, or synthase); and/or one or more polynucleotides coding for enzymes in a pathway that catalyze a conversion of 3-hydroxy-4-pentenoic acid to butadiene (e.g., a 3-hydroxy-4-pentenoic acid decarboxylase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to acetyl-CoA and 3-hydroxypropionyl-CoA and one or more polynucleotides coding for enzymes in a pathway that catalyze a conversion of acetyl-CoA and 3-hydroxypropionyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyze a conversion of pyruvate to acryloyl-CoA; one or more polynucleotides coding for enzymes in a pathway that catalyze a conversion of acryloyl-CoA to 3-hydroxypropionyl-CoA; one or more polynucleotides coding for enzymes in a pathway that catalyze a conversion of pyruvate to 3-hydroxypropionate; one or more polynucleotides coding for enzymes in a pathway that catalyze a conversion of 3-hydroxypropionate to 3-hydroxypropionyl-CoA; one or more polynucleotides coding for enzymes in a pathway that catalyze a conversion of acetyl-CoA and 3-hydroxypropionyl-CoA to 5-hydroxy-3-ketovaleryl-CoA (e.g., a thiolase); one or of more polynucleotides coding for enzymes in a pathway that catalyze a conversion of 5-hydroxy-3-ketovaleryl-CoA to (R) or (S) 3,5-dihydroxy-valeryl-CoA (e.g., a 5-hydroxy-3-ketovaleryl-CoA dehydrogenase); one or more polynucleotides coding for enzymes in a pathway that catalyze a conversion of (R) or (S) 3,5-dihydroxy-valeryl-CoA to 3,5-hydroxypentanoic acid (e.g., a 3,5-hydroxypentanoic acid kinase); one or more polynucleotides coding for enzymes in a pathway that catalyze a conversion of 3,5-hydroxypentanoic acid to 3,5-hydroxypentanoic acid phosphate (e.g., a 3,5-hydroxypentanoic acid kinase); one or more polynucleotides coding for enzymes in a pathway that catalyze a conversion of 3,5-hydroxypentanoic acid phosphate to 3,5-hydroxypentanoic acid diphosphate (e.g., a 3,5-hydroxypentanoic acid phosphate kinase); one or more polynucleotides coding for enzymes in a pathway that catalyze a conversion of 3,5-hydroxypentanoic acid diphosphate to 1-butenyl-4-diphosphate (e.g., a hydroxypentanoic acid diphosphate decarboxylase); and/or one or more polynucleotides coding for enzymes in a pathway that catalyze a conversion of 1-butenyl-4-diphosphate to butadiene (e.g., a butadiene synthase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to ethyl-malonyl-CoA and one or more polynucleotides coding for enzymes in a pathway that catalyze a conversion of ethyl-malonyl-CoA to butadiene including, but are not limited to: one or more polynucleotides coding for enzymes in a pathway that catalyze a conversion of a fermentable carbon source (e.g., glucose) to pyruvate; one or more polynucleotides coding for enzymes in a pathway that catalyzes a conversion of pyruvate to acetyl-CoA; one or more polynucleotides coding for enzymes in a pathway that catalyzes a conversion of acetyl-CoA to acetoacetyl-CoA (e.g., an acetoacetyl-CoA thiolase); one or more polynucleotides coding for enzymes in a pathway that catalyzes a conversion of acetoacetyl-CoA to 3-hydroxybutyryl-CoA (e.g., a 3-hydroxybutyryl-CoA dehydrogenase); one or more polynucleotides coding for enzymes in a pathway that catalyzes a conversion of 3-hydroxybutyryl-CoA to crotonyl-CoA (e.g., a crotonase); one or more polynucleotides coding for enzymes in a pathway that catalyzes a conversion of crotonyl-CoA to ethyl-malonyl-CoA (e.g., a crotonyl-CoA carboxylase/reductase); one or more polynucleotides coding for enzymes in a pathway that catalyzes a conversion of crotonyl-CoA to butyric acid (e.g., butyryl-CoA dehydrogenase); one or more polynucleotides coding for enzymes in a pathway that catalyzes a conversion of butyric acid to ethyl-malonyl-CoA (e.g., a butanoyl-CoA:carbon-dioxide ligase); one or more polynucleotides coding for enzymes in a pathway that catalyze a conversion of ethyl-malonyl-CoA to 2-hydroxymethyl-butanoic acid (e.g., an ethyl-malonyl-CoA reductase, an alcohol dehydrogenase, or a aldehyde dehydrogenase); one or more polynucleotides coding for enzymes in a pathway that catalyze a conversion of 2-hydroxymethyl-butanoic acid to 2-butenyl 4-diphosphate (e.g., a 2-hydroxymethyl-butanoate kinase, a hydroxymethyl butanoate-phosphate kinase, or a 2-hydroxymethyl butanoate-diphosphate decarboxylase); one or more polynucleotides coding for enzymes in a pathway that catalyze a conversion of 2-hydroxymethyl-butanoic acid to 2-butenyl 4-phosphate; one or more polynucleotides coding for enzymes in a pathway that catalyze a conversion of 2-butenyl 4-phosphate to butadiene, and/or one or more polynucleotides coding for enzymes in a pathway that catalyze a conversion of 2-butenyl 4-diphosphate to butadiene (e.g., butadiene synthetase). In some embodiments, a microorganism is provided that comprises one or more of the above polynucleotides including, all, of the polynucleotides above.

A microorganism is also provided that comprises one or more polynucleotides coding for enzymes in a pathway that catalyze a conversion of a fermentable carbon source (e.g., glucose) to lactate and acetyl-CoA and oxalacetate and one or more polynucleotides coding for enzymes in a pathway that catalyze a conversion of lactate and acetyl-CoA and oxalacetate to butadiene including, but are not limited to: one or more polynucleotides coding for enzymes in a pathway that catalyze a conversion of a fermentable carbon source (e.g., glucose) to PEP; one or more polynucleotides coding for enzymes in a pathway that catalyze a conversion of PEP to pyruvate; one or more polynucleotides coding for enzymes in a pathway that catalyze a conversion of pyruvate to acetyl-CoA; one or more polynucleotides coding for enzymes in a pathway that catalyze a conversion of lactate to lactoyl-CoA (e.g., a lactate CoA-transferase); one or more polynucleotides coding for enzymes in a pathway that catalyze a conversion of lactoyl-CoA to acryloyl-CoA (e.g., a lactoyl-CoA dehydratase); one or more polynucleotides coding for enzymes in a pathway that catalyze a conversion of acryloyl-CoA to propionyl-CoA (e.g., an acryloyl-CoA oxidoreductase); one or more polynucleotides coding for enzymes in a pathway that catalyze a conversion of propionyl-CoA to ketovaleryl-CoA (e.g., a thiolase); one or more polynucleotides coding for enzymes in a pathway that catalyze a conversion of ketovaleryl-CoA to 2-pentenoyl-CoA (e.g., a ketovaleryl-CoA dehydratase); one or more polynucleotides coding for enzymes in a pathway that catalyze a conversion of 2-pentenoyl-CoA to 2-pentenoic acid (e.g., a pentenoyl-CoA hydrolase, transferase, or synthase); one or more polynucleotides coding for enzymes in a pathway that catalyze a conversion of 2 pentenoic acid to butadiene (e.g., a 4-pentenoic acid decarboxylase); one or more polynucleotides coding for enzymes in a pathway that catalyze a conversion of 2-pentenoic acid to 4-pentenoic acid (e.g., a transposing C═C bonds isomerase); one or more polynucleotides coding for enzymes in a pathway that catalyze a conversion of 4-pentenoic acid to butadiene (e.g., a 4-pentenoic acid decarboxylase); one or more polynucleotides coding for enzymes in a pathway that catalyze a conversion of oxalacetate to malate (e.g., a malate dehydrogenase); one or more polynucleotides coding for enzymes in a pathway that catalyze a conversion of malate to fumarate (e.g., a fumarase); one or more polynucleotides coding for enzymes in a pathway that catalyze a conversion of fumarate to succinate (e.g., a fumarate reductase); one or more polynucleotides coding for enzymes in a pathway that catalyze a conversion of succinate to succynil-CoA (e.g., a succinyl-CoA transferase synthase); one or more polynucleotides coding for enzymes in a pathway that catalyze a conversion of succynil-CoA to succinate semialdehyde (e.g., a succinyl-CoA reducatase); one or more polynucleotides coding for enzymes in a pathway that catalyze a conversion of succinate semialdehyde to 4-hydroxybutyrate (e.g., a 4 hydroxybutyrate dehydrogenase); one or more polynucleotides coding for enzymes in a pathway that catalyze a conversion of 4-hydroxybutyrate to 4-hydroxybutyril-CoA (e.g., a 4-hydroxybutyryl-CoA transferase, or a 4-hydroxybutyryl-CoA synthase); one or more polynucleotides coding for enzymes in a pathway that catalyze a conversion of 4-hydroxybutyril-CoA to crotonyl-CoA (e.g., a 4-hydroxybutyryl-CoA dehydratase); one or more polynucleotides coding for enzymes in a pathway that catalyze a conversion of crotonyl-CoA to crotonaldehyde (e.g., a crotonaldehyde dehydrogenase); one or more polynucleotides coding for enzymes in a pathway that catalyze a conversion of crotonyl-CoA to crotonyl-alcohol (e.g., a crotonyl-CoA reductase or a bifunctional alcohol dehydrogenase); one or more polynucleotides coding for enzymes in a pathway that catalyze a conversion of crotonaldehyde to crotonyl-alcohol (e.g., an alcohol dehydrogenase); and/or one or more polynucleotides coding for enzymes in a pathway that catalyze a conversion of crotonyl-alcohol to butadiene (e.g., a crotonyl alcohol dehydratase).

Any of the microorganisms provided herein may optionally comprise one or more polynucleotides coding for enzymes that permit for a redox balanced conversion of a fermentable carbon source to butadiene.

The microorganism may be an archea, bacteria, or eukaryote. In some embodiments, the bacteria is a *Propionibacterium, Propionispira, Clostridium, Bacillus, Escherichia, Pelobacter*, or *Lactobacillus* including, for example, *Pelobacter propionicus, Clostridium propionicum, Clostridium acetobutylicum, Lactobacillus, Propionibacterium acidipropionici* or *Propionibacterium freudenreichii*. In some embodiments, the eukaryote is a yeast, filamentous fungi, protozoa, or algae. In some embodiments, the yeast is *Saccharomyces cerevisiae, Zymomonas mobilis*, or *Pichia pastoris*.

In some embodiments, the disclosure contemplates the modification (e.g., engineering) of one or more of the enzymes provided herein. Such modification may be performed to redesign the substrate specificity of the enzyme and/or to modify (e.g., reduce) its activity against others substrates in order to increase its selectivity for a given substrate. Additionally or alternatively, one or more enzymes as provided herein may be engineered to alter (e.g., enhance including, for example, increase its catalytic activity or its substrate specificity) one or more of its properties.

Any of the enzymes (e.g., the polynucleotide coding for the enzyme) may be modified (e.g., mutagenized or diversified) to expand or alter its substrate specificity (e.g., change the substrate specificity of an enzyme from one substrate to another substrate) by any method known in the art. Such methods include, but are not limited to EpPCR Pritchard et al., J. Theor. Biol. 234:497-509 (2005)); Error-prone Rolling Circle Amplification (epRCA) Fujii et al., Nucleic Acids Res. 32:e145 (2004); and Fujii et al., Nat. Protoc. 1:2493-2497 (2006)); DNA or Family Shuffling Stemmer, Proc. Natl. Acad. Sci. U.S.A. 91:10747-10751 (1994); and Stemmer, Nature 370:389-391 (1994)); Staggered Extension (StEP) Zhao et al., Nat. Biotechnol. 16:258-261 (1998)); and/or Random Priming Recombination (RPR) Shao et al., Nucleic Acids Res 26:681-683 (1998)).

Additional exemplary methods for mutagenesis of a polynucleotide include Heteroduplex Recombination (Volkov et al., Nucleic Acids Res. 27:e18 (1999); and Volkov et al., Methods Enzymol. 328:456-463 (2000)); Random Chimeragenesis on Transient Templates (RACHITT) (Coco et al., Nat. Biotechnol. 19:354-359 (2001)); Recombined Extension on Truncated templates (RETT) (Lee et al., J. Molec. Catalysis 26:119-129 (2003)); Degenerate Oligonucleotide Gene Shuffling (DOGS) (Bergquist and Gibbs, Methods Mol. Biol. 352:191-204 (2007); Bergquist et al., Biomol. Eng. 22:63-72 (2005); Gibbs et al., Gene 271:13-20 (2001)); Incremental Truncation for the Creation of Hybrid Enzymes (ITCHY) (Ostermeier et aL, Proc. Natl. Acad. Sci. U.S.A. 96:3562-3567 (1999); and Ostermeier et al., Nat. Biotechnol. 17:1205-1209 (1999)); Thio-Incremental Truncation for the Creation of Hybrid Enzymes (THIO-ITCHY) (Lutz et al., Nucleic Acids Res. 29:E16 (2001)); SCRATCHY (Lutz et al., Proc. Natl. Acad. Sci U.S.A. 98:11248-11253 (2001)); Random Drift Mutagenesis (RNDM) (Bergquist et al., Biomol. Eng. 22:63-72 (2005)); Sequence Saturation Mutagenesis (SeSaM) (Wong et al., Biotechnol. J. 3:74-82 (2008); Wong et al., Nucleic Acids Res. 32:e26 (2004); and Wong et al., Anal. Biochem. 341:187-189 (2005)); Synthetic Shuffling (Ness et al., Nat. Biotechnol. 20:1251-1255 (2002)); Nucleotide Exchange and Excision Technology NexT (Muller et al., Nucleic Acids Res. 33:e117 (2005)). Additional exemplary methods include Sequence Homology-Independent Protein Recombination (SHIPREC) (Sieber et al., Nat. Biotechnol. 19:456-460 (2001)); Gene Site Saturation Mutagenesis™ (GSSM™) (Kretz et al., Methods Enymol. 388:3-11 (2004)); Combinatorial Cassette Mutagenesis (CCM) (Reidhaar-Olson et al. Methods Enzymol. 208:564-586 (1991); and Reidhaar-Olson et al. Science 241:53-57 (1988)); Combinatorial Multiple Cassette Mutagenesis (CMCM) (Reetz et al., Angew. Chem. Int. Ed Engl. 40:3589-3591 (2001)); and the Mutator Strains technique (Selifonova et al., Appl. Environ. Microbiol. 67:3645-3649 (2001); Low et al., J. Mol. Biol. 260:359-3680 (1996)). Further exemplary methods include Look-Through Mutagenesis (LTM) (Rajpal et al., Proc. Natl. Acad. Sci. U.S.A. 102:8466-8471 (2005)); Gene Reassembly (Tunable GeneReassembly™ (TGR™) Technology supplied by Verenium Corporation), in Silico Protein Design Automation (PDA) (Hayes et al., Proc. Natl. Acad. Sci. U.S.A. 99:15926-15931 (2002)); and Iterative Saturation Mutagenesis (ISM) (Reetz et al., Nat. Protoc. 2:891-903 (2007); and Reetz et al., Angew. Chem. Int. Ed Engl. 45:7745-7751 (2006)).

In some embodiments, sequence alignment and comparative modeling of proteins may be used to alter one or more of the enzymes disclosed herein. Homology modeling or comparative modeling refers to building an atomic-resolution model of the desired protein from its primary amino acid sequence and an experimental three-dimensional structure of a similar protein. This model may allow for the enzyme substrate binding site to be defined, and the identification of specific amino acid positions that may be replaced to other natural amino acid in order to redesign its substrate specificity.

Variants or sequences having substantial identity or homology with the polynucleotides encoding enzymes as disclosed herein may be utilized in the practice of the disclosure. Such sequences can be referred to as variants or modified sequences. That is, a polynucleotide sequence may be modified yet still retain the ability to encode a polypeptide exhibiting the desired activity. Such variants or modified sequences are thus equivalents. Generally, the variant or modified sequence may comprise at least about 40%-60%, preferably about 60%-80%, more preferably about 80%-90%, and even more preferably about 90%-95% sequence identity with the native sequence.

In some embodiments, a microorganism may be modified to express including, for example, over express, one or more enzymes as provided herein. The microorganism may be modified by genetic engineering techniques (i.e., recombinant technology), classical microbiological techniques, or a combination of such techniques and can also include naturally occurring genetic variants to produce a genetically modified microorganism. Some of such techniques are generally disclosed, for example, in Sambrook et al., 1989, Molecular Cloning: A Laboratory Manual, Cold Spring Harbor Labs Press.

A microorganism may include a microorganism in which a polynucleotide has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, over expression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

Where desired, the expression of one or more of the enzymes provided herein are under the control of a regulatory sequence that controls directly or indirectly the expression of the enzyme in a time-dependent fashion during a fermentation reaction.

In some embodiments, a microorganism is transformed or transfected with a genetic vehicle such as, an expression vector comprising an exogenous polynucleotide sequence coding for the enzymes provided herein.

Polynucleotide constructs prepared for introduction into a prokaryotic or eukaryotic host may typically, but not always, comprise a replication system (i.e. vector) recognized by the host, including the intended polynucleotide fragment encoding the desired polypeptide, and may preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, mRNA stabilizing sequences, nucleotide sequences homologous to host chromosomal DNA, and/or a multiple cloning site. Signal peptides may also be included where appropriate, preferably from secreted polypeptides of the same or related species, which allow the protein to cross and/or lodge in cell membranes or be secreted from the cell.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

The manipulation of polynucleotides of the present disclosure including polynucleotides coding for one or more of the enzymes disclosed herein is typically carried out in recombinant vectors. Numerous vectors are publicly available, including bacterial plasmids, bacteriophage, artificial chromosomes, episomal vectors and gene expression vectors, which can all be employed. A vector of use according to the disclosure may be selected to accommodate a protein coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the disclosure.

Vectors, including cloning and expression vectors, may contain nucleic acid sequences that enable the vector to replicate in one or more selected host cells. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

A cloning or expression vector may contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli* (e.g., strain TB1 or TG1, DH5α, DH10β, JM110). An *E. coli*-selectable marker, for example, the β-lactamase gene that confers resistance to the antibiotic ampicillin, may be of use. These selectable markers can be obtained from *E. coli* plasmids, such as pBR322 or a pUC plasmid such as pUC18 or pUC19, or pUC119.

Expression vectors may contain a promoter that is recognized by the host organism. The promoter may be operably linked to a coding sequence of interest. Such a promoter may be inducible or constitutive. Polynucleotides are operably linked when the polynucleotides are in a relationship permitting them to function in their intended manner.

Promoters suitable for use with prokaryotic hosts may include, for example, the α-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Moreover, host constitutive or inducible promoters may be used. Promoters for use in bacterial systems will also generally contain a Shine-Dalgarno sequence operably linked to the coding sequence.

Viral promoters obtained from the genomes of viruses include promoters from polyoma virus, fowlpox virus, adenovirus (e.g., Adenovirus 2 or 5), herpes simplex virus (thymidine kinase promoter), bovine papilloma virus, avian sarcoma virus, cytomegalovirus, a retrovirus (e.g., MoMLV, or RSV LTR), Hepatitis-B virus, Myeloproliferative sarcoma virus promoter (MPSV), VISNA, and Simian Virus 40 (SV40). Heterologous mammalian promoters include, e.g., the actin promoter, immunoglobulin promoter, heat-shock protein promoters.

The early and late promoters of the SV40 virus are conveniently obtained as a restriction fragment that also contains the SV40 viral origin of replication (see, e.g., Fiers et al., Nature, 273:113 (1978); Mulligan and Berg, Science, 209:1422-1427 (1980); and Pavlakis et al., Proc. Natl. Acad. Sci. USA, 78:7398-7402 (1981)). The immediate early promoter of the human cytomegalovirus (CMV) is conveniently obtained as a Hind III E restriction fragment (see, e.g., Greenaway et al., Gene, 18:355-360 (1982)). A broad host range promoter, such as the SV40 early promoter or the Rous sarcoma virus LTR, is suitable for use in the present expression vectors.

Generally, a strong promoter may be employed to provide for high level transcription and expression of the desired product. Among the eukaryotic promoters that have been identified as strong promoters for high-level expression are the SV40 early promoter, adenovirus major late promoter, mouse metallothionein-I promoter, Rous sarcoma virus long terminal repeat, and human cytomegalovirus immediate early promoter (CMV or CMV IE). In an embodiment, the promoter is a SV40 or a CMV early promoter.

The promoters employed may be constitutive or regulatable, e.g., inducible. Exemplary inducible promoters include jun, fos and metallothionein and heat shock promoters. One or both promoters of the transcription units can be an inducible promoter. In an embodiment, the GFP is expressed from a constitutive promoter while an inducible promoter drives transcription of the gene coding for one or more enzymes as disclosed herein and/or the amplifiable selectable marker.

The transcriptional regulatory region in higher eukaryotes may comprise an enhancer sequence. Many enhancer sequences from mammalian genes are known e.g., from globin, elastase, albumin, α-fetoprotein and insulin genes. A suitable enhancer is an enhancer from a eukaryotic cell virus. Examples include the SV40 enhancer on the late side of the replication origin (bp 100-270), the enhancer of the cytomegalovirus immediate early promoter (Boshart et al. Cell 41:521 (1985)), the polyoma enhancer on the late side of the replication origin, and adenovirus enhancers (see also, e.g., Yaniv, Nature, 297:17-18 (1982) on enhancing elements for activation of eukaryotic promoters). The enhancer sequences may be introduced into the vector at a position 5' or 3' to the gene of interest, but is preferably located at a site 5' to the promoter.

Yeast and mammalian expression vectors may contain prokaryotic sequences that facilitate the propagation of the vector in bacteria. Therefore, the vector may have other components such as an origin of replication (e.g., a nucleic acid sequence that enables the vector to replicate in one or more selected host cells), antibiotic resistance genes for selection in bacteria, and/or an amber stop codon which can permit translation to read through the codon. Additional eukaryotic selectable gene(s) may be incorporated. Generally, in cloning vectors the origin of replication is one that enables the vector to replicate independently of the host chromosomal DNA, and includes origins of replication or autonomously replicating sequences. Such sequences are well known, e.g., the ColE1 origin of replication in bacteria. Various viral origins (e.g., SV40, polyoma, adenovirus, VSV or BPV) are useful for cloning vectors in mammalian cells. Generally, a eukaryotic replicon is not needed for expression in mammalian cells unless extrachromosomal (episomal) replication is intended (e.g., the SV40 origin may typically be used only because it contains the early promoter).

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

The plasmids may be propagated in bacterial host cells to prepare DNA stocks for subcloning steps or for introduction into eukaryotic host cells. Transfection of eukaryotic host cells can be any performed by any method well known in the art. Transfection methods include lipofection, electroporation, calcium phosphate co-precipitation, rubidium chloride or polycation mediated transfection, protoplast fusion and microinjection. Preferably, the transfection is a stable transfection. The transfection method that provides optimal transfection frequency and expression of the construct in the particular host cell line and type, is favored. Suitable methods can be determined by routine procedures. For stable transfectants, the constructs are integrated so as to be stably maintained within the host chromosome.

Vectors may be introduced to selected host cells by any of a number of suitable methods known to those skilled in the art. For example, vector constructs may be introduced to appropriate cells by any of a number of transformation methods for plasmid vectors. For example, standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used may depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation. Immortalized host cell cultures amenable to transfection and in vitro cell culture and of the kind typically employed in genetic engineering are preferred. Examples of useful mammalian host cell lines are monkey kidney CV1 line transformed by SV40 (COS-7, ATCC CRL 1651); human embryonic kidney line (293 or 293 derivatives adapted for growth in suspension culture, Graham et al., J. Gen Virol., 36:59 (1977); baby hamster kidney cells (BHK, ATCC CCL 10); DHFR-Chinese hamster ovary cells (ATCC CRL-9096); dp12.CHO cells, a derivative of CHO/DHFR-(EP 307,247 published 15 Mar. 1989); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); PEER human acute lymphoblastic cell line (Ravid et al. Int. J. Cancer 25:705-710 (1980)); MRC 5 cells; FS4 cells; human hepatoma line (Hep G2), human HT1080 cells, KB cells, JW-2 cells, Detroit 6 cells, NIH-3T3 cells, hybridoma and myeloma cells. Embryonic cells used for generating transgenic animals are also suitable (e.g., zygotes and embryonic stem cells).

Suitable host cells for cloning or expressing polynucleotides (e.g., DNA) in vectors may include, for example, prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), *E. coli* JM110 (ATCC 47,013) and *E. coli* W3110 (ATCC 27,325) are suitable.

In addition to prokaryotes, eukaryotic microbes such as filamentous fungi or yeast may be suitable cloning or expression hosts for vectors comprising polynucleotides coding for one or more enzymes. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

When the enzyme is glycosylated, suitable host cells for expression may be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk moth) have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, tobacco, *lemna*, and other plant cells can also be utilized as host cells.

Examples of useful mammalian host cells are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for production of one or more enzymes as disclosed herein or with polynucleotides coding for one or more enzymes as disclosed herein and cultured in conventional nutrient media modified as appropriate for inducing promoters, selecting transformants, or amplifying the genes encoding the desired sequences.

Host cells containing desired nucleic acid sequences coding for the disclosed enzymes may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44, (1979); Barnes et al., Anal. Biochem. 102: 255 (1980); U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adeNOSine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides and Encoded Enzymes

Any known polynucleotide (e.g., gene) that codes for an enzyme or variant thereof that is capable of catalyzing an enzymatic conversion including, for example, an enzyme as set forth in any one of Tables 1-3 or FIGS. 1-3, is contemplated for use by the present disclosure. Such polynucleotides may be modified (e.g., genetically engineered) to modulate (e.g., increase or decrease) the substrate specificity of an encoded enzyme, or the polynucleotides may be modified to change the substrate specificity of the encoded enzyme (e.g., a polynucleotide that codes for an enzyme with specificity for a substrate may be modified such that the enzyme has specificity for an alternative substrate). Preferred microorganisms may comprise polynucleotides coding for one or more of the enzymes as set forth in any one of Tables 1-3 and FIG. 1-3.

In some embodiments, the microorganism may comprise an oxidoreductase such as a hydroxyvaleryl-CoA dehydrogenase, a crotonyl-CoA reductase (bifunctional), a crotonaldehyde dehydrogenase, a crotonyl alcohol dehydrogenase, a 3,5-ketovaleryl-CoA dehydrogenase, or an oxidoreductase as set forth in SEQ ID NOs: 103-123. In some embodiments, the microorganism may comprise a transferase such as a pentenoyl-CoA transferase, a pent-2,4-dienoyl-CoA transferase, a formyl-CoA transferase, a 3-hydroxy-4-pentenoyl-CoA transferase, or a transferase as set forth in SEQ ID NOs: 1-28. In some embodiments, the microorganism may comprise a hydrolase such as a pentenoyl-CoA hydrolase, a pent-2,4-dienoyl-CoA hydrolase, a 3-hydroxy-4-pentenoyl-CoA hydrolase, or a hydrolase as set forth in SEQ ID NOs: 29-33. In some embodiments, the microorganism may comprise a CoA synthase such as a formyl-CoA synthase or a CoA synthase as set forth in SEQ ID NOs: 34-36. In some embodiments, the microorganism may comprise a ketothiolase such as a thiolase, an acetyl-CoA:formate C-acetyltransferase, an acetoacetyl-CoA thiolase, a 3,5-ketovaleryl-CoA thiolase, or a ketothiolase as set forth in SEQ ID NOs: 58-78. In some embodiments, the microorganism may comprise a dehydrogenase such as a pentenoyl-CoA dehydrogenase, a formate dehydrogenase, or a dehydrogenase as set forth in SEQ ID NOs: 124-139. In some embodiments, the microorganism may comprise a dehydratase such as a hydroxyvaleryl CoA dehydratase, a crotonyl alcohol dehydratase, a 3,5-hydroxyvaleryl-CoA dehydratase, or a dehydratase as set forth in SEQ ID NOs: 37-55. In some embodiments, the microorganism may comprise an isomerase such as a transposing C=C bonds isomerase, or an isomerase as set forth in SEQ ID NOs: 99-102. In some embodiments, the microorganism may comprise a decarboxylase such as a 2-pentenoic acid decarboxylase, a 4-pentenoic acid decarboxylase, a pent,2,4-dienoic acid decarboxylase, a 3-hydroxy-4-pentenoic acid decarboxylase, or a decarboxylase as set forth in SEQ ID NOs: 79-98.

Enzymes for catalyzing the conversions in FIGS. 1-3 are categorized in Table 4 by Enzyme Commission (EC) number, function, and the step in FIGS. 1-3 in which they catalyze a conversion (Table 4).

TABLE 4

EC number for employed enzymes

| EC Number | Function | FIG. (Number) and Step (Letter) |
|---|---|---|
| 1.1.1. | Oxidoreductase | 1B, 2A, 2B, 2C, 3F, 3G |
| 2.8.3. | Transferase | 1D, 1I, 3C, 3I |
| 3.1.2. | Hydrolase | 1D, 1I, 3I |
| 6.2.1 | CoA Synthetase | 3C |
| 2.3.1. | Ketothiolase | 1A, 3B, 3D, 3E |
| 1.3.1. or 1.2.99 | Dehydrogenase | 1H, 3A |
| 4.2.1. | Dehydratase | 1C, 2D, 3H |
| 5.3.3. | Isomerase | 1F |
| 4.1.1. | Decarboxylase | 1E, 1G, 1J, 3J |

Steps D and I of FIG. 1, and steps C and I in FIG. 3 can be catalyzed by transferases in EC 2.8.3 including, for example, a transferase that catalyzes the reversible transfer of a CoA moiety from one molecule to another. Any known polynucleotide coding for a CoA transferase enzyme including, for example, those polynucleotides set forth in Table 5 below, is contemplated for use by the present disclosure.

TABLE 5

Exemplary genes coding for enzymes in EC 2.8.3

| Gene | Gene ID | Organism | SEQ ID NO: |
|---|---|---|---|
| atoA | 2492994 | *Escherichia coli* K12 | 1 |
| atoD | 2492990 | *Escherichia coli* K12 | 2 |
| actA | 62391407 | *Corynebacterium glutamicum* ATCC 13032 | 3 |
| Cg0592 | 62289399 | *Corynebacterium glutamicum* ATCC 13032 | 4 |
| ctfA | 15004866 | *Clostridium acetobutylicum* | 5 |
| ctfB | 15004867 | *Clostridium acetobutylicum* | 6 |
| Ach1 | 60396828 | *Roseburia* sp. A2-183 | 7 |
| Pct | 7242549 | *Clostridium propionicum* | 8 |
| Cbei_4543 | 150019354 | *Clostridium beijerinchii* | 9 |
| pcaI | 50084858 | *Acinetobacter* sp. ADP1 | 10 |
| PcaJ | 141776 | *Acinetobacter* sp. ADP1 | 11 |
| pcaI | 24985644 | *Pseudomonas putida* | 12 |
| pcaJ | 141776 | *Pseudomonas putida* | 13 |
| ScoA | 16080950 | *Bacillus subtilis* | 14 |
| ScoB | 16080949 | *Bacillus subtilis* | 15 |
| Cat1 | 729048 | *Clostridium kluyveri* | 16 |
| Cat2 | 172046066 | *Clostridium kluyveri* | 17 |
| Cat3 | 146349050 | *Clostridium kluyveri* | 18 |
| gctA | 559392 | *Acidaminococcus fermentans* | 19 |
| gctB | 559393 | *Acidaminococcus fermentans* | 20 |

TABLE 5-continued

| Exemplary genes coding for enzymes in EC 2.8.3 | | | |
|---|---|---|---|
| Gene | Gene ID | Organism | SEQ ID NO: |
| frc | 12931869 | *Escherichia coli* | 21 |
| BBta_3113 | 5149017 | *Bradyrhizobium* sp. | 22 |
| RPA1945 | 2688995 | *Rhodopseudomonas palustris* | 23 |
| SDY_2572 | 3797090 | *Shigella dysenteriae* | 24 |
| RPB_3427 | 3911229 | *Rhodopseudomonas palustris* | 25 |
| frc | 8191935 | *Methylobacterium extorquens* | 26 |
| H16_B1711 | 4455693 | *Ralstonia eutropha* H16 | 27 |
| Bxe_B2760 | 4006524 | *Burkholderia xenovorans* | 28 |

Steps D and I of FIG. 1, and step I of FIG. 3 can be catalyzed by hydrolases in EC 3.1.2 including, for example, hydrolases with broad substrate ranges capable of hydrolyzing 2-petentenoyl-CoA, 2,4-pentenoyl-CoA, and 3-hydroxypentenoyl-CoA to their corresponding acids. Any known polynucleotide coding for a hydrolase including, for example, those polynucleotides set forth in Table 6 below, is contemplated for use by the present disclosure.

TABLE 6

| Exemplary genes coding for enzymes in EC 3.1.2. | | | |
|---|---|---|---|
| Gene | Gene ID | Organism | SEQ ID NO: |
| Orf1 | 23664428 | *Azoarcus evansii* | 29 |
| COG0824 | 46200680 | *Magnetospirillum magnetotacticum* | 30 |
| Jann_0674 | 89052491 | *Jannaschia* sp. CCS1 | 31 |
| SSE37_24444 | 126729407 | *Sagittula stellata* | 32 |
| entH | 1786813 | *Escherichia coli* | 33 |

Step C in FIG. 3 may be catalyzed by a CoA synthetase in EC 6.2.1., including, for example, a CoA synthetase with a broad substrate range capable of activating formic acid to formyl-CoA. Any known polynucleotide coding for a CoA synthetase including, for example, those polynucleotides set forth in Table 7 below, is contemplated for use by the present disclosure.

TABLE 7

| Exemplary genes coding for enzymes in EC 6.2.1. | | | |
|---|---|---|---|
| Gene | Gene ID (GI) | Organism | SEQ ID NO: |
| acs | 8434601 | *Acetobacter pasteurianus* | 34 |
| Avin_10660 | 7760010 | *Azotobacter vinelandii* | 35 |
| acs | 8657923 | *Dehalococcoides* sp. | 36 |

The hydration of a double bond can be catalyzed by hydratase enzymes in EC 4.2.1 and the removal of water to form a double bond can be catalyzed by dehydratase enzymes in EC 4.2.1. Hydratase enzymes are sometimes reversible and may also catalyze dehydration. Likewise, dehydratase enzymes are sometimes reversible and may also catalyze hydration. The addition or removal of 7 water from a given substrate is required by step C in FIG. 1, step D in FIG. 2, and step H in FIG. 3. Any known polynucleotide coding for a hydratase or dehydratase including, for example, those polynucleotides set forth in Table 8 below, is contemplated for use by the present disclosure.

For example, the linalool dehydratase-isomerase from *Castellaniella defragrans* strain 65Phen (E.C. 4.2.1.127; SEQ ID NO: 55) catalyzes the stereospecific hydration of beta-myrcene to (3S)-linalool, the isomerization of (3S)-linalool to geraniol, and is involved in the initial steps of the anaerobic degradation of the monoterpene beta-myrcene. Additionally, this linalool dehydratase-isomerase catalyzes the reverse reactions, i.e. the isomerization of geraniol to linalool and the dehydration of linalool to myrcene. In this direction, the formation of myrcene from geraniol may be seen as a detoxification process for the monoterpene alcohol. Thus, linalool dehydratase represents a suitable candidate for step D in FIG. 2 below.

TABLE 8

| Exemplary genes coding for enzymes in EC 4.2.1. | | | |
|---|---|---|---|
| Gene | Gene ID | Organism | SEQ ID NO: |
| mhpD | 87081722 | *Escherichia coli* | 37 |
| ctmF | 1263188 | *Pseudomonas putida* | 38 |
| todG | 1263188 | *Pseudomonas putida* | 39 |
| hpaH | 7150958100 | *Klebsiella pneumoniae* | 40 |
| hpaH | 8178258 | *Escherichia coli* | 41 |
| cnbE | 6386628 | *Comamonas testosteroni* | 42 |
| leuD | 2122345 | *Methanocaldococcus jannaschii* | 43 |
| dmdA | 9884634 | *Eubacterium limosum* | 44 |
| dmdB | 9884633 | *Eubacterium limosum* | 45 |
| Olhyd_maccj | 7390838 | *Macrococcus caseolyticus* | 46 |
| ech | 1047000 | *Pseudomonas putida* | 47 |
| crt | 1118895 | *Clostridium acetobutylicum* | 48 |
| phaB | 1046931 | *Pseudomonas putida* | 49 |
| fadA | 12934462 | *Escherechia coli* | 50 |
| fadB | 12934454 | *Escherechia coli* | 51 |
| fadI | 12933009 | *Escherechia coli* | 52 |
| fadJ | 12931539 | *Escherechia coli* | 53 |
| fadR | 12931108 | *Escherechia coli* | 54 |
| ldi | 302064203 | *Castellaniella defragrans* | 55 |

In some embodiments, a dehydratase-isomerase including, 4-hydroxybutyryl-CoA dehydratase/vinylacetyl-CoA-Delta-isomerase may be engineered by standard methods to increase its selectivity for crotonyl-alcohol. Exemplary genes that can be engineered to increase its selectivity for crotonyl-alcohol are set forth in Table 9 below and represent a suitable candidate for step D in FIG. 2 below:

TABLE 9

| Exemplary genes that can be engineered to increase its selectivity for crotonyl-alcohol. | | | |
|---|---|---|---|
| Gene | Gene ID | Organism | SEQ ID NO: |
| ldi | 302064203 | *Castellaniella defragrans* | 56 |
| abdD | 1453964 | *Sulfolobus solfataricus* | 57 |

Step A of FIG. 1, and steps C, D and E of FIG. 3 require condensation of either acetyl-CoA or acetoacetyl-CoA with formyl-CoA or propionyl-CoA. Such a condensation can be catalyzed with a ketothiolase set forth in EC 2.3.1. However, any known polynucleotide coding for a ketothiolase including, for example, those polynucleotides set forth in Table 10 below, is contemplated for use by the present disclosure.

TABLE 10

Exemplary genes coding for enzymes in EC 2.3.1.

| Gene | Gene ID | Organism | SEQ ID NO: |
|---|---|---|---|
| paaJ | 12934018 | *Escherichia coli* | 58 |
| phaD | 1046928 | *Pseudomonas putida* | 59 |
| pcaF | 10441755 | *Pseudomonas putida* | 60 |
| pcaF | 11639550 | *Acinetobacter calcoaceticus* | 61 |
| fadA | 4490319 | *Aeromonas hydrophila* | 62 |
| AtoB | 4997503 | *Aeromonas salmonicida* | 63 |
| pcaF | 4383639 | *Pseudomonas aeroginosa* | 64 |
| bktB | 428815 | *Ralstonia eutropha* | 65 |
| pimB | 2692199 | *Rhodopseudomonas palustris* | 66 |
| syn_02642 | 3882984 | *Syntrophus aciditrophicus* | 67 |
| phaA | 10921806 | *Cupriavidus necator* | 68 |
| atoB | 12934272 | *Escherichia coli* | 69 |
| thlA | 1119056 | *Clostridium acetobutylicum* | 70 |
| thlB | 1116083 | *Clostridium acetobutylicum* | 71 |
| ERG10 | 856079 | *Saccahromyces cerevisiae* | 72 |
| pflB | 12931841 | *Escherichia coli* | 73 |
| pflA | 12930359 | *Escherichia coli* | 74 |
| pfl | 15671982 | *Lactococcus lactis* | 75 |
| pfl | 3168596 | *Streptococcus equinus* | 76 |
| act | 14141682 | *Streptococcus equinus* | 77 |
| Clo1313_1716 | 12421448 | *Clostridium thermocellum* | 78 |

Steps E, G, and J in FIG. 1, and step J in FIG. 2 can be catalyzed by a decarboxylase enzyme as set forth in EC class 4.1.1 Numerous decarboxylases have been characterized and shown to decarboxylate structurally similar substrates to 2-pentenoic acid, 2,4-pentedienoic acid (FIG. 1) and 3-hydroxypentenoic acid (FIG. 3). Exemplary enzymes for step J of FIG. 1 include sorbic acid decarboxylase and aconitate decarboxylase as set forth in EC 4.1.1.16. Exemplary enzymes for steps G and E of FIG. 1 may include p450 fatty acid decarboxylase from *Jeotgalicoccus*. Exemplary enzymes for step J of FIG. 3 may include those enzymes as set forth in EC 4.1.1.33 such as diphosphomevalonate decarboxylase. However, any known polynucleotide coding for a decarboxylase including, for example, those polynucleotides set forth in Table 11 below, is contemplated for use by the present disclosure.

TABLE 11

Exemplary genes coding for enzymes in EC 4.1.1.

| Gene | Gene ID | Organism | SEQ ID NO: |
|---|---|---|---|
| $OleT_{JE}$ | 320526717 XXX | *Jeotgalicoccus* sp; ATCC8456 | 79 |
| PadA1 | 145235767 | *Aspergillus niger* | 80 |
| ohbA1 | 145235771 | *Aspergillus niger* | 81 |
| sdrA | 145235769 | *Aspergillus niger* | 82 |
| padA1 | 169786362 | *Aspergillis oryzae* | 83 |
| ohbA1 | 169768360 | *Aspergillis oryzae* | 84 |
| sdrA | 169768362 | *Aspergillis oryzae* | 85 |
| Mvd | 2845318 | *Picrophilus torridus* | 86 |
| mvd | 2845209 | *Picrophilus torridus* | 87 |
| mvd | 855779 | *Saccharomyces cerevisiae* | 88 |
| mvd | 162312575 | *Schizosaccharomyces pombe* | 89 |
| mvd | 257051090 | *Halorhabdus utahensis* | 90 |
| mvd | 8741675 | *Haloterrigena turkmenica* | 91 |
| mvd | 9132821 | *Leuconostoc kimchii* | 92 |
| dvd | 1447408 | *Halobacterium salinarum* | 93 |
| dfd | 121708954 | *Aspergillus clavatus* | 94 |
| | 4593483 | *Neosartorya fischeri* | 95 |
| mvaD | 11027973 | *Streptococcus pseudopneumoniae* | 96 |
| mvaD | 8433456 | *Lactobacillus rhamnosus* | 97 |
| mvaD | 12158799 | *Borrelia afzelii* | 98 |

Step F of FIG. 1 involves an isomerase enzyme as set forth in EC 5.3.3. Exemplary enzymes for the step include the isopentenyl-diphosphate delta-isomerase. However, any known polynucleotide coding for an isomerase including, for example, those polynucleotides set forth in Table 12 below, is contemplated for use by the present disclosure.

TABLE 12

Exemplary genes coding for enzymes in EC 5.3.3.

| Gene | Gene ID | Organism | SEQ ID NO: |
|---|---|---|---|
| ldi | 12930440 | *Escherichia coli* | 99 |
| ldi1 | 855986 | *Saccharomyces cerevisiae* | 100 |
| fni | 1028286 | *Streptococcus mutans* | 101 |
| fni | 938985 | *Bacillus subtilis* | 102 |

Step B of FIG. 1, steps A, B and C of FIG. 2, and steps F and G of FIG. 3 involve the reduction of a ketone to an alcohol and can be catalyzed by oxidoreductase enzymes in EC class 1.1.1. However, any known polynucleotide coding for an oxidoreductase including, for example, those polynucleotides set forth in Table 13 below, is contemplated for use by the present disclosure.

TABLE 13

Exemplary genes coding for enzymes in EC 1.1.1.

| Gene | Gene ID | Organism | SEQ ID NO: |
|---|---|---|---|
| mdh | 6059112 | *Escherichia coli* | 103 |
| idhA | 5591397 | *Escherichia coli* | 104 |
| idh | 113866693 | *Ralstonia eutropha* | 105 |
| adh | 60592974 | *Clostridium beijerinckii* | 106 |
| Adh | 113443 | *Thermoanaerobacter brockii* | 107 |
| Sadh | 21615552 | *Rhodococcus ruber* | 108 |
| adhA | 3288810 | *Pyrococcus furiosus* | 109 |
| adhE | 12930611 | *Escherichia coli* | 110 |
| adhE2 | 12958626 | *Clostridium acetobutylicum* | 111 |
| adhE | 55818563 | *Leuconostoc mesenteroides* | 112 |
| HMG1 | 854900 | *Saccharomyces cerevisiae* | 113 |
| CtCNB1_3119 | 8560791 | *Comamonas testosteroni* | 114 |
| DKAM_0720 | 7170894 | *Desulfurococcus kamchatkensis* | 115 |
| mvaA | 1004602 | *Staphylococcus aureus* | 116 |
| LJ1608 | 2742117 | *Lactobacillus johnsonii* | 117 |
| acr1 | 2879608 | *Acinetobacter* sp. ADP1 | 118 |
| acr1 | 1684885 | *Acinetobacter baylyi* | 119 |
| sucD | 5394466 | *Clostridium kluyveri* | 120 |
| sucD | 2551522 | *Porphyromonas gingivalis* | 121 |
| bld | 31075383 | *Clostridium saccharoperbutylacetonicum* | 122 |
| Cbei_3832 | 5294993 | *Clostridium beijerinckii* | 123 |

Step I of FIG. 1, and step A of FIG. 3 involve a dehydrogenase as set forth in EC 1.3.1 or 1.2.99. However, any known polynucleotide coding for a dehydrogenase including, for example, those polynucleotides set forth in Table 14 below, is contemplated for use by the present disclosure.

TABLE 14

Exemplary genes coding for enzymes in EC 1.3.1 or 1.2.99.

| Gene | Gene ID | Organism | SEQ ID NO: |
|---|---|---|---|
| Msed_1426 | 5104797 | *Metallosphaera sedula* | 124 |
| ST0480 | 1458422 | *Sulfolobus tokodaii* | 125 |
| Mcup_0809 | 10493000 | *Metallosphaera cuprina* | 126 |
| RBRH_02090 | 9986550 | *Streptomyces clavuligerus* | 127 |
| RSP_1434 | 3718801 | *Rhodobacter sphaeroides* | 128 |
| acrA | JN244654.1 | *Clostridium propionicum* | 129 |
| acrB | JN244655 | *Clostridium propionicum* | 130 |
| Fdh1 | 2276464 | *Candida boidinii* | 131 |
| Fdh1 | 854570 | *Saccharomyces cerevisiae* | 132 |
| Fdh2 | 1370568 | *Saccharomyces cerevisiae* | 133 |
| fdsC | 4248880 | *Cupriavidus necator* | 134 |
| fdsA | 4248878 | *Cupriavidus necator* | 135 |
| fdsB | 4248879 | *Cupriavidus necator* | 136 |
| fdsD | 4248881 | *Cupriavidus necator* | 137 |
| fdsG | 4248882 | *Cupriavidus necator* | 138 |
| fdsR | 4248883 | *Cupriavidus necator* | 139 |

Methods for the Production of Butadiene

Butadiene (e.g., fermentation product) may be produced by contacting one or more genetically modified microorganisms provided herein with a fermentable carbon source. Such methods may preferably comprise contacting a fermentable carbon source with a microorganism comprising one or more polynucleotides coding for enzymes in a pathway that catalyzes a conversion of the fermentable carbon source to any of the intermediates provided in Tables 1-3 or FIGS. 1-3 and one or more polynucleotides coding for enzymes in a pathway that catalyze a conversion of the one or more intermediates provided in Tables 1-3 or FIGS. 1-3 to butadiene in a fermentation media including, under sufficient conditions and for a suitable period of time; and expressing the one or more polynucleotides coding for the enzymes in the pathway that catalyzes a conversion of the fermentable carbon source to the one or more intermediates provided in Tables 1-3 or FIGS. 1-3 and one or more polynucleotides coding for enzymes in a pathway that catalyze a conversion of the one or more intermediates provided in Tables 1-3 or FIGS. 1-3 to butadiene in the microorganism to produce butadiene. In some embodiments, the conversion of the fermentable carbon source to butadiene is ATP positive (e.g., generates a net of ATP per mol of butadiene produced; produces ATP as a byproduct) and when combined with a NADH consuming pathway it can provide an anaerobic process for butadiene production. For example, the conversion of a fermentable carbon source such as glucose or fructose to butadiene may produce a net of 1 mol of ATP per mol of butadiene produced.

Exemplary fermentable carbon sources may include, but are not limited to, sugarcane juice, sugarcane molasses, hydrolyzed starch, hydrolyzed lignocellulosic materials, glucose, sucrose, fructose, lactate, lactose, xylose, pyruvate, or glycerol in any form or mixture thereof. In some embodiments, the carbon source is a monosaccharide, oligosaccharide, or polysaccharide.

Metabolic pathways that lead to the production of industrially important compounds such as butadiene involve oxidation-reduction (redox) reactions. For example, during fermentation, glucose is oxidized in a series of enzymatic reactions into smaller molecules with the concomitant release of energy. The electrons released are transferred from one reaction to another through universal electron carriers, such Nicotinamide Adenine Dinucleotide (NAD) and Nicotinamide Adenine Dinucleotide Phosphate (NAD(P)), which act as cofactors for oxidoreductase enzymes. In microbial catabolism, glucose is oxidized by enzymes using the oxidized form of the cofactors (NAD(P)+ and/or NAD+) as cofactor thus generating reducing equivalents in the form of the reduced cofactor (NAD(P)H and NADH). In order for fermentation to continue, redox-balanced metabolism is required, i.e., the cofactors must be regenerated by the reduction of microbial cell metabolic compounds. In some embodiment, the novel pathways disclosed herein are advantageous in that they provide for the conversion of a fermentable carbon source to butadiene through a pathway that redistributes the end products to achieve a redox balance.

Some key parameters for efficient fermentation of a fermentable carbon source by one or more modified microorganisms as disclosed herein include: the ability to grow microorganisms to a greater cell density, increased yield of desired products, increased amount of volumetric productivity, removal of unwanted co-metabolites, improved utilization of inexpensive carbon and nitrogen sources, adaptation to varying fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Inefficiencies in any of these parameters can result in high manufacturing costs, inability to capture or maintain market share, and/or failure to bring fermented end-products to market.

The methods of the present disclosure can be adapted to conventional fermentation bioreactors (e.g., batch, fed-batch, cell recycle, and continuous fermentation). In some embodiments, a microorganism (e.g., a genetically modified microorganism) as provided herein is cultivated in liquid fermentation media (i.e., a submerged culture) which leads to excretion of the fermented product(s) into the fermentation media. Fermentation may occur in a bioreactor configured as a stirred tank, a bubble column, an airlift reactor or any other suitable configuration known in the art. In one embodiment, the fermented end product(s) can be isolated from the fermentation media using any suitable method known in the art.

In some embodiments, formation of the fermented product may occur during an initial, fast growth period of the microorganism. In one embodiment, formation of the fermented product may occur during a second period in which the culture is maintained in a slow-growing or non-growing state. In one embodiment, formation of the fermented product may occur during more than one growth period of the microorganism. In such embodiments, the amount of fermented product formed per unit of time is generally a function of the metabolic activity of the microorganism, the physiological culture conditions (e.g., pH, temperature, medium composition), and the amount of microorganisms present in the fermentation process.

In some embodiments, the fermentation product is recovered from the periplasm or culture medium as a secreted metabolite. In one embodiment, the fermentation product is extracted from the microorganism, for example when the microorganism lacks a secretory signal corresponding to the fermentation product. In one embodiment, the microorganisms are ruptured and the culture medium or lysate is centrifuged to remove particulate cell debris. The membrane and soluble protein fractions may then be separated if necessary. The fermentation product of interest may then be purified from the remaining supernatant solution or suspension by, for example, distillation, fractionation, chromatography, precipitation, filtration, and the like. In one embodiment, fermentation products are extracted by one or more of: distillation, reactive distillation, azeotropic distillation and extractive distillation.

The methods of the present disclosure are preferably preformed under anaerobic conditions. Both the degree of reduction of a product as well as the ATP requirement of its synthesis determines whether a production process is able to proceed aerobically or anaerobically. To produce butadiene via anaerobic microbial conversion, or at least by using a process with reduced oxygen consumption, redox imbalances should be avoided. Several types of metabolic conversion steps involve redox reactions including some of the conversions as set forth in Table 1-3 or FIGS. 1-3. Such redox reactions involve electron transfer mediated by the participation of redox cofactors such as NADH, NADPH and ferredoxin. Since the amounts of redox cofactors in the cell are limited to permit the continuation of metabolic processes, the cofactors have to be regenerated. In order to avoid such redox imbalances, alternative ways of cofactor regeneration may be engineered, and in some cases additional sources of ATP generation may be provided. Alternatively, oxidation and reduction processes may be separated spatially in bioelectrochemical systems (Rabaey and. Rozendal, 2010, Nature reviews, Microbiology, vol 8: 706-716).

In some embodiment, redox imbalances may be avoided by using substrates (e.g., fermentable carbon sources) that are more oxidized or more reduced. for example, if the utilization of a substrate results in a deficit or surplus of electrons, a requirement for oxygen can be circumvented by using substrates that are more reduced or oxidized, respectively. For example, glycerol which is a major byproduct of biodiesel production is more reduced than sugars, and is therefore more suitable for the synthesis of compounds whose production from sugar results in cofactor oxidation, such as succinic acid. In some embodiments, if the conversion of a substrate to a product results in an electron deficit, co-substrates can be added that function as electron donors (Babel 2009, Eng. Life Sci. 9, 285-290). An important criterion for the anaerobic use of co-substrates is that their redox potential is higher than that of NADH (Geertman et al., 2006, FEMS Yeast Res. 6, 1193-1203). If the conversion of substrate to produce results in an electron surplus, co-substrates can be added that function as electron acceptors.

Methods for the Production of Polybutadiene and Other Compounds from Butadiene

Butadiene is gaseous at room temperature or in fermentative conditions (20-45° C.), and their production from a fermentation process results in a gas that could accumulate in the headspace of a fermentation tank, and be siphoned and concentrated. Butadiene may be purified from fermentation of gases, including gaseous alcohol, $CO2$ and other compound by solvent extraction, cryogenic processes, distillation, fractionation, chromatography, precipitation, filtration, and the like.

Butadiene produced via any of the processes or methods disclosed herein may be converted to polybutadiene. Alternatively, butadiene produced via methods disclosed herein may be polymerized with other olefins to form copolymers such as acrylonitrile-butadiene-styrene (ABS), acrylonitrile-butadiene (ABR), or styrene-butadiene (SBR) copolymers, BR butyl rubber (RB), poly butadiene rubber (PBR), nitrile rubber and polychloroprene (Neoprene). Those synthetic rubbers or plastic elastomers applications include productions of tires, plastic materials, sole, shoe hills, technical goods, home appliance, neoprene, paper coatings, gloves, gaskets and seals.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1: Modification of Microorganism for Production of Butadiene

A microorganism such as a bacterium may be genetically modified to produce butadiene from a fermentable carbon source including, for example, glucose.

In an exemplary method, a microorganism may be genetically engineered by any methods known in the art to comprise: i.) one or more polynucleotides coding for enzymes in a pathway that catalyze a conversion of the fermentable carbon source to acetyl-CoA and propionyl-CoA, and/or one or more polynucleotides coding for enzymes in a pathway that catalyze a conversion of acetyl-CoA and propionyl-CoA to butadiene; ii.) one or more polynucleotides coding for enzymes in a pathway that catalyze a conversion of the fermentable carbon source to crotonyl-CoA, and/or one or more polynucleotides coding for enzymes in a pathway that catalyze a conversion of crotonyl-CoA to butadiene; or iii.) one or more polynucleotides coding for enzymes in a pathway that catalyze a conversion of the fermentable carbon source to formic acid, and/or one or more polynucleotides coding for enzymes in a pathway that catalyze a conversion of formic acid to butadiene.

Alternatively, a microorganism that lacks one or more enzymes (e.g., one or more functional enzymes that are catalytically active) for the conversion of a fermentable carbon source to butadiene may be genetically modified to comprise one or more polynucleotides coding for enzymes (e.g., functional enzymes including, for example any enzyme disclosed herein) in a pathway that the microorganism lacks to catalyze a conversion of the fermentable carbon source to butadiene.

Example 2: Fermentation of a Carbon Source by a Genetically Modified Microorganism to Produce Butadiene A genetically modified microorganism, as produced in Example 1 above, may be used to ferment a carbon source, to produce butadiene.

In an exemplary method, a previously-sterilized culture medium comprising a fermentable carbon source (e.g., 9 g/L glucose, 1 g/L $KH2PO4$, 2 g/L $(NH4)2HPO4$, 5 mg/L $FeSO4.7H2O$, 10 mg/L $MgSO4.7H2O$, 2.5 mg/L $MnSO4.H2O$, 10 mg/L $CaCl2.6H2O$, 10 mg/L $CoCl2.6H2O$, and 10 g/L yeast extract) is charged in a bioreactor.

During fermentation, anaerobic conditions are maintained by, for example, sparging nitrogen through the culture medium. A suitable temperature for fermentation (e.g., about 30° C.) is maintained using any method known in the art. A near physiological pH (e.g., about 6.5) is maintained by, for example, automatic addition of sodium hydroxide. The bioreactor is agitated at, for example, about 50 rpm. Fermentation is allowed to run to completion.

The produced butadiene is then recovered from the culture medium using conventional methods. When the fermentation products are recovered by distillation, the butadiene fraction may be optionally polymerized to form polybutadiene. Distillation fractions containing other intermediates along the butadiene pathway (if any) may be subjected to a subsequent fermentation in a bioreactor to produce additional butadiene.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method for producing butadiene, the method comprising: contacting a fermentable carbon source with a genetically modified microorganism comprising one or more polynucleotides encoding enzymes in a pathway that catalyzes a conversion of crotonyl alcohol to butadiene, wherein the pathway comprises a crotonaldehyde dehydrogenase, a crotonyl alcohol dehydrogenase, and an enzyme, wherein the enzyme has an amino acid sequence at least 70% identical to the enzymes encoded by SEQ ID NOs: 37, 41, 43, 44, 46, 47, 48, 50, 51 and 55, and has a dehydratase activity.

2. The method of claim 1, wherein the enzyme is at least 80% identical to linalool dehydratase (GI: 302064203).

3. The method of claim 1, wherein the enzyme is at least 95% identical to linalool dehydratase (GI: 302064203).

4. The method of claim 1, wherein the enzyme is linalool dehydratase (GI: 302064203) or (EC 4.2.1.127).

5. The method of claim 1, wherein the enzyme accepts crotonyl alcohol as a substrate.

6. The method of claim 1, wherein the enzyme has dehydratase activity.

7. The method of claim 1, wherein the enzyme has isomerase activity.

8. The method of claim 1, wherein the enzyme has dehydratase and isomerase activity.

9. The method of claim 1, wherein the method is performed in a microorganism.

* * * * *

SEQUENCE LISTING

```
<160> NUMBER OF SEQ ID NOS: 139

<210> SEQ ID NO 1
<211> LENGTH: 651
<212> TYPE: DNA
<213> ORGANISM: Escherichia coli K12

<400> SEQUENCE: 1

atggatgcga aacaacgtat tgcgcgccgt gtggcgcaag agcttcgtga tggtgacatc      60

gttaacttag ggatcggttt acccacaatg gtcgccaatt atttaccgga gggtattcat     120
```

```
atcactctgc aatcggaaaa cggcttcctc ggtttaggcc cggtcacgac agcgcatcca    180

gatctggtga acgctggcgg gcaaccgtgc ggtgttttac ccggtgcagc catgtttgat    240

agcgccatgt catttgcgct aatccgtggc ggtcatattg atgcctgcgt gctcggcggt    300

ttgcaagtag acgaagaagc aaacctcgcg aactgggtag tgcctgggaa aatggtgccc    360

ggtatgggtg gcgcgatgga tctggtgacc gggtcgcgca aagtgatcat cgccatggaa    420

cattgcgcca aagatggttc agcaaaaatt ttgcgccgct gcaccatgcc actcactgcg    480

caacatgcgg tgcatatgct ggttactgaa ctggctgtct ttcgttttat tgacggcaaa    540

atgtggctca ccgaaattgc cgacgggtgt gatttagcca ccgtgcgtgc caaaacagaa    600

gctcggtttg aagtcgccgc cgatctgaat acgcaacggg gtgatttatg a             651


<210> SEQ ID NO 2
<211> LENGTH: 663
<212> TYPE: DNA
<213> ORGANISM: Escherichia coli K12

<400> SEQUENCE: 2

atgaaaacaa aattgatgac attacaagac gccaccggct tctttcgtga cggcatgacc     60

atcatggtgg gcggatttat ggggattggc actccatccc gcctggttga agcattactg    120

gaatctggtg ttcgcgacct gacattgata gccaatgata ccgcgtttgt tgataccggc    180

atcggtccgc tcatcgtcaa tggtcgagtc cgcaaagtga ttgcttcaca tatcggcacc    240

aacccggaaa caggtcggcg catgatatct ggtgagatgg acgtcgttct ggtgccgcaa    300

ggtacgctaa tcgagcaaat tcgctgtggt ggagctggac ttggtggttt tctcacccca    360

acgggtgtcg gcaccgtcgt agaggaaggc aaacagacac tgacactcga cggtaaaacc    420

tggctgctcg aacgcccact gcgcgccgac ctggcgctaa ttcgcgctca tcgttgcgac    480

acacttggca acctgaccta tcaacttagc gcccgcaact ttaacccccct gatagccctt    540

gcggctgata tcacgctggt agagccagat gaactggtcg aaaccggcga gctgcaacct    600

gaccatattg tcacccctgg tgccgttatc gaccacatca tcgtttcaca ggagagcaaa    660

taa                                                                  663


<210> SEQ ID NO 3
<211> LENGTH: 1509
<212> TYPE: DNA
<213> ORGANISM: Corynebacterium glutamicum ATCC 13032

<400> SEQUENCE: 3

atgtctgatc gcattgcttc agaaaagctg cgctccaagc tcatgtccgc cgacgaggcg     60

gcacagtttg ttaaccacgg tgacaaggtt ggtttctccg gcttcaccgg cgctggctac    120

ccaaaggcac tgcctacggc aatcgctaac cgggctaaag aagcacacgg tgcaggcaac    180

gactacgcaa tcgacctgtt cactggcgca tcgaccgccc ctgactgcga tggcgtactt    240

gcagaagctg acgctatccg ctggcgcatg ccatacgcat ctgatccaat catgcgtaac    300

aagatcaact ccggctccat gggatactcc gatatccacc tgtcccactc cggccagcag    360

gttgaagagg gcttcttcgg ccagctcaac gtagctgtca ttgaaatcac ccgcatcact    420

gaagagggct acatcatccc ttcttcctcc gtgggtaaca acgttgagtg gctcaacgct    480

gcagagaagg tcatcctcga ggttaactct tggcagtctg aagacctcga aggtatgcac    540

gacatctggt ctgttcctgc cctgccaaac cgcattgccg tgccaatcaa caagccaggc    600

gaccgcatcg gtaagaccta catcgagttc gacaccgaca aggttgttgc tgttgttgag    660
```

accaacaccg cagaccgcaa cgcaccattc aagcctgtcg acgacatctc taagaagatc 720
gctggcaact tcctcgactt cctggaaagc gaagttgctg caggtcgcct gtcctacgac 780
ggctacatca tgcagtccgg cgtgggcaac gtgccaaacg cggtgatggc aggcctgctg 840
gaatccaagt ttgagaacat ccaggcctac accgaagtta tccaggacgg catggtggac 900
ctcatcgacg ccggcaagat gaccgttgca tccgcaactt ccttctccct gtctcctgag 960
tacgcagaga agatgaacaa cgaggctaag cgttaccgcg agtccattat cctgcgccca 1020
cagcagatct ctaaccaccc agaggtcatc cgccgcgttg gcctgatcgc caccaacggt 1080
ctcatcgagg ctgacattta cggcaacgtc aactccacca acgtttctgg ctcccgcgtc 1140
atgaacggca tcggcggctc cggcgacttc acccgtaacg gctacatctc cagcttcatc 1200
accccttcag aggcaaaggg cggcgcaatc tctgcgatcg ttcctttcgc atcccacatc 1260
gaccacaccg agcacgatgt catggttgtt atctctgagt acggttacgc agaccttcgt 1320
ggtctggctc cacgtgagcg cgttgccaag atgatcggcc tggctcaccc tgattaccgc 1380
ccactgctcg aggagtacta cgctcgcgca acctccggtg acaacaagta catgcagacc 1440
cctcatgatc ttgcaaccgc gtttgatttc cacatcaacc tggctaagaa cggctccatg 1500
aaggcataa 1509

<210> SEQ ID NO 4
<211> LENGTH: 378
<212> TYPE: DNA
<213> ORGANISM: Corynebacterium glutamicum ATCC 13032

<400> SEQUENCE: 4
atgaatggta tcggcggctc gggcgatttc acgcgtaacg cctttgcttc cacatttatc 60
tctccctcgg cagccaaagt tgatgcgatt tccgcgattg tgcctttcgc gtcccatatc 120
gatcacacgg aacatgatgc gatggttgtc attactgaat atggctacgc agacctgcgc 180
gggctatcgc caaaacaacg agtccccaaa atgattgcca tcgcccaccc ggactatcga 240
ccactgctgg aagcatactt tgaccgggcg ctgaacagtg ctgattccta tcagcacacc 300
ctgcatgatc tgcgcaccgc cttcgatttc cataatcgct tgaactcaca aggaaccatg 360
aaaatcgaaa aagcatag 378

<210> SEQ ID NO 5
<211> LENGTH: 657
<212> TYPE: DNA
<213> ORGANISM: Clostridium acetobutylicum

<400> SEQUENCE: 5
atgaactcta aaataattag atttgaaaat ttaaggtcat tctttaaaga tgggatgaca 60
attatgattg gaggtttttt aaactgtggc actccaacca aattaattga ttttttagtt 120
aatttaaata taaagaattt aacgattata agtaatgata catgttatcc taatacaggt 180
attggtaagt taatatcaaa taatcaagta aaaaagctta ttgcttcata tataggcagc 240
aacccagata ctggcaaaaa actttttaat aatgaacttg aagtagagct ctctccccaa 300
ggaactctag tggaaagaat acgtgcaggc ggatctggct taggtggtgt actaactaaa 360
acaggtttag gaactttgat tgaaaaagga aagaaaaaaa tatctataaa tggaacggaa 420
tatttgttag agctacctct tacagccgat gtagcattaa ttaaaggtag tattgtagat 480
gaggccggaa acaccttcta taaaggtact actaaaaact ttaatcccta tatggcaatg 540

-continued gcagctaaaa ccgtaatagt tgaagctgaa aatttagtta gctgtgaaaa actagaaaag 600
gaaaaagcaa tgaccccgg agttcttata aattatatag taaaggagcc tgcataa 657

<210> SEQ ID NO 6
<211> LENGTH: 666
<212> TYPE: DNA
<213> ORGANISM: Clostridium acetobutylicum

<400> SEQUENCE: 6
atgattaatg ataaaaacct agcgaaagaa ataatagcca aaagagttgc aagagaatta 60
aaaaatggtc aacttgtaaa cttaggtgta ggtcttccta ccatggttgc agattatata 120
ccaaaaaatt tcaaaattac tttccaatca gaaaacggaa tagttggaat gggcgctagt 180
cctaaaataa atgaggcaga taaagatgta gtaaatgcag gaggagacta tacaacagta 240
cttcctgacg gcacattttt cgatagctca gtttcgtttt cactaatccg tggtggtcac 300
gtagatgtta ctgttttagg ggctctccag gtagatgaaa agggtaatat agccaattgg 360
attgttcctg gaaaaatgct ctctggtatg ggtggagcta tggatttagt aaatggagct 420
aagaaagtaa taattgcaat gagacataca aataaaggtc aacctaaaat tttaaaaaaa 480
tgtacacttc ccctcacggc aaagtctcaa gcaaatctaa ttgtaacaga acttggagta 540
attgaggtta ttaatgatgg tttacttctc actgaaatta ataaaaacac aaccattgat 600
gaaataaggt ctttaactgc tgcagattta ctcatatcca atgaacttag acccatggct 660
gtttag 666

<210> SEQ ID NO 7
<211> LENGTH: 1753
<212> TYPE: DNA
<213> ORGANISM: Roseburia sp. A2-183

<400> SEQUENCE: 7
agaaatctgc tacgaactgg gaacctattt tgtgggacag cgcgactacg cggaagcggt 60
tctctggttc tacaatgccg cctatgagac ggaaagcatc ctggacgttc acacaagcgg 120
ggatcttccg ctgctcggtc ttgtcgaatg ttacgagacg ctcctcgccg gggaggaagc 180
caaaattcct tccgacacag cgcttaccat ccagtacgaa atgatgctcg acaaataccg 240
ggaggcttcc agagactggc ggatgccgga ggagacctga tcttacaaat ctccggaaat 300
acgctccggc agggcttgta aaatacgaca taaagtgata ggatgaaact atggtaaaat 360
tttaacaatc ttttgtgtgg gaggtatttg agatggattt tcgtgaagaa tacaaacaga 420
agcttgtctc cgcagatgag gcggtaaagc tcatcaaatc cggagactgg gtagattacg 480
gctggtgcac caacaccgtt gacgcactgg atcaggctct cgcaaagcgc accgacgaac 540
tgacagacgt caagctgcgc ggcggtatcc tgatgaagcc gctggctgtt tttgcacgtg 600
aggatgcagg tgagcatttc tgctggaact cctggcatat gtccggtatc gagcgcaaga 660
tgataaacag aggcgtggct tactactgtc cgatccgcta ctccgagctg ccgcgctact 720
accgcgagct tgactgcccg gatgacgttg ccatgttcca ggttgctccg atggatgcgc 780
acggctactt taacttcggt ccgagtgcct cacatctggg tgcaatgtgc gagcgcgcaa 840
agcacatcat cgtagaagtc aatgaaaata tgccacgctg cctcggcggt accgagtgtg 900
gcatccacat ttccgatgtc acctacatcg tggaaggctc caacccgcca atcggtgaac 960
tgggtgcagg cggtcctgct acagatgtgg ataaggctgt cgcaaagctg atcgtcgatg 1020
agattccgaa cggtgcctgc ttacagctcg gtatcggcgg catgccaaac gctgtcggtt 1080
ccctgattgc agagtccgac ttgaaggatc tcggcgttca cactgagatg tacgtggatg 1140
catttgtcga tattgcaaag gcaggtaaga tcaacggttc caaaaagaat atcgaccgtt 1200
accgccagac ctacgctttc ggcgccggca ccaagaaaat gtacgattat ctggacgaca 1260
acccggaact gatgagcgct ccggtcgact acacgaacga catccgctcg atctccgcac 1320
tggataactt tatttccatc aacaatgccg tggatattga tctctatggt caggtaaatg 1380
cagagtctgc aggcatcaag cagatcagcg gcgcaggcgg acagcttgac ttcgtgctcg 1440
gagcttatct gtccaagggc ggcaagagct ttatctgctt atcctctacc ttcaagacca 1500
aggacggtca ggtgcagtcc cgtatccgcc cgacgctggc aaacggttcc atcgttaccg 1560
acgcaagacc gaatacacac tatgttgtaa ccgaatacgg caaggtgaac ttaaagggtc 1620
tgtctacctg gcagagagcc gaggctctga tctcgatcgc gcatcccgat ttccgcgacg 1680
acctcatcaa agaggcggag cagatgcaca tctggagaag aagcaaccgc tagtaccgga 1740
ggacgactga cgg 1753

<210> SEQ ID NO 8
<211> LENGTH: 1000
<212> TYPE: DNA
<213> ORGANISM: Clostridium propionicum

<400> SEQUENCE: 8
gaattcaaaa ttgctatcgt tgatgacgat ttggctcagg aatccagaca gattcgtgtt 60
gacgttctgg atggcgaagg tggccctctt tatagaatgg caaaagcttg gcagcaaatg 120
tacggttgct ctcttgcaac tgatacaaag aaaggccgcg gcagaatgct gatcaacaag 180
acaattcaga caggtgcaga tgctatcgtt gttgcgatga tgaaattctg tgatcctgaa 240
gaatgggatt accctgtaat gtacagagaa tttgaagaaa aaggcgttaa gagtctgatg 300
atcgaagttg atcaggaagt ttcttccttc gaacagatca agacaagact gcagtctttc 360
gtagaaatgc tgtaatttga acaatcgttt gctgaaaaac tgtacactgg ggtgggtgac 420
tgctccagtg tattgtaata agcaaataag caaaaatcga taagatttag gaggattttc 480
gacaatgaga aaggttccca ttattaccgc agatgaggct gcaaagctta ttaaagacgg 540
tgatacagtt acaacaagtg gtttcgttgg aaatgcaatc cctgaggctc ttgatagagc 600
tgtagaaaaa agattcttag aaacaggcga acccaaaaac attacatatg tttattgtgg 660
ttctcaaggt aacagagacg gaagaggtgc tgagcacttt gctcatgaag gccttttaaa 720
acgttacatc gctggtcact gggctacagt tcctgctttg ggtaaaatgg ctatggaaaa 780
taaaatggaa gcatataatg tatctcaggg tgcattgtgt catttgttcc gtgatatagc 840
ttctcataag ccaggcgtat ttacaaaggt aggtatcggt actttcattg accccagaaa 900
tggcggcggt aaagtaaatg atattaccaa agaagatatt gttgaattgg tagagattaa 960
gggtcaggaa tatttattct accctgcttt tcctattcat 1000

<210> SEQ ID NO 9
<211> LENGTH: 1554
<212> TYPE: DNA
<213> ORGANISM: Clostridium beijerinchii

<400> SEQUENCE: 9
gtgagaaaag taaaagtttt aacaagtcgc gaagcagtac aaatagtgaa ggatggagat 60
gtgttagtaa ctggcggatt tgttggtagt tgtgcacctg aaactcttag ttgtgcttta 120

-continued

```
gaaaaacgtt tcattgaaac aaatcatccg caaaatataa ctttatttca tgcagcagga    180
caaggcgata gtaaggggaa aggttcagat cattatgccc acgaaggctt acttaagaga    240
gtggttgcag gtcattataa tttagcaccg aaaattggaa agttaattaa tgaaaataaa    300
atagaagctt ataatctacc acaagggaca atttctcaat tatttagaga tattgcggga    360
aaaagaattg ggacaataac tcacgttgga ttgaatacat ttgtggatcc aagaattagt    420
ggtggaaaat taaatgaaaa aacaaaagaa gatctagtaa agctaataaa tatagaaggt    480
gaagaaaaat tattatacaa atcaattcca gttaatgtct gcttcttaag aggatctttt    540
gcagatgaat acggtaatgt atcattagaa aaagaaatag ctacacttga ggatacgtca    600
atagcccaag cttgtaagaa taatggcgga aaagtaatag ttcaagtaga aaaagtagtt    660
gaagcaggat ctttagaccc acgtcttata aaaattccag gtatatatgt agatgcggtt    720
gtaatctcaa ctcccgaaga gcatgaacaa tccttcgaat gcccatttaa tccagcagta    780
acaggtgaaa tgagaattcc attaaacagt gtagaaaaag ctccattaaa tgagagaaag    840
ataattgcga gaagagcagc tatggaatta aagaaagata cggtagtaaa tttaggtata    900
gggataccag aagttatttc tttagttgcg aatgaagaag gaattggtga atatatgaca    960
ttaactgtag aagccggtcc aataggaggt ataccacaag gatgcacagc ttttggagcg   1020
agtataaatc cagaagctat tatagatcag ccatatcaat ttgattttta tgatggtgga   1080
ggcgtcgata tagcattttt aggactagct caggttgatg aacatggaaa tttgaatgta   1140
agtaagtttg ggcctagaat tgctggatgt ggtggattca taaatataac tcaaaatgct   1200
aagaaagtgt tattttgtgg aacattcact gcaggaggct taaaagtagt aacaggagat   1260
ggcaaattag aaattaaaca agaaggaaaa gctaaaaaat tcattaagga tgtagagcaa   1320
attacattta gtggagatta tgcaagaagg atggatcaac aagttatgta tataactgag   1380
agagcagtat ttgagttaag gaaagatgga ttatacctta cagaaatagc gcctgggata   1440
gatctaaaaa aggatgtatt ggatttaatg gatttcaaac ctaaaatgga tggagtacct   1500
agactaatga atggaagaat attttatgat aagttgatgg gattaaggga gtaa         1554
```

```
<210> SEQ ID NO 10
<211> LENGTH: 687
<212> TYPE: DNA
<213> ORGANISM: Acinetobacter sp. ADP1

<400> SEQUENCE: 10

atgatagata aaagtgcagc gaccctaacg gaagcgctct cccagatcca cgacggtgcc     60
accatcctga ttggtggttt tggaacagcc ggccaacccg ccgagctgat tgacggactg    120
attgaactag gtcgcaagaa cctaaccatc gtcagcaaca acgccggcaa tggagactat    180
ggactggcca agctgctaaa aactggcgcc gtcaaaaaga tcatctgttc cttcccacgt    240
caggccgact cctacgtatt tgacgagcta taccgtgcgg gcaaaattga acttgaaatc    300
gtgccgcagg gcaatctggc ctgtcgtata caggccgccg gcatggggct ggggccgatc    360
tacaccccaa ccggttttgg cactttactc gcagaaggta aacctaccct gaactttgat    420
ggcaaagact acgtactgga aaacccgatc aaggccgact ttgccctgat caaagcctac    480
aagggcgacc gctggggcaa tctggtctat cgcaaatcag cacgaaactt cggcccgatc    540
atggccatgg ccgccaacgt gaccatcgca caagtgagcg aagtggtggc actaggagaa    600
ctcgacccgg aaaacgtggt gaccccaggc atctttgttc aacacgttgt accagtccaa    660
tctaccccag caagcgctgc accataa                                        687
```

-continued

<210> SEQ ID NO 11
<211> LENGTH: 654
<212> TYPE: DNA
<213> ORGANISM: Acinetobacter sp. ADP1

<400> SEQUENCE: 11
atgagttatc acaaactgac ccgtgaccag atcgcccagc gcgttgccca agacattccg 60
gaaggctcct atgtcaatct tggcattggc ctgccgacca agattgccag ctatctgcct 120
gccgacaaag acgtatttct acattcagaa aacggactgc tggcctttgg cccaccacca 180
gcggccggcg aagaagatcc ggaactgatc aacgcaggca aagaatacgt aaccatgctc 240
gaaggcggtt gcttctttca ccatggcgac tccttcgcca tgatgcgcgg tggacatctg 300
gatatctgcg tattaggcgc attccagatc gccgccaatg gagacctggc caactggcac 360
accggtgcac cggatgccat accgtcggtc ggtggagcca tggatcttgc ggttggggca 420
aaaaaagttt ttgtaaccac cgatcatgtc accaaaaaag gtgagccgaa gattgtagct 480
gaactgacgt atccagccac gggtcagaaa tgtgtcgacc ggatctacac cgacctgtgc 540
atcatcgatg tggtgccaga aggactgaaa gtgatcgaga aagtcgaagg cttaagcttt 600
gaagaactac aacgcctgac cggtgcaaca ctgatcgatg cgacacaagg ctaa 654

<210> SEQ ID NO 12
<211> LENGTH: 696
<212> TYPE: DNA
<213> ORGANISM: Pseudomonas putida

<400> SEQUENCE: 12
ttgatcaata aaacgtacga gtccatcgcc agcgcggtgg aagggattac cgacggttcg 60
accatcatgg tcggtggctt cggcacggct ggcatgccgt ccgagctgat cgatggcctc 120
attgccaccg gtgcccgcga cctgaccatc atcagcaaca acgccggcaa cggcgagatc 180
ggcctggccg ccctgctcat ggcaggcagc gtgcgcaagg tggtctgctc gttcccgcgc 240
cagtccgact cctacgtgtt cgacgaactg taccgcgccg gcaagatcga gctggaagtg 300
gtcccgcagg gcaacctggc cgagcgtatc cgcgccgcag gctccggcat tggtgcgttc 360
ttctcgccaa ccggctacgg caccctgctg gccgagggca aggaaacccg tgagatcgat 420
ggccgcatgt acgtgctgga aatgccgctg cacgccgact tcgcactgat caaggcgcac 480
aagggtgacc gttggggcaa cctgacctac cgcaaggccg cccgcaactt cggcccgatc 540
atggccatgg ctgccaagac cgccatcgcc caggtcgacc aggtcgtcga actcggtgaa 600
ctggacccgg aacacatcat caccccgggt atcttcgtcc agcgcgtggt cgccgtcacc 660
ggtgctgccg cttcttcgat tgccaaagct gtctga 696

<210> SEQ ID NO 13
<211> LENGTH: 642
<212> TYPE: DNA
<213> ORGANISM: Pseudomonas putida

<400> SEQUENCE: 13
atgaccatca ccaaaaagct ctcccgcacc gagatggccc aacgcgtggc cgcagacatc 60
caggaaggcg cgtatgtaaa cctgggtatc ggcgcaccaa ccctggtggc caactacctg 120
ggcgacaagg aagtgttcct gcacagcgaa aacggcctgc tgggcatggg cccaagccct 180
gcgccgggcg aggaagacga tgacctgatc aacgccggca agcagcacgt caccctgctg 240

-continued

```
accggtggtg ccttcttcca ccatgccgat tcgttctcga tgatgcgtgg cggccacctg    300

gacatcgccg tactgggtgc cttccaggtg tcggtcaagg gcgacctggc caactggcac    360

acgggtgccg aaggttcgat cccggccgta ggcggcgcaa tggacctggc caccggcgcc    420

cgccaggtgt tcgtgatgat ggaccacctg accaagaccg gcgaaagcaa gctggtgccc    480

gagtgcacct acccgctgac cggtatcgcg tgcgtcagcc gcatctacac cgacctggcc    540

gtgctggaag tgacaccgga agggctgaaa gtggtcgaaa tctgcgcgga catcgacttt    600

gacgaactgc agaaactcag tggcgtgccg ctgatcaagt aa                       642
```

<210> SEQ ID NO 14
<211> LENGTH: 717
<212> TYPE: DNA
<213> ORGANISM: Bacillus subtilis

<400> SEQUENCE: 14

```
atgggaaaag tgctgtcatc aagcaaggaa gctgcgaaac tgattcatga tggggatacg     60

ctgatcgcgg gagggtttgg gctgtgcggc atccctgaac agctcatttt gtctataaga    120

gatcagggag taaaggattt aaccgttgtc agcaataact gcggagtcga tgactggggg    180

cttggtttgc ttctggctaa caagcaaatc aagaaaatga tcgcttccta tgtcggtgaa    240

aataaaattt ttgagcggca gtttttaagc ggagagcttg aggtagagct tgttccccaa    300

ggaacgctcg ctgagagaat tcgtgcaggc ggtgcaggca taccgggatt ttatacggcg    360

acaggcgtcg gcacctccat agccgaggga aaagaacata aaacattcgg cggccggact    420

tatgtgctgg agcgaggcat taccggcgat gtggcgatcg tcaaagcgtg gaaagcggac    480

accatgggca atttgatttt taggaaaacg gcgagaaatt tcaatcccat tgccgccatg    540

gcaggcaaga tcacgattgc cgaggcggaa gaaatcgtgg aagcaggaga gctcgatcca    600

gatcacatcc atacgccggg aatttacgta cagcatgtcg tgcttggcgc gagccaagaa    660

aaacggattg aaaaacgaac agttcagcaa gcatcgggaa agggtgaggc caagtga       717
```

<210> SEQ ID NO 15
<211> LENGTH: 651
<212> TYPE: DNA
<213> ORGANISM: Bacillus subtilis

<400> SEQUENCE: 15

```
gtgaaggaag cgagaaaacg aatggtcaaa cgggctgtac aagaaatcaa ggacggcatg     60

aatgtgaatc tcgggattgg aatgccgacg cttgtcgcaa atgagatacc cgatggcgtt    120

cacgtcatgc ttcagtcgga aaacggcttg ctcggaattg gcccctatcc tctggaagga    180

acggaagacg cggatttgat caatgcggga aaggaaacga tcactgaagt gacaggcgcc    240

tcttattttg acagcgctga gtcattcgcg atgataagag gcgggcatat cgatttagct    300

attctcggcg gaatggaggt ttcggagcag gggggatttgg ccaattggat gatcccgggc   360

aaaatggtaa aagggatggg cggcgccatg gatctcgtca acggggcgaa acgaatcgtt    420

gtcatcatgg agcacgtcaa taagcatggt gaatcaaagg tgaaaaaaac atgctccctt    480

ccgctgacag gccagaaagt cgtacacagg ctgattacgg atttggctgt atttgatttt    540

gtgaacggcc gcatgacact gacggagctt caggatggtg tcacaattga agaggtttat    600

gaaaaaacag aagctgattt cgctgtaagc cagtctgtac tcaattctta a             651
```

<210> SEQ ID NO 16
<211> LENGTH: 1617

-continued

<212> TYPE: DNA
<213> ORGANISM: Clostridium kluyveri

<400> SEQUENCE: 16

```
atgagtaaag ggataaagaa ttcacaattg aaaaaaaaga atgtaaaggc tagtaatgtg      60
gcagaaaaga ttgaagagaa agttgaaaaa acagataagg ttgttgaaaa ggcagctgag     120
gttacagaaa aacgaattag aaacttgaag cttcaggaaa aagttgtaac agcagatgtg     180
gcagctgata tgatagaaaa cggtatgatt gttgcaatta gcggatttac tccttccggg     240
tatcctaaag aagtacctaa agcattgact aaaaaagtta atgccttaga ggaagaattc     300
aaggtaacac tttatacagg ttcatctaca ggagccgata tagacggaga atgggcaaaa     360
gcaggaataa tagaaagaag aattccatat cagacaaatt ctgatatgag gaaaaaaata     420
aatgatggtt ctattaagta tgctgatatg catttaagcc atatggctca atatattaat     480
tattctgtaa ttcctaaagt agatatagct ataatagagg cagtagctat tacagaagaa     540
ggggatatta ttccttcaac aggaattgga aatacagcta cttttgtgga aaatgcagat     600
aaggtaatag tggaaattaa tgaggctcaa ccgcttgaat tggaaggtat ggcagatata     660
tatacattaa aaaaccctcc aagaagagag cccataccta tagttaatgc aggcaatagg     720
atagggacca catatgtgac ctgtggttct gaaaaaatat gcgctatagt gatgacaaat     780
acccaggata aaacaagacc tcttacagaa gtgtctcctg tatctcaggc tatatccgat     840
aatcttatag gatttttaaa taaagaggtt gaagagggaa aattacctaa gaacctgctt     900
cctatacagt caggagttgg aagtgtagca aatgcagttt tggccggact ttgtgaatca     960
aattttaaaa atttgagttg ttatacagaa gttatacagg attctatgct gaagcttata    1020
aaatgtggta aagcagatgt ggtgtcaggc acttccataa gtccttcacc ggagatgttg    1080
cctgagttca taaaggacat aaatttcttt agagaaaaga tagtattaag accacaggaa    1140
ataagtaata atccagagat agcaagaaga ataggagtta tatccataaa cactgctttg    1200
gaagtagata tatatggtaa tgtaaactcc actcatgtta tgggaagcaa aatgatgaat    1260
ggtataggcg gttctggaga ctttgccaga aatgcatatt tgactatatt cactacagag    1320
tctatcgcca aaaaaggaga tatatcatct atagttccta tggtatccca tgtggatcat    1380
acagaacatg atgtaatggt aattgttaca gaacagggag tagcagattt aagaggtctt    1440
tctcctaggg aaaaggccgt ggctataata gaaaattgtg ttcatcctga ttacaaggat    1500
atgcttatgg aatattttga agaggcttgt aagtcatcag gtggaaatac accacataat    1560
cttgaaaaag ctctttcctg gcatacaaaa tttataaaaa ctggtagtat gaaataa       1617
```

<210> SEQ ID NO 17
<211> LENGTH: 1290
<212> TYPE: DNA
<213> ORGANISM: Clostridium kluyveri

<400> SEQUENCE: 17

```
atggagtggg aagagatata taaagagaaa ctggtaactg cagaaaaagc tgtttcaaaa      60
atagaaaacc atagcagggt agtttttgca catgcagtag gagaacccgt agatttagta     120
aatgcactag ttaaaaataa ggataattat ataggactag aaatagttca catggtagct     180
atgggcaaag gtgaatatac aaaagagggt atgcaaagac attttagaca taatgcttta     240
tttgtaggcg gatgtactag agatgcagta aattcaggaa gagcagatta tacaccttgt     300
tttttctatg aagtgccaag tttgtttaaa gaaaaacgtt tgcctgtaga tgtagcactt     360
```

-continued

```
attcaggtaa gtgagccaga taaatatggc tactgcagtt ttggagtttc caatgactat    420

accaagccag cagcagaaag tgctaagctt gtaattgcag aagtgaataa aaacatgcca    480

agaactcttg gagattcttt tatacatgta tcagatattg attatatagt ggaagcttca    540

cacccattgt tagaattgca gcctcctaaa ttgggagatg tagaaaaagc cataggagaa    600

aactgtgcat ctttaattga agatggagct actcttcagc ttggaatagg tgctatacca    660

gatgcggtac ttttattctt aaagaacaaa aagaatttag gaatacattc tgagatgata    720

tcagatggtg tgatggaact ggtgaaggca ggggttatca ataacaagaa aaagaccctc    780

catccaggca aaatagttgt aacattttta atgggaacaa aaaaattata tgattttgta    840

aacaataatc caatggtaga aacttattct gtagattatg taaataatcc actggtaatt    900

atgaaaaatg acaatatggt ttcaataaat tcttgtgttc aagtagactt aatgggacaa    960

gtatgttctg aaagtatagg attgaaacag ataagtggag tgggaggcca ggtagatttt   1020

attagaggag ctaatctatc aaagggtgga aaggctatta tagctatacc ttccacagct   1080

ggaaaaggaa aagtttcaag aataactcca cttctagata ctggtgctgc agttacaact   1140

tctagaaatg aagtagatta tgtagttact gaatatggtg ttgctcatct taagggcaaa   1200

actttaagaa atagggcaag agctctaata aatatcgctc atccaaaatt cagagaatca   1260

ttaatgaatg aatttaaaaa gagattttag                                     1290
```

<210> SEQ ID NO 18
<211> LENGTH: 1314
<212> TYPE: DNA
<213> ORGANISM: Clostridium kluyveri

<400> SEQUENCE: 18

```
atggttttta aaaattggca ggatctttat aaaagtaaaa ttgttagtgc agacgaagct     60

gtatctaaag taagctgtgg agatagcata attttaggca atgcttgtgg agcatctctt    120

acacttttag atgccttggc tgcaaataag gaaaagtata agagtgtaaa gatacacaat    180

cttatactta attataaaaa tgatatatat actgatccgg aatcagaaaa gtatattcat    240

ggaaatactt tctttgtaag tggaggtaca aaggaagcag ttaattgtaa tagaacagat    300

tatactccat gctttttta tgaaatacca aaattattaa aacaaaagta tataaatgca    360

gatgtagctt ttattcaagt aagtaagcct gatagccatg gatactgtag ctttggagta    420

tcaaccgatt attcacaggc aatggtacag tctgcaaagc ttataattgc agaagtaaac    480

gatcagatgc caagagtttt aggagacaat tttatacaca tttctgatat ggattacata    540

gtagaaagtt cacgtccaat tctagaattg actcctccta aaataggaga agtagagaag    600

acaataggaa aatactgtgc atctcttgta gaagatggtt ctacacttca gcttggaata    660

ggagctattc cagatgcagt acttttattc ttgaaggata aaaaggattt gggtatacat    720

tcagaaatga tatccgatgg tgttgttgaa ttagttgaag caggggtaat tacaaataag    780

aaaaagtccc ttcatccagg aaaaataatt attacattct taatgggaac taagaaatta    840

tatgatttca taaatgataa tcctatggta gaaggatacc ctgtagatta tgtaaatgat    900

cctaaggtta ttatgcaaaa ttctaagatg gtatgtataa actcctgtgt agaagtggat    960

ttcacaggac aagtgtgtgc tgaaagtgta ggatttaaac aaataagcgg tgtaggtgga   1020

caagttgatt acatgagagg agctagcatg gctgatggag gaaaatcaat tcttgctata   1080

ccatctactg cagctggcgg caaaatttca agaatagttc ctattttaac tgaaggagcg   1140

gggggttacta cttcaagata tgatgttcaa tatgttgtta cagaatatgg tattgcactt   1200
```

ctcaagggca aatccataag agaaagagct aaggagctta taaaaattgc acatcctaaa 1260
tttagggaag aattaacagc tcaatttgaa aaaagattca gttgtaagct ttaa 1314

<210> SEQ ID NO 19
<211> LENGTH: 963
<212> TYPE: DNA
<213> ORGANISM: Acidaminococcus fermentans

<400> SEQUENCE: 19
ttgagtaaag taatgacgtt aaaagacgca atcgccaagt atgtgcacag tggtgatcac 60
attgctctgg gtggttttac gacggaccgt aaaccctatg cggctgtgtt cgaaatcctg 120
agacagggta tcacggatct gaccggtctg ggcggcgctg ccggcggcga ctgggatatg 180
ctgatcggca acggccgtgt gaaagcctac atcaactgct acaccgccaa ctccggtgtg 240
accaacgttt ccagacggtt cagaaaatgg ttcgaagccg gcaaactgac catggaagac 300
tattcccagg atgttatcta catgatgtgg catgccgccg ctctgggcct gcccttcctg 360
cctgtaaccc tgatgcaggg ctccggcctg accgatgaat ggggcatcag caaggaagtc 420
cgtaaaaccc tggacaaagt tcctgatgac aaattcaaat acatcgacaa ccccttcaaa 480
ccgggtgaaa aagtcgtggc tgttcctgtt ccgcaggttg atgtggccat catccatgcc 540
cagcaggctt ctcccgatgg caccgttcgc atctggggcg gcaaattcca ggatgtggat 600
attgctgaag cagccaaata caccatcgtt acctgcgaag aaatcatttc tgatgaagaa 660
atcagaagag atcccaccaa gaacgatatc cccggcatgt gcgtagatgc tgttgtcctg 720
gctccttacg gtgcacatcc ttctcagtgc tatggcctgt acgactacga caatccgttc 780
ctgaaagtct atgacaaggt ctccaagacc caggaagact tcgatgcctt ctgcaaggaa 840
tgggtgttcg acctgaagga tcatgacgaa tacctgaaca aactgggtgc cactcgtctg 900
atcaacctga aggttgttcc tggtctgggc taccacatcg acatgacgaa ggaggacaaa 960
taa 963

<210> SEQ ID NO 20
<211> LENGTH: 963
<212> TYPE: DNA
<213> ORGANISM: Acidaminococcus fermentans

<400> SEQUENCE: 20
ttgagtaaag taatgacgtt aaaagacgca atcgccaagt atgtgcacag tggtgatcac 60
attgctctgg gtggttttac gacggaccgt aaaccctatg cggctgtgtt cgaaatcctg 120
agacagggta tcacggatct gaccggtctg ggcggcgctg ccggcggcga ctgggatatg 180
ctgatcggca acggccgtgt gaaagcctac atcaactgct acaccgccaa ctccggtgtg 240
accaacgttt ccagacggtt cagaaaatgg ttcgaagccg gcaaactgac catggaagac 300
tattcccagg atgttatcta catgatgtgg catgccgccg ctctgggcct gcccttcctg 360
cctgtaaccc tgatgcaggg ctccggcctg accgatgaat ggggcatcag caaggaagtc 420
cgtaaaaccc tggacaaagt tcctgatgac aaattcaaat acatcgacaa ccccttcaaa 480
ccgggtgaaa aagtcgtggc tgttcctgtt ccgcaggttg atgtggccat catccatgcc 540
cagcaggctt ctcccgatgg caccgttcgc atctggggcg gcaaattcca ggatgtggat 600
attgctgaag cagccaaata caccatcgtt acctgcgaag aaatcatttc tgatgaagaa 660
atcagaagag atcccaccaa gaacgatatc cccggcatgt gcgtagatgc tgttgtcctg 720

-continued gctccttacg gtgcacatcc ttctcagtgc tatggcctgt acgactacga caatccgttc 780
ctgaaagtct atgacaaggt ctccaagacc caggaagact tcgatgcctt ctgcaaggaa 840
tgggtgttcg acctgaagga tcatgacgaa tacctgaaca aactgggtgc cactcgtctg 900
atcaacctga aggttgttcc tggtctgggc taccacatcg acatgacgaa ggaggacaaa 960
taa 963

<210> SEQ ID NO 21
<211> LENGTH: 1251
<212> TYPE: DNA
<213> ORGANISM: Escherichia coli

<400> SEQUENCE: 21
atgtcaactc cacttcaagg aattaaagtt ctcgatttca ccggtgtgca atctggccca 60
tcttgtactc aaatgctggc ctggtttggc gctgacgtta ttaaaattga acgtcccggc 120
gttggtgacg taacgcgtca ccagctgcga gatattcctg atatcgatgc gctttacttc 180
accatgctta acagtaacaa acgttctatt gagttaaata ccaaaacagc ggaaggcaaa 240
gaggtaatgg aaaagctgat ccgcgaagct gatatcttag tcgagaactt tcatccaggg 300
gccattgatc acatgggctt cacctgggag catattcaag aaatcaatcc acgtctgatt 360
tttggttcga tcaaagggtt tgatgagtgt tcgccttatg tgaatgtaaa agcctatgaa 420
aacgttgctc aggcagcggg tggcgcggca tccactacgg gtttttggga tggtccgccg 480
ctggtaagcg ctgcagcgtt gggtgacagc aacaccggaa tgcatttgct gatcggttta 540
cttgctgctt tgctgcatcg cgaaaaaacg gggcgtgggc aacgagtcac catgtcaatg 600
caggatgccg tattgaacct ttgccgcgtg aaattacgtg accagcagcg tctcgataaa 660
ttgggttatc tggaagaata cccgcagtat ccgaatggta catttggtga tgcagttccc 720
cgcggtggta atgcaggtgg tggcggtcag cctggctgga tcctgaaatg taaaggctgg 780
gaaaccgatc ctaacgccta tatttatttc actattcagg agcaaaactg ggaaaacacc 840
tgtaaagcca tcggcaaacc agaatggatt accgatccgg catacagtac agcccatgca 900
cgacagccac atattttcga tatttttgct gaaatcgaaa aatacactgt cactattgat 960
aaacatgaag cggtggccta tttgactcag tttgatattc cttgtgcacc ggttttaagt 1020
atgaaagaaa tttcacttga tccctctttg cgccaaagtg gcagtgttgt tgaagtggaa 1080
caaccgttgc gtggaaaata tctgaccgtt ggttgtccaa tgaaattctc tgcctttacg 1140
ccggatatta aagctgcgcc gctattaggt gaacataccg ctgctgtatt gcaggagctg 1200
ggttatagcg acgatgaaat tgctgcaatg aagcaaaacc acgccatctg a 1251

<210> SEQ ID NO 22
<211> LENGTH: 1278
<212> TYPE: DNA
<213> ORGANISM: Bradyrhizobium sp.

<400> SEQUENCE: 22
atgaccaagg cgctcgaggg cgttcgcatt ctcgacttca cccacgtcca gtccggaccg 60
acctgcaccc agctgctggc ctggttcggc gccgacgtga tcaaggtcga gcggccgggc 120
gtgggtgaca tcacccgcgg ccagctgcag gacattccca acgtggacag cctgtatttc 180
acgatgctga accacaacaa gcggtcgatc acgctcgaca ccaagaaccc caagggcaag 240
gaggttctga ccgagctgat caagaagtgc gacgtgctgg tcgagaattt cggccccggc 300
gtgcttgacc gcatgggctt cccctgggag aagatccagg ccatcaaccc gaagatgatc 360

-continued

```
gtcgcctcga tcaagggttt cggccctggc ccttacgagg actgcaaggt ctacgagaac    420
gtcgcgcagt gcaccggcgg cgccgcctcg accaccggct tccgtgacgg cctgccgctg    480
gtcaccggcg cgcagatcgg cgattccggc accggcctgc acctcgcgct cggcatcgtc    540
accgcgctct atcagcgcac ccataccggc aagggccagc gcgtcacggc tgcgatgcag    600
gacggcgtgc tcaacctctg ccgtgtcaag ctgcgcgacc agcagcgcct ggagcgcggc    660
ccgctcaagg aatacagcca gttcggtgag ggcgttccgt tcggcgacgc cgtgccgcgc    720
gccggcaacg attccggcgg tggccagccg ggccgcatcc tgaagtgcaa gggctgggag    780
accgacccga acgcctacat ctacttcatc acccaggccc cggtctggga gaagatctgc    840
gacgtgatcg gcgagcccac ctggaagacc gatccgaact acgccaagcc ggccgcccgc    900
ctgccgcgcc tgaacgagat cttcggccgc atcgagcagt ggaccatgac caagaccaag    960
ttcgaggcca tggacatcct caacgagttc gacatcccct gcggcccgat cctgtcgatg   1020
aaggagatcg ccgaggacga gtcgctgcgc aagaccggca ccctggtcga ggtcgaccac   1080
ccgacccgcg gcaaatatct ctcggtcggc aacccgatca agctgtcgga cagcccggcc   1140
gaggtgaccc gctcgccttt gctcggcgag cacaccgatg agatcctgcg ccaggtgctt   1200
ggcttcagcg accaccaggt cgccgagatc cacgactccg gcgcgctcga tccaccgcgt   1260
aaggaagctg cggagtaa                                                 1278
```

<210> SEQ ID NO 23
<211> LENGTH: 1326
<212> TYPE: DNA
<213> ORGANISM: Rhodopseudomonas palustris

<400> SEQUENCE: 23

```
atgggagaga tgccgcttcg gcgcgcaaga gacaacagga gcacgaccat gaccaaggcg     60
ctcgacggcg ttcgcgttct cgacttcacc cacgtccaat ccggcccgac ctgcacgcag    120
ctcttggcgt ggttcggtgc cgacgtgatc aaggtggagc gccccggcag cggcgacatc    180
acccgcggtc agctgcagga catcccgaag gtggacagcc tgtatttcac catgctgaac    240
cacaacaagc ggtcgatcac gctcgacacc aagaacccga agggcaagga ggtgctgacc    300
gcgctgatcc gcacctgcga cgtgctggta gagaatttcg gccccggtgt gctcgaccgg    360
atgggcttca cctgggagaa gatccaggag atcaacccgc ggatgatcgt cgcctcgatc    420
aagggcttcg gtcccggccc gtatgaagac tgcaaggtgt acgagaacgt tgcgcagtgc    480
accggcggcg ccgcctcgac caccggattc cgcgaaggcc tgccgctggt caccggcgcg    540
cagatcggcg atagcggcac cggcctgcat ctcgcgctcg gcatcgtcac cgcgctgtat    600
cagcgccacc acaccggccg cggccagcgc gtcaccgcgg cgatgcagga cggcgtgctg    660
aacctctgcc gcgtcaagct gcgcgatcag cagcgcctcg accatggtcc gctgaaggaa    720
tacagccagt tcggcgaagg catcccgttc ggcgatgcgg tgccgcgtgc cggcaacgat    780
tccggtggcg gccagcccgg ccgcatcctg aagtgcaagg gctgggagca ggatccgaac    840
gcctacatct acgtcatcac ccaggcgccg gtgtgggaga agatctgcga cgtgatcggc    900
gagaccggct ggaagacgca ccccgactac gccacgccgc cggcgcggct gtcgcggctc    960
aacgagatct tcgcgcgcat tgagcaatgg accatgacca agaccaagtt cgaggccatg   1020
gagatcctca acgccgacga catcccctgc ggcccgatcc tgtcgatgaa ggaactcgcc   1080
gaagatcagt cgctgcgcgc caccggcacc atcgtcgagg tcgatcaccc gacccgcggc   1140
```

aagtatctgt cggtcggcaa cccgatcaag ctgtcggact ccccgaccga ggtgaagcgc 1200
tcgccgctac tcggtgaaca caccgacgaa atcctgcgcg acgtcctcgg ctacagcgac 1260
gcgcacgtcg cagagatcca cgactccggc gcgaccgctc cgccgcgcaa gcaagcggcg 1320
gagtaa 1326

<210> SEQ ID NO 24
<211> LENGTH: 1251
<212> TYPE: DNA
<213> ORGANISM: Shigella dysenteriae

<400> SEQUENCE: 24
atgtcaactc cacttcaagg aattaaagtt ctcgatttca ccggtgtgca atctggccca 60
tcttgtactc aaatgctggc ctggtttggc gctgacgtca ttaaaattga acgccccggc 120
gttggtgacg taacgcgtca ccagctgcga gatattcctg atatcgatgc gctttacttc 180
accatgctta acagtaacaa acgttctatt gagttaaata ccaaaacagc ggaaggcaaa 240
gaggtaatgg aaaagctgat ccgcgaagct gatatcttag tcgagaactt tcatccaggg 300
gccattgatc acatgggctt cacctgggag catattcaag aaatcaatcc acgtctgatt 360
tttggttcga tcaaagggtt tgacgagtgt tcgccttatg tgaatgtaaa agcctatgaa 420
aacgttgctc aggcagcggg tggcgcggca tccactacgg gtttttggga cggtccgccg 480
ctggtaagcg ctgcagcgtt aggagacagc aacaccggaa tgcatttgct gatcggttta 540
cttgctgctt tgctgcatcg cgaaaaaacg gggcgtgggc aacgagtcac catgtcaatg 600
caggatgccg tattgaacct ttgccgcgtg aaattacgcg accagcagcg tctcgataaa 660
ttgggttatc tggaagaata cccgcagtat ccgaatggta catttggtga tgcagttccc 720
cgcggaggta atgcgggtgg tggcggtcaa cctggatgga tcctgaaatg taaaggctgg 780
gaaacagatc ctaacgccta tatttatttc actattcagg agcaaaactg ggaaaacacc 840
tgtaaagcca tcggcaaacc agattggatt accgatccgg catacagtac agcccatgcc 900
cgacagccac atattttcga tatttttgct gaaatcgaaa aatacactgt cactattgat 960
aaacatgaag cggtggccta tttgactcag tttgatattc cttgtgcacc ggttttaagt 1020
atgaaagaaa tttcacttga tccctcttta cgccaaagtg gcagtgttgt cgaagtggaa 1080
caaccgttgc gtggaaaata tctgacagtt ggttgtccaa tgaaattctc tgcctttacg 1140
ccagatatta aagctgcgcc gctattaggt gaacataccg ctgctgtatt acaggagctg 1200
ggttatagcg acgatgaaat tgctgcaatg aagcaaaacc acgccatctg a 1251

<210> SEQ ID NO 25
<211> LENGTH: 1278
<212> TYPE: DNA
<213> ORGANISM: Rhodopseudomonas palustris

<400> SEQUENCE: 25
atgaccaagg cgctcgacgg cgttcgcatt ctcgatttca cccacgtcca gtccggcccg 60
acctgcaccc agttgctggc gtggttcggc gccgacgtca tcaaggtcga gcgtcccggc 120
accggcgaca tcacccgcgg gcagttgcag gacatcccga aggtggacag cctgtatttc 180
accatgctga accacaacaa gcgctcgatc acgctcgaca ccaagaaccc caagggcaag 240
gaggtgctga ccgcgctgat ccgctcctgc gacgtgctgg tggagaattt cggccccggc 300
gtgctcgatc gcatgggctt cacctgggac aagatccagg agatcaaccc gcggatgatc 360
gtcgcctcga tcaagggttt cggcccgggt ccctatgaag actgcaaggt ctacgagaac 420

```
gtcgcgcaat gcaccggcgg cgccgcctcg accaccggct tccgcgacgg cccgccgctg    480

gtcaccggcg cacagatcgg cgactcgggc accgggctgc atctcgcgct cggcatcgtc    540

accgcgctgt atcagcgcca tcacaccggc cgcggccagc gcgtcaccgc cgcgatgcag    600

gacggcgtgc tcaatttgtc gcgcgtcaag ctgcgcgatc agcagcgcct cgcccacggc    660

ccgctcaagg aatacagcca gttcggcgaa ggcattccgt tcggcgacgc ggtgccgcgc    720

gccggcaatg attccggcgg cggccagccc ggccgcatcc tgaaatgcaa gggctgggag    780

accgatccca acgcctacat ctacttcatc gcgcaggccc cggtgtggga gaagatctgc    840

gacgtgatcg gcgagaccgg ctggaagacc catccggact acgcgacgcc gccggcgcgg    900

ctgaagcacc tcaacgacat cttcgcccgc atcgaacaat ggaccatgac caagaccaag    960

ttcgaggcga tggacatcct caacagggac gacattccct gcgggccgat cctgtcgatg   1020

aaggaactcg ccgaggacgc ctcgctgcgc gccaccggca cgatcgtcga ggtcgatcat   1080

ccgacccgcg gcaaatatct gtcggtcggc aacccgatca aactgtcgga ctcgccgacc   1140

catgtcgagc gctcgccgct tctcggcgag cacaccgacg aaattctgcg cgacgtcctc   1200

ggcttcaacg atcatcaggt cgctgaaatc cacgattccg gcgcactcgc tccgccgcgc   1260

aagcaggccg cagagtaa                                                 1278
```

<210> SEQ ID NO 26
<211> LENGTH: 1290
<212> TYPE: DNA
<213> ORGANISM: Methylobacterium extorquens

<400> SEQUENCE: 26

```
atgagcaagg caccgggcaa ggccctcgag ggcgttcgca tcctcgattt cacccatgtt     60

caatcggggc cgacctgcac gcaattgctc gcgtggttcg gggccgacgt catcaaggtc    120

gagcggccgg gtgcgggcga cgcgacgcgc cagcagcttc aggaccttcc cggcgtggac    180

agcctctatt tcacgatgct gaaccacaac aagcgttcga tcacgctcga cggcaagaac    240

cccaagggca acgcgatcct ctggcggctc attgccgagt gcgacgtgct ggtcgagaac    300

ttcgcccccg gtgcgctcga ccgcatgggg ctgacctggg agaagctgca ggccgccaat    360

ccgggcctga tcctggcctc ggtgaagggc ttcgggcccg gccgctacca ggattgcaag    420

gtctacgaga acgtcgccca atgcgtcggc ggcgcggcct ccaccaccgg ctggcgcgac    480

ggcgtgccga tggtgtcggg ggcgcagatc ggcgattccg gcaccggcct gcatctggcg    540

ctcggcatcg tcacggccct ctaccagcgc acccagacgg ggcagggcca gcgcgtcgat    600

tgtgccatgc aggacggggt gctcaacctc tgccgggtga agctgcggga ccagcagcgc    660

ctcgcccacg gcccgctgat ggaatacagc cagtacggcg agggcgtccc cttcggcgag    720

gcggtgccgc gggccggcaa cgattccggc ggggggcagc ccggccgcat cctcaagtgc    780

aagggctggg agcaggatcc caacgcttac atctacttca tcacgcaggg cgcggtctgg    840

gggccgatct gcgacatcat cggcgagccg gactggaaga ccgatccggc ctacgcgacg    900

ccgaaagccc gcctgccgca tctcaacgag atcttcacgc gcatcgaagc gtggacgatg    960

aagcacgaca agctcgaggc gatggagatc ctcaacgcct acgagatccc gtgcggaccg   1020

atcctgtcga tgcgggagat cgccgaggat ccgatgctgc gggcgaacgg cacggtggtc   1080

gaggtcgagc acccgacccg cggggcctat ctgacggtgg gcaacccgat caagctgtcg   1140

gcgagcccca ccgagatcac ccgcgcgccg ctgctcggcg agcataccga cgagatcctg   1200
```

cgcgaggtgc tgggctgcac cgatacggaa atcagcgaca tcctcggttc gggtgcggtg 1260
ggcggcgtcc accgcatcgc cgcggagtag 1290

<210> SEQ ID NO 27
<211> LENGTH: 1251
<212> TYPE: DNA
<213> ORGANISM: Ralstonia eutropha H16

<400> SEQUENCE: 27
gtgaacctcc cactcaacgg catcaagatc atcgacttca cgcacgtcca ggccggtccc 60
gcctgcacgc agcttctcgc gtggttcggt gcggacgtga tcaaggtcga gcgccccggt 120
tccggcgacg tgacgcgcac ccagctgcgc gacatcccgg atgtcgatgc cctgtacttc 180
accatgctca acagcaacaa gcgcagcctg acgctggata ccaagaagcc ggaaggcaag 240
aagatcctgg agcagctgat ccgcgagtcg gacgtgctgg tcgagaactt cggcccgggc 300
gcgctggacc gcatggggtt ctcgtgggaa cgcatcaacg aactgaaccc gaagatgatc 360
gtggcttcgg tcaagggctt cagcgacggc caccactatg aagacctgaa ggtctacgag 420
aacgtggccc agtgcgccgg cggcgcggcc tcgaccaccg gcttctggga tggcccgccg 480
acggtgtccg ccgcggcgct gggcgattcc aacaccggca tgcacctggc catcggcatc 540
ctcaccgcgc tgatcggccg cgacaagacc ggcaagggcc agaaggtggc tgtgtcgatg 600
caggatgcgg tgctgaacct gtgccgggtc aagctgcgcg accagcagcg cctggaccgc 660
ctgggctacc tggaggagta cccgcagtat ccgcacggca gcttcagcga cgtggtgccg 720
cgcggcggca acgcgggcgg cggcggccag ccgggctggg tgctgaagtg caaggggtgg 780
gaaaccgacc ccaacgccta tatctacttc accatccagg gccatgcctg ggagccgatc 840
tgcaaggcgc tgggcaagcc ggaatggatt tccgatccca actacgccac cgccaaggct 900
cgccagccgc atatcttcga tatcttcaac accatcgagg aatggctggc cgacaagacc 960
aagtacgagg ccgtggacat cctgcgcaag ttcgacatcc cgtgctcgcc ggtgctgtcg 1020
atgaaggaaa tcgccgccga tccgtcgctg cgcgccagcg gcagcatcac cgaggtgccg 1080
cacaaggagc gcggtaccta cctgacggtg ggcagcccga tcaagttctc cgacctcaag 1140
ccggagatca ccgggtcgcc actgctgggc gagcatagcg aagaggtgct ggccggcctg 1200
ggctacggcg cggacgacat caagcgcctg cgcgagtccc aggtgatctg a 1251

<210> SEQ ID NO 28
<211> LENGTH: 1251
<212> TYPE: DNA
<213> ORGANISM: Burkholderia xenovorans

<400> SEQUENCE: 28
atgaccaaac ctctcgaagg catccggatc atcgacttca cccatgttca agccggccct 60
gcatgcaccc agttgctcgc ctggttcggc gcggacgtca tcaaggttga acggccgggt 120
tcgggcgacg tgacgcgcaa ccagttgcgc gatattcccg acgccgacgc gttgtacttc 180
acgatgctca acagcaacaa gaaatcgctg acgttggaca caaaaaaacc cgaaggcaag 240
gaagtactcg aaaagctgat tcgcgaatcc gacgtgctgg tggagaattt cggcccgggc 300
gcgttggacc gcatgggctt ttcgtgggaa cggctgaatg aactcaatcc gaagatgatc 360
gtcgcctcgg tgaaaggctt cagcgacggc caccactacg acgacctgaa ggtctacgaa 420
aacgtggcgc aatgcgcggg cggtgcggcc tccaccaccg gcttctggga cggtccgccc 480
accatcagcg ccgccgcgct cggcgacagc aataccggta tgcatctggc catcggcatt 540

-continued ctgaccgcgc tgctcggtcg cgacaaaacc ggcaaaggcc agaaggtcgc agtgtccatg 600
caggacagcg tgctgaatct gtgccgcgtg aagcttcgtg accagcagcg gctggaacgc 660
gttggctatc tcgaggagta tccgcaatat ccgcacggcg aattcagcga cgtggtaccg 720
cgcggcggca atgcaggcgg cggcggccag ccgggttggg tgctcaaatg caaaggctgg 780
gaaacggatc cgaacgccta catctacttc acgattcagg gccatgcgtg ggagcccatc 840
tgcaaggcgc tcggcaagcc cgagtggatc gacgacccgg cctacaagac tgcggaagcg 900
cgtcaaccgc atatcttcga tatcttccag accatcgaaa cctggctcgc ggacaaaacc 960
aagttcgaag cggtcgacat cttgcgcaag ttcgacattc cgtgcgcacc ggtgctgacc 1020
atgaaggaac tggccaacga tccgtcgttg cgcgcgagcg gcacgatcgt cgaagtaccg 1080
cacaagaaac gcggcacgta tctgactgtc ggcagcccga tcaagttttc ggatctgaag 1140
ccggaagtca ccgcgtcgcc gctgctcggc gaacacaccg acgaggtgct ggcgagcctt 1200
ggctacagcc agcagcaaat cttcaacctg cgcgaagtca aggcagttta a 1251

<210> SEQ ID NO 29
<211> LENGTH: 423
<212> TYPE: DNA
<213> ORGANISM: Azoarcus evansii

<400> SEQUENCE: 29
tcagtccttc ggcggttcca gatagcgccc gaagcgctcg cgccattcgt cgtcgatcaa 60
ggtcgcgcgc ggggcgccgc cgaggtcggc ccacacgacc gtctgcttcg cgcggaagcg 120
cacctgctcg cccatcgacg cggtcgtgac gatgtccatc gagctgccgc cgatgcgcgc 180
gacgtagagc gtgaaggtga gctcatcgcc gtgcatgctc ggtgcgaaaa agtcgacttc 240
gaggtggcgc atcggcacgc cgcggcggat ctccgcgtgc agcttgtaga agtccacgcc 300
gatgccgcgg tcgaaccagt cctcgaccac ctcattgcac agcaccaggc actgcgggta 360
gaagacgatg ccggccgggt cgcagtggtg gaaacggatg gatttcttgc attcgaagat 420
cat 423

<210> SEQ ID NO 30
<211> LENGTH: 432
<212> TYPE: DNA
<213> ORGANISM: Magnetospirillum magnetotacticum

<400> SEQUENCE: 30
tcattgggcc gcaacctcca ccagccgggt gcgataggct tccaggcgtt cgcgcatggg 60
accgggcatg ggaaccgcct tcaccttttc ctgatcggcg acgacacaga cgaaactggt 120
ctcgaaggcc accacgccgt caccccgcgc gccgatggtg cggaaatgaa tggaagagcc 180
ccccaccctg tccaccagga ccgagatatc cacccggtcg ccgggccgaa gcggcgattt 240
gatctccatg ccgatcttga cgaagggcgt gccgaagccg tgttccttgt tgatggtgta 300
ccagtcatag ccgatgacat cggccatgaa gacctccagc gcctccatgg cgtattccag 360
gaagcggggc gtatagacga tgcgcgccgc gtcggaatcg ccgaaatgga cccggcggcg 420
gtgaatgaac ac 432

<210> SEQ ID NO 31
<211> LENGTH: 411
<212> TYPE: DNA
<213> ORGANISM: Jannaschia sp. CCS1

<400> SEQUENCE: 31
atgacccacc tctggcccct gcgcgtctac tatgaagacg tcgatctggc ggggatcgtc 60
tactacgcca actacctgaa atacctggag cgggggcgct ctgaaatggt gcgtgaggcc 120
ggcatttccc agctcgacat gaaagctgcg gggctggtct ttgccgtgcg gcgggtggag 180
gcggaatacc tcaaacccgc caaatacgat gatgagctgg tcgtggagac gcagctggac 240
cgcctgaaag gggccagttt cgacatgccc cagcgggtcc tgcgcggcga tgacgtgctg 300
ctggacgcgc ggatcaaggt tgtgatcctc aacgcggacg gccgggcggc gcgacttccg 360
gcggatattc gcgcaaaagt cacagccgtc gcggcaagtg atggcccgta a 411

<210> SEQ ID NO 32
<211> LENGTH: 432
<212> TYPE: DNA
<213> ORGANISM: Sagittula stellata

<400> SEQUENCE: 32
atgtcgcagg aggaagccgt ggggcagccg ttcgagcatg agatccgggt gacctggggg 60
gactgcgatc ccgcgcggat cgcctatacg gcgcgcatcc cctggttcgc gctggatgcg 120
atcaacgcct ggtgggagga gaagctgggc ggcggctggt tccagatgga gctggaccgc 180
ggtgtcggca cgccgttcgt caacatgacc atcgatttcc gcagtccggt cacgccgcgc 240
caccggctgc tctgcgccgt gcgcccggtg cggctgggcg agacctcggt cagtttcgaa 300
gtgctgggac ggcaggacgg tgtgctgtgt ttcgaggggc ggttcacctg cgtgttcatc 360
gccgtgccgc gttttcgcaa ggcgccgccg ccggaggata tccgggcggt ggtggaggcg 420
catctgaact ag 432

<210> SEQ ID NO 33
<211> LENGTH: 414
<212> TYPE: DNA
<213> ORGANISM: Escherichia coli

<400> SEQUENCE: 33
atgatctgga aacgccattt aacgctcgac gaactgaacg ccaccagcga taacacaatg 60
gtggcgcatc tgggaattgt gtatacccgt ctgggcgatg atgtgctgga agccgaaatg 120
ccggttgata cccgtactca tcagccgttc ggtttactac atggcggcgc gtcggcggcg 180
ctggcggaaa cgctgggatc gatggccgga tttatgatga cccgcgacgg acagtgtgtg 240
gtaggcacag aacttaatgc aacacaccat cgcccggtgt ctgagggaaa ggtacgcggc 300
gtctgccagc cgctgcatct tggtcggcaa aatcagagct gggaaatcgt cgttttcgat 360
gaacaggggc ggcgttgctg cacttgtcgg ctgggtacgg cagttttggg atga 414

<210> SEQ ID NO 34
<211> LENGTH: 1989
<212> TYPE: DNA
<213> ORGANISM: Acetobacter pasteurianus

<400> SEQUENCE: 34
atgtcggaaa acatcactat cctgcctaca cagtatgcag attacccggc tctgatgcca 60
cctgcggaac tggccgccat gcagcgctat gcacgccgag acccggatgg tttttggctg 120
caacaggccc ggcgtgtgca ctggcaccgc aagcctaggc gaggctttac gggcagcttt 180
acgggtgatg tgtccataag ctggtttgaa gatggcctta tcaacgcatc cgtatgctgt 240
attgataagc atctgacaga caaggctgat cagattgccc ttatcagcca ccgtgaaggc 300

```
cgggccgagg cagaaaaaat tacatatgcc atgctgcatg aacgggtttg ccgcctgtct    360
aacgcgctgg tgcatttggg ggtggaggaa gggcaccgcg ttgccatttg cctgcccatg    420
atttcagaag ccgtggtggc catgctggcc tgtgcgcgta ttggcgcggt gcatgtggtg    480
ctgtttggtg gtttttcggc agaaggtatt gcagaacgta ttatagatag cggcgcagtt    540
gcggtaatta ccgccagcga aagcatgcgc ggcaacaaga tcgtgccctt taaagcgatt    600
atggatgaag ccctgtgcaa ggcaggtgca gaaagtggcg tgcgggctgt tctagttgtg    660
cgcacgtctg atgcacctgt tcccatgctg cctggtaggg attacgattt tcatgatttt    720
gtagattcgt ttgaggcaga ttttgtgccc gttgtcatgc gggcagaagc accattattt    780
atgctctaca catctggcag cacaggcaag cccaaagcag ttgtgcatgc cactggtggc    840
tatatggtgt gggcagctta cactatggac atggtgtacc atcatcaacc tggtgatgtg    900
ctgtggtgca cggcagatgt ggcatggata accgggcata catccgttgt gtatggcccg    960
ctggccaatg gcggaaccac catgatttcc gatagcctgc cttcataccc cgctccgggc   1020
agatggttgg atctgataga tgagcataag gtgaccatgc tgtttaccgc ccccacagcc   1080
gtgcgcgcca tgatggccga tggtgatgat gtggtgaacg cccgcaatct ggagtctctg   1140
cgtttgctgg gtgtggcggg ggagcccata agcccggatg cgtggctatg gtatcacgat   1200
gttgtgggta aaaagcgttg ccccgtggtg gatacatggt ggcagacaga aaccgccggc   1260
attgtgctgg ggccagtgcc gggtgtgcaa ccgcttaaac ccggctctgc cagcacgccg   1320
ctgccggggt tggaaatggt catagccgat acgcagggca ggccggtgca ggggcctgca   1380
gaaggtagcc tgtgcattgc gcgttcatgg ccggggcagg cccgcacaat ctggaaagat   1440
catgctcgct tctgccagac atattttggt atggttccgg ggcattattt cacgggtgat   1500
ggcgcacggc gagatgccga tggctattac tggattacgg ggcgcatgga cgatgttatc   1560
aatattgcag ggcaccgttt gggtacagca gaagtggaag atgcgttggc agcagatcat   1620
cgtattgtgg aatctgctgc agtgggcatc ccgcacccgg taaaggggca ggcgctggcg   1680
gtatttgtta tccagcgcca gaacgtggct acggaactga cagaaaaagg cataagccgc   1740
cttatctccg gtatgttggg gcgttatgcc acgccagagg ccgtttatct ggtgccagat   1800
ctgcctcgca cgcgctctgg caagattgta cgccgcctgc tgcgcaaaat tgccagtggg   1860
gaaatggata atctgggaga tctttcatcg ctgaatgatc cttccatcgt gcgtatgctg   1920
tgtgacagag tatggagcca catggctttt gatgaggaat ctgcacctcg cacacaggca   1980
agggcctga                                                          1989
```

<210> SEQ ID NO 35
<211> LENGTH: 1890
<212> TYPE: DNA
<213> ORGANISM: Azotobacter vinelandii

<400> SEQUENCE: 35

```
atgaactatc agcactacca tgaacgctcc atcgccgatc ccgccggttt ctgggccgaa     60
caggcgcagg ccgtgcgctg gttccgccag ccgacggaaa ttctccgcgc cctggcggac    120
ggcacgcacc agtggttcgc cgacggccgg ttgaacagtt gctatctggc cctggatcat    180
cagatcgaac agggccgtgg cgagcagacg gccctgatcc acgactcgcc ggtcaccggc    240
ggcaaggccc gctacagcta ccgcgaactg cgcgacgaag tggcgcgcct ggccggcgcc    300
ctgcgcgagc tgggcgtgga aaagggcgac cgggtcatca tctacatgcc gatggtgccg    360
```

caagcggcca tggccatgct cgcctgcgcg cggatcggcg cggtgcactc ggtggtgttc 420
ggcggcttcg cccctcacga actggcgctg cgcatcgacg acgcccggcc caaactgctg 480
ctcaccgcgt cctgcggcct ggagttcgac cgggtcatcg aatacaaacc gctggtcgac 540
aaggccctgg aactggccag ccaccagccc gggcacgtac tggtgctgca acggccacaa 600
gcgagcgccg cgctgctccc agggcgcgac ctggactggc aggccagggt cccgctggcc 660
gcgccggtgg agcccgtgcc cctggacagc ggcgatccgc tgtacatcat gtacacctcc 720
ggcaccaccg gaaaacccaa gggcgtcgtg cgcgacaacg gcggcaacgc ggtggccctg 780
agcttcgcca tgcgccatgt ctacgccatg cgggccggcg acgtctggtg gggcatctcc 840
gacgtcggct gggtggtcgg ccattcgctg atcgtctacg gcccgctgat gaacggatgc 900
accagcatcc tctacgaagg caagccggtc cgcacgcccg acgccggcgc ctactggcgg 960
gtgatcgagg aatacggcgt caacggcctg ttctgcgcgc cgacggcgat ccgcgccatg 1020
cgcaaggaag atccttcggg cgaactgagc gggcgccacg acctgggctc gctgcggcac 1080
ctgttcctgg ccggcgagaa gctcgattcg agcacccacc ggtggctgga ggaactgacc 1140
gggaagccgg tgcacgacca ctggtggcag accgagaccg gctggccggt caccgctccc 1200
tgcgccgggc tggagggcca caccgcacgc cacggttcga gcaaccgccc ggtgcccggc 1260
tatcgcgtcc aggtgatgga cgaacagggt cacctgctcg gagcgaaccg gcagggctcg 1320
atcgtcatcg ccctgcccct gccgccgggc tgcgcgcaga ccctgtggaa cgaccacgag 1380
cgctatctgc gctcttatct gagctcctat cccggctact accacaccgg cgacggcggc 1440
tacctggacg acgagggctt cgtctacatc atgggccgca ccgacgacgt gataaacgtg 1500
gccggccacc gcctctccac cggagaaatg gaagacctgg tggcccggca tccggcggtg 1560
gccgaatgcg cggtgatcgg catccccgac gcgatcaagg gacaggtgcc gctgggcctg 1620
atcgtcctca aggacggcag ccgaatccgc gaggagcaac tgcagcggga gttgaccgcc 1680
tcgatccgcg agcagatcgg cgcgctggcc tgcttccagc ggatagcgac ggtcaagcgc 1740
ctgccgaaga cccgttcggg caaaatcctc cgggcggtgc tgcgcaagat cgccaacggc 1800
gaggaggtgg ccacgcccat gaccatcgac gatccggcga tactcgggga aatcggcgcc 1860
gccctggcgt tgtacacgcg cgccagttga 1890

<210> SEQ ID NO 36
<211> LENGTH: 1959
<212> TYPE: DNA
<213> ORGANISM: Dehalococcoides sp.

<400> SEQUENCE: 36
atgagtaccg aagaaaagaa gtttgacacg caaaacctgc ctaccaagac ttatttctgg 60
ccgctgaaaa gataccagga cctttataac agctcactgg ctgacccgga ggctttctgg 120
gccaaacact cagacgtgct ttcatgggaa aagccttggg aaaaagtact ggactggaat 180
ccgccttatg cccgctggtt tgtaggcggc aagctgaata tgtcttacca atgcgtagac 240
cgccatgcca aaagctggcg taagagcaag gtagctatct attgggaagg cgaaaacggg 300
gatacccaga ccataagcta ttcagacctt tacgaaaatg taaaccgtta tgcatccgtc 360
ctgaaaaagc tgggcatatg caagggtgac agggtaactg tctacctgcc catgatacct 420
gaaatggtct atattctatt agcctgcaac cgggttggag ccgtccataa cgtaatattc 480
tcaggtttct cttcccagtc tatcgcagac agggtaaatg actccggttc aaaaatggtt 540
gttaccgcca gcggcggaca ccgccgcggt aagatactgc ctcttaaaga aatcgtagat 600
gaggctgtaa aatccacccc gactatagaa catgtactgg ttattaaata taccggccac 660
gaagtagcca tggaccccac cagagacgta tgggcacatg atctgctgaa agatgcagat 720
aaatacgtag cccctgaagc tatggaatcc accgacccgc tttttatcct gtacacctca 780
ggcactaccg gtaaaccgaa gggtattctg catggtaccg gcggctacgg cgtctgggcg 840
tgcaataccc ttaagtgggc tttcaaaccc acggacgaat cagtcttctg gtgcacggca 900
gacgtaggct ggattaccgg gcacacatat gttgtatatg ccccgctggc gctgggactt 960
acccaggtta tttacgaggg agctccggat tatccttcag tagaccgctg gtgggagatt 1020
attgataaat acggggtaag catattctat acctcgccta ccgccatacg catgtttatg 1080
cgccacggcg aggagttgcc tgccagacac gaccttggca ctctggaaat gctgggaagc 1140
gtgggcgaac ccattaaccc tgaagcctgg gaatggtatt acaagaatat aggccatgag 1200
aactgcccca tttccgatac ttggtggcag accgaaacag gcggttttat gattaccccc 1260
tgccccggca tacaatcctt cccgctcaaa ccgggctcag ccactttgcc tctaccggga 1320
gttgacccgg tagtggtaga tgctgaaggc aaggaactgc cggctaatga aaccgggttt 1380
attgccatcc gcaaaccttg gccgggcata atgctgggta tatataacgg tgatgaactt 1440
tataaaaaga cctactggag ccgtttcccc ggctggtatt gtccgggaga cttttcaatg 1500
aaagattctg acggatatct gtggctgctg ggacgggctg acgaagttat caaggtagcc 1560
ggtcaccgca taagcaccgc cgaattggag catgctctgg taggccatag ttcagttgcc 1620
gaagcggcag tagcctcccg ccctgacgaa gtaaagggtg aagctattgt ggttttcgtc 1680
accctgaaaa aaggtgtaga agcctctgcg gaagtaaaga gagagcttac ccatcacctc 1740
cgctctgcta tcggcactat agccaccccg gaagagatca ttttcgtgga gaaactgccc 1800
aaaacccgtt cgggcaagat tatgcgccgc ctgctgaagg ccgttgccaa cgaagtaccc 1860
attggtgata ccactacact tgatgatgag acttcggtaa atgaggccag agcggctttt 1920
gatgaactgc tggcagcacg caaacaccac aaacactaa 1959

<210> SEQ ID NO 37
<211> LENGTH: 810
<212> TYPE: DNA
<213> ORGANISM: Escherichia coli

<400> SEQUENCE: 37
atgacgaagc atactcttga gcaactggcg gcggatttac gccgcgccgc agagcagggc 60
gaagcgattg caccgctgcg cgatctgatt ggtatcgata acgctgaagc ggcttacgcc 120
attcagcaca taaatgtgca acatgacgtt gcgcaggggc gtcgcgtggt agggcgtaaa 180
gtgggcctga cacatccgaa agtgcaacaa caactgggcg ttgatcaacc ggattttggg 240
acgttatttg ccgacatgtg ttatggcgat aacgaaatca ttcctttttc ccgtgttctg 300
caaccccgca ttgaagcgga gatcgcactg gtgttgaacc gcgatttgcc cgcaaccgat 360
atcaccttcg acgaattgta taacgccatt gaatgggtac ttccggcgct ggaagtggtg 420
gggagccgca ttcgcgactg gtcgattcag tttgtcgata ccgtggcaga taacgcctcc 480
tgtggggtgt atgtcatcgg cggtccggcg caacgtccgg cggggttaga cctgaaaaac 540
tgcgccatga agatgacgcg taataacgaa gaggtttcta gcgggcgcgg cagcgaatgc 600
ctgggacatc cgcttaatgc ggccgtctgg ctggcacgca aaatggccag tctgggtgaa 660
ccgctgcgca ccggagatat cattcttacc ggggcattag gtccgatggt ggcggtgaat 720

-continued gcgggcgatc gttttgaagc ccatattgaa ggcataggtt cagttgctgc gacattttca 780
agcgcagccc caaaaggaag tctgtcatga 810

<210> SEQ ID NO 38
<211> LENGTH: 789
<212> TYPE: DNA
<213> ORGANISM: Pseudomonas putida

<400> SEQUENCE: 38
atgaatgaag ccaacgtgat tgcgaacctg ttatgggatg cgcagcggca aaagctgccc 60
tgtgcaccgg tgcgggaata tttcgagggg aagagcgagg ttgaccaggc gctattggcc 120
tatgccgtac agcaggtgaa tgttcagcgc caggtggagg gcggccgacg tatcgtcggt 180
cgcaagatcg gccttacctc tccggcagtg cagaagcaat tgggtgtaga tcggccggac 240
ttcggcacgt tgctggacga catggcgatc gtcgatggcg agccgatcaa cactgcgcgt 300
cttctgcagc ccaaggtcga agctgagatc gccctggtac tcgagcgtga cctcgatcgg 360
gagcgtcata cagtcgccga cctgatcgac gcgacagcgt atgcacttgc tgcaatcgag 420
gtggtggata gccgtatcac cggttggaac atccgctttg ttgacaccgt ggcagacaac 480
gcctcatcgg gcttgttcgt actcggtact cagcctgttg gcctgtcgaa gcttgatctg 540
gccggtatgt cgatgcgcat ggcgcgtggc gaagagcttg tatcgcaagg ggctggagct 600
gcctgccttg gcaacccgtt gaacgcagcg cgttggcttg ctgacacgtt ggtccaagtg 660
ggcacgccat tgcgtgccgg cgatgtggtt ctgaccggcg ctctggggcc aatggtcgcg 720
gtcgagtccg gtcacaccta tacggcatgg atcgatggct tcgccccggt acgagcaatt 780
ttctcctga 789

<210> SEQ ID NO 39
<211> LENGTH: 807
<212> TYPE: DNA
<213> ORGANISM: Pseudomonas putida

<400> SEQUENCE: 39
atgagcgaac tagataccgc gcggacaggt gccgtgcgta aagctgccga cctgctgtac 60
gaagccaccc ggtccggtgt ggccgtggtg ccggtgcgca atctgatcgg cgagacggat 120
ttggaggcag cctatgcagt acaggaggtt aatacacaga gagcattggt tgccgggcgg 180
cgcctggttg gacgcaagat tgggctgacc tctgtcgctg tacagaagca gctcggagtg 240
gaacagcccg actatggcat gttgttcgca gacatggcgc gtaccgaggg ggaggaaatc 300
gcccttgatg acgtgctcca acctaaagtc gaagccgaga tcgcctttgt cctgggacgt 360
gacctcgatg gcgatcaatt gacggtggcc gacctctttc gcgccatcga gttcgccgtt 420
ccggcgatcg agatcgtggg ttcgcggata accaattggg atatccgtat cacggacacc 480
attgctgaca atgcttcgtc tggcctgtat gtgctgggct ccacgccgaa gcgcttgtgc 540
gattttgact cgcgccaggc aggcatggtg atggagcggc aaggcatacc ggtgtcttcc 600
ggggtagggg ccgcctgcct tggagcgcct ctcaacgcag tcctttggtt ggccagggtc 660
atggctcgag cgggccgtcc gttgcgcact ggcgacacgg tgctttccgg tgcgctgggc 720
cccatggtgc cagtggcagg aggagatgta ttcgatgtgc ggatagccgg gcttggatcg 780
gtgaccgccg cttttgcaaa ggcataa 807

<210> SEQ ID NO 40
<211> LENGTH: 804

<212> TYPE: DNA
<213> ORGANISM: Klebsiella pneumoniae

<400> SEQUENCE: 40
atgctcgata aacagacccg taccctgatt gcccagcggc tgaaccaggc cgaaaagcag 60
cgtgaacaga tccgcgcgat ctcgctggat tatccgtcga tcaccattga ggacgcctac 120
gccgtccagc gcgagtgggt cgagatgaag atcgccgaag gccgcgtgct caaaggccac 180
aagatcggcc tgacctctaa agcgatgcag gccagttcgc agatcagcga gccggactac 240
ggcgcgctgc tcgacgatat gttcttccac gacggcagcg atattcccac cgaccgcttt 300
atcgttccgc gtatcgaagt cgagctggcc ttcgtgctgg ccaaaccgct gcgcggcccg 360
aactgtacgc tgtttgatgt ctacaacgcc accgactacg ttatcccggc gctggagctt 420
atcgacgcgc gctgccacaa catcgacccg gaaacccagc gtccgcgcaa agtgttcgac 480
accatctccg acaacgccgc caacgccggg gtgatcctcg gcggccggcc gattaaaccg 540
gacgagctcg acctgcgctg gatctccgcc ctgctgtatc gcaacggcgt aattgaagag 600
accggcgtcg ccgcgggcgt actcaatcat ccggccaacg gcgtggcctg gctggccaac 660
aagctggcgc cgtacgatgt ccagctcgaa gccgggcaga ttatcctcgg cggctccttc 720
acccgcccgg tcccggcgcg caagggcgat accttccacg tcgactacgg caacatgggc 780
gtcatcagct gccggtttgt ctag 804

<210> SEQ ID NO 41
<211> LENGTH: 804
<212> TYPE: DNA
<213> ORGANISM: Escherichia coli

<400> SEQUENCE: 41
atgttcgaca aacacaccca caccctgatc gcccagcgtc tggatcaggc agaaaaacag 60
cgcgaacaga tccgcgcgat ctcgctggat tacccggaga tcaccatcga agacgcttac 120
gcggtgcagc gtgaatgggt tcgactgaaa atcgccgaag gtcgcacgct gaaaggccac 180
aaaatcggcc tgacttcgaa agcgatgcag gccagctcgc agatcagcga accggattac 240
ggtgcactgc tggacgacat gttcttccac gatggcagcg atatcccgac cgatcgcttt 300
atcgtgccgc gcattgaagt ggagctggct tttgtgctgg caaaaccgct gcgtggacca 360
aactgcacgc tgttcgacgt ttacaacgcc acggactatg tgatcccggc gctggagctg 420
atcgacgctc gctgccacaa catcgatccg gaaacccagc gcccgcgtaa agtgttcgac 480
accatttctg ataacgccgc caatgccggg gtgatcctcg gtggtcgtcc cattaagccc 540
gatgagttgg atctacgttg gatctccgcc ctgatgtatc gcaatggcgt gattgaagaa 600
accggcgtcg ccgctggcgt gctgaatcat ccggcaaacg gcgtggcctg gctggcgaac 660
aaactcgccc cctatgacgt acaactggaa gccgggcaaa tcattctcgg cggttcgttc 720
acccgcccgg ttccggcgcg taagggcgac accttccacg tcgattacgg caacatgggc 780
tccattagct gccgctttgt ttaa 804

<210> SEQ ID NO 42
<211> LENGTH: 840
<212> TYPE: DNA
<213> ORGANISM: Comamonas testosteroni

<400> SEQUENCE: 42
atgaaccgaa cacaagccaa agtagtcgaa ggcaaatttc ccacacagaa caccatggac 60

-continued

```
aactccaaga tccagcacta cggcgacgag ctctaccagt cgctgctcga ccgccaaccc    120

gtcgctccgc tgaccgaccg cgaagcggac atcaccatcg aggacgccta ccagatccag    180

ctgcgcatga tccagcgccg gctggacgcg ggcgagcgcg tggtgggcaa gaaaataggc    240

gtgacgagca aggtcgtgat ggacatgctc aaggtcaacc agcccgactt cggccacctg    300

ctctcgggca tggtctacaa cgaaggccag cccatcccgg tgagcagcat gatcgcgccc    360

aaggccgagg cagaggtcgc cttcatcctg gcgcgcgacc tcgaaggccc cggcgtcacc    420

gcggccgacg tgctgcgcgc caccgactgc gtgatgccgt gcttcgagat cgtcgactcg    480

cgcatcaagg actggaagat caagatccag gacaccgtgg ccgacaacgc ctcctgcggc    540

gtgctcacgc tcggcggcct gcgcaagagc ccgcgcgacc tcgacctcgc gctggccggc    600

atggtgctgg aaaagaacgg cgaaatcatc agcacgtcct gcggcgcatc ggtgcagggc    660

tcgccggtca acgcggtggc ctggctggcc aacacgctcg gccgtctggg catcggcctc    720

aaggccggcg acatcatcct ctctggctcg cagtcgccgc tggtgccggt ggtcgcgggc    780

gacagcctgt attgcagcgt cggcggcctg ggcggcacgt cggtgcgttt cgtcgcctga    840
```

<210> SEQ ID NO 43
<211> LENGTH: 507
<212> TYPE: DNA
<213> ORGANISM: Methanocaldococcus jannaschii

<400> SEQUENCE: 43

```
atgagaagta taataaaggg aagagtttgg aagtttggaa ataacgtaga tacagatgct     60

atattaccag caaggtattt agtttataca aaaccagagg aattagctca gtttgttatg    120

actggggcag acccagattt tccaaagaag gttaagccag gagatataat agttggagga    180

aagaactttg gatgtggttc aagtagagag catgccccat taggattaaa aggagctgga    240

atcagctgtg ttattgctga gagcttcgca agaatatttt atagaaatgc cataaatgtt    300

ggattaccat taattgaatg taagggcatt tcagagaaag tcaatgaagg ggatgagtta    360

gaggttaatt tagagactgg agagattaaa aacttaacca ctggagaggt tttaaaaggt    420

caaaaattac cagaattcat gatggaaatt ttagaggctg gaggattaat gccatactta    480

aagaaaaaga tggctgaaag ccaataa                                        507
```

<210> SEQ ID NO 44
<211> LENGTH: 1263
<212> TYPE: DNA
<213> ORGANISM: Eubacterium limosum

<400> SEQUENCE: 44

```
ttgggtatga caatgactca gaaaatattg gcggcacatg ctggtctgga atccgtaaaa     60

ccgggtgatt tgatcatggc agacctggat ctggtgttgg ggaatgatat tacctcaccg    120

gtagccatca atgtttttaa aaatattaat aaggaaaccg tttttgacaa agacaaggtt    180

gcgctggtcc cagaccattt tgcgccgaac aaggatatta aggctgcgga gcagtgcaaa    240

caggtgcgct gttttgcctg tgagcaggat gtcaccaact attttgaaat cggcgaaatg    300

ggtgtagagc atgctctgct gccggaaaag ggactggtcg ttgccggcga tgtcgtgatt    360

ggggcagatt cgcacacctg tacctatggt gcgcttgggg ctttctcaac cggtgtgggt    420

tctaccgaca tggccgttgg tatggcaacc ggtaaagcct ggtttaaggt accgtctgcc    480

attaaattca atctgactgg cgctttcaaa gaaggtgttt caggaaaaga cctgattctt    540

cacattatcg gaatgattgg tgtggatggt gcgctttata aatcaatgga atttgccgga    600
```

gagggtgtgt caagcctgac gatggatgat cgcttcacca ttgcgaatat ggccattgaa 660
gctggcggta aaaatggtat cttccctgtc gacgataaga ccatcgaata tatgaaggag 720
cattctacca aggaatacaa ggcctttgaa gcagacgcag acgccgagta tgacgctgtg 780
tacgatatta atctggcaga tatcaagtct acggtagcat tcccgcactt gcctgaaaac 840
actaaaaccg ttgatgaaat tactgaaccg gttaagattg accaggttgt tatcggctca 900
tgcaccaatg gacgtttctc agactttaaa aaggccgcag atctgatgcg cggtaagcat 960
gttgccaaag gaatccgtgt tttgattatc ccagcaactc agcagattta cctggattgt 1020
atggaagcgg gatatttaaa agactttatt gaagcgggcg caacggtgag cacaccgacc 1080
tgcgggccat gcctgggcgg acatatgggg attctggcag cgggagaacg ctgcgtttcc 1140
acaacaaacc gtaactttgt cggacgcatg ggccatgtgg actcggaagt ctatctggcg 1200
agccccgagg ttgcggcggc atctgctatc ctgggccgta ttgccggacc agaagaatta 1260
taa 1263

<210> SEQ ID NO 45
<211> LENGTH: 492
<212> TYPE: DNA
<213> ORGANISM: Eubacterium limosum

<400> SEQUENCE: 45
atgaaagcaa aaggaaaagt atttagatat ggcaacaatg ttgatacaga cgttattatt 60
cccgcaagat acctgaacac cagcgatcct ctggaattag cggagcattg tatggaggat 120
attgacaagg attttataaa acgcgtggag gacggcgata tcatcgtcgc tgatgataat 180
tttggctgcg gctcttcaag agagcatgcg cccattgcca tcaaagcctc aggtgtctcc 240
tgtgtaatcg ccaatagctt tgcgcgtatt ttttatcgca attccatcaa tatcgggctg 300
ccgattctgg aatgtccgga agcggtggca gcgattgaag caggcgacga agtagaagtg 360
gattttgact ctggcgttat cactgacgtg accaagggac agagcttcca gggacaggca 420
ttccctgaat ttatgcagaa gctgatcgca gcaggcggcc tggtaaatta cgtcaacgag 480
aatctcattt ag 492

<210> SEQ ID NO 46
<211> LENGTH: 1770
<212> TYPE: DNA
<213> ORGANISM: Macrococcus caseolyticus

<400> SEQUENCE: 46
atgtactata gtaatggaaa ctatgaagca tttgcaagac cgaagaagcc ggaaggggta 60
gataataagt ctgcatattt agttggttct ggtttagcgt cattagcagc ggcaagtttt 120
ttaatacgag atggtcaaat gaaaggtgaa aatattcata tattagaaga actcgatctc 180
cctggaggaa gcttggatgg aatattgaat cctgaacgtg gctatataat gcgtggcggt 240
cgtgagatgg agaatcattt tgaatgttta tgggatttat ttcgttcagt accatcattg 300
gaagtcgaag atgcttctgt tctggatgaa ttttactggt taaataaaga agatccaaac 360
tattcgaagt gccgcgtaat agaaaatcgt ggacaacgcc tagaatcaga tggaaaaatg 420
actctaacaa aaaaagcaaa taaagaaatt atccagctgt gcttaatgaa agaagaacag 480
ctgaatgatg tgaagatctc tgatgtcttc agtaaagact tcttagactc aaacttctgg 540
atctactgga aaacgatgtt tgcatttgaa ccttggcatt ctgctatgga gatgcgtcga 600

```
tatttaatgc gtttcatcca tcatattggt ggacttgcag acttttcagc tctaaaattt    660

acgaagttca atcagttcga atcacttgtt atgcctctga ttgagcatct taaagcgaag    720

aacgttacat ttgaatatgg tgtaactgtt aagaatatac aagttgaatg ttcaaaagag    780

tcaaaagttg caaaggcaat agacatcgtg cgcagaggta acgaggaatc aattccttta    840

actgaaaatg atttagtatt tgtaacaaat ggcagtatca ctgaaagtac tacttatgga    900

gataatgaca cacctgcacc gcctacatca aaacctggtg gcgcatggca actatgggaa    960

aacttaagta cgcaatgtga ggagtttggt aatccagcta aattctataa agatttacca   1020

gaaaaaagct ggttcgtgtc tgctacagca acaacaaata acaaagaagt tatagattat   1080

attcaaaaaa tttgtaaacg cgatccatta tcaggtcgta cagtaactgg cggtatcgtt   1140

actgtagatg attcaaattg gcagttaagc tttacgctaa atcgacaaca gcagtttaaa   1200

aatcaacctg atgatcaagt gagtgtatgg atttacgcac tttattcaga tgaacgtgga   1260

gaacgtacaa ataaaacaat tgttgagtgt tctggtaaag aaatttgtga agaatggctt   1320

tatcatatgg gtgttcctga agagaagatt tcagcactag cagcagaatg taatacaatt   1380

ccaagctata tgccgtacat taccgcttac tttatgccgc gtaaagaagg agatcgtcct   1440

ttagtagtac cacatggttc aaagaatatt gcatttatag gtaactttgc agaaacagaa   1500

agagataccg tatttacaac agaatattca gtaagaactg ctatggaagc ggtgtataaa   1560

cttctagaag tagaccgtgg agtgcctgaa gtattcgctt cagtatacga tgtgagaatt   1620

ttattacatg cgttatctgt actgaatgat ggcaagaaac tagatgaaat tgatatgcca   1680

ttctatgaaa gattggtaga aaaacgcttg ttgaagaaag catctggtac gttcattgaa   1740

gaactgttag aagaagcaaa tttgatataa                                     1770
```

```
<210> SEQ ID NO 47
<211> LENGTH: 831
<212> TYPE: DNA
<213> ORGANISM: Pseudomonas putida

<400> SEQUENCE: 47

atgagcaaat acgaaggccg ctggaccacc gtgaaggtcg aactggaagc gggcatcgcc     60

tgggtgaccc tcaatcgccc ggaaaaacgc aatgccatga gccccaccct gaaccgggaa    120

atggtcgacg tgctggaaac ccttgagcag gacgctgacg ctggcgtgct ggtattgacc    180

ggtgccggcg agtcctggac cgccggcatg gacctgaagg agtacttccg cgaggtggac    240

gccggcccgg aaatcctcca ggaaaagatt cgtcgcgaag cctcgcaatg gcaatggaag    300

ttgctgcgtc tgtatgccaa accgaccatc gccatggtca acggctggtg cttcggcggc    360

ggcttcagcc cactggtggc atgcgacctg gcgatctgcg ccaacgaagc gaccttcggc    420

ctgtcggaaa tcaactgggg catcccgcct ggtaacctgg tcagcaaggc catggccgat    480

accgttggcc atcgtcagtc gctgtactac atcatgaccg gcaagacctt cgatggtcgc    540

aaggctgccg agatgggcct ggtgaacgac agtgtgccgc tggccgagct gcgtgaaacc    600

acccgcgagt tggcgctgaa cctgctggaa aagaacccgg tggtgctgcg tgccgcgaag    660

aatggcttca agcgttgccg cgagctgacc tgggaacaga acgaggacta cctctacgcc    720

aagctcgacc agtcgcgcct gctggacact accggcggcc gcgagcaggg catgaagcag    780

ttcctcgacg acaagagcat caagccaggc ctgcaggcct acaagcgctg a             831

<210> SEQ ID NO 48
<211> LENGTH: 786
```

<212> TYPE: DNA
<213> ORGANISM: Clostridium acetobutylicum

<400> SEQUENCE: 48
atggaactaa acaatgtcat ccttgaaaag gaaggtaaag ttgctgtagt taccattaac 60
agacctaaag cattaaatgc gttaaatagt gatacactaa aagaaatgga ttatgttata 120
ggtgaaattg aaaatgatag cgaagtactt gcagtaattt taactggagc aggagaaaaa 180
tcatttgtag caggagcaga tatttctgag atgaaggaaa tgaataccat tgaaggtaga 240
aaattcggga tacttggaaa taaagtgttt agaagattag aacttcttga aaagcctgta 300
atagcagctg ttaatggttt tgctttagga ggcggatgcg aaatagctat gtcttgtgat 360
ataagaatag cttcaagcaa cgcaagattt ggtcaaccag aagtaggtct cggaataaca 420
cctggttttg gtggtacaca aagactttca agattagttg gaatgggcat ggcaaagcag 480
cttatattta ctgcacaaaa tataaaggca gatgaagcat taagaatcgg acttgtaaat 540
aaggtagtag aacctagtga attaatgaat acagcaaaag aaattgcaaa caaaattgtg 600
agcaatgctc cagtagctgt taagttaagc aaacaggcta ttaatagagg aatgcagtgt 660
gatattgata ctgctttagc atttgaatca gaagcatttg gagaatgctt ttcaacagag 720
gatcaaaagg atgcaatgac agctttcata gagaaaagaa aaattgaagg cttcaaaaat 780
agatag 786

<210> SEQ ID NO 49
<211> LENGTH: 792
<212> TYPE: DNA
<213> ORGANISM: Pseudomonas putida

<400> SEQUENCE: 49
atgactttcc agcacatcct gttttccatc gaggacggcg ttgccttcct ttcattgaac 60
cgccccgagc agctgaacag cttcaatacg gccatgcacc tggaggtgcg cgaagcgctc 120
agacaagtgc gccagagcag tgacgcgcgg gtgctgctgc tgacggctga aggccgcggc 180
ttctgcgccg gccaggacct gtccgaccgc aacgttgccc caggcgccga gatgccagac 240
ctgggccagt cgatcgacaa gttctacaac ccgctggtgc gcaccctgcg cgacctgcct 300
ttgccggtga tatgtgcggt caacggcgtg gcggccggtg ccggtgccaa cattcccttg 360
gcctgcgacc tggtgctggc cgcccgctcg gccagtttca tccaggcctt ctgcaagatc 420
ggcctggtgc cggactccgg cggtacttgg ctgctgccgc gcttggtcgg catggcccgg 480
gccaaggcgc tggccatgct gggcgagcgc cttggcgccg aacaggccga gcaatggggg 540
ctgatctacc gcgtggtgga tgatgcagcg ctgcgtgatg aagccctcac cctcgcccgc 600
cacctcgccg cccagcccac ctacggcctg acactgatca agcgcagcct caatgccagt 660
ttcgacaatg gttttgaggc gcagctggag ctggagcgcg acctgcagcg cctggcaggg 720
cgcagcgagg actaccgcga aggcgtgaac gccttcatga acaaacgcac gccagccttc 780
aaggggcgct ga 792

<210> SEQ ID NO 50
<211> LENGTH: 1164
<212> TYPE: DNA
<213> ORGANISM: Escherechia coli

<400> SEQUENCE: 50
atggaacagg ttgtcattgt cgatgcaatt cgcaccccga tgggccgttc gaagggcggt 60

-continued

```
gcttttcgta acgtgcgtgc agaagatctc tccgctcatt taatgcgtag cctgctggcg    120

cgtaacccgg cgctggaagc ggcggccctc gacgatattt actggggttg tgtgcagcag    180

acgctggagc agggttttaa tatcgcccgt aacgcggcgc tgctggcaga agtaccacac    240

tctgtcccgg cggttaccgt taatcgcttg tgtggttcat ccatgcaggc actgcatgac    300

gcagcacgaa tgatcatgac tggcgatgcg caggcatgtc tggttggcgg cgtggagcat    360

atgggccatg tgccgatgag tcacggcgtc gattttcacc ccggcctgag ccgcaatgtc    420

gccaaagcgg cgggcatgat gggcttaacg gcagaaatgc tggcgcgtat gcacggtatc    480

agccgtgaaa tgcaggatgc ctttgccgcg cggtcacacg cccgcgcctg ggccgccacg    540

cagtcggccg catttaaaaa tgaaatcatc ccgaccggtg gtcacgatgc cgacggcgtc    600

ctgaagcagt ttaattacga cgaagtgatt cgcccggaaa ccaccgtgga agccctcgcc    660

acgctgcgtc cggcgtttga tccagtaaac ggtatggtaa cggcgggcac atcttctgca    720

ctttccgatg gcgcagctgc catgctggtg atgagtgaaa gccgcgccca tgaattaggt    780

cttaagccgc gcgctcgtgt gcgttcgatg gcggtcgttg gttgtgaccc atcgattatg    840

ggttacggcc cggttccggc ctcgaaactg gcgctgaaaa aagcggggct ttctgccagc    900

gatatcggcg tgtttgaaat gaacgaagcc tttgccgcgc agatcctgcc atgtattaaa    960

gatctgggac taattgagca gattgacgag aagatcaacc tcaacggtgg cgcgatcgcg   1020

ctgggtcatc cgctgggttg ttccggtgcg cgtatcagca ccacgctgct gaatctgatg   1080

gaacgcaaag acgttcagtt tggtctggcg acgatgtgta tcggtctggg tcagggtatt   1140

gcgacggtgt ttgagcgggt ttaa                                          1164
```

<210> SEQ ID NO 51
<211> LENGTH: 2190
<212> TYPE: DNA
<213> ORGANISM: Escherechia coli

<400> SEQUENCE: 51

```
atgctttaca aaggcgacac cctgtacctt gactggctgg aagatggcat tgccgaactg     60

gtatttgatg ccccaggttc agttaataaa ctcgacactg cgaccgtcgc cagcctcggc    120

gaggccatcg gcgtgctgga acagcaatca gatctaaaag ggctgctgct gcgttcgaac    180

aaagcagcct ttatcgtcgg tgctgatatc accgaatttt tgtccctgtt cctcgttcct    240

gaagaacagt taagtcagtg gctgcacttt gccaatagcg tgtttaatcg cctggaagat    300

ctgccggtgc cgaccattgc tgccgtcaat ggctatgcgc tgggcggtgg ctgcgaatgc    360

gtgctggcga ccgattatcg tctggcgacg ccggatctgc gcatcggtct gccggaaacc    420

aaactgggca tcatgcctgg ctttggcggt tctgtacgta tgccacgtat gctgggcgct    480

gacagtgcgc tggaaatcat tgccgccggt aaagatgtcg gcgcggatca ggcgctgaaa    540

atcggtctgg tggatggcgt agtcaaagca gaaaaactgg ttgaaggcgc aaaggcggtt    600

ttacgccagg ccattaacgg cgacctcgac tggaaagcaa aacgtcagcc gaagctggaa    660

ccactaaaac tgagcaagat tgaagccacc atgagcttca ccatcgctaa agggatggtc    720

gcacaaacag cggggaaaca ttatccggcc cccatcaccg cagtaaaaac cattgaagct    780

gcggcccgtt ttggtcgtga agaagcctta aacctggaaa acaaaagttt tgtcccgctg    840

gcgcatacca acgaagcccg cgcactggtc ggcattttcc ttaacgatca atatgtaaaa    900

ggcaaagcga agaaactcac caaagacgtt gaaaccccga aacaggccgc ggtgctgggt    960

gcaggcatta tgggcggcgg catcgcttac cagtctgcgt ggaaaggcgt gccggttgtc   1020
```

atgaaagata tcaacgacaa gtcgttaacc ctcggcatga ccgaagccgc gaaactgctg 1080
aacaagcagc ttgagcgcgg caagatcgat ggtctgaaac tggctggcgt gatctccaca 1140
atccacccaa cgctcgacta cgccggattt gaccgcgtgg atattgtggt agaagcggtt 1200
gttgaaaacc cgaaagtgaa aaaagccgta ctggcagaaa ccgaacaaaa agtacgccag 1260
gataccgtgc tggcgtctaa cacttcaacc attcctatca gcgaactggc caacgcgctg 1320
gaacgcccgg aaaacttctg cgggatgcac ttctttaacc cggtccaccg aatgccgttg 1380
gtagaaatta ttcgcggcga gaaaagctcc gacgaaacca tcgcgaaagt tgtcgcctgg 1440
gcgagcaaga tgggcaagac gccgattgtg gttaacgact gccccggctt ctttgttaac 1500
cgcgtgctgt tcccgtattt cgccggtttc agccagctgc tgcgcgacgg cgcggatttc 1560
cgcaagatcg acaaagtgat ggaaaaacag tttggctggc cgatgggccc ggcatatctg 1620
ctggacgttg tgggcattga taccgcgcat cacgctcagg ctgtcatggc agcaggcttc 1680
ccgcagcgga tgcagaaaga ttaccgcgat gccatcgacg cgctgtttga tgccaaccgc 1740
tttggtcaga agaacggcct cggtttctgg cgttataaag aagacagcaa aggtaagccg 1800
aagaaagaag aagacgccgc cgttgaagac ctgctggcag aagtgagcca gccgaagcgc 1860
gatttcagcg aagaagagat tatcgcccgc atgatgatcc cgatggtcaa cgaagtggtg 1920
cgctgtctgg aggaaggcat tatcgccact ccggcggaag cggatatggc gctggtctac 1980
ggcctgggct tccctccgtt ccacggcggc gcgttccgct ggctggacac cctcggtagc 2040
gcaaaatacc tcgatatggc acagcaatat cagcacctcg gcccgctgta tgaagtgccg 2100
gaaggtctgc gtaataaagc gcgtcataac gaaccgtact atcctccggt tgagccagcc 2160
cgtccggttg gcgacctgaa aacggcttaa 2190

<210> SEQ ID NO 52
<211> LENGTH: 702
<212> TYPE: DNA
<213> ORGANISM: Escherechia coli

<400> SEQUENCE: 52
atgacaacct taagctgtaa agtgacctcg gtagaagcta tcacggatac cgtatatcgt 60
gtccgcatcg tgccagacgc ggccttttct tttcgtgctg gtcagtattt gatggtagtg 120
atggatgagc gcgacaaacg tccgttctca atggcttcga cgccggatga aaaagggttt 180
atcgagctgc atattggcgc ttctgaaatc aacctttacg cgaaagcagt catggaccgc 240
atcctcaaag atcatcaaat cgtggtcgac attccccacg gagaagcgtg gctgcgcgat 300
gatgaagagc gtccgatgat tttgattgcg ggcggcaccg ggttctctta tgcccgctcg 360
attttgctga cagcgttggc gcgtaaccca aaccgtgata tcaccattta ctggggcggg 420
cgtgaagagc agcatctgta tgatctctgc gagcttgagg cgctttcgtt gaagcatcct 480
ggtctgcaag tggtgccggt ggttgaacaa ccggaagcgg gctggcgtgg gcgtactggc 540
accgtgttaa cggcggtatt gcaggatcac ggtacgctgg cagagcatga tatctatatt 600
gccggacgtt ttgagatggc gaaaattgcc cgcgatctgt tttgcagtga gcgtaatgcg 660
cgggaagatc gcctgtttgg cgatgcgttt gcatttatct ga 702

<210> SEQ ID NO 53
<211> LENGTH: 2145
<212> TYPE: DNA
<213> ORGANISM: Escherechia coli

<400> SEQUENCE: 53

```
atggaaatga catcagcgtt tacccttaat gttcgtctgg acaacattgc cgttatcacc     60
atcgacgtac cgggtgagaa aatgaatacc ctgaaggcgg agtttgcctc gcaggtgcgc    120
gccattatta agcaactccg tgaaaacaaa gagttgcgag gcgtggtgtt tgtctccgct    180
aaaccggaca acttcattgc tggcgcagac atcaacatga tcggcaactg caaaacggcg    240
caagaagcgg aagctctggc gcggcagggc caacagttga tggcggagat tcatgctttg    300
cccattcagg ttatcgcggc tattcatggc gcttgcctgg gtggtgggct ggagttggcg    360
ctggcgtgcc acggtcgcgt ttgtactgac gatcctaaaa cggtgctcgg tttgcctgaa    420
gtacaacttg gattgttacc cggttcaggc ggcacccagc gtttaccgcg tctgataggc    480
gtcagcacag cattagagat gatcctcacc ggaaaacaac ttcgggcgaa acaggcatta    540
aagctggggc tggtggatga cgttgttccg cactccattc tgctggaagc cgctgttgag    600
ctggcaaaga aggagcgccc atcttcccgc cctctacctg tacgcgagcg tattctggcg    660
gggccgttag gtcgtgcgct gctgttcaaa atggtcggca agaaaacaga acacaaaact    720
caaggcaatt atccggcgac agaacgcatc ctggaggttg ttgaaacggg attagcgcag    780
ggcaccagca gcggttatga cgccgaagct cgggcgtttg gcgaactggc gatgacgcca    840
caatcgcagg cgctgcgtag tatctttttt gccagtacgg acgtgaagaa agatcccggc    900
agtgatgcgc cgcctgcgcc attaaacagc gtggggattt taggtggtgg cttgatgggc    960
ggcggtattg cttatgtcac tgcttgtaaa gcggggattc cggtcagaat taaagatatc   1020
aacccgcagg gcataaatca tgcgctgaag tacagttggg atcagctgga gggcaaagtt   1080
cgccgtcgtc atctcaaagc cagcgaacgt gacaaacagc tggcattaat ctccggaacg   1140
acggactatc gcggctttgc ccatcgcgat ctgattattg aagcggtgtt tgaaaatctc   1200
gaattgaaac aacagatggt ggcggaagtt gagcaaaatt gcgccgctca taccatcttt   1260
gcttcgaata cgtcatcttt accgattggt gatatcgccg ctcacgccac gcgacctgag   1320
caagttatcg gcctgcattt cttcagtccg gtggaaaaaa tgccgctggt ggagattatt   1380
cctcatgcgg ggacatcggc gcaaaccatc gctaccacag taaaactggc gaaaaaacag   1440
ggtaaaacgc caattgtcgt gcgtgacaaa gccggttttt acgtcaatcg catcttagcg   1500
ccttacatta atgaagctat ccgcatgttg acccaaggtg aacgggtaga gcacattgat   1560
gccgcgctag tgaaatttgg ttttccggta ggcccaatcc aacttttgga tgaggtagga   1620
atcgacaccg ggactaaaat tattcctgta ctggaagccg cttatggaga acgttttagc   1680
gcgcctgcaa atgttgtttc ttcaattttg aacgacgatc gcaaaggcag aaaaaatggc   1740
cggggtttct atctttatgg tcagaaaggg cgtaaaagca aaaaacaggt cgatcccgcc   1800
atttacccgc tgattggcac acaagggcag gggcgaatct ccgcaccgca ggttgctgaa   1860
cggtgtgtga tgttgatgct gaatgaagca gtacgttgtg ttgatgagca ggttatccgt   1920
agcgtgcgtg acggggatat tggcgcggta tttggcattg gttttccgcc atttctcggt   1980
ggaccgttcc gctatatcga ttctctcggc gcgggcgaag tggttgcaat aatgcaacga   2040
cttgccacgc agtatggttc ccgttttacc ccttgcgagc gtttggtcga gatgggcgcg   2100
cgtggggaaa gtttttggaa aacaactgca actgacctgc aataa                   2145
```

<210> SEQ ID NO 54
<211> LENGTH: 720
<212> TYPE: DNA
<213> ORGANISM: Escherechia coli

<400> SEQUENCE: 54
atggtcatta aggcgcaaag cccggcgggt ttcgcggaag agtacattat tgaaagtatc 60
tggaataacc gcttccctcc cgggactatt ttgcccgcag aacgtgaact ttcagaatta 120
attggcgtaa cgcgtactac gttacgtgaa gtgttacagc gtctggcacg agatggctgg 180
ttgaccattc aacatggcaa gccgacgaag gtgaataatt tctgggaaac ttccggttta 240
aatatccttg aaacactggc gcgactggat cacgaaagtg tgccgcagct tattgataat 300
ttgctgtcgg tgcgtaccaa tatttccact atttttattc gcaccgcgtt tcgtcagcat 360
cccgataaag cgcaggaagt gctggctacc gctaatgaag tggccgatca cgccgatgcc 420
tttgccgagc tggattacaa catattccgc ggcctggcgt ttgcttccgg caacccgatt 480
tacggtctga ttcttaacgg gatgaaaggg ctgtatacgc gtattggtcg tcactatttc 540
gccaatccgg aagcgcgcag tctggcgctg ggcttctacc acaaactgtc ggcgttgtgc 600
agtgaaggcg cgcacgatca ggtgtacgaa acagtgcgtc gctatgggca tgagagtggc 660
gagatttggc accggatgca gaaaaatctg ccgggtgatt tagccattca ggggcgataa 720

<210> SEQ ID NO 55
<211> LENGTH: 1000
<212> TYPE: DNA
<213> ORGANISM: Castellaniella defragrans

<400> SEQUENCE: 55
atgcggttca cattgaagac gacggcgatt gtgtcggccg ccgccctgct ggccggtttc 60
gggccgccgc cccgcgcggc ggaactgccg ccggggcggc tcgccaccac cgaggactat 120
ttcgcgcagc aggcgaagca ggccgtcacc cccgacgtga tggcccagct ggcctacatg 180
aactacatcg atttcatctc gcccttctac agccggggct gctccttcga ggcctgggag 240
ctcaagcaca cgccgcagcg ggtcatcaag tattcgatcg ccttctatgc gtatggcctg 300
gccagcgtgg cgctcatcga cccgaagctg cgtgcgctcg ccggccatga cctggacatc 360
gcggtctcca agatgaagtg caagcgggtc tggggcgact gggaggaaga cgggttcggc 420
accgacccga tcgagaaaga gaacatcatg tacaagggcc acctgaacct gatgtacggc 480
ctctatcagc tggtgaccgg cagccgccgg tacgaagccg agcatgccca cctcacccgc 540
atcatccatg acgagatcgc ggccaacccc tttgccggca tcgtctgcga gccggacaat 600
tattttgtcc agtgcaattc ggtcgcctac ctgagcctgt gggtctatga ccggctgcat 660
ggcaccgact accgggcggc caccagggcc tggctggatt tcatccagaa ggacctgatc 720
gatcccgagc ggggcgcctt ctacctgtcc tatcaccccg agtccggcgc ggtgaagccg 780
tggatctcgg cgtatacgac agcctggacg ctcgccatgg tgcacggcat ggaccccgcc 840
ttttccgagc gctactaccc ccggttcaag cagaccttcg tcgaggtcta cgacgagggc 900
cgcaaggccc gggtgcgcga gacggccggc acggacgacg cggatggcgg ggtgggcctg 960
gcttcggcgt tcaccctgct gctggcccgc gagatgggcg 1000

<210> SEQ ID NO 56
<211> LENGTH: 1000
<212> TYPE: DNA
<213> ORGANISM: Castellaniella defragrans

<400> SEQUENCE: 56
atgcggttca cattgaagac gacggcgatt gtgtcggccg ccgccctgct ggccggtttc 60

-continued

```
gggccgccgc cccgcgcggc ggaactgccg ccggggcggc tcgccaccac cgaggactat    120

ttcgcgcagc aggcgaagca ggccgtcacc cccgacgtga tggcccagct ggcctacatg    180

aactacatcg atttcatctc gcccttctac agccggggct gctccttcga ggcctgggag    240

ctcaagcaca cgccgcagcg ggtcatcaag tattcgatcg ccttctatgc gtatggcctg    300

gccagcgtgg cgctcatcga cccgaagctg cgtgcgctcg ccggccatga cctggacatc    360

gcggtctcca agatgaagtg caagcgggtc tggggcgact gggaggaaga cgggttcggc    420

accgacccga tcgagaaaga gaacatcatg tacaagggcc acctgaacct gatgtacggc    480

ctctatcagc tggtgaccgg cagccgccgg tacgaagccg agcatgccca cctcacccgc    540

atcatccatg acgagatcgc ggccaacccc tttgccggca tcgtctgcga gccggacaat    600

tattttgtcc agtgcaattc ggtcgcctac ctgagcctgt gggtctatga ccggctgcat    660

ggcaccgact accgggcggc caccagggcc tggctggatt tcatccagaa ggacctgatc    720

gatcccgagc ggggcgcctt ctacctgtcc tatcaccccg agtccggcgc ggtgaagccg    780

tggatctcgg cgtatacgac agcctggacg ctcgccatgg tgcacggcat ggaccccgcc    840

ttttccgagc gctactaccc ccggttcaag cagaccttcg tcgaggtcta cgacgagggc    900

cgcaaggccc gggtgcgcga gacggccggc acggacgacg cggatggcgg ggtgggcctg    960

gcttcggcgt tcaccctgct gctggcccgc gagatgggcg                         1000
```

<210> SEQ ID NO 57
<211> LENGTH: 1392
<212> TYPE: DNA
<213> ORGANISM: Sulfolobus solfataricus

<400> SEQUENCE: 57

```
atgagatcaa aagaagattt cctaaagtcc ttaaaagatg gaagaaattt gtattatagg     60

gggaagttag tagaagatat aacaacacat cagatcttaa agacagccgc attgcacgca    120

gctaagttat atgaatacgc tgatagagtc tatgaggata ataaaatggg aaaaatgagc    180

aagttcttta aggtaccttg gacatctcaa gatttgctag atagacataa actaatttac    240

gatttaacga tgtattgtaa tggggtattt aacatttcac aagcaatagg aagtgatgcg    300

atctttgccc ttatgatcac ggcaaaacaa gttgatagaa aatacggaac tgattactca    360

aaacgtgttg aaaaatattt tgagagagtt gctaaagaag atttaacgtt agccactgcc    420

cagactgacg ttaagggaga tcgaagtaag aggccttctg aacaagttga tccagatatg    480

tatgttagag tagttgatgt gaaaagcgat ggaatagttg ttagaggagc aaaggctcat    540

acaactcaat ctgcggtatc tgatgagatt attgtcatac caaccagagt aatgagggat    600

agcgataaag attacgcagt agcctttgcg gttccagcta atactaaagg tttgaagatg    660

tatattagac caattgatga aattgagggc aattcctcct cagtactcag tagaaaagat    720

tatgagctag aaacattaac cgtcttcaac gacgttttcg ttccttggga tagggtattt    780

ttatttaagg aatacgacta cgctggaaca ttggctatgc tatttgcaac cttccatagg    840

tttactgcat tatcgtatag gtcagcgacc atgaatctat atttgggagc atctaaagtg    900

gcatctcaag taaatggcat tgagaatgaa aagcatgtga gagatgatat agttgatata    960

attctctaca aggaaattat gaggagtagc gcgatagctg cggctgtgta tccagtaaac   1020

atggagggta tagctgtgcc caacccgctt tttactaatg ttggtaaatt atactccaat   1080

atgcatttcc atgatgttgt aagagattta attgacattg ctgggggggat aatagctact   1140

atgccctctc aagaagattt ggaaagtgat gaaggaaaga atattgttaa atatttaagg   1200
```

ggctcagttg atggagagga aagagcaaaa gtgttaaaac tagctaagga attaggggct 1260
agtacgttta ctggctattt gctaactggt atgatacatg cggaaggttc tatggaagct 1320
agcaaaatag agctattcag aagttataat tttaaggagg ccgagaactt agttaaaagg 1380
gtattaagct ag 1392

<210> SEQ ID NO 58
<211> LENGTH: 1206
<212> TYPE: DNA
<213> ORGANISM: Escherichia coli

<400> SEQUENCE: 58
atgcgtgaag cctttatttg tgacggaatt cgtacgccaa ttggtcgcta cggcggggca 60
ttatcaagtg ttcgggctga tgatctggct gctatccctt tgcgggaact gctggtgcga 120
aacccgcgtc tcgatgcgga gtgtatcgat gatgtgatcc tcggctgtgc taatcaggcg 180
ggagaagata accgtaacgt agcccggatg gcgactttac tggcggggct gccgcagagt 240
gtttccggca caaccattaa ccgcttgtgt ggttccgggc tggacgcact ggggtttgcc 300
gcacgggcga ttaaagcggg cgatggcgat ttgctgatcg ccggtggcgt ggagtcaatg 360
tcacgggcac cgtttgttat gggcaaggca gccagtgcat tttctcgtca ggctgagatg 420
ttcgatacca ctattggctg gcgatttgtg aacccgctca tggctcagca atttggaact 480
gacagcatgc cggaaacggc agagaatgta gctgaactgt taaaaatctc acgagaagat 540
caagatagtt ttgcgctacg cagtcagcaa cgtacggcaa aagcgcaatc ctcaggcatt 600
ctggctgagg agattgttcc ggttgtgttg aaaaacaaga aaggtgttgt aacagaaata 660
caacatgatg agcatctgcg cccggaaacg acgctggaac agttacgtgg gttaaaagca 720
ccatttcgtg ccaatggggt gattaccgca ggcaatgctt ccggggtgaa tgacggagcc 780
gctgcgttga ttattgccag tgaacagatg gcagcagcgc aaggactgac accgcgggcg 840
cgtatcgtag ccatggcaac cgccggggtg gaaccgcgcc tgatggggct tggtccggtg 900
cctgcaactc gccgggtgct ggaacgcgca gggctgagta ttcacgatat ggacgtgatt 960
gaactgaacg aagcgttcgc ggcccaggcg ttgggtgtac tacgcgaatt ggggctgcct 1020
gatgatgccc cacatgttaa ccccaacgga ggcgctatcg ccttaggcca tccgttggga 1080
atgagtggtg cccgcctggc actggctgcc agccatgagc tgcatcggcg taacggtcgt 1140
tacgcattgt gcaccatgtg catcggtgtc ggtcagggca tcgccatgat tctggagcgt 1200
gtttga 1206

<210> SEQ ID NO 59
<211> LENGTH: 1221
<212> TYPE: DNA
<213> ORGANISM: Pseudomonas putida

<400> SEQUENCE: 59
atgaatgaac cgacccacgc cgatgccttg atcatcgacg ccgtgcgcac gcccattggc 60
cgctatgccg gggccctgag cagcgtgcgc gccgacgacc tggcggccat cccgctcaaa 120
gccttgatcc agcgtcaccc cgaactggac tggaaagcca ttgatgacgt tatcttcggc 180
tgtgccaacc aggctggcga agacaaccgc aacgtggccc acatggcgag cctgctggcc 240
gggctgccac tcgaagtacc agggaccacg atcaaccgcc tgtgcggttc cggtctggat 300
gccatcggta atgcggcacg tgccctgcgc tgcggtgaag cggggctcat gctggccggt 360

-continued

```
ggtgtggagt ccatgtcgcg tgcaccgttt gtgatgggta agtcggagca ggcattcggg    420

cgtgcggccg agctgttcga caccaccatc ggctggcgtt tcgtcaaccc gctgatgaag    480

gccgcctacg gcatcgattc gatgccggaa acggctgaaa acgtggccga acagttcggc    540

atctcgcgcg ccgaccagga tgcctttgcc ctgcgcagcc agcacaaagc cgcagcagct    600

caggcccgcg gccgcctggc gcgggaaatc gtgccggtcg aaatcccgca acgcaaaggc    660

ccagccaaag tggtcgagca tgacgagcac ccgcgcggcg acacgaccct ggagcagctg    720

gctcggctcg ggacgccgtt tcgtgaaggc ggcagcgtaa cggcgggtaa tgcctccggc    780

gtgaatgacg gcgcttgcgc cctgctgctg gccagcagcg ccgcggcccg ccgccatggg    840

ttgaaggccc gcggccgcat cgtcggcatg gcggtggccg gggttgagcc caggctgatg    900

ggcattggtc cggtgcctgc gacccgcaag gtgctggcgc tcaccggcct ggcactggct    960

gacctggatg tcatcgaact caatgaggcc tttgccgccc aagggctggc cgtgttgcgc   1020

gagctgggcc tggccgacga cgacccgcga gtcaaccgca acggcggcgc catcgccctg   1080

ggccatcccc tgggcatgag cggtgcccgg ttggtgacca ctgccttgca cgagcttgaa   1140

gaaacggccg gccgctacgc cctgtgcacc atgtgcatcg gcgtaggcca aggcattgcc   1200

atgatcatcg agcgcctctg a                                             1221
```

<210> SEQ ID NO 60
<211> LENGTH: 1203
<212> TYPE: DNA
<213> ORGANISM: Pseudomonas putida

<400> SEQUENCE: 60

```
atgcacgacg tattcatctg tgacgccatc cgtaccccga tcggccgctt cggcggcgcc     60

ctggccagcg tgcgggccga cgacctggcc gccgtgccgc tgaaggcgct gatcgagcgc    120

aaccctggcg tgcagtggga ccaggtagac gaagtgttct tcggctgcgc caaccaggcc    180

ggtgaagaca accgcaacgt ggcccgcatg gcactgctgc tggccggcct gccggaaagc    240

atcccgggcg tcaccctgaa ccgtctgtgc gcgtcgggca tggatgccgt cggcaccgcg    300

ttccgcgcca tcgccagcgg cgagatggag ctggtgattg ccggtggcgt cgagtcgatg    360

tcgcgcgccc cgttcgtcat gggcaaggct gaaagcgcct attcgcgcaa catgaagctg    420

gaagacacca ccattggctg gcgtttcatc aacccgctga tgaagagcca gtacggtgtg    480

gattccatgc cggaaaccgc cgacaacgtg gccgacgact atcaggtttc gcgtgctgat    540

caggacgctt tcgccctgcg cagccagcag aaggctgccg ctgcgcaggc tgccggcttc    600

tttgccgaag aaatcgtgcc ggtgcgtatc gctcacaaga agggcgaaat catcgtcgaa    660

cgtgacgaac acctgcgccc ggaaaccacg ctggaggcgc tgaccaagct caaaccggtc    720

aacggcccgg acaagacggt caccgccggc aacgcctcgg gcgtgaacga cggtgctgcg    780

gcgatgatcc tggcctcggc cgcagcggtg aagaaacacg gcctgactcc gcgtgcccgc    840

gttctgggca tggccagcgg cggcgttgcg ccacgtgtca tgggcattgg cccggtgccg    900

gcggtgcgca aactgaccga gcgtctgggg atagcggtaa gtgatttcga cgtgatcgag    960

cttaacgaag cgtttgccag ccaaggcctg gcggtgctgc gtgagctggg tgtggctgac   1020

gatgcgcccc aggtaaaccc taatggcggt gccattgccc tgggccaccc cctgggcatg   1080

agcggtgcac gcctggtact gactgcgttg caccagctgg agaagagtgg cggtcgcaag   1140

ggcctggcga ccatgtgtgt gggtgtcggc caaggtctgg cgttggccat cgagcgggtt   1200

tga                                                                 1203
```

<210> SEQ ID NO 61
<211> LENGTH: 1212
<212> TYPE: DNA
<213> ORGANISM: Acinetobacter calcoaceticus

<400> SEQUENCE: 61
atgacattaa aaaacgctta tatcatcgat gccatccgta ctccattcgg tcgttatgcc 60
ggtggccttg cacctgtccg tgcagatgac cttggtgctg tgccgattaa agccctcatg 120
caacgtaacc caagtgtaga ttgggaacag gtcgatgatg tgatctatgg ctgtgccaac 180
caagccggtg aagataaccg taatgtcggt cgtatgtcag cacttcttgc aggtttacca 240
tatcaggtac cggcaaccac tattaaccgt ttatgcggtt cttcactcga tgccattgcc 300
attgcagccc gtgctattaa agcaggtgaa gcgaacttgg tgattgcagg tggtgtagaa 360
agcatgagcc gtgcgcctta tgtaatgggt aagtcagaca gtgcttttgg ccgtagccag 420
aagattgaag acaccaccat gggctggcgt tttattaacc caaaacttaa agaattgtat 480
ggtgtagaca ccatgcccca gactgccgaa aacgtggctg aacagtttaa cgtcaatcgt 540
gcagatcagg accagtttgc cttggtgagc caacaacgca ccgcaagcgc gcaagccaaa 600
ggcttttttt ctaaagaaat cgtggcagtt gaaatccctc agcgtaaggg tgatgctgtt 660
gtgattgata ctgatgaaca tccacgtgca tcaaccaccc ttgaaggttt aagcaaactt 720
aaatctgtgg ttaaagcaga tggcacagta acagcaggca atgcttcagg tattaatgat 780
ggtgcagcag ctctactgat tgcttctgat gaagcagttc aggcatacaa cctaaaaccc 840
cgcgccaaga ttattgcttc aacagcggtg ggtgtagaac cacggattat gggctttgct 900
ccagcaccag ccattaaaaa attacttaaa caagctaacc tgactttaga tcagatggat 960
gtaattgagc tcaatgaagc ttttgctgct caggctttgg cagtgacccg tgatttaggt 1020
ttgccagatg attctcacaa ggtaaaccca aatggtggtg ccattgcttt gggtcatcca 1080
cttggtgctt caggtgcacg catcgtgact acagccttga accagcttga acaaacaggt 1140
ggtcgctacg ctttgtgttc aatgtgtatt ggggtgggcc aaggcatcgc attgattatt 1200
gagagagtct aa 1212

<210> SEQ ID NO 62
<211> LENGTH: 1164
<212> TYPE: DNA
<213> ORGANISM: Aeromonas hydrophila

<400> SEQUENCE: 62
atgaaagacg tagtcattgt cgactgtatc cggaccccga tgggccggtc caagggcggc 60
gccttccgca acgtgcgtgc agaagacttg tccgcgcacc tgatgaaatc catcctgctg 120
cgcaacccca acctcgaccc gaacgagatc gaggatatct actggggctg cgtgcagcag 180
accctggagc agggcttcaa catcgcccgc aacgcagcct tgctggccgg cattcccaag 240
caggtggggg cggtcaccgt caaccgcctg tgcggctcca gcatgcaggc gctgcacgat 300
gcctcccgcg ccattcaggt aggtgatggg gatatcttca tcatcggcgg tgtcgagcac 360
atgggccacg tgccgatgag ccacggggtg gacttccacc ccggcatggc caagtcggtg 420
gcgaaagcct ccggcatgat ggggctgacc gccgagatgc tcggcaagct gcacggcatc 480
agtcgtcagc agcaggacga gtttgccgcc cgctcccatc gtcgcgctca cgccgccacc 540
gtggaaggac gtttcgccaa ggagatcgtc gggctggaag gccatgacgc cagcggcgcc 600

```
cgcttcttct acgactacga cgaggtgatc cgcccccgaga ccacggtgga aaccctgagc    660

cagctgcgcc cggtgttcga cccggtcaac ggcaccgtca ccgccggcac ctcgtcggcc    720

ctgtccgatg gcgccgccgc catgctggtg atgagtgcgg accgcgccaa ggcgctcggc    780

ctcaccccgc gcgccaagat acgtgccatg gccgtcgccg gctgcgatgc cgccatcatg    840

ggttacggcc cggtaccggc cacccagaag gcgctcaagc gggccggcct gaccatcggc    900

gacatcgacc tgttcgagct gaacgaggcg tttgccgccc agtccctgcc ttgcgtgaag    960

gatctgggtc tgcaagacgt ggtggatgag aaggtgaacc tgaacggcgg cgccatcgcc   1020

ctgggtcacc cgctcggctg ctccggcgcc cgcatctcca ccaccctgct caacctgatg   1080

gaagagaagg acgccaccct gggggttgcc accatgtgca tcggcctggg tcagggcatc   1140

gccaccgtgt tcgaacgagt gtaa                                          1164


<210> SEQ ID NO 63
<211> LENGTH: 1005
<212> TYPE: DNA
<213> ORGANISM: Aeromonas salmonicida

<400> SEQUENCE: 63

atggatattg tgattgttgc ggccaagcgt acccccatgg gggccttcca gggagccttg     60

gccaacctga ctgcccccga gcttggcgct tgcgccattg ctgccgccat agcacaagcc    120

gggctcaagg gggagcagat cgatgaagcc tacatgggca atgtgctcag tgccggggtg    180

gggcaggcac ccgcccgtca ggctgtgttg aaggcaggtt tgccggagag tgtgccatgc    240

accactgtca acaaggtgtg tggttccggc atgaaggcgg tgatgctggc ggcagacagc    300

ttgcgtctgg gtgacaccga catagtgatc gccggtggca tggagagcat gagccgggcg    360

ccttacctgc tcgacaaggc gcgcagcggt tttcgcatgg ggcatcagag cgtgctggat    420

catatgttcc tcgatggctt gcaggatgct tacgaaggcc agttgatggg gcattatgcc    480

cagttgagtg cggatcgcgc cggtctggcc cgctccgaca tggacgcttt tgccatcgct    540

tccctgacgc gtgcgctggc tgcccagcag agcggtgctt tcaaggccga gctggcccag    600

gttactgtcg gtgacaccct gctgctcgcc gaggatgagc agcctgccaa ggccaggccc    660

gacaagatcc ctcatctgaa accggcattc agcaagcagg gcaccataac ggctgccaat    720

gccagctcca tctcggacgg agcggcggcg ctcatcctga tgcgagccga gacggcggcg    780

cagctgggcc tgcctgtgct ggccatggcg ggttgcaacc tgcctcatga caaggtgaac    840

gtgaacggcg gggcctgcgc actggggcat ccactggggg cgagtggtgc ccgtattctg    900

gttacgctca ttcatgcact gcatgcgcgc agtctgaaac ggggtgtggc aagcctgtgt    960

atcggtggag gggaggcgac tgccgtcgcc atcgagttga gctaa                   1005


<210> SEQ ID NO 64
<211> LENGTH: 1206
<212> TYPE: DNA
<213> ORGANISM: Pseudomonas aeroginosa

<400> SEQUENCE: 64

atgagccgcg aggtattcat ctgcgatgcc gtgcgcacgc cgatcggccg tttcggcggc     60

agtctttccg cggtgcgcgc cgacgacctc gcggcggtgc cgctgaaggc cctggtcgag    120

cgcaacccgg gggtcgactg gtcggcgctg gacgaggtgt tcctcggctg cgccaaccag    180

gccggcgagg acaaccgtaa cgtggcgcgc atggcgctgc tgctggccgg tttgccggag    240

agcgtgcccg gcgtcaccct caaccgcctc tgcgcctcgg ggatggacgc catcggcacg    300
```

gcgttccgcg ccatcgcctg cggcgagatg gagctggcca tcgccggcgg cgtcgagtcg 360
atgtcgcgcg cgccgtacgt gatgggcaag gccgatagcg ccttcgggcg cggccagaag 420
atcgaggaca ccaccatcgg ctggcgcttc gtcaacccgc tgatgaagga gcagtacggc 480
atcgacccga tgccgcagac cgccgacaac gtcgccgacg actatcgcgt gtcgcgtgcc 540
gaccaggatg ccttcgccct gcgcagccag cagcgcgccg gcagggcgca ggcggccggt 600
ttcttcgccg aggaaatcgt cccggtgacg attcgcgggc gcaagggcga caccctggtc 660
gagtacgacg agcatccgcg tcccgacacc accctggagg cgctggcccg gctcaagccg 720
gtcaacgggc cggagaagac cgtcaccgcc ggcaacgcgt ccggggtcaa cgacggcgcc 780
gccgcgctgg tcctggcctc cgccgaggca gtggagaagc acggcctgac tccgcgcgcg 840
cgggtgctgg gcatggccag cgccggcgtc gccccacgga tcatgggcat cggcccggtg 900
ccggcggtgc gcaagctgct gcggcgcctg gacctggcga tcgacgcctt cgacgtgatc 960
gaactcaacg aagccttcgc cagccagggc ctggcctgcc tgcgcgaact gggcgtggcc 1020
gacgacagtg agaaggtcaa cccgaacggc ggtgccatcg ccctcggcca cccgctgggg 1080
atgagcggtg cgcggctggt cctcaccgcg ctccatcaac ttgagaagag cggcggccgg 1140
cgcggcctgg cgaccatgtg cgtaggcgtc ggccaaggcc tggcgctggc catcgagcgg 1200
gtctga 1206

<210> SEQ ID NO 65
<211> LENGTH: 1185
<212> TYPE: DNA
<213> ORGANISM: Ralstonia eutropha

<400> SEQUENCE: 65
atgacgcgtg aagtggtagt ggtaagcggt gtccgtaccg cgatcgggac ctttggcggc 60
agcctgaagg atgtggcacc ggcggagctg ggcgcactgg tggtgcgcga ggcgctggcg 120
cgcgcgcagg tgtcgggcga cgatgtcggc cacgtggtat tcggcaacgt gatccagacc 180
gagccgcgcg acatgtatct gggccgcgtc gcggccgtca acggcggggt gacgatcaac 240
gcccccgcgc tgaccgtgaa ccgcctgtgc ggctcgggcc tgcaggccat tgtcagcgcc 300
gcgcagacca tcctgctggg cgataccgac gtcgccatcg gcggcggcgc ggaaagcatg 360
agccgcgcac cgtacctggc gccggcagcg cgctggggcg cacgcatggg cgacgccggc 420
ctggtcgaca tgatgctggg tgcgctgcac gatcccttcc atcgcatcca catgggcgtg 480
accgccgaga atgtcgccaa ggaatacgac atctcgcgcg cgcagcagga cgaggccgcg 540
ctggaatcgc accgccgcgc ttcggcagcg atcaaggccg gctacttcaa ggaccagatc 600
gtcccggtgg tgagcaaggg ccgcaagggc gacgtgacct tcgacaccga cgagcacgtg 660
cgccatgacg ccaccatcga cgacatgacc aagctcaggc cggtcttcgt caaggaaaac 720
ggcacggtca cggccggcaa tgcctcgggc ctgaacgacg ccgccgccgc ggtggtgatg 780
atggagcgcg ccgaagccga gcgccgcggc ctgaagccgc tggcccgcct ggtgtcgtac 840
ggccatgccg gcgtggaccc gaaggccatg ggcatcggcc cggtgccggc gacgaagatc 900
gcgctggagc gcgccggcct gcaggtgtcg gacctggacg tgatcgaagc caacgaagcc 960
tttgccgcac aggcgtgcgc cgtgaccaag gcgctcggtc tggacccggc caaggttaac 1020
ccgaacggct cgggcatctc gctgggccac ccgatcggcg ccaccggtgc cctgatcacg 1080
gtgaaggcgc tgcatgagct gaaccgcgtg cagggccgct acgcgctggt gacgatgtgc 1140

```
atcggcggcg ggcagggcat tgccgccatc ttcgagcgta tctga                 1185


<210> SEQ ID NO 66
<211> LENGTH: 1188
<212> TYPE: DNA
<213> ORGANISM: Rhodopseudomonas palustris

<400> SEQUENCE: 66

atgaccgagg ccgttatcgt ttcaaccgcg cgcacgccga tcggcaaggc gtatcgcggc     60

gccctcaacg ccaccgaggg tgccacactg ctcggccacg ccatcgagca cgcggtgaag    120

cgcgccggta tcgacccgaa ggaggtcgag gacgtggtga tgggcgcggc gatgcagcag    180

ggcgccaccg gcggcaacat cgcccgcaag gcgctgctgc gcgccggcct gccggtgact    240

accgccggca ccaccatcga tcggcagtgc gcctccggcc tgcaggcgat cgcgctcgcc    300

gctcgctcgg tgctgttcga cggcgtcgag atcgcggtcg gcggtggcgg cgagtcgatc    360

tcgctcgtcc agaacgacaa gatgaacacc ttccacgccg tcgatccggc gctcgaggcg    420

atcaagggcg acgtctacat ggcgatgctc gacaccgccg aaaccgtggc gaagcgctac    480

ggcatctcgc gcgagcgcca ggacgagtat tcgctggaaa gccagcgccg caccgcggct    540

gcgcagcagg gcggcaagtt caacgacgag atcgcgccga tctcgaccaa gatgggcgtc    600

gtcgacaagg ccaccggcgc ggtgtcgttc aaggatatca cgctgtcgca ggacgaaggc    660

ccgcggccgg aaaccaccgc tgaaggtctc gccggtctta aggccgtgcg tggtgaaggc    720

ttcaccatca ctgccggcaa tgccagccag ctgtcggacg gcgcctcggc cacggtgatc    780

atgagcgaca agacggcggc cgcgaagggc ctcaagccgc tcggcatctt ccgcggcatg    840

gtctcctacg gctgcgagcc ggacgagatg ggcatcggcc cggtgttcgc ggtgccgcgc    900

ctgttgaagc gccatggtct cagcgtcgac gacatcggtc tgtgggagct gaacgaagcc    960

ttcgccgtgc aggtgctgta ctgccgcgac aagctcggca tcgatccgga gaagctcaat   1020

gtcaacggcg gcgcgatctc ggtcggccac ccctacggca tgtcgggtgc acgcctcgcc   1080

ggccacgcgc tgatcgaagg ccgtcgccgc aaggcgaagt acgcggtggt cacgatgtgc   1140

gtcggcggcg gcatgggctc cgccggcctg ttcgagatcg tgcactga                1188


<210> SEQ ID NO 67
<211> LENGTH: 1293
<212> TYPE: DNA
<213> ORGANISM: Syntrophus aciditrophicus

<400> SEQUENCE: 67

atgaaagatg tcgtcatcgt aagcggcgcc agaaccgccg tgggtgcttt tggcggatcg     60

ctgaaaggcg tgagagttac ggatttggga gcgctggtca tcaaagaggc catcaagaga    120

gcggggctgc ggccggccat cagtgaagaa gtgaaaggct gccgttgcga taccttcgga    180

gaattcgaca agaccgaaat caacaagaaa tattatgatt acgatgaatc cctgaccccc    240

gtttatttcg acgagtgcat catggggaac tgcctgatcg ccggcctggg acagaatccc    300

ggccgtcagt ccagcatcta tgccggtctg cccgaagaaa cgaacaccat cacagtgaac    360

aaggtctgcg catccggcat gaaagccatc accctggccg cccagatcat caaagccggc    420

gatgccgaca tcatggtggc cggcggcatg gaaaacatga gcaatgtacc ctacgccctg    480

cccgacgccc gctggggata ccggatgaac atgcctacgg gttccatcat cgacctcatg    540

gttcatgatg gtctctggga aatcttcaac ggctatcaca tgggattcac ggcggaaaat    600

atcgcctccc gttatggaat cagccgtcag gcccaggacg agctggccct catgagccat    660
```

```
cagcgcgccc gtgcggccat cgccagcggc gccgtcgccg atgaaatcat ccccgttccg    720
ctgcccgtga agaaaggcgc ggctccgcag tttttctccg tcgacgagcg tcccatggac    780
accagcctgg aaaagatggc gaagctggcc ccagtcttca agaaggacgg aaccgtcacg    840
gcggccaacg cctcgggtat caatgacggt gcggcggctg tcgtcgtgat gagcgccgac    900
aaggcaaagg aactgggcct caaaccgctg gcgaagatcc tcggctatgc ctccggcggc    960
gtcgatccgg catacatggg tctgggtccg attccggcaa cccgcaaggt cttcaagaaa   1020
ctcggcctga ccatgaagga catggacatc gtggaactga acgaggcctt tgcatcccag   1080
gccctgggct gcgtccagga aatgggtgtg gatctggaca aaaccaatct caacggcagc   1140
gggatctcca tcggtcaccc cgtcggctgc accggcgccc ggatcaccta cagcttggcc   1200
atgcagctgc agaagaagaa cgcgcacctc ggactcgcca cgctgtgtat cggtggcgga   1260
caggggatgg ccattgtcct ggaaagagtg taa                                1293
```

<210> SEQ ID NO 68
<211> LENGTH: 1209
<212> TYPE: DNA
<213> ORGANISM: Cupriavidus necator

<400> SEQUENCE: 68

```
atgcgcagag ctgcaatcgt cactcccctc cgcacgcccg tcggcacctt cggcggcagc     60
ctgcgcccgg tgcccgtgga ggagctggcc gccaccgccg tgcgcgccgt ggtggaacgc    120
agcggcatcg atcccgcgcg tatcgatgac gtggtctttg cccagtccta cgccaacagc    180
gaagtgccct gcgtcggccg ctgggccgcg ctgcaggccg gcctgccggt cgaagtgccg    240
ggcatgcagc tggaccgccg ctgcggcggc ggcctgcagg ccatcgtcac ggcctcgatg    300
atggtgcaaa gcggcgccgc cgacgtggtg atcgcgggcg gcgtcgagag catgagcaat    360
atcgagtact acaccaccga catgcgctgg ggcgcgcgct cgggcaatgt gcgcttcttc    420
gaccgcctcg accgcggccg tgaacgctcc cagccggtcg agcgcttcgg caagatctcc    480
gggatgatcg agacggccga gaacctggcg cgcgactacg gcatcagccg cgaagcggcc    540
gatgtcttcg ccgcccgcag ccacgcacgc gccgcggcag cctgggaggc cggccgcttc    600
gatgccgagg tcgtccccgt gcaggtgccc cagcgcaagg gcgatccggt gcggttcgcg    660
cgcgacgaag gtttccgccc ggaaaccacg cgtgaaagcc tgggcaagct gcgcacgctg    720
atgccgaacg gtaccgtcac cgccggcaac gccagccagc agaacgacgc ctcggccgcg    780
tgcctgatcg tggccgaaga caagctggcc gaattgggcc tcacccccat ggcctcgctg    840
gtgggctggg cggcggctgg ctgcgagccc tcgcacatgg gcatcggccc ggtgcccgcg    900
gtgaagaagc tgctggcgcg cctgaacctg acgctggacc ggatggacct ggtcgagctg    960
aacgaagcct tcgcctgcca ggtgctggcc gtgctcaagg gctgggaatg gcatgaccag   1020
gacgcgatcg agcagaagct caacgtgaac ggctcgggca tctcgcttgg ccatccgatc   1080
ggcgccaccg gcgtgcgcat cctggccacg ctgctgcacg aactgcagcg ccgcggcggc   1140
cgctatggcc tggaaaccat gtgcatcggc ggcggccagg gtattgccgc ggtcttcgaa   1200
cgctactga                                                           1209
```

<210> SEQ ID NO 69
<211> LENGTH: 1185
<212> TYPE: DNA
<213> ORGANISM: Escherichia coli

<400> SEQUENCE: 69
atgaaaaatt gtgtcatcgt cagtgcggta cgtactgcta tcggtagttt taacggttca 60
ctcgcttcca ccagcgccat cgacctgggg gcgacagtaa ttaaagccgc cattgaacgt 120
gcaaaaatcg attcacaaca cgttgatgaa gtgattatgg gtaacgtgtt acaagccggg 180
ctggggcaaa atccggcgcg tcaggcactg ttaaaaagcg ggctggcaga aacggtgtgc 240
ggattcacgg tcaataaagt atgtggttcg ggtcttaaaa gtgtggcgct tgccgcccag 300
gccattcagg caggtcaggc gcagagcatt gtggcggggg gtatggaaaa tatgagttta 360 gcccccctact tactcgatgc aaaagcacgc tctggttatc gtcttggaga cggacaggtt 420
tatgacgtaa tcctgcgcga tggcctgatg tgcgccaccc atggttatca tatggggatt 480
accgccgaaa acgtggctaa agagtacgga attacccgtg aaatgcagga tgaactggcg 540
ctacattcac agcgtaaagc ggcagccgca attgagtccg gtgcttttac agccgaaatc 600
gtcccggtaa atgttgtcac tcgaaagaaa accttcgtct tcagtcaaga cgaattcccg 660
aaagcgaatt caacggctga agcgttaggt gcattgcgcc cggccttcga taaagcagga 720
acagtcaccg ctgggaacgc gtctggtatt aacgacggtg ctgccgctct ggtgattatg 780
gaagaatctg cggcgctggc agcaggcctt acccccctgg ctcgcattaa aagttatgcc 840
agcggtggcg tgccccccgc attgatgggt atggggccag tacctgccac gcaaaaagcg 900
ttacaactgg cggggctgca actggcggat attgatctca ttgaggctaa tgaagcattt 960
gctgcacagt tccttgccgt tgggaaaaac ctgggctttg attctgagaa agtgaatgtc 1020
aacggcgggg ccatcgcgct cgggcatcct atcggtgcca gtggtgctcg tattctggtc 1080
acactattac atgccatgca ggcacgcgat aaaacgctgg ggctggcaac actgtgcatt 1140
ggcggcggtc agggaattgc gatggtgatt gaacggttga attaa 1185

<210> SEQ ID NO 70
<211> LENGTH: 1179
<212> TYPE: DNA
<213> ORGANISM: Clostridium acetobutylicum

<400> SEQUENCE: 70
atgaaagaag ttgtaatagc tagtgcagta agaacagcga ttggatctta tggaaagtct 60
cttaaggatg taccagcagt agatttagga gctacagcta taaaggaagc agttaaaaaa 120
gcaggaataa aaccagagga tgttaatgaa gtcattttag gaaatgttct tcaagcaggt 180
ttaggacaga atccagcaag acaggcatct tttaaagcag gattaccagt tgaaattcca 240
gctatgacta ttaataaggt ttgtggttca ggacttagaa cagttagctt agcagcacaa 300
attataaaag caggagatgc tgacgtaata atagcaggtg gtatggaaaa tatgtctaga 360
gctccttact tagcgaataa cgctagatgg ggatatagaa tgggaaacgc taaatttgtt 420
gatgaaatga tcactgacgg attgtgggat gcatttaatg attaccacat gggaataaca 480
gcagaaaaca tagctgagag atggaacatt tcaagagaag aacaagatga gtttgctctt 540
gcatcacaaa aaaaagctga agaagctata aaatcaggtc aatttaaaga tgaaatagtt 600
cctgtagtaa ttaaaggcag aaagggagaa actgtagttg atacagatga gcaccctaga 660
tttggatcaa ctatagaagg acttgcaaaa ttaaaacctg ccttcaaaaa agatggaaca 720
gttacagctg gtaatgcatc aggattaaat gactgtgcag cagtacttgt aatcatgagt 780
gcagaaaaag ctaaagagct tggagtaaaa ccacttgcta agatagtttc ttatggttca 840
gcaggagttg acccagcaat aatgggatat ggacctttct atgcaacaaa agcagctatt 900

```
gaaaaagcag gttggacagt tgatgaatta gatttaatag aatcaaatga agcttttgca    960

gctcaaagtt tagcagtagc aaaagattta aaatttgata tgaataaagt aaatgtaaat   1020

ggaggagcta ttgcccttgg tcatccaatt ggagcatcag gtgcaagaat actcgttact   1080

cttgtacacg caatgcaaaa aagagatgca aaaaaaggct tagcaacttt atgtataggt   1140

ggcggacaag gaacagcaat attgctagaa aagtgctag                          1179
```

<210> SEQ ID NO 71
<211> LENGTH: 1179
<212> TYPE: DNA
<213> ORGANISM: Clostridium acetobutylicum

<400> SEQUENCE: 71

```
atgagagatg tagtaatagt aagtgctgta agaactgcaa taggagcata tggaaaaaca     60

ttaaaggatg tacctgcaac agagttagga gctatagtaa taaaggaagc tgtaagaaga    120

gctaatataa atccaaatga gattaatgaa gttatttttg gaaatgtact tcaagctgga    180

ttaggccaaa acccagcaag acaagcagca gtaaaagcag gattaccttt agaaacacct    240

gcgtttacaa tcaataaggt ttgtggttca ggtttaagat ctataagttt agcagctcaa    300

attataaaag ctggagatgc tgataccatt gtagtaggtg gtatggaaaa tatgtctaga    360

tcaccatatt tgattaacaa tcagagatgg ggtcaaagaa tgggagatag tgaattagtt    420

gatgaaatga taaaggatgg tttgtgggat gcatttaatg gatatcatat gggagtaact    480

gcagaaaata ttgcagaaca atggaatata acaagagaag agcaagatga attttcactt    540

atgtcacaac aaaaagctga aaaagccatt aaaaatggag aatttaagga tgaaatagtt    600

cctgtattaa taaagactaa aaaaggtgaa atagtctttg atcaagatga atttcctaga    660

ttcggaaaca ctattgaagc attaagaaaa cttaaaccta ttttcaagga aaatggtact    720

gttacagcag gtaatgcatc cggattaaat gatggagctg cagcactagt aataatgagc    780

gctgataaag ctaacgctct cggaataaaa ccacttgcta agattacttc ttacggatca    840

tatggggtag atccatcaat aatgggatat ggagcttttt atgcaactaa agctgcctta    900

gataaaatta atttaaaacc tgaagactta gatttaattg aagctaacga ggcatatgct    960

tctcaaagta tagcagtaac tagagattta aatttagata tgagtaaagt taatgttaat   1020

ggtggagcta tagcacttgg acatccaata ggtgcatctg gtgcacgtat tttagtaaca   1080

ttactatacg ctatgcaaaa aagagattca aaaaaaggtc ttgctactct atgtattggt   1140

ggaggtcagg gaacagctct cgtagttgaa agagactaa                          1179
```

<210> SEQ ID NO 72
<211> LENGTH: 1197
<212> TYPE: DNA
<213> ORGANISM: Saccahromyces cerevisiae

<400> SEQUENCE: 72

```
atgtctcaga acgtttacat tgtatcgact gccagaaccc caattggttc attccagggt     60

tctctatcct ccaagacagc agtggaattg ggtgctgttg ctttaaaagg cgccttggct    120

aaggttccag aattggatgc atccaaggat tttgacgaaa ttatttttgg taacgttctt    180

tctgccaatt tgggccaagc tccggccaga caagttgctt tggctgccgg tttgagtaat    240

catatcgttg caagcacagt taacaaggtc tgtgcatccg ctatgaaggc aatcattttg    300

ggtgctcaat ccatcaaatg tggtaatgct gatgttgtcg tagctggtgg ttgtgaatct    360
```

atgactaacg caccatacta catgccagca gcccgtgcgg gtgccaaatt tggccaaact 420
gttcttgttg atggtgtcga aagagatggg ttgaacgatg cgtacgatgg tctagccatg 480
ggtgtacacg cagaaaagtg tgcccgtgat tgggatatta ctagagaaca acaagacaat 540
tttgccatcg aatcctacca aaaatctcaa aaatctcaaa aggaaggtaa attcgacaat 600
gaaattgtac ctgttaccat taagggattt agaggtaagc ctgatactca agtcacgaag 660
gacgaggaac ctgctagatt acacgttgaa aaattgagat ctgcaaggac tgttttccaa 720
aaagaaaacg gtactgttac tgccgctaac gcttctccaa tcaacgatgg tgctgcagcc 780
gtcatcttgg tttccgaaaa agttttgaag gaaaagaatt tgaagccttt ggctattatc 840
aaaggttggg gtgaggccgc tcatcaacca gctgatttta catgggctcc atctcttgca 900
gttccaaagg ctttgaaaca tgctggcatc gaagacatca attctgttga ttactttgaa 960
ttcaatgaag ccttttcggt tgtcggtttg gtgaacacta agattttgaa gctagaccca 1020
tctaaggtta atgtatatgg tggtgctgtt gctctaggtc acccattggg ttgttctggt 1080
gctagagtgg ttgttacact gctatccatc ttacagcaag aaggaggtaa gatcggtgtt 1140
gccgccattt gtaatggtgg tggtggtgct tcctctattg tcattgaaaa gatatga 1197

<210> SEQ ID NO 73
<211> LENGTH: 2283
<212> TYPE: DNA
<213> ORGANISM: Escherichia coli

<400> SEQUENCE: 73
atgtccgagc ttaatgaaaa gttagccaca gcctgggaag gttttaccaa aggtgactgg 60
cagaatgaag taaacgtccg tgacttcatt cagaaaaact acactccgta cgagggtgac 120
gagtccttcc tggctggcgc tactgaagcg accaccaccc tgtgggacaa agtaatggaa 180
ggcgttaaac tggaaaaccg cactcacgcg ccagttgact ttgacaccgc tgttgcttcc 240
accatcacct ctcacgacgc tggctacatc aacaagcagc ttgagaaaat cgttggtctg 300
cagactgaag ctccgctgaa acgtgctctt atcccgttcg gtggtatcaa aatgatcgaa 360
ggttcctgca aagcgtacaa ccgcgaactg gatccgatga tcaaaaaaat cttcactgaa 420
taccgtaaaa ctcacaacca gggcgtgttc gacgtttaca ctccggacat cctgcgttgc 480
cgtaaatctg gtgttctgac cggtctgcca gatgcatatg gccgtggccg tatcatcggt 540
gactaccgtc gcgttgcgct gtacggtatc gactacctga tgaaagacaa actggcacag 600
ttcacttctc tgcaggctga tctggaaaac ggcgtaaacc tggaacagac tatccgtctg 660
cgcgaagaaa tcgctgaaca gcaccgcgct ctgggtcaga tgaaagaaat ggctgcgaaa 720
tacggctacg acatctctgg tccggctacc aacgctcagg aagctatcca gtggacttac 780
ttcggctacc tggctgctgt taagtctcag aacggtgctg caatgtcctt cggtcgtacc 840
tccaccttcc tggatgtgta catcgaacgt gacctgaaag ctggcaagat caccgaacaa 900
gaagcgcagg aaatggttga ccacctggtc atgaaactgc gtatggttcg cttcctgcgt 960
actccggaat acgatgaact gttctctggc gacccgatct gggcaaccga atctatcggt 1020
ggtatgggcc tcgacggtcg taccctggtt accaaaaaca gcttccgttt cctgaacacc 1080
ctgtacacca tgggtccgtc tccggaaccg aacatgacca ttctgtggtc tgaaaaactg 1140
ccgctgaact tcaagaaatt cgccgctaaa gtgtccatcg acacctcttc tctgcagtat 1200
gagaacgatg acctgatgcg tccggacttc aacaacgatg actacgctat tgcttgctgc 1260
gtaagcccga tgatcgttgg taaacaaatg cagttcttcg gtgcgcgtgc aaacctggcg 1320

```
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca agtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga aagttaaacc gattcgtgac gaagacggtc tggctatcga cttcgaaatc   1680
gaaggcgaat acccgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac gggtaacacc   1860
ccagacggtc gtcgtgctgg cgcgccgttc ggaccgggtg ctaacccgat gcacggtcgt   1920
gaccagaaag gtgcagtagc ctctctgact tccgttgcta aactgccgtt tgcttacgct   1980
aaagatggta tctcctacac cttctctatc gttccgaacg cactgggtaa agacgacgaa   2040
gttcgtaaga ccaacctggc tggtctgatg gatggttact tccaccacga agcatccatc   2100
gaaggtggtc agcacctgaa cgttaacgtg atgaaccgtg aaatgctgct cgacgcgatg   2160
gaaaacccgg aaaaatatcc gcagctgacc atccgtgtat ctggctacgc agtacgtttc   2220
aactcgctga ctaaagaaca gcagcaggac gttattactc gtaccttcac tcaatctatg   2280
taa                                                                2283
```

<210> SEQ ID NO 74
<211> LENGTH: 741
<212> TYPE: DNA
<213> ORGANISM: Escherichia coli

<400> SEQUENCE: 74

```
atgtcagtta ttggtcgcat tcactccttt gaatcctgtg gaaccgtaga cggcccaggt     60
attcgcttta tcaccttttt ccagggctgc ctgatgcgct gcctgtattg tcataaccgc    120
gacacctggg acacgcatgg cggtaaagaa gttaccgttg aagatttgat gaaggaagtg    180
gtgacctatc gccactttat gaacgcttcc ggcggcggcg ttaccgcatc cggcggtgaa    240
gcaatcctgc aagctgagtt tgttcgtgac tggttccgcg cctgcaaaaa agaaggcatt    300
catacctgtc tggacaccaa cggttttgtt cgtcgttacg atccggtgat tgatgaactg    360
ctggaagtaa ccgacctggt aatgctcgat ctcaaacaga tgaacgacga gatccaccaa    420
aatctggttg gagtttccaa ccaccgcacg ctggagttcg ctaaatatct ggcgaacaaa    480
aatgtgaagg tgtggatccg ctacgttgtt gtcccaggct ggtctgacga tgacgattca    540
gcgcatcgcc tcggtgaatt tacccgtgat atgggcaacg ttgagaaaat cgagcttctc    600
ccctaccacg agctgggcaa acacaaatgg gtggcaatgg gtgaagagta caaactcgac    660
ggtgttaaac caccgaagaa agagaccatg gaacgcgtga aaggcattct tgagcagtac    720
ggtcataagg taatgttcta a                                              741
```

<210> SEQ ID NO 75
<211> LENGTH: 2364
<212> TYPE: DNA
<213> ORGANISM: Lactococcus lactis

<400> SEQUENCE: 75

```
atgaaaaccg aagttacgga aaatatcttt gaacaagctt gggatggttt taaaggaacc     60
```

-continued

```
aactggcgcg ataaagcaag cgttactcgc tttgtacaag aaaactacaa accatatgat    120
ggtgatgaaa gctttcttgc tgggccaaca gaacgtacac ttaaagtaaa gaaaattatt    180
gaagatacaa aaaatcacta cgaagaagta ggatttccct tcgatactga ccgcgtaacc    240
tctattgata aaatccctgc tggatatatc gatgctaatg ataaagaact tgaactcatc    300
tatgggatgc aaaatagcga acttttccgc ttgaatttca tgccaagagg tggacttcgt    360
gttgctgaaa agattttgac agaacacggt ctctcagttg acccaggctt gcatgatgtt    420
ttgtcacaaa caatgacttc tgtaaatgat ggaatctttc gtgcttatac ttcagcaatt    480
cgtaaagcac gtcatgctca tactgtaaca ggtttgccag atgcttactc tcgtggacgt    540
atcattggtg tctatgcacg tcttgccctt tacggtgctg attaccttat gaaggaaaaa    600
gcaaaagaat gggatgcaat cactgaaatt aacgaagaaa acattcgtct taaagaagaa    660
attaatatgc aataccaagc tttgcaagaa gttgtaaact ttggtgcttt atatggtctt    720
gatgtttcac gtccagctat gaacgtaaaa gaagcaatcc aatgggttaa catcgcttat    780
atggcagtat gtcgtgtcat taatggagct gcaacttcac ttggacgtgt tccaatcgtt    840
cttgatatct ttgcagaacg tgaccttgct cgtggaacat ttactgaaca agaaattcaa    900
gaatttgttg atgatttcgt tttgaagctt cgtacaatga aatttgcgcg tgcagctgct    960
tatgatgaac tttattctgg tgacccaaca ttcatcacaa catctatggc tggtatgggt   1020
aatgacggac gtcaccgtgt cactaaaatg gactaccgtt tcttgaacac acttgataca   1080
atcggaaatg ctccagaacc aaacttgaca gtcctttggg attctaaact tccttactca   1140
ttcaaacgtt attcaatgtc tatgagccac aagcattctt ctattcaata tgaaggtgtt   1200
gaaacaatgg ctaaagatgg atatggcgaa atgtcatgta tctcttgttg tgtctcacca   1260
cttgatccag aaaatgaaga aggacgtcat aacctccaat actttggtgc gcgtgtaaac   1320
gtcttgaaag caatgttgac tggtttgaac ggtggttatg atgacgttca taaagattat   1380
aaagtattcg acatcgaacc tgttcgtgac gaaattcttg actatgatac agttatggaa   1440
aactttgaca aatctctcga ctggttgact gatacttatg ttgatgcaat gaatatcatt   1500
cattacatga ctgataaata taactatgaa gcagttcaaa tggccttctt gcctactaaa   1560
gttcgtgcta acatgggatt tggtatctgt ggattcgcaa atacagttga ttcactttca   1620
gcaattaaat atgctaaagt taaaacattg cgtgatgaaa atggctatat ctacgattac   1680
gaagtagaag gtgatttccc tcgttatggt gaagatgatg atcgtgctga tgatattgct   1740
aaacttgtca tgaaaatgta ccatgaaaaa ttagcttcac acaaacttta caaaaatgct   1800
gaagctactg tttcactttt gacaattaca tctaacgttg cttactctaa acaaactggt   1860
aattctccag tacataaagg agtattcctc aatgaagatg gtacagtaaa taaatctaaa   1920
cttgaattct tctcaccagg tgctaaccca tctaataaag ctaagggtgg ttggttgcaa   1980
aatcttcgct cattggctaa gttggaattc aaagatgcaa atgatggtat ttcattgact   2040
actcaagttt cacctcgtgc acttggtaaa actcgtgatg aacaagtgga taacttggtt   2100
caaattcttg atggatactt cacaccaggt gctttgatta atggtactga atttgcaggt   2160
caacacgtta acttgaacgt aatggacctt aaagatgttt acgataaaat catgcgtggt   2220
gaagatgtta tcgttcgtat ctctggttac tgtgtcaata ctaaatacct cacaccagaa   2280
caaaaacaag aattaactga acgtgtcttc catgaagttc tttcaaacga tgatgaagaa   2340
gtaatgcata cttcaaacat ctaa                                          2364
```

<210> SEQ ID NO 76
<211> LENGTH: 2325
<212> TYPE: DNA
<213> ORGANISM: Streptococcus equinus

<400> SEQUENCE: 76

```
atggcgactg ttaaaacaaa tgcagatgtt tttgaaaaag cctgggaagg ctttaaaggt     60
actgactgga aagaaaaagc cagcgtttct cgcttcgttc aagctaacta cacaccatat    120
gatggtgatg aaagcttctt agcaccagct actgaacgct ctcttaaaat caagaaaatc    180
attgaagaca ctaaagctga atacgaagca actcgtttcc caatggacac tcgtccaaca    240
tcaatcgcag atattcctgc cggctatatt caaaaagacg atgaattaat ctacggtatt    300
caaaatgatg agttgttcaa attgaatttc atgccaaaag gtggtatccg tatggcagaa    360
acagcactta aagaacatgg ttatgaacca gatcctgctg ttcatgaaat tttcacaaaa    420
tacactacta cagtaaatga cggaattttc cgcgcttata catctaatat ccgccgtgcc    480
cgtcacgctc acacagtaac tggtcttcca gatgcttact cacgcggacg tatcatcggt    540
gtttatgctc gtcttgctct ttatggtgca gactacttga tgcaagaaaa agttaacgac    600
tggaacgcta tcacagaaat cgacgaagaa tctattcgtc ttcgcgaaga agttaacatg    660
caataccaag ctcttggtga agttgttaaa cttggtgacc tttacggact tgatgtccgt    720
aaaccagcca tgaacgttaa agaagctatc caatgggtaa acatcgcctt catggccgta    780
tgtcgtgtta tcaacggtgc tgctacttct cttggacgtg tgccaatcgt tcttgatatc    840
tttgctgaac gtgaccttgc tcgtggtact ttcacagaat cagaaatcca agaatttgtc    900
gatgactttg tcttgaaact tcgtactgta aaatttgctc gtactaaagc ttacgacgaa    960
ctttactctg gtgacccaac attcatcact acatctatgg ctggtatggg tgctgacggt   1020
cgtcaccgtg ttactaaaat ggactaccgt ttcttgcaca cacttgataa tatcggtaac   1080
gctccagaac caaacttgac agttctttgg actgataaat tgccatattc attccgtcgc   1140
tactgtatga aaatgtcaca caaacactcg tcaatccaat acgaaggtgt gacaacaatg   1200
gctaaagatg gttacggtga aatgtcatgt atctcatgtt gtgtatcacc acttgaccca   1260
gaaaacgaag aacaacgtca caacatccaa tactttggtg ctcgtgtaaa cgtccttaaa   1320
gctcttctta ctggtttgaa cggtggttat gacgacgtcc acaaagacta caaagtattt   1380
gatatcgaac cagttcgtga tgaaatcctt gatttcgaaa cggttaaagc taatttcgaa   1440
aaatctcttg attggttgac ttcaacttac gtagatgccc ttaacatcat tcactacatg   1500
actgataaat acaactacga agctgttcaa atggcattct tgccaactaa acaacgtgcc   1560
aacatgggat tcggtatctg tggtttcgct aataccgttg atactttatc agcaatcaaa   1620
tacgctactg ttaaaccaat ccgtgacgaa gatggttaca tctacgacta cgaaacaact   1680
ggtgacttcc ctcgttgggg tgaagatgac cctcgttcta acgaacttgc tgaatggttg   1740
gtagaagctt acactactcg tcttcgtagc cacaaacttt acaagaacgc tgaagctact   1800
gtatcacttc ttacaatcac ttcaaacgtt gcttattcta aacaaactgg taactctcca   1860
gttcacaaag gtgtttacct taacgaagat ggtactgtaa acctttctaa acttgaattc   1920
ttctcaccag gtgccaaccc atctaacaaa gctcgtggtg gttggttgca aaacttgaac   1980
tctcttgcaa gccttgactt ctcatatgct gcagatggta tctcacttac aactcaagtt   2040
tctccacgcg ctcttggtaa gacatttgat gaacaagttg ataacttggt aactatcctt   2100
gatggttact tcgaaaacgg tggacaacac gttaacttga acgtcatgga ccttaaagat   2160
```

gtttatgaca agattatgaa tggtgaagat gttatcgttc gtatatcagg ttactgtgtc 2220
aacactaaat accttactaa agaacaaaag acagaattga cacaacgcgt cttccacgaa 2280
gttctttcaa tggatgatgt tgctgaaact gttgctgcta aataa 2325

<210> SEQ ID NO 77
<211> LENGTH: 789
<212> TYPE: DNA
<213> ORGANISM: Streptococcus equinus

<400> SEQUENCE: 77
atgactgaaa tagattacgg aaaagtgaca ggaatgattc attcaacaga aagttttggt 60
tctgtggatg ggcctggtgt tcgctttgtc atttttatgc aaggctgcaa gatgcgttgc 120
caatattgtc acaatccaga tacttgggca ttagagacaa ataattctcg tgaacgcact 180
gttgatgatg ttttagcaga agctttgcgt tatcgacatt tctggggtga aaatggtggg 240
attaccgttt caggtggtga agccatgttg caaattgagt ttgtaacagc ccttttttacc 300 aaggctaaag aattaggaat tcattgcacg cttgatacgt gtggttttac gttccgagat 360
acgcctgaat atcacgaaat tgtggataag ttactagctg tgacggattt agttctttta 420
gatttaaaag aaatcaatcc taaacaacac attgttgtaa cacgtcaacc caatactaat 480
attctagctt ttgctcgtta tttgtctgat aagggtgttc cagtctggat tcgtcatgtc 540
ttggttccag gattgaccga ttttgatgaa gacttaattg agctagggaa atttgttgaa 600
acgttaaaaa acgtggataa atttgaaatt ttgccttatc ataccttggg tgaattcaag 660
tggcgtgaat tgggaattcc ttataccctt gaaggggtta aaccaccgac tagagaacgt 720
gtccaaaatg ctaaaaagct tatgcataca gagtcttaca cagactacat gaaacgcatt 780
catcactag 789

<210> SEQ ID NO 78
<211> LENGTH: 717
<212> TYPE: DNA
<213> ORGANISM: Clostridium thermocellum

<400> SEQUENCE: 78
atgacattaa agggcaggat acactcattt gaatcttttg ggacactgga cggaccgggt 60
ataagatttg tggttttcat gcagggctgt cccttgcgtt gtatatattg ccacaacagg 120
gatacctggg atgttaatgc ggggagtgag tacactcccc ggcaagtaat tgatgaaatg 180
atgaaataca tagactatat aaaggtctcc ggaggcggaa taactgttac cggcggggag 240
cctgttctcc aggccgattt tgtggccgag gtgttcagac ttgcaaaaga gcagggagtg 300
catacggcgc tggataccaa tggatttgct gacatagaga aggttgaaag gcttataaaa 360
tacaccgatc ttgtattgct ggatataaag catgcccggg aggataaaca taagataatt 420
accggtgtgt ccaacgaaaa aatcaagcgt tttgcgctgt atctttcgga ccagggagtg 480
cctatctgga taagatatgt ccttgtcccc ggatataccg acgatgaaga tgaccttaaa 540
atggcggctg atttcataaa aaagcttaaa acggtggaaa aaatcgaagt tcttccttat 600
cacaacatgg gagcatacaa atgggaaaaa cttggtcaga aatacatgct tgaaggagta 660
aaggggccga gtgcgcaaga ggtggaaaaa gcaaagagga ttctgtcagg caaataa 717

<210> SEQ ID NO 79
<211> LENGTH: 1269
<212> TYPE: DNA
<213> ORGANISM: Jeotgalicoccus sp; ATCC8456

<400> SEQUENCE: 79
atggcaacac ttaagaggga taagggctta gataatactt tgaaagtatt aaagcaaggt 60
tatctttaca caacaaatca gagaaatcgt ctaaacacat cagttttcca aactaaagca 120
ctcggtggta aaccattcgt agttgtgact ggtaaggaag gcgctgaaat gttctacaac 180
aatgatgttg ttcaacgtga aggcatgtta ccaaaacgta tcgttaatac gctttttggt 240
aaaggtgcaa tccatacggt agatggtaaa aaacacgtag acagaaaagc attgttcatg 300
agcttgatga ctgaaggtaa cttgaattat gtacgagaat taacgcgtac attatggcat 360
gcgaacacac aacgtatgga aagtatggat gaggtaaata tttaccgtga atctatcgta 420
ctacttacaa aagtaggaac acgttgggca ggcgttcaag caccacctga agatatcgaa 480
agaatcgcaa cagacatgga catcatgatc gattcattta gagcacttgg tggtgccttt 540
aaaggttaca aggcatcaaa agaagcacgt cgtcgtgttg aagattggtt agaagaacaa 600
attattgaga ctcgtaaagg gaatattcat ccaccagaag gtacagcact ttacgaattt 660
gcacattggg aagactactt aggtaaccca atggactcaa gaacttgtgc gattgactta 720
atgaacacat tccgcccatt aatcgcaatc aacagattcg tttcattcgg tttacacgcg 780
atgaacgaaa acccaatcac acgtgaaaaa attaaatcag aacctgacta tgcatataaa 840
ttcgctcaag aagttcgtcg ttactatcca ttcgttccat tccttccagg taaagcgaaa 900
gtagacatcg acttccaagg cgttacaatt cctgcaggtg taggtcttgc attagatgtt 960
tatggtacaa cgcatgatga atcactttgg gacgatccaa atgaattccg cccagaaaga 1020
ttcgaaactt gggacggatc accatttgac cttattccac aaggtggtgg agattactgg 1080
acaaatcacc gttgtgcagg tgaatggatc acagtaatca tcatggaaga aacaatgaaa 1140
tactttgcag aaaaaataac ttatgatgtt ccagaacaag atttagaagt ggacttaaac 1200
agtatcccag gatacgttaa gagtggcttt gtaatcaaaa atgttcgcga agttgtagac 1260
agaacataa 1269

<210> SEQ ID NO 80
<211> LENGTH: 684
<212> TYPE: DNA
<213> ORGANISM: Aspergillus niger

<400> SEQUENCE: 80
atgttcaact cacttctatc cggtactact acaccaaact ccggccgtgc atctcctccc 60
gccagcgaaa tgcccatcga taatgatcac gtggccgttg cccgtccagc tccccgccgc 120
cgccgcattg tagtagccat gacgggtgcc actggagcca tgctcggcat caaagtccta 180
attgctctgc gccgtctaaa tgtggagaca cacctggtga tgagtaaatg ggcggaggct 240
acgatcaaat acgagactga ctaccatccc tcaaacgtgc gagcgctggc cgactacgtg 300
cacaacatca atgacatggc cgccccagta tccagcggct cattccgcgc ggacggaatg 360
attgtggtac cgtgcagcat gaaaacattg gctgctatcc actcgggctt ttgcgacgat 420
ctcatttcaa ggacagcaga tgtgatgctc aaggagcgca ggcggttggt gctagtagcg 480
cgggagacgc cattgagcga gatccatctg cgaaacatgt tggaggttac acgcgctggg 540
gcagtcatct tccccccagt accggcgttc tacatcaagg ccggaagtat cgaggacctc 600
atcgaccaga gtgttggacg aatgttggat ttatttgacc tcgacacggg ggattttgaa 660
cgttggaatg gatgggaaaa ataa 684

<210> SEQ ID NO 81
<211> LENGTH: 1555
<212> TYPE: DNA
<213> ORGANISM: Aspergillus niger

<400> SEQUENCE: 81
atgtctgcgc aacctgctca cctgtgtttc cgctccttcg tcgaagccct caaggtcgac 60
aacgaccttg ttgaaatcaa taccccaatt gaccccaatc tcgaagctgc tgctattacc 120
cgccgagtat gtgagaccaa cgacaaggct cctttattca acaacctcat cggcatgaaa 180
aatggcctct tccgtatact tggggctcct ggctctctca ggaagtcgtc tgctgatcgc 240
tacggccgcc ttgctcgtca cctagccctc ccacctacgg cctcaatgcg tgagattctc 300
gataagatgc tctccgccag cgatatgcct cccatccctc cgaccattgt tcccaccggg 360
ccatgcaagg agaacagctt agatgactct gaattcgacc ttaccgaact ccccgttcct 420
cttattcaca aatcggatgg tggtaaatac atccaaacct atggcatgca cattgtgcag 480
tctccggatg gaacctggac caactggtct attgcccgtg cgatggtcca tgacaagaac 540
catctgaccg gcctggttat tccccctcag cacatctggc agattcacca gatgtggaag 600
aaggaaggcc gcagtgacgt tccctgggct ttggcctttg gtgtcccacc cgctgccatt 660
atggcctcta gcatgcctat tcccgatggt gtcaccgaag ctgggtacgt gggagctatg 720
acgggatcct ccctggagct tgttaaatgt gatacgaacg atctatatgt ccccgctacc 780
tcagaaatcg ttctcgaggg cacactctct atcagcgaga caggcccaga gggacctttc 840
ggtgagatgc atggttacat cttccccggg gatactcacc tcggcgccaa atacaaggtt 900
aaccggatca cctaccgcaa caacgccatc atgcccatgt cttcttgtgg ccgcttgacg 960
gatgaaacgg taagtttagt ccctgtcctg ccatttatag ccaaggacta acacggtcta 1020
gcacaccatg atcggctctc tggctgcggc ggagatccgt aagctctgcc agcagaatga 1080
cctccctatc actgatgcct tcgctccttt cgagtctcaa gttacctggg ttgctctgcg 1140
ggtcgatact gagaagctac gtgccatgaa gacaacgtct gagggattcc gcaagagagt 1200
gggagacgtc gtcttcaacc acaaggccgg atacaccatt catcgtctgg tgttggtcgg 1260
tgacgacatt gatgtctatg aaggaaagga tgtgctctgg gcgttctcca cccgttgccg 1320
tcctggtatg gacgagactt tgtttgagga tgttcgtggg ttccccttga ttccgtatat 1380
gggacacggg aatgggcccg cccaccgcgg cggaaaggtt gtgtccgacg ctcttatgcc 1440
gactgagtac accactggtc gcaactggga ggctgctgac ttcaaccaat cttatcccga 1500
ggatctgaag cagaaggtgt tggacaactg gacgaagatg ggtttcagca actaa 1555

<210> SEQ ID NO 82
<211> LENGTH: 2224
<212> TYPE: DNA
<213> ORGANISM: Aspergillus niger

<400> SEQUENCE: 82
atgggcaccc cgataaatcg tgaagagatt gaccgcgtgc tgcgaatgaa acgcaatcag 60
cgcgaggctc gagcgtgtta tccttgccgc cagcgcaagg tgaaatgcga cagcactcag 120
ccgtgtcgaa catgtcgccg acgaggccat ccccaaatat gtgtgtatga ccaagattcg 180
tctgggtcta aaaaggctcg tagcaccggc caaagacgtt cctctgctgc ttctcgtgga 240
acaaatcaga caccaaccgc cgagcaggca ttcgatgccg aaccacaatc tctgccctca 300
gcgcgcagtt taccagaagt ccagccaaaa acaagacagt actatagtac tcgaatcccg 360
tcttccgatg gccccgataa tgatcttatc tactcgggcg acaactcggt attgtcttat 420
ttgcgcaacc ggacgcaaga taccaatggc tccatgaccc gtgaggtggg ctctgttcta 480
ggcctgcaaa atacctacgg cagttatcca tttatggact ttcggacacc ccaggaccgg 540
tggaaggagc ttctacgtat tattccgcag cgagcggaac tgttgaagta agcacatctt 600
attgttgttt ttgataacct ctaacggata gcaggttctt ccatttctac agaatatcag 660
cttacccttt caatccgatc atacttgaca ttgagagatt tgagcaagat gtgtgttcat 720
acctcaatga tcttgcagca ggagagctgc agaacacttc aaagatttgc gaacgttggg 780
ccactgatcg gtctgtcggg ctgatcagcc tgctacttgc ggccttggct tccggtgcgc 840
attattctga cctggattac atgcaaagaa cagagctatg ccaggatttt ggtacgtaac 900
cagtatcttt acctatgcat gtttgactaa acaggagaag caaaacgatc ctttcaagct 960
cttcgactag ccaattttct tttccgtccg acgatggata taatacaagc acttctaatc 1020
ataggaaaca ctctgcaaaa caatggccag tctgatgcag catgggtttt gttagggaca 1080
acagtccgtc tcgcgcagac attaggtctt cacacagaaa agagtgtagc acgcctaccg 1140
gatcatgtca aatacaaagc acgaaagcta tggtacataa accatgctac aggtaacgac 1200
acaagctgac gcggctacag gtacactgtc gtttggcaag attgcctgct ctgtttatgt 1260
tacgaccggc ctcgcgtagt ctctatgacc gggtgggctc cagattattc aatcctctcg 1320
agcagcgaac tatctttcac agaagctatg tattttctat gccaaactgc cttaaatatg 1380
atcacaacag acggaccgga gatatcggaa aatgcgcgac agcttgacat tttggccacg 1440
attgatagcc tcaaccaacg cactcagcca tatctgcgtg accgccagga atgcaaaacc 1500
ctccaacaca atctggagca cctggcgtta cgaatgcaca tgtctctagt tatttccgtc 1560
ctgacacgtc cagcactgaa gcgcactgta atgcaagacg cgtcctatga catcttgcgc 1620
acccgcgcca aattgagcct gatcgacgcc tctagggcct ttttggattt tcaggctctg 1680
agtgtggtac ccctccgaag ctggtcaatg gtgcacacgg tgcttagttc cactttactt 1740
ctctgcattt gggaggagac ccgaaacgat cccgagtgtc gtgatttaca gcaaaaggtg 1800
attgaggtct tttctgccgc tggcacagtg ggcacagtgg agaacacagc atcggagaat 1860
gggcaatggc tatcggaacg gcatatacga gcgctaatca cactgcgcaa ttcggtccga 1920
acggcagtcg aacgtgaaaa gggggaggca agcgttggga cagaacgcgc ggagcagccc 1980
cagccttttt ttcctgtcta tgggtatgtg cacccgctat tgtctgataa gtggagctgt 2040
gcgatggatg ctgattttgc agtatgccga acgggatccc ggatgacttc ggtcaagact 2100
tctcaccagc aagctatctt gactccatta tgaacggtat gctgaggctc ccgactattt 2160
atcgatcgaa ctaaccgtcg tagtacccat gtttgactta tcccaagagc tgggttttct 2220
ttga 2224

<210> SEQ ID NO 83
<211> LENGTH: 723
<212> TYPE: DNA
<213> ORGANISM: Aspergillis oryzae

<400> SEQUENCE: 83
atgctctcct ccttccttcc ttccggcacc aacacatcaa actccggtca tcacagcccc 60
gacaatgcat ccgaaacaca atcaaccaca cagtccgcac cactcgagca catatccacc 120
gcaatgccac cagtcccaac caaaggtcga cgcaaacgaa tcgtcgtagc catgaccgga 180
gccaccggct caatcctggg aatcaaagtc ctcatcgccc ttcgccgcct caacatcgaa 240
acccacctcg taatcagcaa atgggccgaa gcaaccataa aatacgaaac agactatcac 300
ccgcggaatg ttcgtgccct agccgactac gtccacaaca taaacgacat ggcggcaccc 360
atatccagcg ggtccttcaa gaccgacggc atgatcgtcg tcccatgttc catgaaaaca 420
ctcgccgcta tcaactccgg gttctgtgaa gatctcatct cccggactgc agacgtcatg 480
ctcaaggagc gcaggaagct ggttcttgtt gctagggaaa cgcctcttag tgatattcat 540
cttcgcaata tgctttctgt gtctcaggct ggggctatta tcttcccgcc tgtgccggcg 600
tactatatca aggcggcgtc tgtggatgaa cttgtggatc agagtgttgg gcgcatgttg 660
gatctgtttg atctggatac ggctgatttt gctagatggg agggttggaa gaaggataac 720
tga 723

<210> SEQ ID NO 84
<211> LENGTH: 1512
<212> TYPE: DNA
<213> ORGANISM: Aspergillis oryzae

<400> SEQUENCE: 84
atggccgcga ttaacgaagt cgatcattcc ttccgcgcct ttgtcgaagc cctcaaggcc 60
gacgatgact tggtcgagat caacaccgag atcgactcta acctggaagc cgccgcgatc 120
actcgtcttg tctgcgagac cgatgacaaa gcccccctct tcaataacct caaaggcatg 180
ggaaagaatg gcctcttccg tatcctgggc gctccgggct ctctcagaaa gtccaaacgt 240
gaccgctacg gccggctcgc ccgccacctg gcgctgcctc ctactgccag catgaaggaa 300
atccttgaca agatgctctc cgcctctcag ctacctccca ttgaccctaa gattgtagag 360
actggtcctg tgaaggacaa ttcccttgaa ggcgacgaaa tcgacctcac tgcgctccca 420
gtgcccatgg tgcacaagtc tgacggcggc aaatatctac aaacatacgg aatgcatgtc 480
gtgcagtctc ctgatggaaa gtggacgaac tggtctatcg cccgtgcgat ggtcaaggac 540
aagaaccatt tgacaggcct ggttattgag ccccagcata tttggcaaat ccaccagatg 600
tggaaaaagg agggaaagga tgtcccgtgg gctctatgct tcggagttcc tcctgccgct 660
atcatggcat catcgatgcc catcccggat ggtgtaactg aggctggcta cgttggtgcc 720
atgactggtc gcgccttgga gctcgtcaag tgcgacacca accatctcta cgtccctgcc 780
aatgcggaga ttgtcctcga gggtaccctc tccatcactg aaaccgccga tgaaggcccc 840
ttcggtgaga tgcacggcta cgtcttcccc ggcgatagcc acaagtgtcc cgtttacaaa 900
gttaacaaga tcacctaccg caccgatgct atcctgccca tgtccgcctg cggtcgtctt 960
accgacgaga cccatactat gattggctcg ttggctgccg ctgagattcg taaaatttgc 1020
caactggccg gcctccccat caccgacacc ttttctccct tcgaggcaca ggttacctgg 1080
gtggctctca aagttgacac cgcaaagctt cgtcaaatga agctagcccc taaagagctt 1140
cagaaatggg tcggagacgt ggtctttaac cacaaggctg ggtacactat ccaccgcctg 1200
gtcctggttg gcgatgatat tgacccgtat gagtggaagg atgtcatgtg ggctttcgca 1260
acacggtgtc gacccaatgc tgatgaaatg ttctttgaag acgtccgtgg tttccccctt 1320
atcccgtata tgggtcacgg cacggggtcg cccaccaagg gtggtaaggt ggtttccgac 1380
gctctgatgc ccacagagta taccacaggt gctgattggg aagctgctga ctttgagcac 1440
tcctatccgg aggagatcaa ggccaaggtg agggccaact gggaggcttt gggattcaga 1500
aaacaggatt aa 1512

<210> SEQ ID NO 85
<211> LENGTH: 723
<212> TYPE: DNA
<213> ORGANISM: Aspergillis oryzae

<400> SEQUENCE: 85

```
atgctctcct ccttccttcc ttccggcacc aacacatcaa actccggtca tcacagcccc     60

gacaatgcat ccgaaacaca atcaaccaca cagtccgcac cactcgagca catatccacc    120

gcaatgccac cagtcccaac caaaggtcga cgcaaacgaa tcgtcgtagc catgaccgga    180

gccaccggct caatcctggg aatcaaagtc ctcatcgccc ttcgccgcct caacatcgaa    240

acccacctcg taatcagcaa atgggccgaa gcaaccataa aatacgaaac agactatcac    300

ccgcggaatg ttcgtgccct agccgactac gtccacaaca taaacgacat ggcggcaccc    360

atatccagcg ggtccttcaa gaccgacggc atgatcgtcg tcccatgttc catgaaaaca    420

ctcgccgcta tcaactccgg gttctgtgaa gatctcatct cccggactgc agacgtcatg    480

ctcaaggagc gcaggaagct ggttcttgtt gctagggaaa cgcctcttag tgatattcat    540

cttcgcaata tgctttctgt gtctcaggct ggggctatta tcttcccgcc tgtgccggcg    600

tactatatca aggcggcgtc tgtggatgaa cttgtggatc agagtgttgg gcgcatgttg    660

gatctgtttg atctggatac ggctgatttt gctagatggg agggttggaa gaaggataac    720

tga                                                                  723
```

<210> SEQ ID NO 86
<211> LENGTH: 1050
<212> TYPE: DNA
<213> ORGANISM: Picrophilus torridus

<400> SEQUENCE: 86

```
ttgaatgatc ttaatgttta tggtgaaaaa ataagaaata tgcttcttga acttggcatt     60

tataataaat cagatgatta ttcacctgat attaaataca ataaaacgtt ccacgcaaat    120

ggatacccaa taacaggtct ttataaattc cttggatact atgataggga taataacata    180

gccaactttc catcgatatc gttcacaacg aacttttcat catgtgatgt tacatgcagg    240

gtattaagat caggcaatga caggatcata ttcaacggga aaaacaatga aaagtattac    300

aaaagggctg aaaaggccct gtcatttctc aggaaaaaat atagaataga tgcagcattt    360

gagtttaaca tcaggataaa tagaagatac agggatgcca aaggccttgg agaatcggca    420

gccgtggcat cggcaaccgc cagggccgtt gccgcagcag tctttggcat ggatgctgca    480

aaagacaggg gttttgtatc atacctggcc aggcatgtct ctggctccgg taccagatct    540

gcggcaggaa acctttcaat gtggctttca tatcctggaa tagacgattt atcttcaatt    600

ggcttcgaaa taagaaaaga cgatttattc catttctatg ccataccaat gagatcaaga    660

atagagacat taaatgcaca tgattatgca tcctcatcaa ttttttataa tgcatgggtc    720

aaatcaaaat tttttgatat aatagacatc attgaaaaca aattcaatac aaggatgatg    780

cttgaatact ccatgaagga tatgtacagg ctgcaggcgc ttttaatatc ctctggatat    840

atcatatatg aaaagcatta tttagacatt ataagaaaat taagatcatc attaaataac    900

tacaaaaacg tttatttcac atctgataca ggaacaagca ttgttgttat gtcaacatca    960

atgaatgagc tttcaaggtt cgttaacgat cttgatcttg atggtataag cggcaatttt   1020

ccagagaaga tcattataga ggaactatga                                    1050
```

<210> SEQ ID NO 87
<211> LENGTH: 975
<212> TYPE: DNA
<213> ORGANISM: Picrophilus torridus

<400> SEQUENCE: 87
atggaaaatt acaatgttaa gacaagggcg ttcccaacaa taggcataat actgcttggt 60
gggatctcgg ataaaaagaa caggataccg ctgcatacaa cggcaggcat agcatatact 120
ggtataaaca atgatgttta cactgagaca aagctttatg tatcaaaaga tgaaaaatgc 180
tatattgatg gaaaggaaat tgatttaaat tcagatagat caccatcgaa ggttattgat 240
aaattcaagc atgaaatact tatgagagta aatcttgatg atgaaaataa cctttcaatt 300
gattcaagga actttaatat attaagtggc agctcagatt ctggggccgc tgcactggga 360
gagtgcatag aatcaatttt tgaatacaat ataaatatat ttacatttga aaacgatctt 420
cagaggatat cagaaagtgt tggaagaagc ctttacggtg gtttaacagt aaactatgcc 480
aatggcaggg aatcattaac agagccatta cttgagcctg aggcatttaa taactttaca 540
ataattggtg cacattttaa cattgataga aaaccatcaa atgagattca tgaaaatatc 600
ataaaacatg aaaattacag ggaaagaata aaaagtgctg agagaaaggc gaaaaaactt 660
gaggagctat caaggaatgc aaacataaag ggtatctttg aacttgcaga atccgataca 720
gtggaatacc ataaaatgct ccatgatgtt ggcgttgaca taataaatga tagaatggag 780
aacctcattg aaagggtaaa agaaatgaaa aataacttct ggaattcata catagttacc 840
ggcggcccga acgtttttgt aataacagag aaaaaggacg ttgataaggc aatggaagga 900
ttaaatgatc tgtgcgatga tataagatta ttaaaagttg caggaaagcc acaggtcatt 960
tcaaaaaact tttaa 975

<210> SEQ ID NO 88
<211> LENGTH: 1191
<212> TYPE: DNA
<213> ORGANISM: Saccharomyces cerevisiae

<400> SEQUENCE: 88
atgaccgttt acacagcatc cgttaccgca cccgtcaaca tcgcaaccct taagtattgg 60
gggaaaaggg acacgaagtt gaatctgccc accaattcgt ccatatcagt gactttatcg 120
caagatgacc tcagaacgtt gacctctgcg gctactgcac ctgagtttga acgcgacact 180
ttgtggttaa atggagaacc acacagcatc gacaatgaaa gaactcaaaa ttgtctgcgc 240
gacctacgcc aattaagaaa ggaaatggaa tcgaaggacg cctcattgcc cacattatct 300
caatggaaac tccacattgt ctccgaaaat aactttccta cagcagctgg tttagcttcc 360
tccgctgctg gctttgctgc attggtctct gcaattgcta agttatacca attaccacag 420
tcaacttcag aaatatctag aatagcaaga aaggggtctg gttcagcttg tagatcgttg 480
tttggcggat acgtggcctg ggaaatggga aaagctgaag atggtcatga ttccatggca 540
gtacaaatcg cagacagctc tgactggcct cagatgaaag cttgtgtcct agttgtcagc 600
gatattaaaa aggatgtgag ttccactcag ggtatgcaat tgaccgtggc aacctccgaa 660
ctatttaaag aaagaattga acatgtcgta ccaaagagat ttgaagtcat gcgtaaagcc 720
attgttgaaa aagatttcgc cacctttgca aaggaaacaa tgatggattc caactctttc 780
catgccacat gtttggactc tttccctcca atattctaca tgaatgacac ttccaagcgt 840
atcatcagtt ggtgccacac cattaatcag ttttacggag aaacaatcgt tgcatacacg 900

```
tttgatgcag gtccaaatgc tgtgttgtac tacttagctg aaaatgagtc gaaactcttt    960

gcatttatct ataaattgtt tggctctgtt cctggatggg acaagaaatt tactactgag   1020

cagcttgagg ctttcaacca tcaatttgaa tcatctaact ttactgcacg tgaattggat   1080

cttgagttgc aaaaggatgt tgccagagtg attttaactc aagtcggttc aggcccacaa   1140

gaaacaaacg aatctttgat tgacgcaaag actggtctac caaaggaata a            1191
```

<210> SEQ ID NO 89
<211> LENGTH: 1182
<212> TYPE: DNA
<213> ORGANISM: Schizosaccharomyces pombe

<400> SEQUENCE: 89

```
atggacaaaa aggtttatca atgcaccgtt agtgcgcctg ttaatattgc agtaattaaa     60

tactggggaa agagagatgt ggcattgaac ttgcctacca atagctcgat cagtgtgacc    120

ctttctcaag atgacttacg tactgttact acagctagtt gtagcgagaa gtttgagaat    180

gatacactgt ggttaaatgg aaacgctgag gaaatctttg ccaataaacg acttcgtgtc    240

tgtgtagagg aactgcgtaa agctagatta gatctcgaag aggaaaatga tgatcttgac    300

aagattggtg cattgaagct tcatgtcgtt tcagaaaaca acttccctac tgctgctggt    360

ttggcatctt cagctgctgg ttatgctgct ttttgtgaag caatcgctag attgtacgat    420

ttaccatgga cacccactca attatctcgc attgctagac aggggtctgg aagtgcttgt    480

cgtagcttgt ttgggggcta tgtagcctgg gagatgggcg agcttcatag cggtgctgat    540

agtgtagcag ttcaagttga acctgttgaa aattggcccg aaatacgtgt tgctgtttta    600

gtagcgtccg ctgccaaaaa aggggtttcc tcaacagctg gcatgcaagc tacagttgca    660

tcttctacct tgttccaaca tcgtattcaa aacatcgttc cacaacgtat ccaagaaatg    720

aagaccgcca ttcgtgagcg tgattttgag acttttgcga agcttaccat gactgattcc    780

aatcaattcc atgcgtgctg ccttgatact ttccccccta tcttttactt gaacgatact    840

tcacgtgcgg ttatccgagt tgttgagaat ataaatgcta ctgctggaaa gaccattgct    900

gcctatacat ttgatgctgg cccaaatgct gttatttact tcttggaaga aaactccgag    960

attgtattaa atacacttta tgctgttact aaaaatgctg aaggatggag caagcagtat   1020

ggctcttccc ccgttactgt tgattctgct gcagccaata ttgtatcatc tggtataagc   1080

cgagttatct taactcgagt gggtaatggg cctcgagttt tgacgattga cgaatctttg   1140

atcgatgcat ctggcaaccc taaatttata ggaagtcatt aa                      1182
```

<210> SEQ ID NO 90
<211> LENGTH: 972
<212> TYPE: DNA
<213> ORGANISM: Halorhabdus utahensis

<400> SEQUENCE: 90

```
atgaaagcga cagcgacggc ccacccgatc caggggctgg tgaagtacca cgggatacgc     60

gaccccgaac tccggacgcc gtatcacgat tcgatcagcc tctgcactgc gccgagtaac    120

tccacgacga cggtcgcctt cgaacccgag cgtcccgagg acgagtacgt catcgacggc    180

gaacacatcg acgggcgcgg ggccgagcgc atccggaccg tcgtcgataa cgttcgcgaa    240

cgggccgatc tcgacgagcg cgtccgcgtc gcaagtgaga acaacttccc gtcgaacgtc    300

ggctttggct cctcggcgtc gggattcgcg gcgctggcga ctgctctcgt tgaggccgct    360
```

```
ggcctggacc tctcacgccc ggagatctcg acgattgccc gccgcggctc gacctcggcg    420
gcgcgggcgg tcacgggtgg cttttcggat ctgcgggcgg gcagtaacga cgccgactgc    480
cgttcgaagc gactcgacgt ccccttggag gatgacgttc gcatcgtcgg cgcagtgatt    540
cctgcataca aagagaccga ggcggcccac gaggaggccg ccgagagcca catgttcgag    600
ggccgactcg cccacgtcca cgagcaactc gcggacatgc gcgacgcgct cggtcgcggg    660
gacttcgagc ggtccttcga gatcgccgaa cacgacacac tctcgctggc ggcgacgacg    720
atgaccggac cgagcggctg ggtctactgg caacccgaga gcctcgaagt cttcgagacg    780
gttcgggacc ttcgcgacga cggggttccc gtctacttct ccggggatac cggcgcaagc    840
atctacgtca acaccacggc cgagtacgtc gaccgcgtcg aatcggcgat cgaaaccctc    900
gggatcgaga cgctcacctg gcgcgtcggt ggccccgcgc gcgtccgtga tcccgagaag    960
gcactgttct ga                                                        972
```

<210> SEQ ID NO 91
<211> LENGTH: 984
<212> TYPE: DNA
<213> ORGANISM: Haloterrigena turkmenica

<400> SEQUENCE: 91

```
atgaaagcga ccgccatggc ccacccgatt caggggctgg tcaagtatca cgggatgcga     60
gacgagatcg agcgcctgcc gtatcacgac agtatcagtc tctgtacggc cccgagccac    120
actcgcacga ccgtggagtt ctcgatggac tacgaggagg acacgttcgt cgtcgacggc    180
gaggaactcg acggccgggc ctacgagcgc gtcgaagccg tcgtcgagaa ggctcgttcg    240
aagtccgacg cggcccacac cgtctatccg gttcgcctcg agagcgagaa cagtttcccg    300
tcgaacgtcg ggctgggctc ctcttcctcg ggcttcgccg ccgccgcgat ggcgctggcc    360
gaggccgccg aactcgacgc ctcccgccag gagatttcga cgatcgctcg cgtcggctcg    420
gcgtcggccg cccgcgcggt caccggcgcg ttttcgcaac tgcacacggg tctgaacgac    480
gaggattgtc gctcgcggcg catcccgagt gaccttcacg aggacctgaa gatcgtcgtc    540
ggcctcgtcc cctaccacaa ggagaccgag gacgcccacc gcgaggccgc cgacagccac    600
atgttccagg cccgcaacgc ccacatccac ggccagatcg ccgagatgcg cgacgccctg    660
cggaacaacg agttcgaccg cgccttcgaa ctcgccgagc aggactccct ctcgctggcc    720
gcgacgacga tgaccggccc ctccgggtgg gtctactggc agcccgctac cctgaagatc    780
ttcaatacgg tgcgggaact ccgcgaggag gaggacatcc ccgtctactt ctcgacggac    840
accggcgcca gcgtctacgt caacaccacc gaggaacacg tcgacgaggt cgaggaggcg    900
gtctcggatt gcggcgtctc caccaccgtc tgggacgtcg gcggccctgc gaagctgcta    960
gacgaggaaa agcacctgtt ctag                                           984
```

<210> SEQ ID NO 92
<211> LENGTH: 951
<212> TYPE: DNA
<213> ORGANISM: Leuconostoc kimchii

<400> SEQUENCE: 92

```
atgcctacaa cagccacagc acatactaat attgcattta ttaaatattg ggtaaaaaa      60
gatgcgcgct taaatttacc gacaaccagt tctttatccc taacactctc acaattttat    120
acaacaacaa cagtcacaca aaacaccgac aaagatcaac ttgttttaaa cggtgagcta    180
gccgacccta ctagaataca tcattttta aatacaatac gtgatatcct tggtgatttt     240
```

```
cctgctgtga cagtcacttc agaaaaccat gtgccaacca gtgcaggtct agcctcttcg    300

gcttcatctt tcgctgcgct aacaggtgca gtaacaagag aaatgggatt tgatttgtct    360

aatcaatcct tatctcggtt agcacgccgt ggatctggtt ccgcctcacg atcgttttac    420

agtcactttg ctatctggca tgctggtatg gatgatgcct catcttttgc tgaaagttta    480

aatgcccctg acatgccgat tgcccttgtc gttgccgaag tgtccacttc agcaaagaaa    540

gtgagctcaa gtgatggcat gcaacgtgca atcacttcac caaactacga tgattggctc    600

aaccgcagcg cgacacaatt tatggatatg cagtctgcca ttcaacaatc agacatcgaa    660

aaaattggta cgcttgctga agaaaacgct ttagctatgc atgcgcttaa tctcactgca    720

cgccataaac cattcaccta tttcacgcaa gaaacccaac aaatacttgc cctagtatca    780

gatttacgac gacaagggat cctagccttc gcaacaatgg atgctggtcc aaacgtcaaa    840

attataacga ctttaaatga tgcaccaaaa attgttacag cactacattc tgctttacca    900

tatatccatc tcgaaactgc tacaagcgga tcaggtatta cctatgacta a             951
```

<210> SEQ ID NO 93
<211> LENGTH: 1005
<212> TYPE: DNA
<213> ORGANISM: Halobacterium salinarum

<400> SEQUENCE: 93

```
atgcgcgcga cacccccgca tcgacgtatg aaagcaaccg cgcgcgcaca ccccatccag     60

ggcctcgtga aataccacgg gatgcgcgac gagtcgcttc gcatgccgta ccacgactcc    120

atcagcgtct gcaccgcgcc cagcaacacc acgacgaccg tcgagttcga tcccgaccgc    180

gacgccgacc agtacgtcgt cgacggcgac acggtcaccg gtcacggcgc ggaccgcatc    240

cgcagtgtgg tcgatgcggt ccgcgaccgc gccgggttcg accaccgcgt gcgcctggag    300

agccagaaca gcttccccac gaacatcggc ctggggtcgt cgtcgtcggg gttcgcggcg    360

gccgcgctgg cgtgcgtccg cgccgccggc ctggatctgg acctcccgac ggtgtcgacg    420

gtcgcgcgcc gcggatcggc gtcggcggcc cgcgccgtca cgggcgggtt ctcggatctg    480

cacgcgggat tgaacgacgc cgactgccgc agcgaacgcc tcgacgcccc cgcggagttc    540

gcgtccgatc tgcgcatcgt cgtgggcgaa gtgcccgcgt acaaggagac ggagtctgcc    600

cacgccgagg ccgccgacag ccacatgttc gacgcgcggc tggcacacgt ccagggccaa    660

ctcgcggaga tgcgtgacgc cgtccgcgcg ggcgacttcc agcgcgtctt cgagaccgcc    720

gaacacgact cgctgtcgct cgcggcgacg acgatgacgg ggccgtccgg gtgggtgtac    780

tggaagcccg agacgctctc gatattcgag accgtgcggg agctccgggc ggacggcgtg    840

ccgacgtact tctcgacgga taccggcgcg acagtgtacg tgaacaccac tgcgagtcac    900

gccgacgagg tcgaggctgc ggtcgccgac tgcggcgtcg acaccgccgt ctgggaggtc    960

ggcgggcctg cccacgaact cgacgagcgc gacgcgatct tctga                   1005
```

<210> SEQ ID NO 94
<211> LENGTH: 1300
<212> TYPE: DNA
<213> ORGANISM: Aspergillus clavatus

<400> SEQUENCE: 94

```
atggcggctg cggactcttc ggtctatagg gccaccacta ctgcccctgt caatattgct     60

gtcatcaagt aagttgactg cccccccccc ctaaataaac caaccgcctc cttttcttct    120
```

-continued atcattaaat ttgtactaac gctgggactt ctctagatac tggggaaaac gggacgcaac 180
tctgaacctg cccaccaatt cttccctctc tgtgaccctt tcccagcgtt cgctccgcac 240
cctcaccacc gcctcctgtt ctgctatcta ccccaccgca gatgagctta tcctcaatgg 300
caagcctcaa gatatccaat cctccaagcg tacgctcgcc tgtctctcca gcctgcgctc 360
tcttcgccag gcgctggaat ctacagactc atcgttgccg aaattatcta cacttccctt 420
gcggattgtt tccgagaaca atttccccac ggccgctggt cttgctagct cagctgctgg 480
gtttgcagcc ctcgttcgtg ctgtagcgaa cctctaccaa cttccgcaat cacctcggga 540
gctcagccgt atcgctcgtc agggatctgg ctctgcttgc cggtctctga tgggcggcta 600
cgtggcttgg cgcgctggag agttggagga cggcagcgat agtcttgctg aggaggttgc 660
acctgcctca cactggcctg agatgcgtgc cattgtcctg gtggtcagcg ccgagaagaa 720
ggatgtcccc agtaccgagg gcatgcagac gacggtcgct acctcgagtc tcttcgctac 780
cagagcgaca tctgttgttc ccgagcggat ggctgccatt gagacagcaa tcctgaacaa 840
ggactttcct gccttcgccg aactcaccat gcgcgactct aacggcttcc acgccacctg 900
ccttgactcc tggcccccaa ttttctatat gaacgacgtt tcccgggctg ctgtcagaat 960
tgtccacgat atcaaccgtg ctattggccg aactgtgtgt gcgtacacct ttgatgctgg 1020
accgaatgct gttatctatt atctggaaaa ggattcggag ctggtcgcag gaactgtcaa 1080
ggcaatcttg accaccaaca ctgacggctg gaatggtcct ttctacgata ttctgaagga 1140
cgtcactgcc ccgggtgttt ctttggataa gattgactct agagccgttg aagttctcaa 1200
ggagggagtc agccgcgtga ttctgaccgg tgttggtgag ggtcctgtca gtgtagaaga 1260
ccacctggtc agcgcaactg gagatgttct ttcgcactaa 1300

<210> SEQ ID NO 95
<211> LENGTH: 1283
<212> TYPE: DNA
<213> ORGANISM: Neosartorya fischeri

<400> SEQUENCE: 95
atggcggcta cttctgatca taccgtctat cgtgctacca ctaccgcccc ggtcaatatt 60
gctgttatta agtgagttga ctatcgcccc ctaatccgtc ctgtggtgat tcttgtttcc 120
tcctaacagg gtcctctagg tattggggta aaagagatgc gtctctgaat ctgccaacca 180
attcctccct ctctgttacc ctctctcagc gctccctccg aaccctcact accgcctcct 240
gctcagctat ctaccccgcc gcagacgagc tcatcttgaa cggcaagcca caggatattc 300
agtcctccaa acgcacactc gcttgtctct ccaacctacg ttccctccgt caggctctcg 360
aaaatgccga cccctcattg cctaaactgt ctgctctccc attgcgaatt gtttccgaga 420
acaacttccc caccgctgct ggtctcgcga gctcagctgc tggtttcgca gcccttgtcc 480
gtgctatagc agatctttat cagcttccac aatctcctct ggagctcagc cgtattgccc 540
gtcagggttc cggctctgct tgtcggtctc tgatgggcgg ttatgttgcc tggcgtgctg 600
gcgagcggga agatggtagc gacagtctgg ctgaggaagt cgctcccgca tctcattggc 660
ctgagatgcg tgcaattatc ctggtggtta gtgccgagaa gaaagacgtc cccagtacag 720
agggtatgca gactacagtt gctacctcga gtctctttgc tacccgggcc gcatctgttg 780
tccctgagcg gatggccgcc attgagacgg caatccagaa caaggacttc gctacctttg 840
cggaaatcac catgcgtgac tctaacagtt tccacgcaac ttgcctcgac tcctggcctc 900
cgatcttcta catgaacgac gtctccagag ctgccgtgag actcgtccac gacatcaacc 960
gtgctgttgg ccggactgtg tgtgcttaca cattcgacgc tggcccgaat gccgttatct 1020
actaccttga gaaagactcg gaggtggtcg caggaaccgt caaggctatt ttgggcccca 1080
acaccgaagg gttcgacggc ccattctatg atatcttgaa gaatgtcact gcttcagtcg 1140
tgcctctgga gaatgttgac tctagagctg tagaagtctt gaagaacggc atcagccgcg 1200
tcattctgac tggtgtcggg gagggtccta tcagcgtgga ggatcacctt gtgagcgcga 1260
cgggtgatat cctcgcttct tga 1283

<210> SEQ ID NO 96
<211> LENGTH: 954
<212> TYPE: DNA
<213> ORGANISM: Streptococcus pseudopneumoniae

<400> SEQUENCE: 96
atggatagag agcctgtaac agtacgttcc tacgcaaata ttgctattat caaatattgg 60
ggaaagaaaa aagaaaaaga gatagtgcct gctactagca gtatttctct aactttggaa 120
aatatgtata cagagacgac cttgtcgcct ttaccagcca atgtaacagc tgacgaattt 180
tacatcaatg ctcagctaca aaatgaggtc gagcatgcca agatgagtaa gattattgac 240
cgttatcgtc cagctggtga gggctttgtc cgtatcgata ctcaaaataa tatgcctacg 300
gcagcgggcc tgtcctcaag ttctagtggt ttgtccgccc tggtcaaggc ttgtaatgct 360
tatttccagc ttggtttgtc tcggagtcag ttggcacagg aggctaagtt tgcctcaggt 420
tcttcttctc ggagttttta tggaccacta ggtgcctggg acaaggatag tgggggaatt 480
taccctgtag agacaaactt gaaactagct atgatcatgt tggtgctaga ggacaagaaa 540
aaaccaatct ctagccgtga cgggatgaaa ctttgtgtgg agacttcgac gacttttgac 600
gactgggttc gtcagtctga gaaggactat caggatatgc tgatttatct caaggaaaat 660
gactttgcca agattggaga attaacggag aaaaatgctc ttgctatgca cgctacgaca 720
aaaacagcat caccagcctt ttcttatctg accgattcat cttatgaagc gatggacttt 780
gttcgtcaac ttcgcgagca aggagaggcc tgctacttta ctatggatgc cggtcctaat 840
gtcaaagttc tttgtcaaga gaaagacttg gagcatttat caaaaatctt cggtcaacgt 900
taccgcttga ttgtgtcaaa aacaaaggat ttgagtcaag atgattgctg ttaa 954

<210> SEQ ID NO 97
<211> LENGTH: 1005
<212> TYPE: DNA
<213> ORGANISM: Lactobacillus rhamnosus

<400> SEQUENCE: 97
atgacaactt atgcacgtgc gcacactaac attgcattga tcaaatattg gggcaaagca 60
aataagcaac tgatgctgcc ggcaaccagc agtatttcgc ttaccttgaa tgacttttac 120
acggacacgg cggtaacttt tgaccctgca ctcgatcagg atcaattcac gttaaatcac 180
caaatgcagt cgcctactgc tgtcagccgc tttttggatc atgttcggca cctggcccaa 240
attgatacac gcgctcgggt caactcgttg aatcatgtac cgactgctgc cggtttggcc 300
agttcggctt ctgcgtttgc ggcactggca ctggctacaa gtcgcgcggc tggcctaaat 360
ttaaccccta ccgctttgtc acggttggca cgtcgcggct cagggtcggc cacccgttca 420
atctttggcg gagcggtaat ttggcaccgt ggcagcgatg atcaatcctc gtttgccgaa 480
cccttaacca ttcagccaac tctgccgctg cggatgttgg tcgtcacggt ttccgatcag 540

```
aaaaaggcag tcagctcccg caccggcatg gccaacacgg ttgcgaccag cccttattac    600

caggcatggg tacaatcgaa tgaagcgtta atttcaccta tgatcacggc attggccgaa    660

aatgatctga cgacgattgg tgcactcacc gaattatcga gtatgcgcat gcacgctgcc    720

attatggctg aggagccgcc gttcacctac tttttgccgg aaactttacg cgcctggcaa    780

ttggtgcaag aacaacgggc actcggcatt ccggcgtttg ccacgatgga tgccggaccc    840

aacgtcaaga tcctcacaac cgcaccgtac gtggatgttc tcatgaccgc cttgcagcct    900

gtttttggcg accggatttt gagcacccgc ctcggcccgg acgcgcaagt gattacaaag    960

gagcaattta atgacacaga gtcagcaatc acatcgcaag gatga                  1005
```

<210> SEQ ID NO 98
<211> LENGTH: 939
<212> TYPE: DNA
<213> ORGANISM: Borrelia afzelii

<400> SEQUENCE: 98

```
atgaaagtaa agtgtaaagc caatgcaagc ttggctttaa ttaaatattg ggaaagaag     60

gatgtttttt taaacattcc agcgacttct agtcttgctg ttagtgttga taaattttat    120

tcaataagtg agcttgaact ttcagatcga gatgaaataa ttttaaattc aaagccagtt    180

atattgcaaa atagagaaaa ggtgtttttt gattatgcaa gaaaaattct tagtgaaccg    240

aatgttagat ttaaaattaa aagtgaaaac aattttccaa cagcagcagg ccttgcaagt    300

tcaagttcag gatttgcttc tattgctgct tgtattttga aatattttga taaatattct    360

tttaatagtg catctaatct tgcaagagta ggatcagctt ctgcagcaag ggctatttac    420

ggagggttta ctattttgaa agaaggttca aaagaatctt ttcaattaag agatgaatct    480

tattttaatg atttgcgcat aatatttgcc ataattgata gtagtgaaaa agaattgtcc    540

tcaagagccg caatgaatat ttgcaaacac catggatttt attatgatgc ttggattgct    600

tctagtaaaa agatttttaa agatgcttta tatttttttt taaaaaaaga ttttgtgcat    660

tttggagcaa ctattgtaaa aagttatcag aatatgtttg ctttaatgtt tgcatcttct    720

attttttatt ttaaaaatag cacaatagat ttaattaaat atgccgctta tttaagaaat    780

aaaggaattt tggtatttga gacaatggat gcgggccccc aagtgaagtt tctttgtttg    840

gagaaaaatt taaatactat tttaaaagga cttaagcaga attttactga cattgagttt    900

attgtttcaa aggttggatg tgacttagaa tggatttga                          939
```

<210> SEQ ID NO 99
<211> LENGTH: 549
<212> TYPE: DNA
<213> ORGANISM: Escherichia coli

<400> SEQUENCE: 99

```
atgcaaacgg aacacgtcat tttattgaat gcacagggag ttcccacggg tacgctggaa     60

aagtatgccg cacacacggc agacacccgc ttacatctcg cgttctccag ttggctgttt    120

aatgccaaag gacaattatt agttacccgc cgcgcactga gcaaaaaagc atggcctggc    180

gtgtggacta actcggtttg tgggcaccca caactgggag aaagcaacga agacgcagtg    240

atccgccgtt gccgttatga gcttggcgtg gaaattacgc ctcctgaatc tatctatcct    300

gactttcgct accgcgccac cgatccgagt ggcattgtgg aaaatgaagt gtgtccggta    360

tttgccgcac gcaccactag tgcgttacag atcaatgatg atgaagtgat ggattatcaa    420

tggtgtgatt tagcagatgt attacacggt attgatgcca cgccgtgggc gttcagtccg    480
```

```
tggatggtga tgcaggcgac aaatcgcgaa gccagaaaac gattatctgc atttacccag    540

cttaaataa                                                            549


<210> SEQ ID NO 100
<211> LENGTH: 867
<212> TYPE: DNA
<213> ORGANISM: Saccharomyces cerevisiae

<400> SEQUENCE: 100

atgactgccg acaacaatag tatgccccat ggtgcagtat ctagttacgc caaattagtg     60

caaaaccaaa cacctgaaga cattttggaa gagtttcctg aaattattcc attacaacaa    120

agacctaata cccgatctag tgagacgtca aatgacgaaa gcggagaaac atgtttttct    180

ggtcatgatg aggagcaaat taagttaatg aatgaaaatt gtattgtttt ggattgggac    240

gataatgcta ttggtgccgg taccaagaaa gtttgtcatt taatggaaaa tattgaaaag    300

ggtttactac atcgtgcatt ctccgtcttt attttcaatg aacaaggtga attactttta    360

caacaaagag ccactgaaaa aataactttc cctgatcttt ggactaacac atgctgctct    420

catccactat gtattgatga cgaattaggt ttgaagggta agctagacga taagattaag    480

ggcgctatta ctgcggcggt gagaaaacta gatcatgaat taggtattcc agaagatgaa    540

actaagacaa ggggtaagtt tcacttttta aacagaatcc attacatggc accaagcaat    600

gaaccatggg gtgaacatga aattgattac atcctatttt ataagatcaa cgctaaagaa    660

aacttgactg tcaacccaaa cgtcaatgaa gttagagact tcaaatgggt ttcaccaaat    720

gatttgaaaa ctatgtttgc tgacccaagt tacaagttta cgccttggtt taagattatt    780

tgcgagaatt acttattcaa ctggtgggag caattagatg acctttctga agtggaaaat    840

gacaggcaaa ttcatagaat gctataa                                        867


<210> SEQ ID NO 101
<211> LENGTH: 996
<212> TYPE: DNA
<213> ORGANISM: Streptococcus mutans

<400> SEQUENCE: 101

atgacaaata gaaaagatga tcatataaaa tatgccttag actatcgttc gccatataat     60

agtttcgatg acatagaact cattcatcat tctttaccag attatgattt agccgagatt    120

gatttgtcta cacattttgc tggtcaggat tttgattttc ctttttatat caacgctatg    180

acaggcggaa gccaaaaagg gaaagaagtt aatgaaaaat tagctcaggt agcggacacc    240

tgtggtcttc tttttgtaac aggttcttac agcacagctc ttaaaaatcc agacgatact    300

tcttatcagg taaaaaaatc cagacctcat ttattactag caaccaatat cggccttgac    360

aaaccttatc aggctggctt acaggcagtt agggatttac agcctttatt tcttcaagtt    420

catattaatc ttatgcaaga gctccttatg ccagaggggg aacgcgaatt taggtcttgg    480

aagaaacatt tatctgacta tgcgaagaaa ctacaacttc cttttatttt aaaagaagtt    540

ggttttggta tggacgttaa aacaatccaa actgctattg acctaggggt taaaactgtc    600

gatatttctg gccgaggcgg aactagtttt gcttatatcg aaaatagacg tggcggaaat    660

cgttcttatc ttaatcaatg gggacaaacc acagcgcaag ttctattaaa tgctcagccg    720

cttatggata aggtagaaat cctggctagc ggcgggattc gtcatccatt ggacataata    780

aaagctttgg tccttggagc caaagcggtc ggtttatctc gaacgatgtt agaattagtt    840
```

```
gaacagcatt ctgttcatga agtcattgct attgtaaatg gttggaaaga agatttgcgc    900

ctgatcatgt gcgcccttaa ctgtcaaacg attgcagaac ttcgaaatgt tgactatctt    960

ttatatgggc gcttaagaga aggacagaga caataa                              996


<210> SEQ ID NO 102
<211> LENGTH: 1050
<212> TYPE: DNA
<213> ORGANISM: Bacillus subtilis

<400> SEQUENCE: 102

gtgactcgag cagaacgaaa aagacaacac atcaatcatg ccttgtccat cggccagaag     60

cgggaaacag gtcttgatga tattacgttt gttcacgtca gtctgcccga tcttgcatta    120

gaacaagtag atatttccac aaaaatcggc gaactttcaa gcagttcgcc gatttttatc    180

aatgcaatga ctggcggcgg cggaaaactt acatatgaga ttaataaatc gcttgcgcga    240

gcggcttctc aggctggaat tccccttgct gtgggatcgc aaatgtcagc attaaaagat    300

ccatcagagc gtctttccta tgaaattgtt cgaaaggaaa acccaaacgg gctgattttt    360

gccaacctgg gaagcgaggc aacggctgct caggcaaagg aagccgttga gatgattgga    420

gcaaacgcac tgcagatcca cctcaatgtg attcaggaaa ttgtgatgcc tgaaggggac    480

agaagcttta gcggcgcatt gaaacgcatt gaacaaattt gcagccgggt cagtgtaccg    540

gtcattgtga aagaagtcgg cttcggtatg agcaaagcat cagcaggaaa gctgtatgaa    600

gctggtgctg cagctgttga cattggcggt tacgggggaa caaatttctc gaaaatcgaa    660

aatctccgaa gacagcggca aatctccttt tttaattcgt ggggcatttc gacagctgca    720

agtttggcgg aaatccgctc tgagtttcct gcaagcacca tgatcgcctc tggcggtctg    780

caagatgcgc ttgacgtggc aaaggcaatt gcgctggggg cctcttgcac cggaatggca    840

gggcattttt taaaagcgct gactgacagc ggtgaggaag gactgcttga ggagattcag    900

ctgatccttg aggaattaaa gttgattatg accgtgctgg gtgccagaac aattgccgat    960

ttacaaaagg cgccccttgt gatcaaaggt gaaacccatc attggctcac agagagaggg   1020

gtcaatacat caagctatag tgtgcgataa                                   1050


<210> SEQ ID NO 103
<211> LENGTH: 939
<212> TYPE: DNA
<213> ORGANISM: Escherichia coli

<400> SEQUENCE: 103

atgaaagtcg cagtcctcgg cgctgctggc ggtattggcc aggcgcttgc actactgtta     60

aaaacccaac tgccttcagg ttcagaactc tctctgtatg atatcgctcc agtgactccc    120

ggtgtggctg tcgatctgag ccatatccct actgctgtga aaatcaaagg tttttctggt    180

gaagatgcga ctccggcgct ggaaggcgca gatgtcgttc ttatctctgc aggcgtagcg    240

cgtaaaccgg gtatggatcg ttccgacctg tttaacgtta acgccggcat cgtgaaaaac    300

ctggtacagc aagttgcgaa aacctgcccg aaagcgtgca ttggtattat cactaacccg    360

gttaacacca cagttgcaat tgctgctgaa gtgctgaaaa aagccggtgt ttatgacaaa    420

aacaaactgt tcggcgttac cacgctggat atcattcgtt ccaacacctt tgttgcggaa    480

ctgaaaggca aacagccagg cgaagttgaa gtgccggtta ttggcggtca ctctggtgtt    540

accattctgc cgctgctgtc acaggttcct ggcgttagtt ttaccgagca ggaagtggct    600

gatctgacca aacgcatcca gaacgcgggt actgaagtgg ttgaagcgaa ggccggtggc    660
```

gggtctgcaa ccctgtctat gggccaggca gctgcacgtt ttggtctgtc tctggttcgt 720
gcactgcagg gcgaacaagg cgttgtcgaa tgtgcctacg ttgaaggcga cggtcagtac 780
gcccgtttct tctctcaacc gctgctgctg ggtaaaaacg gcgtggaaga gcgtaaatct 840
atcggtaccc tgagcgcatt tgaacagaac gcgctggaag gtatgctgga tacgctgaag 900
aaagatatcg ccctgggcga agagttcgtt aataagtaa 939

<210> SEQ ID NO 104
<211> LENGTH: 990
<212> TYPE: DNA
<213> ORGANISM: Escherichia coli

<400> SEQUENCE: 104
atgaaactcg ccgtttatag cacaaaacag tacgacaaga agtacctgca acaggtgaac 60
gagtcctttg gctttgagct ggaatttttt gactttctgc tgacggaaaa aaccgctaaa 120
actgccaatg gctgcgaagc ggtatgtatt ttcgtaaacg atgacggcag ccgcccggtg 180
ctggaagagc tgaaaaagca cggcgttaaa tatatcgccc tgcgctgtgc cggtttcaat 240
aacgtcgacc ttgacgcggc aaaagaactg gggctgaaag tagtccgtgt tccagcctat 300
gatccagagg ccgttgctga acacgccatc ggtatgatga tgacgctgaa ccgccgtatt 360
caccgcgcgt atcagcgtac ccgtgacgct aacttctctc tggaaggtct gaccggcttt 420
actatgtatg gcaaaacggc aggcgttatc ggtaccggta aaatcggtgt ggcgatgctg 480
cgcattctga aaggttttgg tatgcgtctg ctggcgttcg atccgtatcc aagtgcagcg 540
gcgctggaac tcggtgtgga gtatgtcgat ctgccaaccc tgttctctga atcagacgtt 600
atctctctgc actgcccgct gacaccggaa aactaccatc tgttgaacga agccgccttc 660
gatcagatga aaaatggcgt gatgatcgtc aataccagtc gcggtgcatt gattgattct 720
caggcagcaa ttgaagcgct gaaaaatcag aaaattggtt cgttgggtat ggacgtgtat 780
gagaacgaac gcgatctgtt ctttgaagat aaatccaacg acgtgatcca ggatgacgta 840
ttccgtcgcc tgtctgcctg ccacaacgtg ctgtttaccg ggcaccaggc attcctgaca 900
gcagaagctc tgaccagtat ttctcagact acgctgcaaa acttaagcaa tctggaaaaa 960
ggcgaaacct gcccgaacga actggtttaa 990

<210> SEQ ID NO 105
<211> LENGTH: 1050
<212> TYPE: DNA
<213> ORGANISM: Ralstonia eutropha

<400> SEQUENCE: 105
atgaagatct ccctcaccag cgcccgccag cttgcccgcg acatcctcgc cgcgcagcag 60
gtgcccgccg acatcgctga cgacgtggcc gagcacctgg tcgaatccga ccgctgcggc 120
tatatcagcc acggcctgtc gatcctgccc aactaccgca ccgccctcga cggccacagc 180
gtcaacccgc aaggccgcgc caaatgcgtg ctggaccagg gcacgctgat ggtgttcgac 240
ggcgacggcg gcttcggcca gcacgtgggc aagtccgtga tgcaagcagc gatcgagcgc 300
gtgcgccagc atggccactg catcgtcact ctgcgccgct cgcaccatct cggccgcatg 360
ggccactacg gcgagatggc ggccgccgcc ggctttgtgc tgctgagctt caccaacgtg 420
atcaaccgcg cgccggtggt ggcgccgttc ggcggccgcg tggcgcggct caccaccaac 480
ccgctgtgtt tcgccggccc gatgcccaac gggcggccgc ctctggtggt ggacatcgcc 540

```
accagcgcga ttgccatcaa caaggcccgt gtgctggccg agaaaggcga gccggcgccc    600

gaaggcagca tcatcggcgc cgacggcaac ccccaccaccg acgcgtcaac catgttcggc    660

gaacaccccg gcgcgctgct gccctttggc ggccacaagg gctacgcact gggcgttgtg    720

gccgagctgc tggcgggcgt gctgtccggc ggcggtacca tccagccaga caatccgcgc    780

ggcggcgtgg ccaccaacaa cctgttcgcg gtgctgctca atcccgcgct ggacctgggc    840

ctggactggc agagcgccga ggtcgaggcg ttcgtgcgct acctgcacga cacaccgccg    900

gcgccgggcg tcgaccgcgt gcagtacccc ggcgagtacg aggccgccaa ccgggcgcag    960

gccagcgaca cgctaaacat caacccggcc atctggcgca atcttgagcg cctggcgcag   1020

tcgctcaacg tggccgtccc cacggcctga                                    1050
```

<210> SEQ ID NO 106
<211> LENGTH: 1056
<212> TYPE: DNA
<213> ORGANISM: Clostridium beijerinckii

<400> SEQUENCE: 106

```
atgaaaggtt ttgcaatgct aggtattaat aagttaggat ggatcgaaaa agaaaggcca     60

gttgcgggtt catatgatgc tattgtacgc ccattagcag tatctccgtg tacatcagat    120

atacatactg tttttgaggg agctcttgga gataggaaga atatgatttt agggcatgaa    180

gctgtaggtg aagttgttga agtaggaagt gaagtgaagg attttaaacc tggtgacaga    240

gttatagttc cttgtacaac tccagattgg agatctttgg aagttcaagc tggttttcaa    300

cagcactcaa acggtatgct cgcaggatgg aaattttcaa atttcaagga tggagttttt    360

ggtgaatatt ttcatgtaaa tgatgcggat atgaatcttg cgattctacc taaagacatg    420

ccattagaaa atgctgttat gataacagat atgatgacta ctggatttca tggagcagaa    480

cttgcagata ttcaaatggg ttcaagtgtt gtggtaattg gcattggagc tgttggctta    540

atgggaatag caggtgctaa attacgtgga gcaggtagaa taattggagt ggggagcagg    600

ccgatttgtg ttgaggctgc aaaattttat ggagcaacag atattctaaa ttataaaaat    660

ggtcatatag ttgatcaagt tatgaaatta acgaatggaa aaggcgttga ccgcgtaatt    720

atggcaggcg gtggttctga aacattatcc caagcagtat ctatggttaa accaggagga    780

ataatttcta atataaatta tcatggaagt ggagatgctt tactaatacc acgtgtagaa    840

tggggatgtg gaatggctca caagactata aaaggaggtc tttgtcctgg gggacgtttg    900

agagcagaaa tgttaagaga tatggtagta tataatcgtg ttgatctaag taaattagtt    960

acacatgtat atcatggatt tgatcacata gaagaagcac tgttattaat gaaagacaag   1020

ccaaaagact taattaaagc agtagttata ttataa                             1056
```

<210> SEQ ID NO 107
<211> LENGTH: 1059
<212> TYPE: DNA
<213> ORGANISM: Thermoanaerobacter brockii

<400> SEQUENCE: 107

```
atgaaaggtt ttgcaatgct cagtatcggt aaagttggct ggattgagaa ggaaaagcct     60

gctcctggcc catttgatgc tattgtaaga cctctagctg tggccccttg cacttcggac    120

attcataccg tttttgaagg cgccattggc gaaagacata acatgatact cggtcacgaa    180

gctgtaggtg aagtagttga agtaggtagt gaggtaaaag attttaaacc tggtgatcgc    240

gttgttgtgc cagctattac ccctgattgg cggacctctg aagtacaaag aggatatcac    300
```

```
cagcactccg gtggaatgct ggcaggctgg aaattttcga atgtaaaaga tggtgttttt    360

ggtgaatttt ttcatgtgaa tgatgctgat atgaatttag cacatctgcc taaagaaatt    420

ccattggaag ctgcagttat gattcccgat atgatgacca ctggttttca cggagctgaa    480

ctggcagata tagaattagg tgcgacggta gcagttttgg gtattggccc agtaggtctt    540

atggcagtcg ctggtgccaa attgcgtgga gccggaagaa ttattgccgt aggcagtaga    600

ccagtttgtg tagatgctgc aaaatactat ggagctactg atattgtaaa ctataaagat    660

ggtcctatcg aaagtcagat tatgaatcta actgaaggca aaggtgtcga tgctgccatc    720

atcgctggag gaaatgctga cattatggct acagcagtta agattgttaa acctggtggc    780

accatcgcta atgtaaatta ttttggcgaa ggagaggttt tgcctgttcc tcgtcttgaa    840

tggggttgcg gcatggctca taaaactata aaaggcgggc tatgccccgg tggacgtcta    900

agaatggaaa gactgattga ccttgttttt tataagcgtg tcgatccttc taagctcgtc    960

actcacgttt tccggggatt tgacaatatt gaaaaagcct ttatgttgat gaaagacaaa   1020

ccaaaagacc taatcaaacc tgttgtaata ttagcataa                          1059
```

<210> SEQ ID NO 108
<211> LENGTH: 2537
<212> TYPE: DNA
<213> ORGANISM: Rhodococcus ruber

<400> SEQUENCE: 108

```
ctgcagggct tcaccctcgg ccactacacc cacgtcttcc ccgagttcgc ggcgaagatg     60

gggccgtggc tcgcggccgg cgacgtggtg ttcgacgaga cgatcgtcga cggcatcggc    120

aactcggtcg atgccttcct cgacctcatg cgcgggcgca acgtcggcaa gatgctcgtc    180

cgaaccgcct gacgtccgga gccggaacgg ccggcgtcgt gcagcggaag attcgctcca    240

gtgccgggcg ggcgcacctt cccggccgta gagtcgggcg catgaaagcc ctccagtaca    300

ccgagatcgg ctccgagccg gtcgtcgtcg acgtccccac cccggcgccc gggccgggtg    360

agatcctgct gaaggtcacc gcggccggct tgtgccactc ggacatcttc gtgatggaca    420

tgccggcaga gcagtacatc tacggtcttc ccctcaccct cggccacgag ggcgtcggca    480

ccgtcgccga actcggcgcc ggcgtcaccg gattcgagac gggggacgcc gtcgccgtgt    540

acgggccgtg gggtgcggt gcgtgccacg cgtgcgcgcg cggccgggag aactactgca     600

cccgcgccgc cgagctgggc atcaccccgc ccggtctcgg ctcgcccggg tcgatggccg    660

agtacatgat cgtcgactcg gcgcgccacc tcgtcccgat cggggacctc gaccccgtcg    720

cggcggttcc gctcaccgac gcgggcctga cgccgtacca cgcgatctcg cgggtcctgc    780

ccctgctggg acccggctcg accgcggtcg tcatcggggt cggcggactc gggcacgtcg    840

gcatccagat cctgcgcgcc gtcagcgcgg cccgcgtgat cgccgtcgat ctcgacgacg    900

accgactcgc gctcgcccgc gaggtcggcg ccgacgcggc ggtgaagtcg ggcgccgggg    960

cggcggacgc gatccgggag ctgaccggcg gtgagggcgc gacggcggtg ttcgacttcg   1020

tcggcgccca gtcgacgatc gacacggcgc agcaggtggt cgcgatcgac gggcacatct   1080

cggtggtcgg catccatgcc ggcgcccacg ccaaggtcgg cttcttcatg atcccgttcg   1140

gcgcgtccgt cgtgacgccg tactggggca cgcggtccga gctgatggac gtcgtggacc   1200

tggcccgtgc cggccggctc gacatccaca ccgagacgtt caccctcgac gagggaccca   1260

cggcctaccg gcggctacgc gagggcagca tccgcggccg cggggtggtc gtcccgggct   1320
```

gacacgacga cgaaggctcc gcactcggat cgagtgcgga gccttcgtcg ggtacgggga 1380
tcagcgagcg aacagcagcg cgcgcttgac ctcctggatc gccttcgtca cctggatgcc 1440
gcgcgggcac gcgtcggtgc agttgaaggt ggtgcggcag cgccacacgc cctcgacgtc 1500
gttgaggatg tcgagacgct cggcggcgcc ctcgtcacgg ctgtcgaaga tgaaccggtg 1560
cgcgttgacg atggcggcgg gaccgaagta gctgccgtcg ttccagtaca ccgggcacga 1620
ggtggtgcag cacgcgcaca ggatgcactt ggtggtgtcg tcgaaccggg cacggtcggc 1680
ctgcgactgg atccgctcgc gggtgggctc gttgcccgtg gcgatgagga acggcttcac 1740
ggcgcggaac gcgtcgaaga agggctccat gtcgacgacg aggtccttct cgaccggcag 1800
gccgcggatc ggctcgacgg tgatggtcac cggcttgccg tccttgggca gcatgtcctt 1860
catcaggatc ttgcaggcca ggcggttgac gccgttgatc cgcatggcgt ccgagccgca 1920
caccccgtgc gcgcagctgc ggcggaacgt gagggtgccg tcgaggtagc ccttcacgta 1980
gagcagcagg ttgagcatgc ggtccgacgg cagcgccgga acctggaagc tgtcccagtg 2040
ctgacccttg ccgtcctcgg ggttgaaccg cgcgatcttg agggtgacca tcgtggcgcc 2100
ctcgggcacg ggtggcaggt tcgagacgtc ggcttcgttc ttctcgaggg ttgtcatcaa 2160
gtacttccgc tccatcggct cgtagcgggt ctgcaccacc ggcttgtagt ccaggcggat 2220
gggggagatc agctccgtcc cctccttgta ggccatggtg tgcttgagga acttctcgtc 2280
gtcgcgcttc gggaagtcct cgcgggcgtg accgccgcgc gattccttcc ggttgagcgc 2340
accggcgacg gtgacctcgg ccatctcgag caggaagccc agctcgacgg cctcgagcag 2400
gtcgctgttg tagcgcttgc ccttgtcctg gacggtgatg ttcttgtacc gctccttcag 2460
cgcgtggatg tcctcgagcg ccttggtgag cgtctcctcg gtgcggaaca ccgaggcgtt 2520
gttgtccatg gactgca 2537

<210> SEQ ID NO 109
<211> LENGTH: 1173
<212> TYPE: DNA
<213> ORGANISM: Pyrococcus furiosus

<400> SEQUENCE: 109
atgtttgaga tatcaattta tcttcccaca gaaatagttt ttggtcctgg gaagcttgaa 60
atgcttccta aactagtgaa gaagcatggg ctttctggga aggccctaat agtaactgga 120
aggagaagca caaaggaaac tggagttctt tatagagttc aagaactact taagcaagct 180
ggggtagaga gcatagtttt tgacaaaatt attccaaatc caatatctac tcatgtggat 240
gaaggggcag agatagcgag aaaagaaaat gttagctttg ttgttggctt gggtggtgga 300
agtgcgatag atagtgcaaa agctatagca atgactgccg ccagtggagg taaatattgg 360
gactatgttc cagctgtggg aggaggaaag aagcctactg gagcgcttcc aatagttgca 420
attccaacaa cccacgggac tggaacggag gctgatcctt atgctgttat aactaatcct 480
gaaacaaagg agaagcaggg aattggatat gatgttctct tccccaaatt ctctatagtt 540
gatccagaac ttatgcttac tcttccaaaa gatcaaacag tgtacacttc aatggatgct 600
ttctaccact ccattgaggc ctttcttaat gttagagcaa atccatattc ggatgttctg 660
gctctcgact caatgaggcg cattgttaca taccttccat tggcctacga aaacttgaga 720
aatcttgaag caagaacgca acttgcctgg gcaagtactg aggctggaat aacggaaacg 780
gtaacgggag ttgtggcaaa tcatgcactt gagcatggtc taagtggatt ctatcctgaa 840
gtgcctcatg gtctgggcct ctgcattcta ggaccctacc tctttgaata cattctcgac 900

```
tatgcctatg aaaagttggc gatagtcgga agagaggtat ttggagttta cgagccaaat    960
gacagaaagg cagcagagct agctattaag aagctacgtg acttccagag cctctttgga   1020
gtaaacaaga agctcagaga attaggggtt aaagaggaag acattccaga gatggctagg   1080
actgcttata gaatgatgaa acctgttata gaggcaacac cgggagattt gaaagttgaa   1140
gacttggaag agatctatag aagagcatac taa                                1173
```

<210> SEQ ID NO 110
<211> LENGTH: 2676
<212> TYPE: DNA
<213> ORGANISM: Escherichia coli

<400> SEQUENCE: 110

```
atggctgtta ctaatgtcgc tgaacttaac gcactcgtag agcgtgtaaa aaaagcccag     60
cgtgaatatg ccagtttcac tcaagagcaa gtagacaaaa tcttccgcgc cgccgctctg    120
gctgctgcag atgctcgaat cccactcgcg aaaatggccg ttgccgaatc cggcatgggt    180
atcgtcgaag ataaagtgat caaaaaccac tttgcttctg aatatatcta caacgcctat    240
aaagatgaaa aaacctgtgg tgttctgtct gaagacgaca cttttggtac catcactatc    300
gctgaaccaa tcggtattat ttgcggtatc gttccgacca ctaacccgac ttcaactgct    360
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga aagatctgat cggctggatc gatcaacctt ctgttgaact gtctaacgca    540
ctgatgcacc acccagacat caacctgatc ctcgcgactg gtggtccggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggcgcgta tcctgattaa caccccagcg   1200
tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg gttatgctga tcagatcact   1500
tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taaacgtatc   1740
tacaagttcc cgaaaatggg cgtgaaagcg aaaatgatcg ctgtcaccac cacttctggt   1800
```

acaggttctg aagtcactcc gtttgcggtt gtaactgacg acgctactgg tcagaaatat 1860
ccgctggcag actatgcgct gactccggat atggcgattg tcgacgccaa cctggttatg 1920
gacatgccga agtccctgtg tgctttcggt ggtctggacg cagtaactca cgccatggaa 1980
gcttatgttt ctgtactggc atctgagttc tctgatggtc aggctctgca ggcactgaaa 2040
ctgctgaaag aatatctgcc agcgtcctac cacgaagggt ctaaaaatcc ggtagcgcgt 2100
gaacgtgttc acagtgcagc gactatcgcg ggtatcgcgt ttgcgaacgc cttcctgggt 2160
gtatgtcact caatggcgca caaactgggt tcccagttcc atattccgca cggtctggca 2220
aacgccctgc tgatttgtaa cgttattcgc tacaatgcga acgacaaccc gaccaagcag 2280
actgcattca gccagtatga ccgtccgcag gctcgccgtc gttatgctga aattgccgac 2340
cacttgggtc tgagcgcacc gggcgaccgt actgctgcta agatcgagaa actgctggca 2400
tggctggaaa cgctgaaagc tgaactgggt attccgaaat ctatccgtga agctggcgtt 2460
caggaagcag acttcctggc gaacgtggat aaactgtctg aagatgcatt cgatgaccag 2520
tgcaccggcg ctaacccgcg ttacccgctg atctccgagc tgaaacagat tctgctggat 2580
acctactacg gtcgtgatta tgtagaaggt gaaactgcag cgaagaaaga agctgctccg 2640
gctaaagctg agaaaaaagc gaaaaaatcc gcttaa 2676

<210> SEQ ID NO 111
<211> LENGTH: 3015
<212> TYPE: DNA
<213> ORGANISM: Clostridium acetobutylicum

<400> SEQUENCE: 111 atttacttt attctaataa tacgtaatac acccacttat aactagtatt tggcaataaa 60
aatagttata atcattaatt attgttaaat gtttgacaat ctttaattac tgttatataa 120
taatattata gaaaataaaa tgactgcata attttactat agaaatacaa gcgttaaata 180
tgtacatatc aacggtttat cacattagaa gtaaataatg taaggaaacc acactctata 240
atttataagg catcaaagtg tgttatataa tacaataagt tttatttgca atagtttgtt 300
aaatatcaaa ctaataataa attttataaa ggagtgtata taaatgaaag ttacaaatca 360
aaaagaacta aaacaaaagc taaatgaatt gagagaagcg caaaagaagt ttgcaaccta 420
tactcaagag caagttgata aaatttttaa acaatgtgcc atagccgcag ctaaagaaag 480
aataaactta gctaaattag cagtagaaga aacaggaata ggtcttgtag aagataaaat 540
tataaaaaat catttttgcag cagaatatat atacaataaa tataaaaatg aaaaaacttg 600
tggcataata gaccatgacg attctttagg cataacaaag gttgctgaac caattggaat 660
tgttgcagcc atagttccta ctactaatcc aacttccaca gcaattttca aatcattaat 720
ttctttaaaa acaagaaacg caatattctt ttcaccacat ccacgtgcaa aaaaatctac 780
aattgctgca gcaaaattaa ttttagatgc agctgttaaa gcaggagcac ctaaaaatat 840
aataggctgg atagatgagc catcaataga actttctcaa gatttgatga gtgaagctga 900
tataatatta gcaacaggag gtccttcaat ggttaaagcg gcctattcat ctggaaaacc 960
tgcaattggt gttggagcag gaaatacacc agcaataata gatgagagtg cagatataga 1020
tatggcagta agctccataa ttttatcaaa gacttatgac aatggagtaa tatgcgcttc 1080
tgaacaatca atattagtta tgaattcaat atacgaaaaa gttaaagagg aatttgtaaa 1140
acgaggatca tatatactca atcaaaatga aatagctaaa ataaaagaaa ctatgtttaa 1200
aaatggagct attaatgctg acatagttgg aaaatctgct tatataattg ctaaaatggc 1260

```
aggaattgaa gttcctcaaa ctacaaagat acttataggc gaagtacaat ctgttgaaaa   1320
aagcgagctg ttctcacatg aaaaactatc accagtactt gcaatgtata aagttaagga   1380
ttttgatgaa gctctaaaaa aggcacaaag gctaatagaa ttaggtggaa gtggacacac   1440
gtcatcttta tatatagatt cacaaaacaa taaggataaa gttaaagaat ttggattagc   1500
aatgaaaact tcaaggacat ttattaacat gccttcttca cagggagcaa gcggagattt   1560
atacaatttt gcgatagcac catcatttac tcttggatgc ggcacttggg gaggaaactc   1620
tgtatcgcaa aatgtagagc ctaaacattt attaaatatt aaaagtgttg ctgaaagaag   1680
ggaaaatatg ctttggttta aagtgccaca aaaaatatat tttaaatatg gatgtcttag   1740
atttgcatta aaagaattaa aagatatgaa taagaaaaga gcctttatag taacagataa   1800
agatcttttt aaacttggat atgttaataa aataacaaag gtactagatg agatagatat   1860
taaatacagt atatttacag atattaaatc tgatccaact attgattcag taaaaaaagg   1920
tgctaaagaa atgcttaact ttgaacctga tactataatc tctattggtg gtggatcgcc   1980
aatggatgca gcaaaggtta tgcacttgtt atatgaatat ccagaagcag aaattgaaaa   2040
tctagctata aactttatgg atataagaaa gagaatatgc aatttcccta aattaggtac   2100
aaaggcgatt tcagtagcta ttcctacaac tgctggtacc ggttcagagg caacaccttt   2160
tgcagttata actaatgatg aaacaggaat gaaataccct ttaacttctt atgaattgac   2220
cccaaacatg gcaataatag atactgaatt aatgttaaat atgcctagaa aattaacagc   2280
agcaactgga atagatgcat tagttcatgc tatagaagca tatgtttcgg ttatggctac   2340
ggattatact gatgaattag ccttaagagc aataaaaatg atatttaaat atttgcctag   2400
agcctataaa aatgggacta acgacattga agcaagagaa aaaatggcac atgcctctaa   2460
tattgcgggg atggcatttg caaatgcttt cttaggtgta tgccattcaa tggctcataa   2520
acttggggca atgcatcacg ttccacatgg aattgcttgt gctgtattaa tagaagaagt   2580
tattaaatat aacgctacag actgtccaac aaagcaaaca gcattccctc aatataaatc   2640
tcctaatgct aagagaaaat atgctgaaat tgcagagtat ttgaatttaa agggtactag   2700
cgataccgaa aaggtaacag ccttaataga agctatttca aagttaaaga tagatttgag   2760
tattccacaa aatataagtg ccgctggaat aaataaaaaa gatttttata atacgctaga   2820
taaaatgtca gagcttgctt ttgatgacca atgtacaaca gctaatccta ggtatccact   2880
tataagtgaa cttaaggata tctatataaa atcattttaa aaaataaaga atgtaaaata   2940
gtctttgctt cattatatta gcttcatgaa gcacatagac tattttacat tttactcttg   3000
tttttatct ttcaa                                                     3015
```

<210> SEQ ID NO 112
<211> LENGTH: 2685
<212> TYPE: DNA
<213> ORGANISM: Leuconostoc mesenteroides

<400> SEQUENCE: 112

```
atgagcaagt aaaggagcaa agattatggc agaagcaatt gcaaagaaac ccgcaaaaaa     60
ggttttgacc cctgaagaaa aagcggaatt acaaacacaa gctgagaaga tgactgttgt    120
attgattgaa aaatcacaaa aggcattgtc tgaattttca acattttcgc aagaacaagt    180
tgataaaatt gttgcagcta tggccttggc aggttctgag aattcacttc tgttagccca    240
tgctgctcac gacgagactg gacgtggggt tgtggaagat aaggatacga aaaatcgttt    300
```

-continued

```
cgcctcagaa tcagtttata acgctattaa gtttgataag actgtgggtg ttattagtga    360
agacaagatt caaggtaagg tagaattagc agccccactt ggtattttgg ctggaatcgc    420
tccaacgaca aatccaacgt cgacaactat tttcaaatca atgttgacag caaagacacg    480
taacacaatt atctttgctt tccatcccca gcctcaaaaa gcatcggttc ttgctgcaaa    540
aattgtttat gatgctgctg ttaaagcagg cgcaccggaa aactttatcc aatggattga    600
aaagccttca ctttatgcaa caagtgcgct gatacaaaat cctcacattg cttcaattct    660
agctactggt gggccatcaa tggttaatgc agctttgaag tcaggaaatc catccatggg    720
tgtcggtgct ggaaacggtg cagtttatat tgatgcaact gttgacacag atcgtgccgt    780
gtctgatttg ttgttatcaa agcgtttcga taatggcatg atttgtgcca cagaaaactc    840
agccgttatt caagcaccaa tctatgacga aattttaact aagttacaag aacaaggtgc    900
ataccttgtt cctaagaaag actacaagaa aattgctgat tatgtcttta agcctaacgc    960
agagggattt ggtattgctg gtcctgttgc tggtatgtca ggacgttgga ttgctgagca   1020
agcaggcgta aagattcctg atggtaaaga tgtacttttg ttcgaattag atcagaagaa   1080
cataggtgaa gcgttatctt ctgaaaagtt atcgccatta ctttcaattt ataaagttga   1140
gaagcgtgaa gaagctattg agactgttca atccttgtta aactatcaag gcgcagggca   1200
caacgcagca attcaaattg gttcacaaga tgatccattc attaaagagt atgctgacgc   1260
tattggtgca tcacgtattt tggttaacca acctgactca atcggtggcg ttggggatat   1320
ttatacagat gctatgcgtc catcgttgac acttggtacc ggatcatggg ggaagaattc   1380
attgtctcat aacttatcaa catacgactt acttaatatt aagaccgtgg ctcgccgccg   1440
taatcgtcct caatgggttc gtttacctaa ggaagtttac tacgaaacca atgccattac   1500
ttacttacaa gacttgccta ctataaaccg tgcatttatt gtcgctgatc ctggtatggt   1560
tcagttcgga tttgttggca gagtactagg tcaacttaag ttacgtcaag aacaggttga   1620
aacaaatatc tatggttcag ttaagcctga cccaactttg tcacaagctg ttgaaattgc   1680
tcgccaaatg gcagacttca aaccagatac agttatttta cttggcggtg gttcggcact   1740
tgacgctggt aaaattggtc ggttcttgta cgaatactcg acacgccatg aaggaatttt   1800
agaagatgac gaggcgatta aagagctatt cttagaacta caacaaaagt ttatggatat   1860
tcgtaagcga atcgttaagt tttaccacgc acgtttgaca caaatggttg cgattccaac   1920
aacttcaggt actggatcag aagtcacacc atttgccgtt attacagatg atgaaacaca   1980
tgtaaagtat ccactagccg attatgaatt gacaccggaa gttgctattg ttgatccaga   2040
atttgttatg accgtaccac aacacacggt atcttggtca ggattagatg ctttgtcaca   2100
tgctttggaa tcgtatgtct cagtgatggc ttctgaattc tcacgtcctt gggcattaca   2160
agctattaag ttgatttttg ataacttaac aaattcatac aattatgatc ctaaacaccc   2220
aactaaggaa ggtcagaatg cacgcacaaa gatgcactat gcgtcaacat tggctggtat   2280
gtcatttgcg aatgccttct tgggacttaa ccactcacta gcacacaaaa ctggtggaga   2340
attcggacta cctcacggta tggcaatcgc tattgcaatg ccacatgtga ttaagtttaa   2400
tgcggtaaca ggaaatgtaa agcgcacacc atacccacga tacgaaacct atacagcaca   2460
aaaagattat gctgatattg cacgttactt aggtttgaaa ggtgaaacag atgctgaatt   2520
ggtcgatgta ttgattgcag aaatcaagaa gttggctgca tcagtgggtg tcaatcaaac   2580
actatctggc aacggtgttt caaagcatga ctttgataca aagttagaaa agatgattga   2640
cttagtttac aatgaccaat gcacgccggg aaaccctcgc caacc                   2685
```

<210> SEQ ID NO 113
<211> LENGTH: 3164
<212> TYPE: DNA
<213> ORGANISM: Saccharomyces cerevisiae

<400> SEQUENCE: 113
atgccgccgc tattcaaggg actgaaacag atggcaaagc caattgccta tgtttcaaga 60
ttttcggcga aacgaccaat tcatataata cttttttctc taatcatatc cgcattcgct 120
tatctatccg tcattcagta ttacttcaat ggttggcaac tagattcaaa tagtgttttt 180
gaaactgctc caaataaaga ctccaacact ctatttcaag aatgttccca ttactacaga 240
gattcctctc tagatggttg ggtatcaatc accgcgcatg aagctagtga gttaccagcc 300
ccacaccatt actatctatt aaacctgaac ttcaatagtc ctaatgaaac tgactccatt 360
ccagaactag ctaacacggt tttgagaaa gataatacaa aatatattct gcaagaagat 420
ctcagtgttt ccaaagaaat ttcttctact gatggaacga aatggaggtt aagaagtgac 480
agaaaaagtc ttttcgacgt aaagacgtta gcatattctc tctacgatgt attttcagaa 540
aatgtaaccc aagcagaccc gtttgacgtc cttattatgg ttactgccta cctaatgatg 600
ttctacacca tattcggcct cttcaatgac atgaggaaga ccgggtcaaa tttttggttg 660
agcgcctcta cagtggtcaa ttctgcatca tcacttttct tagcattgta tgtcacccaa 720
tgtattctag gcaaagaagt ttccgcatta actcttttg aaggtttgcc tttcattgta 780
gttgttgttg gtttcaagca caaaatcaag attgcccagt atgccctgga gaaatttgaa 840
agagtcggtt tatctaaaag gattactacc gatgaaatcg tttttgaatc cgtgagcgaa 900
gagggtggtc gtttgattca agaccatttg ctttgtattt ttgcctttat cggatgctct 960
atgtatgctc accaattgaa gactttgaca aacttctgca tattatcagc atttatccta 1020
atttttgaat tgattttaac tcctacattt tattctgcta tcttagcgct tagactggaa 1080
atgaatgtta tccacagatc tactattatc aagcaaacat tagaagaaga cggtgttgtt 1140
ccatctacag caagaatcat tttaaagcag aaaagaaatc cgtatcttct ttcttaaatc 1200
tcagtgtggt tgtcattatc atgaaactct ctgtcatact gttgtttgtc ttcatcaact 1260
tttataactt tggtgcaaat tgggtcaatg atgccttcaa ttcattgtac ttcgataagg 1320
aacgtgtttc tctaccagat tttattacct cgaatgcctc tgaaaacttt aaagagcaag 1380
ctattgttag tgtcacccca ttattatatt acaaacccat taagtcctac caacgcattg 1440
aggatatggt tcttctattg cttcgtaatg tcagtgttgc cattcgtgat aggttcgtca 1500
gtaaattagt tctttccgcc ttagtatgca gtgctgtcat caatgtgtat ttattgaatg 1560
ctgctagaat tcataccagt tatactgcag accaattggt gaaaactgaa gtcaccaaga 1620
agtcttttac tgctcctgta caaaaggctt ctacaccagt tttaaccaat aaaacagtca 1680
tttctggatc gaaagtcaaa agtttatcat ctgcgcaatc gagctcatca ggaccttcat 1740
catctagtga ggaagatgat tcccgcgata ttgaaagctt ggataagaaa atacgtcctt 1800
tagaagaatt agaagcatta ttaagtagtg gaaatacaaa acaattgaag aacaaagagg 1860
tcgctgcctt ggttattcac ggtaagttac ctttgtacgc tttggagaaa aaattaggtg 1920
atactacgag agcggttgcg gtacgtagga aggctctttc aattttggca gaagctcctg 1980
tattagcatc tgatcgttta ccatataaaa attatgacta cgaccgcgta tttggcgctt 2040
gttgtgaaaa tgttataggt tacatgcctt tgcccgttgg tgttataggc cccttggtta 2100

-continued

```
tcgatggtac atcttatcat ataccaatgg caactacaga gggttgtttg gtagcttctg   2160
ccatgcgtgg ctgtaaggca atcaatgctg gcggtggtgc aacaactgtt ttaactaagg   2220
atggtatgac aagaggccca gtagtccgtt tcccaacttt gaaaagatct ggtgcctgta   2280
agatatggtt agactcagaa gagggacaaa acgcaattaa aaaagctttt aactctacat   2340
caagatttgc acgtctgcaa catattcaaa cttgtctagc aggagattta ctcttcatga   2400
gatttagaac aactactggt gacgcaatgg gtatgaatat gatttctaaa ggtgtcgaat   2460
actcattaaa gcaaatggta gaagagtatg gctgggaaga tatggaggtt gtctccgttt   2520
ctggtaacta ctgtaccgac aaaaaaccag ctgccatcaa ctggatcgaa ggtcgtggta   2580
agagtgtcgt cgcagaagct actattcctg gtgatgttgt cagaaaagtg ttaaaaagtg   2640
atgtttccgc attggttgag ttgaacattg ctaagaattt ggttggatct gcaatggctg   2700
ggtctgttgg tggatttaac gcacatgcag ctaatttagt gacagctgtt ttcttggcat   2760
taggacaaga tcctgcacaa aatgttgaaa gttccaactg tataacattg atgaaagaag   2820
tggacggtga tttgagaatt tccgtatcca tgccatccat cgaagtaggt accatcggtg   2880
gtggtactgt tctagaacca caaggtgcca tgttggactt attaggtgta agaggcccgc   2940
atgctaccgc tcctggtacc aacgcacgtc aattagcaag aatagttgcc tgtgccgtct   3000
tggcaggtga attatcctta tgtgctgccc tagcagccgg ccatttggtt caaagtcata   3060
tgacccacaa caggaaacct gctgaaccaa caaaacctaa caatttggac gccactgata   3120
taaatcgttt gaaagatggg tccgtcacct gcattaaatc ctaa                    3164
```

<210> SEQ ID NO 114
<211> LENGTH: 1290
<212> TYPE: DNA
<213> ORGANISM: Comamonas testosteroni

<400> SEQUENCE: 114

```
atggccgtcg attcgcgtct tcccaatttc cgagctctca cccccgcaca gcgctgggag     60
catgtcgcca ccgcatgcaa tctcagcgcc gaagaacgca atctactgac ccaggcgggc    120
gccctgcccg ccaccttggc tgacggcatg atcgaaaatg tggtgggcac gttcgagcta    180
cccatgggca tcgcaggcaa cttccgcatc aacggtcgcg atgtgctgat tccgctcgca    240
gtggaagagc cctccatcat cgctgctgct tcgtatatgg ccaagctggc ccgtgaagac    300
ggaggctttg aaacgtcgag caccttgccg ctgatgcgtg cgcaggtgca aatcgtcggc    360
atcagcgacc cctatggtgc aagactggcg ttgttcaagg cccgcgatga gatcctcgcg    420
caagccaata gccgagacaa ggtgctgatc agcctgggcg gtggctgcaa ggacatcgaa    480
atccacgtct tcccagattc tccgcgcggc cctatggtcg tgatgcactt gatcgtggac    540
gtgcgcgatg ccatgggtgc caacaccgtg aacaccatgg ccgaatcagt ctcgccactg    600
gtggaaaaga ttaccggtgg ttcggtgcgc ctgcgcattc tctcgaacct ggcagacctg    660
cgcctggccc gtgctcgtgt acgcctgaca ccgcaaacct tggccaccaa agagcgcagc    720
ggcgaagcaa ttattgaagg cgtgctcgac gcctacactt tcgccgccat tgacccctac    780
cgcgccgcta cccacaacaa gggcatcatg aacggtatcg accccgtcat cgtcgctaca    840
ggcaacgatt ggcgcgcggt cgaagccggt gcccatgcct atgccagccg caacggccaa    900
tacacctcgc tgacgcactg ggaaaaagac aatgccggcg ccttggtggg aacgatcgag    960
ctacccatgc ccgtgggctt ggtgggcggt gccaccaaga cccatccgct ggcgcgcctg   1020
gcgctcaaga tcatggaggt gaagtctgcc caggaactgg gcgagattgc cgccgcagtg   1080
```

ggtctggccc agaacctggg tgctttgcgc gcgctggcca ccgaaggcat tcagcgcggc 1140
catatggcac ttcatgctcg caatattgcg caggtcgcag gagccgtggg tgaagaagta 1200
gagatcgtcg ccaagcgcct ggctaccgag catgacgtgc gcaccgatcg cgcactggaa 1260
gtgctgcaag aaattcgcgc ccagcgctaa 1290

<210> SEQ ID NO 115
<211> LENGTH: 1284
<212> TYPE: DNA
<213> ORGANISM: Desulfurococcus kamchatkensis

<400> SEQUENCE: 115
atggagaaga caagccgtat acagggcttc tacaagcttc cccttgaaga aagacggagg 60
atagtctgcg agtgggctgg gctaacagag gaagagtgca ggacactgag cgaattcggt 120
aatctaccag ttaagatagg ggacagcatg attgagaacg ttataggcgc gatgagctat 180
cccttcgcag tagcgacaaa cttcctgatc aatgggaggg attaccttgt cccaatggtt 240
atagaggaga caagcgtcgt agcggctgca agcaatgcgg ccaggatgct taggcatggg 300
aaagggatac ttgcaaatgc tgagagacag gagatgatca gccaaataca cctggttaaa 360
gtaaactccc cacgctttaa agccatgaag attatcgagg ccaagaagga gctactggac 420
tacgcggcac agcaggatcc aaccctgcta aagtacggcg ggggtcccag ggacctcgag 480
gtaagagcaa tggagcaccc tgctttaggc ggggtcataa tagtccacct agtagtagac 540
gtcagagacg ccatgggtgc taacactgtt aacacgatgg ctgaagcgat agccccgctt 600
ctagagaaga taacgggtgg ggaagcaagg ctcagaatag tttcaaacca cgcagtatac 660
agggttacac gggcatgggc tgcgacacct gtcgaagaag tgggaggcct tgaagtagcc 720
aggaggataa tggaggcatc tatactcgcc gagatagatc cctatagggc ggtaacccat 780
aacaagggca taatgaatgg agtaatagca gtagccctcg cgacgggaca ggatcaccgc 840
gccatagagg ctggagccca tgcatacgcc tctagaacgg gggtctacaa gcccctcagc 900
tactgggagg taacaagcga taactatctt gcgggaagcc ttgagatacc tctccaaata 960
ggcgttgttg gaggagcagt caaggtacac cctgtggcaa agatagcatt gaagatccta 1020
ggggtaaaca cggctaggga gctcgccgag gtaatggctg cggtagggct agcccagaac 1080
ctagccgctc taagagccct cgtgacagag ggtattcaga aaggccatat gaggctccac 1140
gccagaaacc tcgctataat ggctggtgca tcaggagatc taatagataa gatagccgag 1200
aaaatgatca gggacggtag aataagatac gactacgcta aacaactagt agagaaagca 1260
ctacagggcg agccattaga ctag 1284

<210> SEQ ID NO 116
<211> LENGTH: 1281
<212> TYPE: DNA
<213> ORGANISM: Staphylococcus aureus

<400> SEQUENCE: 116
atgcaaaatt tagataagaa ttttcgacat ttatctcgta aagaaaagtt acaacaattg 60
gttgataagc aatggttatc agaagaacaa ttcgacattt tactgaatca tccattaatc 120
gatgaagaag tagccaatag tttaattgaa aatgtcatcg cgcaaggtgc attacccgtt 180
ggattattac cgaatatcat tgtggacgat aaggcatatg ttgtacctat gatggtggaa 240
gagccttcag ttgtcgctgc agctagttat ggtgcaaagc tagtgaatca gactggcgga 300

```
tttaaaacgg tatcttctga acgtattatg ataggtcaaa tcgtctttga tggcgttgac    360
gatactgaaa aattatcagc agacattaaa gctttagaaa agcaaattca taaaattgcg    420
gatgaggcat atccttctat taaagcgcgt ggtggtggtt accaacgtat agcgattgat    480
acatttcctg agcaacagtt actatcttta aaagtatttg ttgatacgaa agatgctatg    540
ggcgctaata tgcttaatac gattttagag gccataactg catttttaaa aaatgaattt    600
ccgcaaagcg acattttaat gagtatttta tccaatcatg caacagcgtc cgttgttaaa    660
gttcaaggcg aaattgatgt taaagattta gcaaggggcg agagaactgg agaagaggtt    720
gccaaacgaa tggaacgtgc ttctgtattg gcacaagtag atattcatcg tgcagcaaca    780
cataataaag gtgttatgaa tggcatacat gctgttgttt tagcaacagg aaatgatacg    840
cgtggtgcag aagcaagtgc gcatgcatac gcaagtcgtg acggacagta tcgtggtatt    900
gctacatggc gttacgatca agatcgtcaa cgattgattg gtacaattga agtgcctatg    960
acattggcaa ttgttggggg tggtacgaaa gtattaccaa tagctaaagc ttcattagag   1020
ctactaaatg tagagtcagc acaagaatta ggtcatgtag ttgctgccgt tggtttagcg   1080
caaaactttg cagcatgtcg cgcgcttgtg tcagaaggta ttcaacaagg tcatatgagt   1140
ttacaatata aatcattagc tattgttgta ggagcaaaag gtgatgaaat tgctaaagta   1200
gctgaagctt tgaaaaaaga accccgtgca aatacacaag cagcggaacg tattttacaa   1260
gatttaagaa gccaacaata g                                              1281
```

```
<210> SEQ ID NO 117
<211> LENGTH: 1236
<212> TYPE: DNA
<213> ORGANISM: Lactobacillus johnsonii

<400> SEQUENCE: 117
```

```
atgaaattag aagaatcatc taaaaagaaa ttttatcaat ggttaccaga ggaaagaaga     60
gtctttttaa ctgaaaaagg aattaaacta agtgagattg agtctgaaac tttggaaaga    120
ctagataaac ttagtgaaaa tgtaattggt caagtccgtc ttcctcttgg tgtgcttcct    180
aagttaatag ttaacgggaa agattatcaa gtaccaatgg ccgtagaaga accatcggtt    240
gttgcagcag caaaccatgc agctaaaatt tttaatcaaa atggtggagc agtagctgat    300
agtagacgaa atggaatata tggtcaaatt gttttagagg taactgataa ttttgattta    360
actaagttta ctactgaatt tcctcaatta attagcttag ctaataaaaa attcgttagc    420
ttagtcaagc atggtggagg agttcgtaaa attgaagctt ctcaaaaaga aaatttagtt    480
tttcttagag ttttggttga cccagcagaa gctatgggag ctaataaaac aaatgctatt    540
ttagaatttt taggaaatga attagagaag cagccagata ttgaacaaac tctgtatgca    600
attttgtcta attatcctac gcaattgact agtgctaaag taagtctttc aattgacagt    660
gtaggaggat taaaagttgc taaaaagata gctttattga gtaaaatagg acaaactgat    720
atttaccggg cagtgactaa taataaagga attatgaatg gtattgatag tgtattggtt    780
gcaactggta atgattatcg tggagttgaa gcagcaactg ctgtttgggc taataaaaat    840
ggtgcctata catctttgag taagtggaaa attgaagaag atagactagt ggggactgta    900
acagttccct tagcaatcgg tgtagtaggt ggctcaatta aggctcgtcg agacgttcaa    960
caaagcttta gtttattagg taatatatct gccaagcaac tagcagaagt tattgcgaca   1020
actggcttag caaataactt ttcagctctt ttagcaattt ctactaaggg aattcaagct   1080
gggcatatga aattgcaggc gagaaattta gtagcaacct taaaagctag tgaaggtgaa   1140
```

aaagcaatag ttttaaaaaa attgcaggaa agtaaaaaat atactcaaga agcagctttt 1200
gaatttttaa gcgaaataag aaaggatcaa aaataa 1236

<210> SEQ ID NO 118
<211> LENGTH: 912
<212> TYPE: DNA
<213> ORGANISM: Acinetobacter sp. ADP1

<400> SEQUENCE: 118
ttgatatcaa tcagggaaaa acgcgtgaac aaaaaacttg aagctctctt ccgagagaat 60
gtaaaaggta aagtggcttt gatcactggt gcatctagtg gaatcggttt gacgattgca 120
aaaagaattg ctgcggcagg tgctcatgta ttattggttg cccgaaccca agaaacactg 180
gaagaagtga aagctgcaat tgaacagcaa gggggacagg cctctatttt tccttgtgac 240
ctgactgaca tgaatgcgat tgaccagtta tcacaacaaa ttatggccag tgtcgatcat 300
gtcgatttcc tgatcaataa tgcagggcgt tcgattcgcc gtgccgtaca cgagtcgttt 360
gatcgcttcc atgattttga acgcaccatg cagctgaatt actttggtgc ggtacgttta 420
gtgttaaatt tactgccaca tatgattaag cgtaaaaatg gccagatcat caatatcagc 480
tctattggtg tattggccaa tgcgacccgt tttctgcttt atgtcgcgtc taaagctgcg 540
ctggatgcct tcagtcgctg tctttcagcc gaggtactca agcataaaat ctcaattacc 600
tcgatttata tgccattggt gcgtacccca atgatcgcac ccaccaaaat ttataaatac 660
gtgcccacgc tttccccaga agaagccgca gatctcattg tctacgccat tgtgaaacgt 720
ccaaaacgta ttgcgacgca cttgggtcgt ctggcgtcaa ttacctatgc catcgcacca 780
gacatcaata atattctgat gtcgattgga tttaacctat tcccaagctc aacggctgca 840
ctgggtgaac aggaaaaatt gaatctgcta caacgtgcct atgcccgctt gttcccaggc 900
gaacactggt aa 912

<210> SEQ ID NO 119
<211> LENGTH: 1670
<212> TYPE: DNA
<213> ORGANISM: Acinetobacter baylyi

<400> SEQUENCE: 119
cagaagatat ggttcggtta tcggttggga ttgaacatat tgatgatttg attgcagatc 60
tggaacaagc attggccaca gtttgagcgt aaattttata aaaaacctct gcaatttcag 120
aggttttttt atatttgctt tattatcgta tgatgttcat aattgatcta gcaaataata 180
aaaattagag caattactct aaaaacattt gtaatttcag atacttaaca ctagattttt 240
taaccaaatc actttagatt aactttagtt ctggaaattt tatttccctt taaccgtctt 300
caatccaaat acaataatga cagcctttac agtttgatat caatcaggga aaaacgcgtg 360
aacaaaaaac ttgaagctct cttccgagag aatgtaaaag gtaaagtggc tttgatcact 420
ggtgcatcta gtggaatcgg tttgacgatt gcaaaaagaa ttgctgcggc aggtgctcat 480
gtattattgg ttgcccgaac ccaagaaaca ctggaagaag tgaaagctgc aattgaacag 540
caagggggac aggcctctat ttttccttgt gacctgactg acatgaatgc gattgaccag 600
ttatcacaac aaattatggc cagtgtcgat catgtcgatt tcctgatcaa taatgcaggg 660
cgttcgattc gccgtgccgt acacgagtcg tttgatcgct tccatgattt tgaacgcacc 720
atgcagctga attactttgg tgcggtacgt ttagtgttaa atttactgcc acatatgatt 780

-continued

```
aagcgtaaaa atggccagat catcaatatc agctctattg gtgtattggc caatgcgacc    840

cgtttttctg cttatgtcgc gtctaaagct gcgctggatg ccttcagtcg ctgtctttca    900

gccgaggtac tcaagcataa aatctcaatt acctcgattt atatgccatt ggtgcgtacc    960

ccaatgatcg cacccaccaa aatttataaa tacgtgccca cgctttcccc agaagaagcc   1020

gcagatctca ttgtctacgc cattgtgaaa cgtccaacac gtattgcgac gcacttgggt   1080

cgtctggcgt caattaccta tgccatcgca ccagacatca ataatattct gatgtcgatt   1140

ggatttaacc tattcccaag ctcaacggct gcactgggtg aacaggaaaa attgaatctg   1200

ctacaacgtg cctatgcccg cttgttccca ggcgaacact ggtaaaattt ataaaagaag   1260

cctctcatac cgagaggctt ttttatggtt acgaccatca gccagattta gaggaaattg   1320

acttttcctg tttttacatc ataaatcgca ccaacaatat caatttcttt gcgatccagc   1380

atatctttaa gtacagaact atgctgaata atgtattgaa tattatagtg aacattcata   1440

gcagtcacct gatcaataaa tgctttgctt aattcacgcg gttgcataat atcaaataca   1500

ctgccaaccg aatgcatgag tggcccaagc acgtattgga tgtgtggcat ttcctgaata   1560

tcggaaatct gcttatgttg caatcttaac tggcatgcgc tggtgaccgc accacagtcg   1620

gtatgtccca aaaccagaat cactttggaa cctttggctt gacaggcaaa              1670
```

<210> SEQ ID NO 120
<211> LENGTH: 1362
<212> TYPE: DNA
<213> ORGANISM: Clostridium kluyveri

<400> SEQUENCE: 120

```
atgagtaatg aagtatctat aaaagaatta attgaaaagg caaaggtggc acaaaaaaaa     60

ttggaagcct atagtcaaga acaagttgat gtactagtaa aagcactagg aaaagtggtt    120

tatgataatg cagaaatgtt tgcaaaagaa gcagttgaag aaacagaaat gggtgtttat    180

gaagataaag tagctaaatg tcatttgaaa tcaggagcta tttggaatca tataaaagac    240

aagaaaactg taggcataat aaaagaagaa cctgaaaggg cacttgttta tgttgctaag    300

ccaaagggag ttgtggcagc tactacgcct ataactaatc cagtggtaac tcctatgtgt    360

aatgcaatgg ctgctataaa gggcagaaat acaataatag tagcaccaca tcctaaagca    420

aagaaagttt cagctcatac tgtagaactt atgaatgctg agcttaaaaa attgggagca    480

ccagaaaata tcatacagat agtagaagca ccatcaagag aagctgctaa ggaacttatg    540

gaaagtgctg atgtagttat tgctacaggc ggtgctggaa gagttaaagc tgcttactcc    600

agtggaagac cagcttatgg cgttggacct ggaaattcac aggtaatagt tgataaggga    660

tacgattata acaaagctgc acaggatata ataacaggaa gaaaatatga caatggaatt    720

atatgttctt cagagcaatc agttatagct cctgctgaag attatgataa ggtaatagca    780

gcttttgtag aaaatggggc attctatgta gaagatgagg aaacagtaga aaagtttaga    840

tcaactttat ttaaagatgg aaaaataaac agcaagatta taggtaaatc cgtccaaatt    900

attgcggatc ttgcaggagt aaaagtacca gaaggtacta aggttatagt acttaagggt    960

aaaggtgcag gagaaaaaga tgtactttgt aaagaaaaaa tgtgtccagt tttagtagca   1020

ttgaaatatg atacttttga agaagcagtt gaaatagcta tggctaatta tatgtatgaa   1080

ggagctggtc atacagcagg catacattct gacaatgacg agaacataag atatgcagga   1140

actgtattac ctataagcag attagttgta aatcagcctg caactactgc tggaggaagt   1200

ttcaataatg gatttaaccc tactactaca ctaggctgcg gatcatgggg cagaaacagt   1260
```

atttcagaaa atcttactta cgagcatctt ataaatgttt caagaatagg gtatttcaat 1320
aaagaagcaa aagttcctag ctatgaggaa atatggggat aa 1362

<210> SEQ ID NO 121
<211> LENGTH: 1356
<212> TYPE: DNA
<213> ORGANISM: Porphyromonas gingivalis

<400> SEQUENCE: 121
atggaaatca aagaaatggt gagccttgca cgcaaggctc agaaggagta tcaagctacc 60
cataaccaag aagcagttga caacatttgc cgagctgcag caaaagttat ttatgaaaat 120
gcagctattc tggctcgcga agcagtagac gaaaccggca tgggcgttta cgaacacaaa 180
gtggccaaga atcaaggcaa atccaaaggt gtttggtaca acctccacaa taaaaaatcg 240
attggtatcc tcaatataga cgagcgtacc ggtatgatcg agattgcaaa gcctatcgga 300
gttgtaggag ccgtaacgcc gacgaccaac ccgatcgtta ctccgatgag caatatcatc 360
tttgctctta agacctgcaa tgccatcatt attgcccccc accccagatc caaaaaatgc 420
tctgcacacg cagttcgtct gatcaaagaa gctatcgctc cgttcaacgt accggaaggt 480
atggttcaga tcatcgaaga acccagcatc gagaagacgc aggaactcat gggcgccgta 540
gacgtagtag ttgctacggg tggtatgggc atggtgaagt ctgcatattc ttcaggaaag 600
ccttctttcg gtgttggagc cggtaacgtt caggtgatcg tggatagcaa catcgatttc 660
gaagctgctg cagaaaaaat catcaccggt cgtgctttcg acaacggtat catctgctca 720
ggcgaacaga gcatcatcta caacgaggct gacaaggaag cagttttcac agcattccgc 780
aaccacggtg catatttctg tgacgaagcc gaaggagatc gggctcgtgc agctatcttc 840
gaaaatggag ccatcgcgaa agatgtagta ggtcagagcg ttgccttcat tgccaagaaa 900
gcaaacatca atatccccga gggtacccgt attctcgttg ttgaagctcg cggcgtagga 960
gcagaagacg ttatctgtaa ggaaaagatg tgtcccgtaa tgtgcgccct cagctacaag 1020
cacttcgaag aaggtgtaga aatcgcacgt acgaacctcg ccaacgaagg taacggccac 1080
acctgtgcta tccactccaa caatcaggca cacatcatcc tcgcaggatc agagctgacg 1140
gtatctcgta tcgtagtgaa tgctccgagt gccactacag caggcggtca catccaaaac 1200
ggtcttgccg taaccaatac gctcggatgc ggatcatggg gtaataactc tatctccgag 1260
aacttcactt acaagcacct cctcaacatt tcacgcatcg caccgttgaa ttcaagcatt 1320
cacatccccg atgacaaaga aatctgggaa ctctaa 1356

<210> SEQ ID NO 122
<211> LENGTH: 1407
<212> TYPE: DNA
<213> ORGANISM: Clostridium saccharoperbutylacetonicum

<400> SEQUENCE: 122
atgattaaag acacgctagt ttctataaca aaagatttaa aattaaaaac aaatgttgaa 60
aatgccaatc taaagaacta caaggatgat tcttcatgtt tcggagtttt cgaaaatgtt 120
gaaaatgcta taagcaatgc cgtacacgca caaaagatat tatcccttca ttatacaaaa 180
gaacaaagag aaaaaatcat aactgagata agaaaggccg cattagaaaa taaagagatt 240
ctagctacaa tgattcttga agaaacacat atgggaagat atgaagataa aatattaaag 300
catgaattag tagctaaata cactcctggg acagaagatt taactactac tgcttggtca 360
ggagataacg ggcttacagt tgtagaaatg tctccatatg gcgttatagg tgcaataact 420

```
ccttctacga atccaactga aactgtaata tgtaatagta taggcatgat agctgctgga    480
aatactgtgg tatttaacgg acatccaggc gctaaaaaat gtgttgcttt tgctgtcgaa    540
atgataaata aagctattat ttcatgtggt ggtcctgaga atttagtaac aactataaaa    600
aatccaacta tggactctct agatgcaatt attaagcacc cttcaataaa actactttgc    660
ggaactggag ggccaggaat ggtaaaaacc ctcttaaatt ctggtaagaa agctataggt    720
gctggtgctg gaaatccacc agttattgta gatgatactg ctgatataga aaaggctggt    780
aagagtatca ttgaaggctg ttcttttgat aataatttac cttgtattgc agaaaaagaa    840
gtatttgttt ttgagaacgt tgcagatgat ttaatatcta acatgctaaa aaataatgct    900
gtaattataa atgaagatca agtatcaaag ttaatagatt tagtattaca aaaaaataat    960
gaaactcaag aatactctat aaataagaaa tgggtcggaa aagatgcaaa attattctta   1020
gatgaaatag atgttgagtc tccttcaagt gttaaatgca taatctgcga agtaagtgca   1080
aggcatccat ttgttatgac agaactcatg atgccaatat taccaattgt aagagttaaa   1140
gatatagatg aagctattga atatgcaaaa atagcagaac aaaatagaaa acatagtgcc   1200
tatatttatt caaaaaatat agacaaccta aataggtttg aaagagaaat cgatactact   1260
atctttgtaa agaatgctaa atcttttgcc ggtgttggtt atgaagcaga aggctttaca   1320
actttcacta ttgctggatc cactggtgaa ggaataactt ctgcaagaaa ttttacaaga   1380
caaagaagat gtgtactcgc cggttaa                                       1407
```

<210> SEQ ID NO 123
<211> LENGTH: 1407
<212> TYPE: DNA
<213> ORGANISM: Clostridium beijerinckii

<400> SEQUENCE: 123

```
atgaataaag acacactaat acctacaact aaagatttaa aagtaaaaac aaatggtgaa     60
aacattaatt taaagaacta caaggataat tcttcatgtt tcggagtatt cgaaaatgtt    120
gaaaatgcta taagcagcgc tgtacacgca caaaagatat tatcccttca ttatacaaaa    180
gagcaaagag aaaaaatcat aactgagata agaaaggccg cattacaaaa taaagaggtc    240
ttggctacaa tgattctaga agaaacacat atgggaagat atgaggataa aatattaaaa    300
catgaattgg tagctaaata tactcctggt acagaagatt taactactac tgcttggtca    360
ggtgataatg gtcttacagt tgtagaaatg tctccatatg gtgttatagg tgcaataact    420
ccttctacga atccaactga aactgtaata tgtaatagca taggcatgat agctgctgga    480
aatgctgtag tatttaacgg acacccatgc gctaaaaaat gtgttgcctt tgctgttgaa    540
atgataaata aggcaattat ttcatgtggc ggtcctgaaa atctagtaac aactataaaa    600
aatccaacta tggagtctct agatgcaatt attaagcatc cttcaataaa acttctttgc    660
ggaactgggg gtccaggaat ggtaaaaacc ctcttaaatt ctggtaagaa agctataggt    720
gctggtgctg gaaatccacc agttattgta gatgatactg ctgatataga aaaggctggt    780
aggagcatca ttgaaggctg ttcttttgat aataatttac cttgtattgc agaaaaagaa    840
gtatttgttt ttgagaatgt tgcagatgat ttaatatcta acatgctaaa aaataatgct    900
gtaattataa atgaagatca agtatcaaaa ttaatagatt tagtattaca aaaaaataat    960
gaaactcaag aatactttat aaacaaaaaa tgggtaggaa aagatgcaaa attattctta   1020
gatgaaatag atgttgagtc tccttcaaat gttaaatgca taatctgcga agtaaatgca   1080
aatcatccat ttgttatgac agaactcatg atgccaatat tgccaattgt aagagttaaa   1140
```

gatatagatg aagctattaa atatgcaaag atagcagaac aaaatagaaa acatagtgcc 1200
tatatttatt ctaaaaatat agacaaccta aatagatttg aaagagaaat agatactact 1260
atttttgtaa agaatgctaa atcttttgct ggtgttggtt atgaagcaga aggatttaca 1320
actttcacta ttgctggatc tactggtgag ggaataacct ctgcaaggaa ttttacaaga 1380
caaagaagat gtgtacttgc cggctaa 1407

<210> SEQ ID NO 124
<211> LENGTH: 999
<212> TYPE: DNA
<213> ORGANISM: Metallosphaera sedula

<400> SEQUENCE: 124
atgaaagctg tcgtagtgaa aggacataaa cagggttatg aggtcaggga agttcaggac 60
ccgaaacctg cttcaggaga agtaatcatc aaggtcagga gagcagccct gtgttatagg 120
gaccttctcc agctacaggg gttctaccct agaatgaagt accctgtggt tctaggacat 180
gaggttgttg ggagatatact ggaggtaggt gagggagtga ccggtttctc tccaggagac 240
agagtaattt cactcctcta tgcgcctgac ggaacctgcc actactgcag acagggtgaa 300
gaggcctact gccactctag gttaggatac tctgaggaac tagatggttt cttctctgag 360
atggccaagg tgaaggtaac cagtctcgta aaggttccaa cgagagcttc agatgaggga 420
gccgttatgg ttccctgcgt cacaggcatg gtgtacagag ggttgagaag ggccaatcta 480
agagagggtg aaactgtgtt agttacggga gcaagcggtg gagttggaat acatgccctg 540
caagtggcaa aggccatggg agccagggta gtgggtgtca cgacgtcgga ggagaaggca 600
tccatcgttg gaaagtatgc tgatagggtc atagttggat cgaagttctc ggaggaggca 660
aagaaagagg acattaacgt ggtaatagac accgtgggaa cgccaacctt cgatgaaagc 720
ctaaagtcgc tctggatggg aggtaggata gtccaaatag gaaacgtgga cccaacccaa 780
tcctatcagc tgaggttagg ttacaccatt ctaaaggata tagccataat tgggcacgcg 840
tcagccacaa ggagggatgc agagggagca ctaaagctga ctgctgaggg gaagataaga 900
ccagtggttg cgggaactgt tcacctggag gagatagaca agggatatga aatgcttaag 960
gataagcaca aagtggggaa agtactcctt accacgtaa 999

<210> SEQ ID NO 125
<211> LENGTH: 1005
<212> TYPE: DNA
<213> ORGANISM: Sulfolobus tokodaii

<400> SEQUENCE: 125
atgaaagcaa ttgtagttcc aggacctaag caagggtata aacttgaaga ggtacctgat 60
cctaagccgg gaaaagatga agtaataatt agggtagata gagctgctct ttgttataga 120
gatttgcttc aactacaagg atattatcca agaatgaaat acccagttat actagggcat 180
gaagttgtag gaaccataga agaagtcgga gaaaatataa agggatttga agtaggtgat 240
aaagtaattt ctttattata tgcaccagat ggtacatgcg aatattgcca aataggtgag 300
gaagcatatt gtcatcatag gttaggctac tcagaagagc tagacggatt ttttgcagag 360
aaagctaaaa ttaaagtaac tagcttagta aaggttccaa aaggtacccc agatgaggga 420
gcagtacttg taccttgtgt aaccggaatg atatatagag gtattagaag ggctggtggt 480
atacgtaaag gggagctagt gttagttact ggtgccagtg gtggagtagg aatacatgca 540
attcaagttg ctaaggcctt aggtgctaaa gttatagggg taacaacatc agaagaaaaa 600

-continued gcaaagataa ttaagcagta tgcggattat gtcatcgttg gtacaaagtt ttctgaagaa 660
gcaaagaaga taggtgatgt tactttagtt attgatactg tgggtactcc tactttcgat 720
gaaagcttaa agtcattgtg gatgggcgga aggattgttc aaatagggaa tgtcgaccct 780
tctcaaatct ataatttaag attgggctac ataatattaa aagatttaaa gatagttggt 840
catgcctcag ctaccaaaaa agatgctgaa gatacactaa aattaacaca agagggaaaa 900
attaaaccag ttattgcagg aacagtcagt cttgaaaata ttgatgaagg ttataaaatg 960
ataaaggata agaataaagt aggcaaagtc ttagtaaaac cataa 1005

<210> SEQ ID NO 126
<211> LENGTH: 999
<212> TYPE: DNA
<213> ORGANISM: Metallosphaera cuprina

<400> SEQUENCE: 126
atgaaagctg ttatcgttaa gggagccaaa caaggttatg aagtcagaga cgttcaagat 60
ccgaaacctc aacctgatga ggtagtaata aaggttaaca gagctgccct atgttacaga 120
gatctccttc aacttcaggg gttttacccc aggatgaaat acccagtggt tctgggacac 180
gaagtgatag gcgaaatcgt tgacgtaggt agagacgtga aggggttcgc catagggat 240 agagtcatat ccttacttta cgctcctgac ggtagctgtc actactgtaa aaggggagag 300
gaggcatact gtcactctag actgggctat tctgaggagc ttgatggatt cttcgcggag 360
atggcaaggg ttaaagtaag tagcctcgtt aaggtacctc ctggagtttc cgatgagggg 420
ggagtcatgg taccttgcgt aaccgggatg atatatagag gtttaagaag agctaactta 480
agcgaagggg agaccgtttt agtgacaggg gccagtggag gagtcggaat acacgccctg 540
caagtcgcga aaggaatggg ggccagagtg attggggtga cgacttcaga ggagaagagt 600
tcgattatag cgaagtactc tgacagggta atagtaggtt ccaagttctc ggaagaggcc 660
aagaaagagg acgtcaacgt gatcattgat accgttggaa ctcctacgtt tgaggaaagc 720
ctcagatcgt tatggatggg aggtagaata gtccagattg gtaacgtaga tcctacacag 780
gcttaccaat tgagattagg ctacacgatt ctcaaagata ttgccataat tgggcatgcc 840
tcagctacca aacgcgatgc tgaagccgct ttaaaactaa cttcagaagg caaggtaagg 900
ccgatagtag ctggaaccgt cagcttagag gagatagata agggttacga aatcctcaag 960
gacaaacaca aagtagggaa ggtattgcta aagccttag 999

<210> SEQ ID NO 127
<211> LENGTH: 1788
<212> TYPE: DNA
<213> ORGANISM: Streptomyces clavuligerus

<400> SEQUENCE: 127
atgggacagt acgctgcacc gttgcgcgac atgcaattcg tcttgcacga attgctgaac 60
gtcgaagccg aactgaagca actgcctaag cacgcggatc tggatgccga tacgatcaat 120
gcggtgctgc aggaggcggg caagttctgc tccgaggtcc tgtttccgtt gaaccaggtt 180
ggcgaccagc agggttgtac gtatgtcggc gacggcgtgg tgaccacgcc cgagggcttc 240
aagcaagcgt accagcagta tatcgaggcc ggctggccgg cgttgggctg cgatccggcc 300
tatggcggcc agggcttgcc cgcgttcgtg aacaacgcgc tgtacgagat gctcaattcg 360
gcgaaccagg catggaccat gtatcctggc ctgtcgcacg gcgcgtacga atgcctgcac 420
gcgcacggca cgccggagct tcaacagcgg tatctaccga agctggtatc cggtcagtgg 480

-continued

```
accggcacga tgtgcttgac cgagccgcat tgcggcaccg accttgggat cttgcgcacg    540
cgggccgagc ccaacggcga cggctcgtac tcgattaccg gcacgaagat ctttatttcg    600
agcggcgagc acgacctcgc cgacaacatc gtccacctgg tgctcgcgcg gttgccggac    660
gcgccggcgg ggaccaaggg catttcattg ttcatcgtgc ccaagttcat cccggacgac    720
aacggcgagc ctgggcagcg caacggcgtc aagtgtggct cgatcgagca caagatgggc    780
atccatggca atgcgacgtg cgtaatcaat ctggatgatg ccaggggctg gctggtcggc    840
gagccgaaca agggcttgaa tgcgatgttc gtgatgatga atgcggcgcg gctcggcgtg    900
ggcatgcaag gcctggggct gaccgaagtc gcgtaccaga actcgctcgc ctacgcgagg    960
cagcggctgc agatgcgctc gcttagcggt cctaaggcgc cggacaaggc ggccgacccg   1020
atcatcgtgc acccggatgt gcgacgcatg ttgttgacgc agaaggccta cgtcgaggcg   1080
gggcgcgcgt tcacgtactg ggcggctctg cagatcgaca aggaactgtc gcacgaggac   1140
gaggcggtgc gccgggatgc ggccgacctg gttgcgttgc tcacaccggt catcaaggcg   1200
ttcctgaccg acaacgcgtt cgaggcgacc aacaacgcca tgcaggtgtt gggcggccat   1260
ggctatatcg ctgagtgggg catcgagcaa tatgtgcgtg atgcgcgcat caacatgatt   1320
tacgaaggca ctaacacgat tcagtcgctg gacctgctgg ggcgcaaggt gctcggcgac   1380
atgggcgcga agctgaagaa gtttggcaag ctcgtgcagg attttgtcca ggccgagggc   1440
atcaaccccg acatgcagga gttcgtcaat ccgctggcgg acatcggcga aaaggtacag   1500
aagctgacga tggaaatcgg catgaaggcg atgcagagcc cggacgaagt tggcgccgcg   1560
gcggtaccgt acctgcgcac ggtcgggcat ttagtgttct cgtacttttg ggcgcgcatg   1620
gcccgtctgg cgctggacaa gcaaggtagc ggcgacccat tctaccggtc caagctcgcg   1680
accgcgcggt tctactttgc gaagctgtta cccgagacgg ccttcacgat ccgcgccgcg   1740
cgtgccggag ccaagccgct gaccgagatc gacgaagcgc tgttttaa               1788
```

<210> SEQ ID NO 128
<211> LENGTH: 981
<212> TYPE: DNA
<213> ORGANISM: Rhodobacter sphaeroides

<400> SEQUENCE: 128

```
gtgagagccg ttctgataga gaaatccgac gatacgcagt ccgtttcggt gacggagctt     60
gccgaggacc agctgcccga gggcgacgtt ctggtcgacg tcgcctattc gaccttgaac    120
tacaaggacg cgctggcgat caccggcaag gcgccggtcg tgcggcgctt ccccatggtg    180
ccgggcatcg acttcacggg cacggtggca caaagcagcc atgccgattt caagcccggc    240
gaccgggtca tcctgaatgg ctggggcgtg ggggaaaaac actggggcgg gctggccgaa    300
cgggcacggg tccgcggcga ctggctggtt ccgctgccgg cgcccctcga cttgcggcag    360
gcggcgatga tcggcacggc gggctatacg gccatgctct gcgttctggc gctcgagcgg    420
cacggggtcg tgcccggcaa tggcgagatc gtcgtgagcg gcgccgctgg cggtgtcggc    480
agcgttgcga cgacacttct tgccgcgaag ggctacgaag ttgctgcggt caccggccgt    540
gcctccgagg cggagtatct gcgcggtctg ggcgccgcgt cggtgatcga ccgcaacgaa    600
ctgaccggca aggtccgtcc gctggggcag gagcgttggg ccggcggcat cgatgttgcg    660
ggcagcacgg tgctggcgaa catgctctcg atgatgaaat accggggcgt cgtcgcggcc    720
tgcggtcttg ccgcgggaat ggatctgccc gcgtcggtgg cgcccttcat cctgcgcggt    780
atgaccctgg ccggggtcga cagcgtcatg tgcccgaaaa ccgaccgcct tgcggcctgg    840
```

gctcggctcg ccagcgatct cgatccggca aagctcgagg agatgacgac cgaactgccc 900
ttctccgagg tcatcgagac cgccccgaag ttccttgacg ggaccgtccg aggacgcatc 960
gtcattccgg tcaccccctg a 981

<210> SEQ ID NO 129
<211> LENGTH: 1104
<212> TYPE: DNA
<213> ORGANISM: Clostridium propionicum

<400> SEQUENCE: 129
atggctttta acagtgctga tataaattcg tttcgagata tttgggtatt ttgcgaacag 60
agagaaggca agcttattaa tacagatttt gagctgattt cagaaggaag aaagctcgct 120
gatgagcggg gctcaaaatt ggttggtatt ttattaggac atgaggtaga agagattgca 180
aaagagctag gtggatatgg tgcagataaa gtgattgttt gcgaccatcc cgaattaaaa 240
ttttatacca cagatgctta tgccaaggta ctttgtgatg tggttatgga ggagaaaccc 300
gaggttattt tgattggtgc aacaaatatt ggccgtgatt taggccccag atgtgcagca 360
cgcttacata cgggtttaac agcagattgt acccatttgg atattgatat gaacaaatat 420
gtggactttc tttccacctc ctcaacattg gatatatcat ccatgacctt tcctatggag 480
gacacaaatt taaaaatgac ccgtcctgcc tttggcggac atttgatggc aactatcatt 540
tgccctagat tccgcccttg tatgtctact gtaagacccg gggttatgaa aaaagcagag 600
tttagccagg aaatggctca ggcttgtcag gttgttacac gccatgtaaa tttatctgat 660
gaggacttaa agacgaaagt aatcaatatt gtgaaagaaa ctaaaaaaat tgttgattta 720
atcggcgccg aaattattgt ttctgttgga cgtggaatca gcaaggatgt gcaaggggggc 780 attgccctag cagaaaagct tgccgatgcg tttgggaatg gtgttgttgg cggttctcgt 840
gcggttattg attccggttg gctccctgcg gatcatcagg ttgggcagac gggaaaaacc 900
gtgcatccta aggtatatgt tgcccttggt atttccggcg ccattcagca taaggcaggt 960
atgcaggatt cagagttgat tattgcggta aataaagacg agactgctcc tattttcgat 1020
tgtgctgatt atggtataac aggggatttg tttaaaattg taccaatgat gattgatgca 1080
attaaggaag gtaaaaatgc ttga 1104

<210> SEQ ID NO 130
<211> LENGTH: 804
<212> TYPE: DNA
<213> ORGANISM: Clostridium propionicum

<400> SEQUENCE: 130
atgagaattt atgtttgtgt aaaacaagtt ccggatacat cgggaaaggt tgctgtaaac 60
cccgatggaa ccttaaaccg tgcatctatg gcggctatta ttaatcccga tgatatgagt 120
gccattgagc aggccttaaa gttgaaggat gaaacaggct gtcaagttac agcccttacc 180
atggggccac ctcctgcgga gggaatgttg cgggaaatta tcgcaatggg cgcagatgat 240
ggcgttttaa tttccgccag agagttcggt ggttccgata ccttcgcaac ctctcaaatt 300
atatcggcgg cgatacataa attagggctt tccaatgagg atatgatttt ttgcggtagg 360
caggcaattg atggagatac agcacaggta ggaccgcaaa ttgcagaaaa attaagcatt 420
cctcaggtga cttatggggc agggattaaa aaaagcggag atttggtttt ggtaaagcgc 480
atgctggaag atggatatat gatgatagag gtggaaacac cctgcttgat tacttgcatt 540

-continued caggataagg ctgtaaaacc acgctatatg actttgaatg gaattatgga atgctatagc 600
aagcctcttt tggtattaga ttatgaagcc cttaaggatg aacccctaat cgaattggat 660
acgatcggtc tgaaaggttc tcctacaaat atatttaaat cctttacgcc gccacaaaag 720
ggtgtaggcg ttatgcttca aggaacagac aaagaaaaag ttgaagattt ggtggacaaa 780
ttgatgcaga agcatgtcat ttaa 804

<210> SEQ ID NO 131
<211> LENGTH: 1562
<212> TYPE: DNA
<213> ORGANISM: Candida boidinii

<400> SEQUENCE: 131
ttcaactaaa aattgaacta tttaaacact atgatttcct tcaattatat taaaatcaat 60
ttcatatttc cttacttctt tttgctttat tatacatcaa taactcaatt aactcattga 120
ttatttgaaa aaaaaaaaca tttattaact taactccccg attatatatt atattattga 180
ctttacaaaa tgaagatcgt tttagtctta tatgatgctg gtaagcacgc tgctgatgaa 240
gaaaaattat atggttgtac tgaaaataaa ttaggtattg ctaattggtt aaaagatcaa 300
ggtcatgaac taattactac ttctgataaa gaaggtgaaa caagtgaatt ggataaacat 360
atcccagatg ctgatattat catcaccact cctttccatc ctgcttatat cactaaggaa 420
agacttgaca aggctaagaa cttaaaatta gtcgttgtcg ctggtgttgg ttctgatcac 480
attgatttag attatattaa tcaaacaggt aagaaaatct cagtcttgga agttacaggt 540
tctaatgttg tctctgttgc tgaacacgtt gtcatgacca tgcttgtctt ggttagaaat 600
ttcgttccag cacatgaaca aattattaac cacgattggg aggttgctgc tatcgctaag 660
gatgcttacg atatcgaagg taaaactatt gctaccattg gtgctggtag aattggttac 720
agagtcttgg aaagattact cccttttaat ccaaaagaat tattatacta cgattatcaa 780
gctttaccaa aagaagctga agaaaaagtt ggtgctagaa gagttgaaaa tattgaagaa 840
ttagttgctc aagctgatat cgttacagtt aatgctccat tacacgcagg tacaaaaggt 900
ttaattaata aggaattatt atctaaattt aaaaaaggtg cttggttagt caataccgca 960
agaggtgcta tttgtgttgc tgaagatgtt gcagcagctt tagaatctgg tcaattaaga 1020
ggttacggtg gtgatgtttg gttcccacaa ccagctccaa aggatcaccc atggagagat 1080
atgagaaata aatatggtgc tggtaatgcc atgactcctc actactctgg tactacttta 1140
gatgctcaaa caagatacgc tgaaggtact aaaaatatct tggaatcatt ctttactggt 1200
aaatttgatt acagaccaca agatattatc ttattaaatg gtgaatacgt tactaaagct 1260
tacggtaaac acgataagaa ataaattttc ttaacttgaa aactataatt gctataacaa 1320
ttcttcaatt tctctttttc ttcctttttt tgaagaattt ttaacaatca aaattttgac 1380
tctttgattt cccgcaatct ctgagctcag catactcatt attattttat tattattatt 1440
attattactt ttattattat tatattttty cttctttaac gatatcgttt gtgttttatc 1500
ttttatgatt taaattttat acgaatttat gaatacaaca aaatatttaa gtttacacaa 1560
tg 1562

<210> SEQ ID NO 132
<211> LENGTH: 1131
<212> TYPE: DNA
<213> ORGANISM: Saccharomyces cerevisiae

<400> SEQUENCE: 132
atgtcgaagg gaaaggtttt gctggttctt tacgaaggtg gtaagcatgc tgaagagcag 60
gaaaagttat tggggtgtat tgaaaatgaa cttggtatca gaaatttcat tgaagaacag 120
ggatacgagt tggttactac cattgacaag gaccctgagc caacctcaac ggtagacagg 180
gagttgaaag acgctgaaat tgtcattact acgccctttt tccccgccta catctcgaga 240
aacaggattg cagaagctcc taacctgaag ctctgtgtaa ccgctggcgt cggttcagac 300
catgtcgatt tagaagctgc aaatgaacgg aaaatcacgg tcaccgaagt tactggttct 360
aacgtcgttt ctgtcgcaga gcacgttatg gccacaattt tggttttgat aagaaactat 420
aatggtggtc atcaacaagc aattaatggt gagtgggata ttgccggcgt ggctaaaaat 480
gagtatgatc tggaagacaa aataatttca acggtaggtg ccggtagaat tggatatagg 540
gttctggaaa gattggtcgc atttaatccg aagaagttac tgtactacga ctaccaggaa 600
ctacctgcgg aagcaatcaa tagattgaac gaggccagca agcttttcaa tggcagaggt 660
gatattgttc agagagtaga gaaattggag gatatggttg ctcagtcaga tgttgttacc 720
atcaactgtc cattgcacaa ggactcaagg ggtttattca ataaaaagct tatttcccac 780
atgaaagatg gtgcatactt ggtgaatacc gctagaggtg ctatttgtgt cgcagaagat 840
gttgccgagg cagtcaagtc tggtaaattg gctggctatg gtggtgatgt ctgggataag 900
caaccagcac caaaagacca tccctggagg actatggaca ataaggacca cgtgggaaac 960
gcaatgactg ttcatatcag tggcacatct ctggatgctc aaaagaggta cgctcaggga 1020
gtaaagaaca tcctaaatag ttacttttcc aaaaagtttg attaccgtcc acaggatatt 1080
attgtgcaga atggttctta tgccaccaga gcttatggac agaagaaata a 1131

<210> SEQ ID NO 133
<211> LENGTH: 438
<212> TYPE: DNA
<213> ORGANISM: Saccharomyces cerevisiae

<400> SEQUENCE: 133
atgtcgaagg gaaaggtttt gctggttctt tatgaaggtg gtaagcatgc tgaagagcag 60
gaaaagttat tggggtgtat tgaaaatgaa cttggtatca gaaatttcat tgaagaacag 120
ggatacgagt tggttactac cattgacaag gaccctgagc caacctcaac ggtagacagg 180
gagttgaaag acgctgaaat tgtcattact acgccctttt tccccgccta catctcgaga 240
aacaggattg cagaagctcc taacctgaag ctctgtgtaa ccgctggcgt cggttcagac 300
catgtcgatt tagaagctgc aaatgaacgg aaaatcacgg tcaccgaagt tactggttct 360
aacgtcgttt ctgtcgcaga gcacgttatg gccacaattt tggttttgat aagaaactat 420
aatggtggtc atcaataa 438

<210> SEQ ID NO 134
<211> LENGTH: 867
<212> TYPE: DNA
<213> ORGANISM: Cupriavidus necator

<400> SEQUENCE: 134
atgatgcgct gcatgcagtc accggaggtg catccggccg cggccggaga cgccgagccg 60
cccactcaca gcaccttcgc cgtcagccgc tggcgccgcg gcgagctgat gctgagcccc 120
gatgaagtgg ccgaggaagt gccggtcgcg ctggtgtaca acggcatctc gcacgcggtg 180
atgctggcga cgccggccga cctggaggac ttcgcactcg gcttcagcct gagcgaaggc 240

```
atcgttaccc gtgccagcga cgtctatgac atcgagatcg acacgcgcga gcacggcatc    300

gccgtgcagc tggagatcgc atcggaagcc ttcatgcggc tcaaggaccg ccgccgctcg    360

ctggccgggc gcaccggctg cgggctgtgc ggcaccgaat cgctggaaca ggtgatgcgc    420

ctgccggcac cggtgcgcag cgatgccagc ttccataccg acgtgatcca ggccgcgttc    480

gtgcaactgc aactgcggca ggaactgcag caacacacgg gtgcgacgca cgctgccgca    540

tggctgcgtg ccgatggcca tgtatcactg gtgcgtgaag acgtgggccg ccacaacgcg    600

ctggacaagc tggcgggcgc gctcgccagc agcggcgagg acatctccag cggcgcggtg    660

ctggtgacca gccgcgccag ctatgaaatg gtgctgaaga ccgccgccat cggcgccggc    720

gtgctcgccg cagtgtccgc accgacggcg ctggccgtgc ggcttgccga acaagccagc    780

atcaccctgg ccggcttcgt gcgcgccggc gcgcacgtgg tctatgccca tccccaacgc    840

ctgcagcacg aagcgagcct ggcatga                                        867
```

<210> SEQ ID NO 135
<211> LENGTH: 2880
<212> TYPE: DNA
<213> ORGANISM: Cupriavidus necator

<400> SEQUENCE: 135

```
atgaacgccc gcaacgagat cgatttcggc acgcccgcca gcccatccac cgaactggtc     60

accctggagg tcgatggcgt cagcgtcacc gtgcccgccg gcacctcggt gatgcgcgcc    120

gcgatggaag cgcagatcgc cgtccccaag ctgtgcgcca ccgacagcct cgaagccttc    180

ggctcgtgcc ggctgtgcct ggtcgagatc gaagggcgcc gcggctatcc ggcatcgtgc    240

accacgccgg tcgaagccgg catgaaggtc aagacccaga gcgacaagct ggccgacctg    300

cgccgcggcg tgatggagct gtatatctcc gaccacccgc tcgattgcct gacctgcccg    360

accaacggca actgcgagct gcaggacatg gccggcgtgg tcggcctgcg tgaagtgcgc    420

tacaacgacg gcggcccgga agctgcgccg atcgcgaccc acacgcagat gaagaaggac    480

gaatccaatc cttacttcac ctacgacccc tccaagtgca tcgtctgcaa ccgctgcgtg    540

cgcgcctgcg aggaaacgca gggcaccttc gccctgacca tcagcggccg cggcttcgat    600

tcccgcgtct cgcccggaac cagccagtcg ttcatggaat cggactgcgt ctcgtgcggc    660

gcctgcgtgc aggcgtgccc gaccgcgacg ctgaccgaga cctcggtgat caagttcggc    720

cagccctcgc acagcaccgt gaccacctgt gcctattgcg gcgtgggctg ttcgttcaag    780

gccgagatga agggcaatga agtggtgcgc atggtgccgt acaaggacgg caaggccaat    840

gaaggccacg cctgcgtcaa gggccgcttt gcctggggct acgccacgca caaggaccgc    900

atcctcaagc cgatgatccg cgccaagatc accgatccgt ggcgcgaggt gtcgtgggaa    960

gaggcgatcg actatgccgc gtcgcagttc aagcgtatcc aggccgagca cggcaaggac   1020

tccatcggcg gcatcgtgtc gtcgcgctgc accaatgaag agggctacct ggtgcagaag   1080

ctggtgcgcg cagccttcgg caacaacaac gtcgacacct gcgcgcgcgt gtgccattcg   1140

ccgaccggct acggcctgaa gcagaccctg ggcgaatcgg ccggcacgca gaccttcaag   1200

tcggtggaga aggccgacgt gatcatggtg atcggtgcca acccgaccga cggccacccg   1260

gtctttgcgt cgcgcatgaa gaagcgcctg cgcgccggcg ccaggctgat cgtggtcgat   1320

ccgcgccgca tcgacctggt cgactccccg catatccgtg ccgactatca cctgcaactg   1380

cgcccgggca ccaacgtggc gctggtgacc tcgctggccc acgtgatcgt caccgaaggc   1440
```

-continued

```
ctgctcaacg aagctttcat cgccgagcgc tgcgaggacc gcgccttcca gcaatggcgc   1500
gatttcgtct cgctgccgga gaactcgccg gaggcgatgg aaagcgtgac cggcattccg   1560
gcggaacagc tgcgcggtgc cgcacgcctg tatgccaccg gcggcaacgc tgcgatctac   1620
tacggcctgg gcgtgaccga gcatgcgcaa ggctcaacca ccgtgatggg cattgccaac   1680
ctcgccatgg ccaccggcaa tatcggccgc gaaggcgtgg gtgtgaaccc gctgcgcggg   1740
cagaacaatg tgcagggctc gtgcgacatc ggttcgttcc cgcatgagct gccgggctat   1800
cgccacgtgt cggactcgac cacgcgcggt ctgttcgaag ccgcgtggaa tgtcgagatc   1860
agccccgagc cgggcctgcg catcccccaat atgtttgaag ccgcgctggc cggcagcttc   1920
aagggcctct actgccaggg cgaggacatt gtccagtccg acccgaacac gcagcacgtg   1980
tccgaggcgc tgtcatcgat ggaatgcatc gtggtgcagg acatcttcct gaacgagacc   2040
gccaagtacg cgcacgtgtt cctgccgggc tcgtccttcc tggaaaagga cggcaccttc   2100
accaacgccg agcgccgcat ctcgcgcgtg cgcaaggtga tgccgcccaa ggcgcgctat   2160
gccgactggg aagccaccat cctgctggcc aatgcgctgg gctacccgat ggactacaag   2220
catccgtcgg agatcatgga cgagatcgcg cgcctgacgc cgaccttcgc cggtgtcagc   2280
tacaagcgcc tggaccagct cggcagcatc cagtggccgt gcaacgccga cgcgccggaa   2340
ggcacgccga ccatgcatat cgacaccttc gtgcgcggca agggcaagtt catcatcacc   2400
aagtacgtgc ccaccaccga gaagatcacg cgcgccttcc cgctgatcct gaccaccggc   2460
cgcatcctgt cgcaatacaa cgtcggcgcg cagacgcgcc gtaccgacaa cgtctactgg   2520
catgccgagg accggctcga gatccatccg cacgatgccg aggagcgcgg catcaaggac   2580
ggcgactggg tcggggtgca gagccgtgcc ggcgacacgg tgctgcgcgc gatcgtcagc   2640
gagcgcatgc agccgggcgt ggtctacacc accttccact tcccggaatc cggcgccaac   2700
gtgatcacca ccgacaactc cgactgggcc accaactgcc cggagtacaa ggtgaccgcg   2760
gtgcaggtgc tgccggtggc gcagccgtcg gcgtggcagc gggagtacca ggagttcaac   2820
gcccagcagc tgcaactgct ggaagccgcc agcgccgacc cggcgcaggc cgtacgctga   2880
```

<210> SEQ ID NO 136
<211> LENGTH: 1563
<212> TYPE: DNA
<213> ORGANISM: Cupriavidus necator

<400> SEQUENCE: 136

```
atgatcacga tcaccaccat cttcgtgccg cgcgattcca ccgcgctggc actgggcgcc     60
gacgacgtcg cccgcgccat cgcgcgtgaa gccgcggcgc gcaacgagca cgtgcgcatt    120
gtgcgcaatg gctcgcgcgg catgttctgg ctggagccgc tggtcgaggt gcagaccgga    180
gccggccgcg tggcctatgg cccggtcagc gccgcagacg tgccggggct gttcgacgcc    240
ggcttgctgc aaggcggcga gcacgcgctg tcgcagggcg tcaccgaaga gatccccttc    300
ctgaagcagc aggagcgcct gaccttcgcc cgcgtcggca tcaccgatcc gctgtcgctg    360
gacgactacc gcgcgcatga gggctttgcc ggcctggagc gcgcgctggc gatgcagccc    420
gccgagatcg tgcaggaggt caccgactcc ggcctgcgcg gccgcggcgg cgcggcgttc    480
ccgaccggca tcaagtggaa gaccgtgctg ggcgcgcagt ccgcggtcaa gtacatcgtc    540
tgcaatgccg acgagggcga ctcgggcacg ttctccgatc gcatggtgat ggaagacgac    600
ccgttcatgc tgatcgaagg catgaccatt gccgcgcttg cggtgggtgc ggagcagggc    660
tacatctact gccgttccga atacccgcac gcgattgccg tgctggaaag cgcgattggt    720
```

atcgccaacg ccgccggctg gctcggcgac gacatccgcg gcagcggcaa gcgcttccac 780
ctcgaagtgc gcaagggcgc cggcgcctat gtctgcggcg aggaaaccgc gctgctggaa 840
agcctggaag gacggcgcgg cgtggtgcgc gccaagccgc cgctgccggc gctgcagggg 900
ctgttcggca agcccacggt gatcaacaac gtgatctcgc tggccaccgt gccggtgatc 960
ctggcgcgcg gcgcgcagta ctaccgcgac tacggcatgg gccgttcgcg cggcacgctg 1020
ccgttccagc ttgccggcaa catcaagcag ggcggactgg tggaaaaggc gttcggcgtg 1080
acgctgcgcg agctgctggt cgactacggc ggcggcacgc gcagcggccg cgccatccgc 1140
gcggtgcagg tgggcgggcc gctgggcgcc tacctgcccg agtcgcgctt cgacgtgccg 1200
ctggactatg aagcctatgc cgcgttcggc ggcgtggtcg gccacggcgg catcgtggtg 1260
ttcgatgaaa ccgtcgacat ggcaaagcag gcccgctacg cgatggagtt ctgcgcgatc 1320
gaatcgtgcg gcaagtgcac cccgtgccgg atcggctcga cccgcggcgt cgaagtgatg 1380
gaccgcatca tcgccggcga gcagccggtc aagcacgtcg ccctggtgcg cgacctgtgc 1440
gacaccatgc tcaacggctc gctgtgcgcg atgggcggca tgaccccgta cccggtgctg 1500
tccgcgctga atgaattccc cgaggacttc ggcctcgcct ccaacccagc caaggccgcc 1560
tga 1563

<210> SEQ ID NO 137
<211> LENGTH: 225
<212> TYPE: DNA
<213> ORGANISM: Cupriavidus necator

<400> SEQUENCE: 137
atgaagatcg acaacctcat caccatggcc aaccagatcg gcagcttctt cgaggccatg 60
ccggatcggg aagaggccgt ctctgatatt gcagggcata tcaagcggtt ttgggagccg 120
cgcatgcgca aggccttgct ggggcatgtg gatgccgagg cagggagcgg gctgctggac 180
atcgtgcgcg aggcgctggg gcggcatcgg gcgatgctgg agtag 225

<210> SEQ ID NO 138
<211> LENGTH: 531
<212> TYPE: DNA
<213> ORGANISM: Cupriavidus necator

<400> SEQUENCE: 138
atgccagaaa tttcccccca cgcaccggca tccgccgatg ccacgcgcat cgccgccatc 60
gtggccgcgc gccaggacat accgggcgcc ttgctgccga tcctgcatga gatccaggac 120
acacagggct atatccccga cgccgccgtg cccgtcattg cccgcgcgct gaacctgtcg 180
cgcgccgagg tgcacggcgt gatcaccttc taccaccatt tccgccagca gccggccggg 240
cgccacgtgg tgcaggtctg ccgcgccgaa gcctgccagt cggtcggcgc cgaagcgctg 300
gccgagcatg cgcagcgcgc acttggctgt ggctttcatg aaaccaccgc ggacgggcag 360
gtgacgctgg agccggttta ttgcctgggc cagtgcgcct gcggccccgc cgtgatggtc 420
ggcgagcagc tgcacggcta tgtcgatgcc aggcgcttcg acgcgctggt gcgctcgctg 480
cgcgagtcgt ccgcggaaaa gaccacggaa gccgcggagg cacaggcatg a 531

<210> SEQ ID NO 139
<211> LENGTH: 1095
<212> TYPE: DNA
<213> ORGANISM: Cupriavidus necator -continued

<400> SEQUENCE: 139

```
atgattcgca tctcgatcca cccgcacctg cagatccggg acgacgccag ccccggtggc      60
gaggccctgg acgtgtcccg cctggtggcc ctgctcggcc atatcgagga atccggcagc     120
atcagccact cggcgcaggc ggtatcgctg tcctaccgct acgcctgggg catcctgcgc     180
gatgccgagg cgctgttcgg cggcccgctg atcgacaaga cccgcgggcg cggcagcgcg     240
ctgacgccgc tggcgcagca gttggtgtgg gccagcaagc ggatcggcgc gcggctgtcg     300
ccgacgctgg acagcctggc gtccgagctg gagatcgagt tgaagaagct gatggaccag     360
cccgaagcca cggcgcggct gcatgccagc cacggcttcg cggtggcggc gctgcgcgac     420
ttcctcgacg agcagcaggt gcggcacgac ctgaagtact gcggcagcgt cgaggccgtg     480
gcggcactgg ccgaaggcgc ctgcgatatc gccggcttcc atgtgccggt gggcgagttc     540
gagcacggca tgtggcggca tttcaccacc tggctcaagc cggacaccca ctgcctggtg     600
cacctggcgg tgcgcagcca gggactgttc gtgcggccgg acaacccgct tggcatccac     660
acgctggaag acctgacccg gcgcgaggtg cgcttcgtca accgccaggt gggctcgggc     720
acgcgcctgc tgctggacct gatgctggcc gcgcgcggca tcgacacggc ccgcatcgag     780
ggctacagca acggtgaatt cacccacgcc gcggtggccg cgtatatcgg cagcggcatg     840
gccgacgtgg gctttggcgt ggaaaccgcg gcgcggcgct tcgggctggc gttcgtgccg     900
gtgatcaagg agcgctactt ctttgcgatc gagcgcgcca agctgcgcag cgcggcactg     960
gccggcgcgg tggacgcgct taccagcgaa gccttccgcc agcgcgtcaa tgcactgccc    1020
ggctacgacg gcacgctgac cggcaccgtg ctgacgctgg aagaagcgtt cccggattac    1080
gctgaggcgc gctag                                                     1095
```